US012806178B2

(12) United States Patent
Charlier et al.

(10) Patent No.: US 12,806,178 B2
(45) Date of Patent: Nov. 24, 2026

(54) CRF1 RECEPTOR ANTAGONIST, PHARMACEUTICAL FORMULATIONS AND SOLID FORMS THEREOF FOR THE TREATMENT OF CONGENITAL ADRENAL HYPERPLASIA

(71) Applicant: Sanofi, Paris (FR)

(72) Inventors: Anne Charlier, Paris (FR); Nathalie Baud, Montpellier (FR)

(73) Assignee: Sanofi, Paris (FR)

( * ) Notice: Subject to any disclaimer, the term of this patent is extended or adjusted under 35 U.S.C. 154(b) by 1074 days.

(21) Appl. No.: 17/311,310

(22) PCT Filed: Dec. 6, 2019

(86) PCT No.: PCT/IB2019/001325

§ 371 (c)(1),
(2) Date: Jun. 4, 2021

(87) PCT Pub. No.: WO2020/115555

PCT Pub. Date: Jun. 11, 2020

(65) Prior Publication Data

US 2022/0023266 A1 Jan. 27, 2022

Related U.S. Application Data

(60) Provisional application No. 62/816,674, filed on Mar. 11, 2019, provisional application No. 62/776,763, filed on Dec. 7, 2018.

(51) Int. Cl.

| | |
|---|---|
| ***A61K 31/426*** | (2006.01) |
| ***A61K 9/00*** | (2006.01) |
| ***A61K 9/107*** | (2006.01) |
| ***A61K 9/28*** | (2006.01) |
| ***A61K 9/48*** | (2006.01) |
| ***A61K 45/06*** | (2006.01) |
| ***A61K 47/10*** | (2017.01) |
| ***A61K 47/14*** | (2017.01) |
| ***A61K 47/22*** | (2006.01) |
| ***A61K 47/26*** | (2006.01) |
| ***A61K 47/32*** | (2006.01) |
| ***C07D 277/42*** | (2006.01) |

(52) U.S. Cl.

CPC .......... *A61K 31/426* (2013.01); *A61K 9/0095* (2013.01); *A61K 9/107* (2013.01); *A61K 9/28* (2013.01); *A61K 9/4833* (2013.01); *A61K 45/06* (2013.01); *A61K 47/10* (2013.01); *A61K 47/14* (2013.01); *A61K 47/22* (2013.01); *A61K 47/26* (2013.01); *A61K 47/32* (2013.01); *C07D 277/42* (2013.01); *C07B 2200/13* (2013.01)

(58) Field of Classification Search

CPC .... A61K 31/426; A61K 9/0095; A61K 9/107; A61K 9/28; A61K 9/4833; A61K 45/06; A61K 47/10; A61K 47/14; A61K 47/22; A61K 47/26; A61K 47/32; C07D 277/42; C07B 2200/13

See application file for complete search history.

(56) References Cited

U.S. PATENT DOCUMENTS

| | | | |
|---|---|---|---|
| 5,464,847 | A | 11/1995 | Courtemanche et al. |
| 6,344,470 | B1 | 2/2002 | Fontaine et al. |
| 6,365,180 | B1 | 4/2002 | Meyer et al. |
| 6,531,475 | B1 | 3/2003 | Haddach et al. |
| 6,586,456 | B1 | 7/2003 | Fontaine et al. |
| 6,610,678 | B2 | 8/2003 | Huang et al. |
| 6,664,261 | B2 | 12/2003 | Chen et al. |
| 6,806,282 | B2 | 10/2004 | Geslin et al. |
| 7,276,526 | B2 | 10/2007 | Termin et al. |
| 7,297,708 | B2 | 11/2007 | Termin et al. |
| 7,951,803 | B2 | 5/2011 | Cole et al. |
| 8,030,304 | B2 | 10/2011 | Chen et al. |
| 8,153,127 | B2 | 4/2012 | Paez-Pereda et al. |
| 8,314,249 | B2 | 11/2012 | Fazekas et al. |
| 8,420,679 | B2 | 4/2013 | Fontaine et al. |
| 9,351,517 | B2 | 5/2016 | Bromley |
| 10,758,490 | B2 | 9/2020 | Viladot Petit et al. |
| 10,849,908 | B2 | 12/2020 | Howerton et al. |
| 10,898,477 | B2 | 1/2021 | Madhavi et al. |

(Continued)

FOREIGN PATENT DOCUMENTS

| | | |
|---|---|---|
| CN | 1370154 | 9/2002 |
| CN | 101381314 | 3/2009 |

(Continued)

OTHER PUBLICATIONS

Kitagawa et al., "Basic Pharmaceutical Science Textbook Series 20," Pharmaceutical Science, 2nd print, Kagaku-Dojin Publishing Co., Inc., 2012, p. 16-19 (with English translation).

(Continued)

*Primary Examiner* — Robert A Wax
*Assistant Examiner* — Olga V. Tcherkasskaya
(74) *Attorney, Agent, or Firm* — Fish & Richardson P.C.

(57) ABSTRACT

Provided are methods related to treating congenital adrenal hyperplasia in a subject in need thereof comprising administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Formula 1), or a pharmaceutically acceptable salt thereof. Further provided are pharmaceutical formulations and solid forms of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, and their use in the treatment of congenital adrenal hyperplasia (CAH).

52 Claims, 45 Drawing Sheets

(56) References Cited

U.S. PATENT DOCUMENTS

| | | | | |
|---|---|---|---|---|
| 10,905,690 | B2 | 2/2021 | Grigoriadis | |
| 11,007,201 | B2 | 5/2021 | Howerton et al. | |
| 11,304,950 | B2 | 4/2022 | Howerton et al. | |
| 11,311,544 | B2 | 4/2022 | Grigoriadis | |
| 11,583,502 | B2 | 2/2023 | Wu et al. | |
| 11,730,739 | B2 | 8/2023 | Grigoriadis | |
| 11,858,932 | B2 | 1/2024 | Barnes et al. | |
| 12,128,033 | B2 | 10/2024 | Becker et al. | |
| 12,214,084 | B2 | 2/2025 | Osaki et al. | |
| 12,383,536 | B2 | 8/2025 | Smith et al. | |
| 2005/0209250 | A1 | 9/2005 | Romano | |
| 2006/0078623 | A1 | 4/2006 | Dhoot et al. | |
| 2007/0281919 | A1 | 12/2007 | Fontaine et al. | |
| 2009/0203755 | A1 | 8/2009 | Richard | |
| 2010/0069463 | A1* | 3/2010 | Paez-Pereda ...... | G01N 33/5041 435/7.1 |
| 2010/0216751 | A1 | 8/2010 | Jacob et al. | |
| 2010/0222339 | A1 | 9/2010 | Chen et al. | |
| 2013/0183383 | A1 | 7/2013 | Phang et al. | |
| 2015/0094310 | A1 | 4/2015 | Holsboer | |
| 2015/0284362 | A1 | 10/2015 | Bersot et al. | |
| 2017/0020877 | A1 | 1/2017 | Grigoriadis | |
| 2019/0231781 | A1 | 8/2019 | Grigoriadis | |
| 2020/0255436 | A1 | 8/2020 | Howerton et al. | |
| 2021/0137926 | A1 | 5/2021 | Grigoriadis | |
| 2021/0361659 | A1 | 11/2021 | Grigoriadis | |
| 2022/0133742 | A1 | 5/2022 | Ghosh et al. | |
| 2022/0211711 | A1 | 7/2022 | Howerton et al. | |
| 2022/0409592 | A1 | 12/2022 | Smith et al. | |
| 2023/0065034 | A1 | 3/2023 | Ashweek et al. | |
| 2023/0233534 | A1 | 7/2023 | Palmer et al. | |
| 2023/0255942 | A1 | 8/2023 | Farber et al. | |
| 2023/0286932 | A1 | 9/2023 | Palmer et al. | |
| 2023/0295161 | A1 | 9/2023 | Barnes et al. | |
| 2024/0024330 | A1 | 1/2024 | Loewen et al. | |
| 2024/0058342 | A1 | 2/2024 | Grigoriadis | |
| 2024/0238257 | A1 | 7/2024 | Becker et al. | |

FOREIGN PATENT DOCUMENTS

| | | |
|---|---|---|
| CN | 102414185 | 4/2012 |
| CN | 106102740 | 11/2016 |
| CN | 107438606 | 12/2017 |
| JP | 2002-030048 | 1/2002 |
| JP | 4949582 | 3/2012 |
| JP | 2012-525368 | 10/2012 |
| JP | 2013-231063 | 11/2013 |
| JP | 2015-516979 | 6/2015 |
| JP | 2018-516231 | 6/2018 |
| RU | 2523793 | 7/2014 |
| RU | 2667977 | 9/2018 |
| WO | WO 1987/005297 | 9/1987 |
| WO | WO 98/08846 | 3/1998 |
| WO | WO 98/11075 | 3/1998 |
| WO | WO 99/10350 | 3/1999 |
| WO | WO 00/59888 | 10/2000 |
| WO | WO 2001/005776 | 1/2001 |
| WO | WO 03/006015 | 1/2003 |
| WO | WO 2003/022820 | 3/2003 |
| WO | WO 2006/044821 | 4/2006 |
| WO | WO 2006/044958 | 4/2006 |
| WO | WO 2006/102194 | 9/2006 |
| WO | WO 2006/107784 | 10/2006 |
| WO | WO 2006/116412 | 11/2006 |
| WO | WO 2006/126718 | 11/2006 |
| WO | WO 2007/069565 | 6/2007 |
| WO | WO 2007/069671 | 6/2007 |
| WO | WO 2007/090631 | 8/2007 |
| WO | WO 2007/104053 | 9/2007 |
| WO | WO 2007/105113 | 9/2007 |
| WO | WO 2007/137227 | 11/2007 |
| WO | WO 2008/036541 | 3/2008 |
| WO | WO 2008/036579 | 3/2008 |
| WO | WO 2008/051533 | 5/2008 |
| WO | WO 2008/082003 | 7/2008 |
| WO | WO 2008/083070 | 7/2008 |
| WO | WO 2008/136377 | 11/2008 |
| WO | WO 2009/008552 | 1/2009 |
| WO | WO 2009/144632 | 12/2009 |
| WO | WO 2010/014280 | 2/2010 |
| WO | WO 2010/014687 | 2/2010 |
| WO | WO 2010/015628 | 2/2010 |
| WO | WO 2010/015655 | 2/2010 |
| WO | WO 2010/062718 | 6/2010 |
| WO | WO 2010/096426 | 8/2010 |
| WO | WO 2010/125414 | 11/2010 |
| WO | WO 2011/043381 | 4/2011 |
| WO | WO 2011/043387 | 4/2011 |
| WO | WO 2011/092290 | 8/2011 |
| WO | WO 2011/092293 | 8/2011 |
| WO | WO 2011/095450 | 8/2011 |
| WO | WO 2011/128783 | 10/2011 |
| WO | WO 2013/155464 | 10/2013 |
| WO | WO 2013/160315 | 10/2013 |
| WO | WO 2013/160317 | 10/2013 |
| WO | WO 2014/151109 | 9/2014 |
| WO | WO 2015/112642 | 7/2015 |
| WO | WO 2015/155664 A1 | 10/2015 |
| WO | WO 2015/159170 | 10/2015 |
| WO | WO 2016/065177 | 4/2016 |
| WO | WO 2016/127133 | 8/2016 |
| WO | WO 2016/156575 A2 | 10/2016 |
| WO | WO 2016/156576 | 10/2016 |
| WO | WO 2017/031325 | 2/2017 |
| WO | WO 2017/218379 A1 | 12/2017 |
| WO | WO 2018/102552 | 6/2018 |
| WO | WO 2018/213634 A1 | 11/2018 |
| WO | WO 2018/219804 | 12/2018 |
| WO | WO 2019/036472 | 2/2019 |
| WO | WO 2019/036503 | 2/2019 |
| WO | WO 2019/210266 | 10/2019 |
| WO | WO 2021/016208 | 1/2021 |
| WO | WO 2021/062246 | 4/2021 |
| WO | WO 2021/111179 | 6/2021 |
| WO | WO 2021/113263 | 6/2021 |
| WO | WO 2021/250468 | 12/2021 |
| WO | WO 2021/252669 | 12/2021 |
| WO | WO 2022/036123 | 2/2022 |
| WO | WO 2022/046905 | 3/2022 |
| WO | WO 2022/153062 | 7/2022 |
| WO | WO 2022/184549 | 9/2022 |
| WO | WO 2024/206769 A1 | 10/2024 |

OTHER PUBLICATIONS

[No Author], "Guidance for Industry: Q3A Impurities in New Drug Substances," U.S. Department of Health and Human Services, Jun. 2008, 17 pages.

Auchus et al., "Crinecerfont Lowers Elevated Biomarkers of Disease Control in Adults with Congenital Adrenal Hyperplasia Due to 21-Hydroxylase Deficiency," submitted to Lancet Apr. 30, 2021, 33 pages.

Auchus et al., "Phase 3 Trial of Crinecerfont in Adult Congenital Adrenal Hyperplasia," The New England Journal of Medicine, Jun. 1, 2024, 11 pages.

Bastin et al., "Salt Selection and Optimisation Procedures for Pharmaceutical New Chemical Entities," Organic Process Research & Development, 2000, 4:427-435.

Byrn et al., "Pharmaceutical Solids: A Strategic Approach to Regulatory Considerations," Pharmaceutical Research, 1995, 12(7):945-954.

Croce et al., "A Simple Procedure for N-Propenylation and N-Propynylation of Secondary Amines," Gazetta Chimica Italiana, 1996, 126(2):107-109.

Habibzadeh, "Statistical Data Editing in Scientific Articles," Journal of Korean Medical Science, Jul. 2017, 32(7):1072-1076.

Hirayama, "[Handbook for manufacturing crystal of organic compound—principle and know-how]," Maruzen, Jul. 2008, 57-84 (with English translation).

(56) References Cited

OTHER PUBLICATIONS

Kojima, "[Effective solid form selection for the pharmaceutical development," Journal of Pharmaceutical Science and Technology, Sep. 1, 2008, 68(5):344-349 (with English translation).
Kumbhar et al., "D-α-tocopheryl polyethylene glycol succinate: A review of multifarious applications in nanomedicines," OpenNano, Mar. 2022, 6:100036, 13 pages.
Lee et al., "Standard deviation and standard error of the mean," Korean Journal of Anesthesiology, Jun. 2015, 68(3):220-223.
Mercado-Asis et al., "Acute Effects of Bromocriptine, Cyproheptadine, and Valproic Acid on Plasma Adrenocorticotropin Secretion in Nelson's Syndrome," Journal of Clinical Endocrinology & Metabolism, 1997, 82(2):514-517.
*Neurocrine Biosciences, Inc*., Petitioner, v. *Spruce Biosciences, Inc*., Patent Owner, Case No. PGR2021-00088, U.S. Pat. No. 10,849,908, Decision Denying Institution of Post-Grant Review 35 U.S.C. § 324, filed Dec. 10, 2021, 36 pages.
*Neurocrine Biosciences, Inc*., Petitioner, v. *Spruce Biosciences, Inc*., Patent Owner, Case No. PGR2021-00088, U.S. Pat. No. 10,849,908, Decision Granting Institution of Post-Grant Review 35 U.S.C. § 324, filed Dec. 1, 2023, 57 pages.
*Neurocrine Biosciences, Inc*., Petitioner, v. *Spruce Biosciences, Inc*., Patent Owner, Case No. PGR2021-00088, U.S. Pat. No. 10,849,908, Decision Vacating the Decision Denying Institution and Remanding to the Patent Trial and Appeal Board Panel for Further Proceedings, filed Aug. 4, 2023, 16 pages.
*Neurocrine Biosciences, Inc*., Petitioner, v. *Spruce Biosciences, Inc*., Patent Owner, Case No. PGR2021-00088, U.S. Pat. No. 10,849,908, Declaration of Adrian Dobs, M.D., M.H.S., filed Mar. 12, 2024, 68 pages.
*Neurocrine Biosciences, Inc*., Petitioner, v. *Spruce Biosciences, Inc*., Patent Owner, Case No. PGR2021-00088, U.S. Pat. No. 10,849,908, Declaration of Gordon B. Cutler, Jr., M.D. in Support of Petition for Post Grant Review of U.S. Pat. No. 10,849,908, filed Jan. 5, 2024, 228 pages.
*Neurocrine Biosciences, Inc*., Petitioner, v. *Spruce Biosciences, Inc*., Patent Owner, Case No. PGR2021-00088, U.S. Pat. No. 10,849,908, Deposition of Dr. Gordon B. Cutler, Jr., Washington, D.C., Thursday, Jul. 25, 2024, 207 pages.
*Neurocrine Biosciences, Inc*., Petitioner, v. *Spruce Biosciences, Inc*., Patent Owner, Case No. PGR2021-00088, U.S. Pat. No. 10,849,908, filed Mar. 12, 2024, 91 pages.
*Neurocrine Biosciences, Inc*., Petitioner, v. *Spruce Biosciences, Inc*., Patent Owner, Case No. PGR2021-00088, U.S. Pat. No. 10,849,908, filed on Jun. 20, 2024, 38 pages.
*Neurocrine Biosciences, Inc*., Petitioner, v. *Spruce Biosciences, Inc*., Patent Owner, Case No. PGR2021-00088, U.S. Pat. No. 10,849,908, filed on Jun. 27, 2024, 9 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner Spruce Biosciences' Motion To Exclude 37 C.F.R. §42.64(c), filed Aug. 14, 2024, 10 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Opposition To Petitioner's Motion To Exclude Evidence 37 C.F.R. §42.64, filed Aug. 20, 2024, 15 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Opposition To Petitioner's Motion To Strike, filed Aug. 28, 2024, 8 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Preliminary Response, filed Sep. 15, 2021, 57 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Reply in Support of Its Motion To Exclude, filed Aug. 23, 2024, 8 pages.
*Neurocrine Biosciences, Inc*., Petitioner, v. *Spruce Biosciences, Inc*., Patent Owner, Case No. PGR2021-00088, U.S. Pat. No. 10,849,908, Patent Owner's Sur-Reply, filed Aug. 12, 2024, 36 pages.
*Neurocrine Biosciences, Inc*., Petitioner, v. *Spruce Biosciences, Inc*., Patent Owner, Case No. PGR2021-00088, U.S. Pat. No. 10,849,908, Petition for Post Grant Review of U.S. Pat. No. 10,849,908, filed May 28, 2021, 90 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Motion To Exclude Evidence, filed Aug. 14, 2024, 16 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Motion To Strike, filed Aug. 22, 2024, 13 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Opposition To Patent Owner's Motion To Exclude Evidence, filed Aug. 20, 2024, 19 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Reply in Support of Its Motion To Exclude Evidence, filed Aug. 23, 2024, 9 pages.
*Neurocrine Biosciences, Inc*., Petitioner, v. *Spruce Biosciences, Inc*., Patent Owner, Case No. PGR2021-00088, U.S. Pat. No. 10,849,908, Petitioner's Request for Rehearing, filed Jan. 10, 2022, 18 pages.
*Neurocrine Biosciences, Inc*., Petitioner, v. *Spruce Biosciences, Inc*., Patent Owner, Case No. PGR2021-00088, U.S. Pat. No. 10,849,908, Reply Declaration of Gordon B. Cutler, Jr., M.D., filed Jun. 20, 2024, 64 pages.
*Neurocrine Biosciences, Inc*., Petitioner, v. *Spruce Biosciences, Inc*., Patent Owner, Case No. PGR2022-00025, U.S. Pat. No. 11,007,201, Decision Denying Institution of Post-Grant Review 35 U.S.C. § 324(a), filed Sep. 15, 2022, 35 pages.
*Neurocrine Biosciences, Inc*., Petitioner, v. *Spruce Biosciences, Inc*., Patent Owner, Case No. PGR2022-00025, U.S. Pat. No. 11,007,201, Decision Granting Institution of Post-Grant Review 35 U.S.C. § 324(a), filed Dec. 1, 2023, 38 pages.
*Neurocrine Biosciences, Inc*., Petitioner, v. *Spruce Biosciences, Inc*., Patent Owner, Case No. PGR2022-00025, U.S. Pat. No. 11,007,201, Declaration of Adrian Dobs, M.D., M.H.S., filed Mar. 12, 2024, 63 pages.
*Neurocrine Biosciences, Inc*., Petitioner, v. *Spruce Biosciences, Inc*., Patent Owner, Case No. PGR2022-00025, U.S. Pat. No. 11,007,201, Declaration of Gordon B. Cutler, Jr., M.D. in Support of Petition for Post Grant Review of U.S. Pat. No. 11,007,201, filed Jan. 5, 2024, 224 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner Spruce Biosciences' Motion To Exclude 37 C.F.R. §42.64(c), filed Aug. 14, 2024, 9 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Objections To Evidence, filed Jun. 27, 2024, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Objections To Evidence, filed on Dec. 15, 2023, 7 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Opposition To Petitioner's Motion To Exclude Evidence 37 C.F.R. §42.64, filed Aug. 20, 2024, 15 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Opposition To Petitioner's Motion To Strike, filed Aug. 28, 2024, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Pre-Institution Sur-Reply, filed Jul. 28, 2022, 8 pages.
*Neurocrine Biosciences, Inc*., Petitioner, v. *Spruce Biosciences, Inc*., Patent Owner, Case No. PGR2022-00025, U.S. Pat. No. 11,007,201, Patent Owner's Preliminary Response, filed Jun. 17, 2022, 72 pages.

(56) References Cited

OTHER PUBLICATIONS

*Neurocrine Biosciences, Inc.*, Petitioner, v. *Spruce Biosciences, Inc.*, Patent Owner, Case No. PGR2022-00025, U.S. Pat. No. 11,007,201, Patent Owner's Reply in Support of Its Motion To Exclude, filed Aug. 23, 2024, 7 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Response, filed Mar. 12, 2024, 93 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Sur-Reply, filed Aug. 12, 2024, 33 pages.
*Neurocrine Biosciences, Inc.*, Petitioner, v. *Spruce Biosciences, Inc.*, Patent Owner, Case No. PGR2022-00025, U.S. Pat. No. 11,007,201, Petition for Post Grant Review of U.S. Pat. No. 11,007,201, filed Feb. 18, 2022, 92 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion To Exclude Evidence, filed Aug. 14, 2024, 16 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion To Strike, filed Aug. 22, 2024, 14 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections To Evidence, filed Aug. 19, 2024, 4 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections To Evidence, filed Mar. 19, 2024, 6 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Opposition To Patent Owner's Motion To Exclude Evidence, filed Aug. 20, 2024, 15 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply in Support of Its Motion To Exclude Evidence, filed Aug. 23, 2024, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply To Patent Owner's Preliminary Response, filed Jul. 14, 2022, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply To Patent Owner's Response, filed Jun. 20, 2024, 36 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Request for Rehearing, filed Oct. 13, 2022, 17 pages.
*Neurocrine Biosciences, Inc.*, Petitioner, v. *Spruce Biosciences, Inc.*, Patent Owner, Case No. PGR2022-00025, U.S. Pat. No. 11,007,201, Reply Declaration of Gordon B. Cutler, Jr., M.D., filed Jun. 20, 2024, 60 pages.
*Neurocrine Biosciences, Inc.*, Petitioner, v. *Spruce Biosciences, Inc.*, Patent Owner, Case Nos. PGR2021-00088 and PGR2022-00025, U.S. Pat. Nos. 10,849,908 and 11,007,201, "Transcript of Feb. 29, 2024 Deposition of Gordon B. Cutler, Jr., M.D.," filed on Mar. 12, 2024, 147 pages.
*Neurocrine Biosciences, Inc.*, Petitioner, v. *Spruce Biosciences, Inc.*, Patent Owner, Case Nos. PGR2021-00088 and PGR2022-00025, U.S. Pat. Nos. 10,849,908 and 11,007,201, "Transcript of Jun. 5, 2024 Deposition of Dr. Adrian Dobs," filed on Jun. 20, 2024, 169 pages.
Recto II et al., "Comparison of the Efficacy and Tolerability of Simvastatin and Atorvastatin in the Treatment of Hypercholesterolemia," Clinical Cardiology, 2000, 23(9):682-688.
Saal et al., "Pharmaceutical salts: A summary on doses of salt formers from the Orange Book," European Journal of Pharmaceutical Sciences, Jul. 16, 2013, 49(4):614-623.
Yanovski et al., "Etiology of the Differences in Corticotropin-Releasing Hormone-Induced Adrenocorticotropin Secretion of Black and White Women," Journal of Clinical Endocrinology & Metabolism, 1996, 81(9):3307-3311.
[No Author Listed], "IUPAC-IUB, Commission on Biochemical Nomenclature—Abbreviated Nomenclature of Synthetic Polypeptides (Polymerized Amino Acids)*—Revised Recommendations (1971)," Biochemistry, 1972, 11(5):942-944.
Allen et al., "Psychometric evaluation and tests of validity of the Medical Outcomes Study 12-item Sleep Scale (MOS sleep)," Sleep Medicine, May 1, 2009;10(5):531-9.
Auchus et al., "A pharmacokinetic and biomarker study of the corticotropin-releasing factor receptor antagonist NBI-77860 in adult females with classic, 21-hydroxylase deficiency, congenital adrenal hyperplasia (CAH)," OR06 HPA Axis and Adrenal: Receptors To Clinical Impact, Platform presentation at the 97th annual meeting of the Endocrine Society (ENDO 2015), Mar. 2015, 1 page.
Auchus et al., "Crinecerfont (NBI-74788), a novel CRF1 receptor antagonist, reduces adrenal androgens and precursors in patients with classic congenital adrenal hyperplasia: Results from a phase 2, multiple-dose study," Poster Presentation, Presented Virtually at The 22nd European Congress of Endocrinology, Sep. 5-9, 2020, 1 page.
Auchus et al., "Crinecerfont lowers elevated hormone markers in adults with 21-hydroxylase deficiency congenital adrenal hyperplasia," The Journal of Clinical Endocrinology & Metabolism, 2022, 107(3):801-812.
Auchus et al., "OR18-4 Crinecerfont (NBI-74788), a Novel CRF1 Receptor Antagonist, Lowers Adrenal Androgens and Precursors in Adolescents with Classic Congenital Adrenal Hyperplasia," Journal of the Endocrine Society. 2022, 6(Supplement_1):A618.
Auchus et al., "Response to Crinecerfont Treatment in Adults with Classic Congenital Adrenal Hyperplasia Is Correlated with Elevated Baseline Hormone Levels But Not Glucocorticoid Dose," Abstract submitted to ECE for consideration at 2023 annual meeting, prepared on Mar. 2023, 2 pages.
Auchus et al., "The effects of crinecerfont (NBI-74788), a novel CRF1 receptor antagonist, on adrenal androgens and precursors in patients with classic congenital adrenal hyperplasia: Results from a multiple-dose phase 2 study," Journal of the Endocrine Society, 2020, 4(Abstract Supplement):A111.
Belza et al., "A systematic review of studies using the multidimensional assessment of fatigue scale," Journal of Nursing Measurement, May 1, 2018;26(1):36-74.
Berge et al., "Pharmaceutical salts," Journal of Pharmaceutical Sciences, 1977, 66(1):1-9.
Blume et al., "Oral medicine acceptance in infants and toddlers: measurement properties of the caregiver-administered Children's acceptance tool (CareCAT)," BMC pediatrics, 2018, 18:117.
Caira, "Crystalline polymorphism of organic compounds," Design of Organic Solids, 1998, pp. 163-208.
Collier et al., "Radiosynthesis and In-Vivo Evaluation of the Psuedopeptide δ-Opioid Antagonist [$^{125}$]-ITIPP(Ψ)," XIIIth International Symposium on Radiopharmaceutical Chemistry, J. Labelled Cpd. Radiopharm., 1999, 42(Suppl. 1):S264-S266.
Cui et al., "Modification of sample size in group sequential clinical trials," Biometrics, 1999, 55(3):853-857.
Dai et al., "A Generic Headspace GC Method for Residual Solvents in Pharmaceuticals: Benefits, Rationale, and Adaptations for New Chemical Entities," LCGC North America, 2010, 28(1):54-66.
De Villiers, "Pharmaceutical solvents and solubilizing agents," Pharmaceutical Excipients, Part 4, 2009, 15 pages.
De Villiers, "Vehicles for Liquid Preparations," A Practical Guide to Contemporary Pharmacy Practice, 3rd Editions, Jan. 2009, 22:267-276 pages.
De Vries et al., "Mental health of a large group of adults with disorders of sex development in six European countries," Psychosomatic Medicine, 2019, 81(7):629-640.
El-Maouche et al., "Adrenal morphology and associated comorbidities in congenital adrenal hyperplasia," Clinical Endocrinology, 2019, 91(2):247-255.

(56) References Cited

OTHER PUBLICATIONS

El-Maouche et al., "Longitudinal assessment of illnesses, stress dosing, and illness sequelae in patients with congenital adrenal hyperplasia," The Journal of Clinical Endocrinology & Metabolism, 2018, 103(6):2336-2345.
Fuqua et al., "Duration of suppression of adrenal steroids after glucocorticoid administration," International Journal of Pediatric Endocrinology, 2010, 2010:1-8.
Grossi et al., "Development and validation of the short version of the Psychological General Well-Being Index (PGWB-S)," Health and Quality of Life Outcomes, 2006, 4(1):1-8.
Gupta al., "Formulation strategies to improve the bioavailability of poorly absorbed drugs with special emphasis on self-emulsifying systems," ISRN Pharmaceutics, 2013, pp. 1-16.
He et al., "Changes in adrenal and gonadal androgens after 14-day treatment with a CRF1 receptor antagonist, crinecerfont (NBI-74788), in men with classic 21-hydroxylase deficiency," Journal of the Endocrine Society, 2021, 5(Supplement_1):A78.
Holm, "A simple sequentially rejective multiple test procedure," Scandinavian Journal of Statistics, 1979, 65-70.
Jenkins-Jones et al., "Poor compliance and increased mortality, depression and healthcare costs in patients with congenital adrenal hyperplasia," European Journal of Endocrinology, 2018, 178(4):309-320.
Jha et al., "SUN-371 Successful Induction of Fertility with Low-Dose Dexamethasone in a Patient with Congenital Adrenal Hyperplasia and Testicular Adrenal Rest Tumor," Journal of the Endocrine Society, 2019, 3(Supplement_1):SUN-371.
Le Bas et al., "Radioiodinated analogs of EP 00652218 for the exploration of the tachykinin NK1 receptor by spect," Journal of Labelled Compounds and Radiopharmaceuticals, 2001, 44(S1):S280-S282.
Lehmacher et al., "Adaptive sample size calculations in group sequential trials," Biometrics, 1999, 55(4):1286-1290.
Li et al., "Use of Spray-Dried Dispersions in Early Pharmaceutical Development: Theoretical and Practical Challenges," AAPS J, Mar. 2017, 19:321-333.
Mehta et al., "Adaptive increase in sample size when interim results are promising: a practical guide with examples," Statistics in Medicine, 2011, 30(28):3267-3284.
Miller et al., "Emergency management of adrenal insufficiency in children: advocating for treatment options in outpatient and field settings," Journal of Investigative Medicine, 2020, 68(1):16-25.
Mullins et al., "Brief psychiatric rating scale for children: quantitative scoring of medical records," Psychiatry Research, 1986, 19(1):43-49.
Newfield et al., "ACTH receptor blockade: A novel approach to treat congenital adrenal hyperplasia, or Cushing's disease," Medical Hypotheses, Apr. 2010, 74(4):705-706.
Newfield et al., "Crinecerfont (NBI-74788), a Novel $CRF_1$ Receptor Antagonist, Lowers Adrenal Androgens and Precursors in Adolescents with Classic Congenital Adrenal Hyperplasia," Abstract submitted to ECE for consideration at 2023 annual meeting, 2 pages.
Newfield et al., "Crinecerfont (NBI-74788), a novel CRF1 receptor antagonist, lowers adrenal androgens and precursors in adolescents with classic congenital adrenal hyperplasia," Presentation Slides presented at the 104th annual meeting and expo of the Endocrine Society (ENDO 2022), Atlanta, GA, Jun. 2022, 13 pages.
Nieves-Remacha et al., "Scale-up of N-alkylation reaction using phase-transfer catalysis with integrated separation in flow," Reaction Chemistry & Engineering, 2019, 4(2):334-345.
Nokoff et al., "Sex differences in effects of obesity on reproductive hormones and glucose metabolism in early puberty," The Journal of Clinical Endocrinology & Metabolism, 2019, 104(10):4390-4397.
Oster et al., "The functional and clinical significance of the 24-hour rhythm of circulating glucocorticoids, " Endocrine Reviews, 2017, 38(1):3-45.
Overall et al., "The Brief Psychiatric Rating Scale (BPRS): recent developments in ascertainment and scaling, " Psychopharmacology Bulletin, 1988, 24(1):97-99.
Overall et al., "The brief psychiatric rating scale," Psychological Reports, 1962, 10(3):799-812.
Peplow et al., "Blood draws up to 3% of blood volume in clinical trials are safe in children," Acta Paediatrica, 2019, 108(5):940-944.
Purnell et al., "Association of 24-hour cortisol production rates, cortisol-binding globulin, and plasma-free cortisol levels with body composition, leptin levels, and aging in adult men and women," The Journal of Clinical Endocrinology & Metabolism, 2004, 89(1):281-287.
Ravens-Sieberer et al., "Feasibility, reliability, and validity of the EQ-5D-Y: results from a multinational study," Quality of Life Research, 2010, 19(6):887-897.
Reisch, "Substitution therapy in adult patients with congenital adrenal hyperplasia," Best Practice & Research Clinical Endocrinology & Metabolism, 2015, 29(1):33-45.
Rief et al., "Mechanisms involved in placebo and nocebo responses and implications for drug trials," Clinical Pharmacology & Therapeutics, 2011, 90(5):722-726.
Ross et al., "Improved biochemical control with dose reduction in chronic glucocorticoid therapy: A phase III extension study of Chronocort (Efmody) in the treatment of Congenital Adrenal Hyperplasia (CAH)," Abstract submitted to ENDO 2023 for consideration, prepared on Dec. 2022, 2 pages.
Ross et al., "Switching patients with Congenital Adrenal Hyperplasia to Modified release hydrocortisone capsules: relative bioavailability and disease control," Abstract submitted to European Congress of Endocrinology 2023 for consideration, prepared on Jan. 2023, 2 pages.
Sarafoglou et al., "Tildacerfont in adults with classic congenital adrenal hyperplasia: results from two phase 2 studies," Manuscript, The Journal of Clinical Endocrinology & Metabolism, 2021, 106(11):e4666-79.
Scott et al., "The use of the EQ-5D-Y health related quality of life outcome measure in children in the Western Cape, South Africa: psychometric properties, feasibility and usefulness—a longitudinal, analytical study," Health and Quality of Life Outcomes, 2017, 15:12.
Smith et al., "Measures of sleep: the insomnia severity index, medical outcomes study (MOS) sleep scale, Pittsburgh sleep diary (PSD), and Pittsburgh sleep quality index (PSQI)," Arthritis Care & Research: Official Journal of the American College of Rheumatology, 2003, 49(S5):S184-S196.
Souron, "New Introduction of Pharmacology," Nanzando Co., 3rd edition, 1987, p. 414-416 (with English translation).
Stewart et al., "Exploring inpatient hospitalizations and morbidity in patients with adrenal insufficiency," The Journal of Clinical Endocrinology & Metabolism, 2016, 101(12):4843-4850.
Varni et al., "PedsQL™ 4.0: Reliability and validity of the Pediatric Quality of Life Inventory™ Version 4.0 Generic Core Scales in healthy and patient populations," Medical Care, 2001, 39(8):800-812.
Varni et al., "The PedsQL™ 4.0 as a school population health measure: feasibility, reliability, and validity," Quality of Life Research, 2006, 15:203-215.
Varni et al., "The PedsQL™ family impact module: preliminary reliability and validity," Health and Quality of Life Outcomes, 2004, 2:55.
Wiens, "A fixed sequence Bonferroni procedure for testing multiple endpoints," Pharmaceutical Statistics: The Journal of Applied Statistics in the Pharmaceutical Industry, 2003, 2(3):211-215.
Zhu et al., "Synthesis and mode of action of $^{125}$I-and $^{3}$H-labeled thieno [2,3-c]pyridine antagonists of cell adhesion molecule expression," The Journal of Organic Chemistry, 2002, 67(3):943-948.
Abdellatif, "Microparticles Formulation as a Targeting Drug Delivery System," J Nanomed Res., 2017, 6(2):00151.
Ambroziak et al., "Congenital adrenal hyperplasia due to 21-hydroxylase deficiency—management in adults," Polish Journal of Endocrinology, 2010, 61:142-155.
Anthenelli et al., "Sex Differences in the ACTH and Cortisol Response to Pharmacological Probes are Stressor-Specific and Occur Regardless of Alcohol Dependence History," Psychoneuroendocrinology, Aug. 2018, 94:72-82.

(56) References Cited

OTHER PUBLICATIONS

Arlt et al., "Health status of adults with congenital adrenal hyperplasia: a cohort study of 203 patients," J Clin Endocrinol Metab., Nov. 2010, 95(11):5110-21.
Arvanitis, AG., et al., "Non-Peptide Corticotropin-Releasing Hormone Antagonists: Syntheses and Structure—Activity Relationships of 2-Anilinopyrimidines and -triazines," J. Med. Chem., 1999, 42(5):805-818.
Auchus et al., "Approach to the patient: the adult with congenital adrenal hyperplasia," J Clin Endocrinol Metab., Jul. 2013, 98(7):2645-55.
Auchus et al., "The Effects of Crinecerfont (NBI-74788), a Novel CRF1 Receptor Antagonist, on Adrenal Androgens and Precursors in Patients with Classic Congenital Adrenal Hyperplasia: Results from A Multiple-Dose Phase 2 Study," J Endocrin Soc., 2020, 4(Supplement 1):OR25-03.
Auchus RJ, et al., "Management of the adult with congenital adrenal hyperplasia," Int J Ped Endocrinol., 2010, Article ID 614107: 1-9.
Bachelot A, et al., "Bone health should be an important concern in the care of patients affected by 21 hydroxylase deficiency," Int J Ped Endocrinol., 2010, Article ID 326275: 1-7.
Bakshi VP, et al., "Reduction of Stress-Induced Behavior by Antagonism of Corticotropin-Releasing Hormone 2 (CRH2) Receptors in Lateral Septum or CRH1 Receptors in Amygdala", J. Neurosci., 2002, 22(7): 2926-2935.
Bale et al., "Overview on Therapeutic Applications of Microparticulate Drug Delivery Systems," Crit Rev Ther Drug Carrier Syst., 2016, 33(4):309-361.
Barreau F. et al., "Pathways involved in gut mucosal barrier dysfunction induced in adult rats by maternal deprivation: corticotrophin-releasing factor and nerve growth factor interplay," Journal of Physiology—London, 2007, 580(1):347-356.
Behan DP et al., "Neurobiology of corticotropin releasing factor (CRF) receptors and CRF-binding protein: implications for the treatment of CNS disorders," Molecular Psychiatry, 1996, 1(4):265-277.
Belza, "Comparison of self-reported fatigue in rheumatoid arthritis and controls," J Rheumatol., Apr. 1995, 22(4):639-643.
Benedetti et al., "The Biochemical and Neuroendocrine Bases of the Hyperalgesic Nocebo Effect," J Neurosci., Nov. 15, 2006, 26(46):12014-12022.
Bleicken B, et al., "Improvement of health-related quality of life in adult women with 21-hydroxylase deficiency over a seven-year period," Endocr J., 2012, 59(10):931-939.
Bonfig et al., "Reduced final height outcome in congenital adrenal hyperplasia under prednisone treatment: deceleration of growth velocity during puberty," J Clin Endocrinol Metab., May 2007, 92(5):1635-1639.
Bonfig W. et al., "Hydrocortisone Dosing During Puberty in Patients With Classical Congenital Adrenal Hyperplasia: An Evidence-Based Recommendation," J Clin Endocrinol Metab., 2009, 94(10):3882-3888.
Bornstein et al., "Chronic effects of a nonpeptide corticotropin-releasing hormone type I receptor antagonist on pituitary-adrenal function, body weight, and metabolic regulation," Endocrinology, 1998, 139(4):1546-1555.
Brazier et al., "Validating the SF-36 health survey questionnaire: new outcome measure for primary care," BMJ, Jul. 18, 1992, 305(6846):160-164.
Brunson KL, et al., "Corticotropin-Releasing Hormone (CRH) Downregulates the Function of Its Receptor (CRF1) and Induces CRF1 Expression in Hippocampal and Cortical Regions of the Immature Rat Brain," Experimental Neurology, 2002, 176(1): 75-86.
Buxton et al., "Pharmacokinetics: The Dynamics of Drug Absorption, Distribution, Metabolism, and Elimination," Goodman & Gilman's The Pharmacological Basis of Therapeutics., Brunton L.L. ed., 12th ed. 2011, Chapter 2, 29 pages.
CAS Registry No., 321839-75-2, Feb. 15, 2001, 1 page.
Chakhtoura Z. et al., "Impact of total cumulative glucocorticoid dose on bone mineral density in patients with 21-hydroxylase deficiency, " Eur J Endocrinol., 2008, 158(6):879-887.
Charmandari et al., "Bioavailability of oral hydrocortisone in patients with congenital adrenal hyperplasia due to 21-hydroxylase deficiency," J Endocrinol, Apr. 2001, 169(1):65-70.
Chatzaki, E, et al., "CRF receptor type 1 and 2 expression and anatomical distribution in the rat colon," Journal of Neurochemistry, 2004, 90: 309-316.
Chen C, et al., "NBI 30775 (R121919), an Orally Active Antagonist of the Corticotropin-releasing Factor (CRF) Type-1 Receptor for the Treatment of Anxiety and Depression," Drug Development Research, 2005, 65(4):216-226.
Chen C, et al., "1-Alkyl-3-amino-5-ary1-1H-[1,2,4]triazoles: novel synthesis via cyclization of N-Acyl-S-methylisothioureas with alkylhydrazines and their potent corticotropin-Releasing factor-1 (CRF1) receptor antagonist activities," Bioorganic & Medicinal Chemistry Letters, 2001, 11(24): 3165-3168.
Chen C, et al., "Design and Synthesis of a Series of Non-Peptide High-Affinity Human Corticotropin-Releasing Factor1 Receptor Antagonists," J. Med. Chem., 1996, 39(22):4358-4360.
Chen C, et al., "Design of 2,5-Dimethyl-3-(6-dimethyl-4-methylpyridin-3-yl)-7-dipropylaminopyrazolo[1,5-a]pyrimidine (NBI 30775/R121919) and Structure-Activity Relationships of a Series of Potent and Orally Active Corticotropin-Releasing Factor Receptor Antagonists," J. Med. Chem., 2004, 47(19): 4787-4798.
Chen C, et al., "Optimization of 3-phenylpyrazolo[1,5-a]pyrimidines as potent corticotropin-releasing factor-1 antagonists with adequate lipophilicity and water solubility" Bioorganic & Medicinal Chemistry Letters, 2004, 14(14): 3669-3673.
Chen Y, et al., "Cellular and molecular mechanisms of hippocampal activation by acute stress are age-dependent," Molecular Psychiatry, 2006, 11: 992-1002.
Chen Y, et al., "Modulation of dendritic differentiation by corticotropin-releasing factor in the developing hippocampus," Proceedings of the National Academy of Sciences, 2004, 101(44): 15782-15787.
Cheng and Speiser, "Treatment outcomes in congenital adrenal hyperplasia," Adv Pediatr., 2012, 59(1):269-281.
Chinese Office Action in Chinese Application No. 20158005270.4, dated Oct. 19, 2018, 12 pages (with English Translation).
Claahsen-van der Grinten et al., "Prevalence of testicular adrenal rest tumours in male children with congenital adrenal hyperplasia due to 21-hydroxylase deficiency," Eur J Endocrinol., Sep. 2007, 157(3):339-344.
Claustre et al., "Effects of the Vasopressin ($V_{1b}$) Receptor Antagonist, SSR149415, and the Corticotropin-Releasing Factor 1 Receptor Antagonist, SSR125543, on FG 7142-induced Increase in Acetylcholine and Norepinephrine Release in the Rat," Neuroscience, 2006, 141:1481-1488.
Clinicaltrials.gov, "A study in patients with irritable bowel syndrome to measure hormone response after dosing with GW876008 and Gsk561679," U.S. National Library of Medicine, Aug. 6, 2007, retrieved on Jun. 11, 2020, retrieved from URL: https://clinicaltrials.gov/ct2/show/NCT00511563?term=NCT00511563&draw=1&rank=1, 5 pages.
Clinicaltrials.gov, "A study of the effects of a new antidepressant treatment (GSK561679) in females with major depressive disorder," U.S. National Library of Medicine, Aug. 13, 2008, retrieved on Jun. 11, 2020, retrieved from URL: https://clinicaltrials.gov/ct2/show/NCT00733980?term=NCT00733980&draw=2&rank=1, 14 pages.
Clinicaltrials.gov, "A study to compare the putative anxiolytic effect of 2 new drugs in subjects with social anxiety disorder," U.S. National Library of Medicine, Nov. 7, 2007, retrieved on Jun. 11, 2020, retrieved from URL: https://clinicaltrials.gov/ct2/show/NCT00555139?term=NCT00555139&draw=2&rank=1, 10 pages.
Clinicaltrials.gov, "CRF1 antagonist GSK561679 in alcoholism," U.S. National Library of Medicine, Aug. 24, 2010, retrieved on Sep. 25, 2020, retrieved from URL: https://clinicaltrials.gov/ct2/show/NCT01187511?term=NCT01187511&draw=2&rank=1, 20 pages.
Clinicaltrials.gov, "Evaluation of GSK561679 in women with post-traumatic stress disorder," U.S. National Library of Medicine, Nov.

(56) References Cited

OTHER PUBLICATIONS 25, 2009, retrieved on Jun. 11, 2020, retrieved from URL: https://clinicaltrials.gov/ct2/show/NCT01018992?term=NCT01018992&draw=2&rank=1, 9 pages.
Cottone P, et al., "CRF system recruitment mediates dark side of compulsive eating," Proceedings of the National Academy of Sciences, 2009, 106(47): 20016-20020.
Curtis AL, et al., "Pharmacological comparison of two corticotropin-releasing factor antagonists: in vivo and in vitro studies," Journal of Pharmacology and Experimental Therapeutics, 1994, 268(1): 359-365.
Dauber et al., "Nocturnal dexamethasone versus Hydrocortisone for the treatment of children with congenital adrenal hyperplasia," Int. J. of Pediatric Endocrinology, 2010, 2010(1):347636.
Deak et al., "The impact of the nonpeptide corticotropin-releasing hormone antagonist antalarmin on behavioral and endocrine responses to stress," Endocrinology, 1999, 140(1):79-86.
*Neurocrine Biosciences, Inc.*, Petitioner, v. *Spruce Biosciences, Inc.*, Patent Owner, Case No. PGR2021-00088, U.S. Pat. No. 10,849,908, Declaration of Robert M. Carey, M.D., dated May 28, 2021, 154 pages.
Derendorf et al., "Pharmacokinetics and oral bioavailability of hydrocortisone," J Clin Pharmacol. May 1991, 31(5):473-476.
Douma et al., "CRF1 receptor antagonists do not reverse pharmacological disruption of prepulse inhibition in rodents," Psychopharmacology, 2014, 231:1289-1303.
Dournes et al., "Deep brain stimulation in treatment-resistant depression in mice: comparison with the $CRF_1$ antagonist, SSR125543," Progress in Neuro-Psychopharmacology & Biological Psychiatry, 2013, 40:213-220.
Doyon et al., "Effects of the $CRF_1$ receptor antagonist SSR125543 on energy balance and food deprivation-induced in neuronal activation in obese Zucker rats," J. of Endocrinology, 2007, 193:11-19.
Dudzinska B, et al., "Sexual Well-Being in Adult Male Patients with Congenital Adrenal Hyperplasia," Int J Endocrinol., 2014, ID 469289: 1-9.
Dunn et al., "Physiological and behavioral responses to corticotropin-releasing factor administration: is CRF a mediator of anxiety or stress responses?" Brain Res Brain Res Rev., May 1990-Aug. 15(2):71-100.
Dyck B, et al., "Potent, Orally Active Corticotropin-Releasing Factor Receptor-1 Antagonists Containing a Tricyclic Pyrrolopyridine or Pyrazolopyridine Core," J. Med. Chem., 2005, 48(12): 4100-4110.
El Maouche et al., "Congenital Adrenal Hyperplasia," Lancet., Nov. 11, 2017, 390:2194-2210.
Elder et al., "The utility of sulfonate salts in drug development," Journal of Pharmaceutical Sciences, Jan. 1, 2010, 99(7):2948-2961.
Elnecave et al., "Bone mineral density in girls with classical congenital adrenal hyperplasia due to CYP21 deficiency," J Pediatr Endocrinol Metab., Dec. 2008, 21(12):1155-62.
Esteban et al., "Daily cortisol production rate in man determined by stable isotope dilution/mass spectrometry," J Clin Endocrinol Metab., Jan. 1991, 72(1):39-45.
EU Clinical Trials Register, "Abbreviated Style Clinical Study Report," Sanofi-Aventis Group, Sep. 5, 2011, 4 pages.
European Office Action in European Application No. 15702917, dated Aug. 16, 2019, 7 pages.
European Office Action in European Application No. 15702917.4, dated Dec. 9, 2018, 7 pages.
Fahmy et al., "Structure and Function of Small Non-Peptide CRF Antagonists and their Potential Clinical Use," Curr Mol Pharmacol., 2017, 10(4):270-281.
Falhammar et al., "Fertility, sexuality and testicular adrenal rest tumors in adult males with congenital adrenal hyperplasia," Eur J Endocrinol., Mar. 2012, 166(3):441-449.
Falhammar et al., "Fractures and bone mineral density in adult women with 21-hydroxylase deficiency," J Clin Endocrinol Metab. Dec. 2007; 92(12):4643-4649.
Falhammar et al., "Increased mortality in patients with congenital adrenal hyperplasia due to 21-hydroxylase deficiency," J Clin Endocrinol Metab., Dec. 2014, 99(12):E2715-21.
Falhammar et al., "Quality of life, social situation, and sexual satisfaction, in adult males with congenital adrenal hyperplasia," Endocrine., 2014, 47:299-307.
Finkielstain et al., "Clinical Characteristics of a Cohort of 244 Patients with Congenital Adrenal Hyperplasia," J Clin Endocrinol Metab, 2012, 97(12):4429-4438.
Fleck et al., "Binding Kinetics Redefine the Antagonist Pharmacology of the Corticotropin-Releasing Factor Type 1 Receptor," The Journal of Pharmacology and Experimental Therapeutics, 2012, 341(2):518-531.
Forest, "Recent advances in the diagnosis and management of congenital adrenal hyperplasia due to 21-hydroxylase deficiency," Human Reproduction Update, 2004, 10(6): 469-485.
Frederic et al., "Radiosynthesis of [C-11]SSR126374, a new selective CRF1 antagonist," Journal of Labelled Compounds & Radiopharmaceuticals, 2011, 54(1):273.
Gilban D, et al., "Health related quality of life of children and adolescents with congenital hyperplasia in Brazil," Health Qual Life Outcomes, 2014, 12:107 (9 pages).
Gilligan et al., "Corticotropin-releasing factor antagonists: recent advances and exciting prospects for the treatment of human diseases," Curr. Opin. In Drug Discov. & Develop., 2004, 7(4)487-497.
Grammatopoulos et al., Functional characteristics of CRH receptors and potential clinical applications of CRH-receptor antagonists, TRENDS in Endocrinology & Metabolism, 2002, 13(10):436-444.
Griebel et al., "4-(2-Chloro-4-methoxy-5-methylpheny1)-N-[(1S)-2-cyclopropyl-1-(3-fluoro-4-methylphenyl)ethy1]5-methyl-N-(2-propynyl)-1,3-thiazol-2-amine Hydrochloride (SSR125543A), a Potent and Selective Corticotrophin-Releasing factor(1) Receptor Antagonist. II. Characterization in Rodent Models of Stress-Related Disorders," J. Pharmacol. Exp. Ther., 2002, 301(1):333-345.
Grigoriadis DE, "Corticotropin-Releasing Factor Receptor Antagonists: Potential Novel Therapies for Human Disease," Celltransmissions, 2003, 19(4): 3-10.
Grigoriadis DE, "The corticotropin-releasing factor receptor: a novel target for the treatment of depression and anxiety-related disorders," Expert Opin. Ther. Targets, 2005, 9(4): 651-684.
Grigoriadis DE, et al., "$^{125}$I-Tyr$^{0}$-Sauvagine: A Novel High Affinity Radioligand for the Pharmacological and Biochemical Study of Human Corticotropin-Releasing Factor $_{2\alpha}$ Receptors," Molecular Pharmacology, 1996, 50:679-686.
Grigoriadis DE, et al., "Drugability of Extracellular Targets: Discovery of Small Molecule Drugs Targeting Allosteric, Functional, and Subunit-Selective Sites on GPCRs and Ion Channels," Neuropsychopharmacology, 2009, 34: 106-125.
Grigoriadis, DE, et al., "The CRF Receptor Structure, Function and Potential for Therapeutic Intervention," Current Medicinal Chemistry—Central Nervous System Agents, 2001, 1(1): 63-97.
Gross RS, et al., "Design and Synthesis of Tricyclic Corticotropin-Releasing Factor-1 Antagonists," J. Med. Chem., 2005, 48(18): 5780-5793.
Gully et al., "4-(2-Chloro-4-methoxy-5-methylpheny1)-N-[(1S)-2-cyclopropyl-1-(3-fluoro-4-methylphenyl)ethy1]5-methyl-N-(2-propyny1)-1,3-thiazol-2-amine Hydrochloride (SSR125543A): A Potent and Selective Corticotrophin-Releasing factor(1) Receptor Antagonist. I. Biochemical and Pharmacological Characterization," J. Pharmacol. Exp. Ther., 2002, 301(1):322-332.
Guo Z, et al., "Design and Synthesis of Tricyclic Imidazo[4,5-b]pyridin-2-ones as Corticotropin-Releasing Factor-1 Antagonists," J. Med. Chem., 2005 , 48(16): 5104-5107.
Habib et al., "Oral administration of a corticotropin-releasing hormone receptor antagonist significantly attenuates behavioral, neuroendocrine, and autonomic responses to stress in primates," Proceedings of the National Academy of Sciences, 2000, 97(11):6079-6084.
Halper et al., "Health-related quality of life in children with congenital adrenal hyperplasia," Health Qual Life Outcomes., 2017, 15(1):194.
Hamilton, "Needle Phobia: A Neglected Diagnosis," J Fam Pract., Aug. 1995, 41(2):169-175.

(56) References Cited

OTHER PUBLICATIONS

Han et al., "Quality of life in adults with congenital adrenal hyperplasia relates to glucocorticoid treatment, adiposity and insulin resistance: United Kingdom Congenital adrenal Hyperplasia Adult Study Executive (CaHASE)" Eur J Endocrinol., May 3, 2013, 168(6):887-893.
Han TS, et al., "Glucocorticoid treatment regimen and health outcomes in adults with congenital adrenal hyperplasia," Clin Endocrinol, 2013, 8:197-203.
Han TS, et al., "Relationship Between Final Height and Health Outcomes in Adults with Congenital Adrenal Hyperplasia: United Kingdom Congenital Adrenal Hyperplasia Adult Study Executive (CaHASE)," J Clin Endocrinol Metab., 2014, 99(8):E1547-E1555.
Han TS, et al., "Treatment and health outcomes in adults with congenital adrenal hyperplasia," Nat Rev Endocrinol., 2014, 10:115-124.
Hannah-Shmouni et al., "Genetics of Congenital Adrenal Hyperplasia," Best Pract Res Clin Endocrinol Metab., Apr. 2009, 23(2):181-192.
Hauger RL, et al., "International Union of Pharmacology. XXXVI. Current Status of the Nomenclature for Receptors for Corticotropin-Releasing Factor and Their Ligands," Pharmacological Reviews, 2003, 55(1): 21-26.
Heinrichs SC, et al., "Brain Penetrance, Receptor Occupancy and Antistress In Vivo Efficacy of a Small Molecule Corticotropin Releasing Factor Type I Receptor Selective Antagonist," Neuropsychopharmacology, 2002, 27:194-202.
Herdman et al., "Development and preliminary testing of the new five-level version of EQ-5D (EQ-5D-5L)," Qual Life Res., Dec. 2011, 20(10):1727-1736.
Hertzberg et al., "Birth prevalence rates of newborn screening disorders in relation to screening practices in the United States," J Pediatr., Oct. 2011, 159(4):555-560.
Hines et al., "Spatial abilities following prenatal androgen abnormality: targeting and mental rotations performance in individuals with congenital adrenal hyperplasia," Psychoneuroendocrinology, Nov. 2003, 28(8):1010-1026.
Hoare et al., "Mechanism of Corticotropin-Releasing Factor Type I Receptor Regulation by Nonpeptide Antagonists," Molecular Pharmacology, 2003, 63(3):751-756.
Hoare SRJ, et al., "Allosteric Ligands for the Corticotropin Releasing Factor Type 1 Receptor Modulate Conformational States Involved in Receptor Activation," Molecular Pharmacology, 2008, 73(5): 1371-1380.
Hoare SRJ, et al., "Conformational states of the corticotropin releasing factor 1 (CRF1) receptor: detection, and pharmacological evaluation by peptide ligands," Peptides, 2003, 24(12): 1881-1897.
Hoare SRJ, et al., "Ligand Affinity for Amino-Terminal and Juxtamembrane Domains of the Corticotropin Releasing Factor Type I Receptor: Regulation by G-Protein and Nonpeptide Antagonists," Biochemistry, 2004, 43(13): 3996-4011.
Hoare SRJ, et al., "Single amino acid residue determinants of non-peptide antagonist binding to the corticotropin-releasing factor1 (CRF1) receptor," Biochemical Pharmacology, 2006, 72(2): 244-255.
Huang CQ, et al., "Design and synthesis of 3-(2-pyridyl)pyrazolo[1,5-a]pyrimidines as potent CRF1 receptor antagonists," Bioorganic & Medicinal Chemistry Letters, 2004, 14(15): 3943-3947.
Huang CQ, et al., "Design, synthesis, and SAR of 2-dialkylamino-4-arylpyrimidines as potent and selective corticotropin-releasing factor1 (CRF1) receptor antagonists," Bioorganic & Medicinal Chemistry Letters, 2004, 14(9): 2083-2086.
Huang CQ, et al., "Synthesis and SAR of 8-Arylquinolines as potent corticotropin-Releasing factor1 (CRF1) receptor antagonists," Bioorganic & Medicinal Chemistry Letters, 2003, 13(19): 3375-3379.
Huang CQ, et al., "Synthesis of 1-methyl-3-phenylpyrazolo[4,3-b]pyridines via a methylation of 4-phthalimino-3-phenylpyrazoles and optimization toward highly potent corticotropin-releasing factor type-1 antagonists," Bioorganic & Medicinal Chemistry Letters, 2003, 13(19): 3371-3374.
International Preliminary Report in International Application No. PCT/IB2019/001325, dated Dec. 23, 2020, 15 pages.
International Search Report and Written Opinion in International Application No. PCT/IB2019/001325, dated Jul. 3, 2020, 24 pages.
Invitation to Pay Fees in International Application No. PCT/IB2019/001325, dated Apr. 17, 2020, 15 pages.
International Search Report and Written Opinion in International Appln. No. PCT/US2015/012315, dated Apr. 21, 2015, 11 pages.
International Preliminary Report in International Application No. PCT/US2015/012315, dated Jul. 26, 2016, 7 pages.
Iranmanesh et al., "Glucose Ingestion Selectively Amplifies ACTH and Cortisol Secretory-Burst Mass and Enhances Their Joint Synchrony in Healthy Men," J Endocrinol and Metab., Sep. 2011, 96(9):2882-2888.
Ising M, et al., "High-Affinity CRF1 Receptor Antagonist NBI-34041: Preclinical and Clinical Data Suggest Safety and Efficacy in Attenuating Elevated Stress Response," Neuropsychopharmacology, 2007, 32:1941-1949.
Israeli Office Action in Israeli Application No. 246783, dated Mar. 9, 2019, 3 pages (with English Translation).
Ivy AS, et al., "Hippocampal Dysfunction and Cognitive Impairments Provoked by Chronic Early-Life Stress Involve Excessive Activation of CRH Receptors," J. Neurosci., 2010, 30(39):13005-13015.
Jain et al., "Spray Drying in Pharmaceutical Industry: A review," Research Journal of Pharmaceutical Dosage Forms and Technology, Apr. 10, 2012, 4(2):74-79.
Japanese Office Action in Japanese Application No. 2016-565135, dated Dec. 11, 2018, 13 pages (with English Translation).
Johannsen et al., "Impaired cognitive function in women with congenital adrenal hyperplasia," J Clin Endocrinol Metab., Apr. 2006, 91(4):1376-1381.
Katkade et al., "Real world data: an opportunity to supplement existing evidence for the use of long-established medicines in health care decision making," J Multidiscip Healthc., 2018, 11:295-304.
Kehne et al., "Therapeutic Utility of Non-Peptidic $CRF_1$ Receptor Antagonists in Anxiety, Depression, and Stress-Related Disorders: Evidence from Animal Models," Pharmacol Ther., Dec. 2010; 128(3):460-487.
Kiddoo DA, et al., "Impact of state of arousal and stress neuropeptides on urodynamic function in freely moving rats," Am J Physiol Regul Integr Comp Physiol, 2006, 290:R1697-R1706.
Kim et al., "Cardiovascular Disease Risk in Adult Women with Congenital Adrenal Hyperplasia Due to 21-hydroxylase Deficiency," Semin Reprod Med, 2009, 27(4):316-321.
King et al., "Long-Term Corticosteroid Replacement and Bone Mineral Density in Adult Women with Classical Congenital Adrenal Hyperplasia," The Journal of Clinical Endocrinology & Metabolism, 2006, 91(3):865-869.
Koelsch et al., "The Impact of Acute Stress on Hormones and Cytokines, and How Their Recovery is Affected by Music-Evoked Positive Mood," Sci Reps., Mar. 2016, 6:1-11.
Koob et al., "Update on Corticotropin-Releasing Factor Pharmacotherapy for Psychiatric Disorders: A Revisionist View ," Neuropsychopharmacology Reviews, 2012, 37:308-309.
Kosoyan HP, et al., "The $CRF_1$ receptor antagonist, NBI-35965, abolished the activation of locus coeruleus neurons induced by colorectal distension and intracisternal CRF in rats," Brain Research, 2005, 1056(1):85-96.
Kulshreshtha B, et al., "Pubertal development among girls with classical congenital adrenal hyperplasia initiated on treatment at different ages," Indian J Endocrinol Metab., 2012, 16(4):599-603.
Lekarev et al., "Adrenal disease in pregnancy," Best Practice & Research, Clinical Endocrinology & Metabolism, Dec. 2011, 25(6):959-973.
Li et al., "The pharmacology of DMP696 and DMP904, non-peptidergic $CRF_1$ receptor antagonists," CNS Drug Reviews, 2005, 11(1):21-52.
Liapakis G, et al., "Members of CRF Family and their Receptors: From Past to Future," Current Medicinal Chemistry, 2011, 18(17):2583-2600.
Linder et al., "Cortisol production rate in childhood and adolescence," J Pediatr, Dec. 1990, 117(6):892-896.

(56) References Cited

OTHER PUBLICATIONS

Liu J, et al., "Corticotropin-Releasing Factor and Urocortin I Modulate Excitatory Glutamatergic Synaptic Transmission," Journal of Neuroscience, 2004, 24(16): 4020-4029.
Loechner et al., "Alternative Strategies for the Treatment of Classical Congenital Adrenal Hyperplasia: Pitfalls and Promises," International Journal of Pediatric Endocrinology, vol. 2010, No. 1, Jun. 8, 2010, Article ID 670960, 10 pages.
Logachev et al., "Congenital Adrenal Hyperplasia: Modern Problems of Terminology and Treatment," Pediatrics, Apr. 19, 2012, 91(3):130-135 pages (with English Translation).
Louis et al., "Antidepressant-like Effects of the Corticotropin-Releasing Factor 1 Receptor Antagonist, SSR125543, and the Vasopressin 1b Receptor Antagonist, SSR149415, in a DRL-72 S Schedule in the Rat," Neuropsychopharmacology, 2006, 31:2180-2187.
Lovenberg TW, et al., "Cloning and characterization of a functionally distinct corticotropin-releasing factor receptor subtype from rat brain," Proceedings of the National Academy of Sciences, 1995, 92(3): 836-840.
Lowe RF, et al., "Rational Design, Synthesis, and Structure—Activity Relationships of Aryltriazoles as Novel Corticotropin-Releasing Factor-1 Receptor Antagonists," J. Med. Chem., 2005, 48(5):1540- 1549.
Maciejewski-Lenoir D, et al., "Selective Impairment of Corticotropin-Releasing Factor1 (CRF1) Receptor-Mediated Function Using CRF Coupled to Saporin, " Endocrinology, 2000, 141(2):498-504.
Mackay, KB, et al., "Neuroprotective Effects of the CRF1 Antagonist R121920 after Permanent Focal Ischemia in the Rat," Journal of Cerebral Blood Flow & Metabolism, 2001, 21(10): 1208-1214.
Malouf et al., "Cognitive outcome in adult women affected by congenital adrenal hyperplasia due to 21-hydroxylase deficiency," Horm Res., 2006, 65(3):142-150.
Martínez V, et al., "Central CRF, urocortins and stress increase colonic transit via CRF1 receptors while activation of CRF2 receptors delays gastric transit in mice," J Physiol., 2004, 556.1: 221-234.
Martinez-Aguayo et al., "Testicular adrenal rest tumors and Leydig and Sertoli cell function in boys with classical congenital adrenal hyperplasia," J Clin Endocrinol Metab., Dec. 2007, 92(12):4583-9.
McCarthy JR, et al., "Chapter 2. Recent Progress in Corticotropin-Releasing Factor Receptor Agents," Annual Reports in Medicinal Chemistry, 1999, 34: 11-20.
McCarthy JR, et al., "Recent advances with the CRF1 receptor: design of small molecule inhibitors, receptor subtypes and clinical indications," Curr Pharm Des., 1999, 5(5):289-315.
Medlineplus.gov, "21-Hydroxylase Deficiency," NIH US National Library of Medicine, Updated Aug. 18, 2020 [retrieved Dec. 13, 2021], retrieved from URL<https://medlineplus.gov/genetics/condition/21-hydroxylase-deficiency/>, 6 pages.
Merke et al., "Congenital adrenal hyperplasia," Lancet, 2005, 365:2125-2136.
Merke et al., "Congenital adrenal hyperplasia: epidemiology, management and practical drug treatment," Paediatr Drugs., 2001, 3(8):599-611.
Merke et al., "Flutamide, testolactone, and reduced hydrocortisone dose maintain normal growth velocity and bone maturation despite elevated androgen levels in children with congenital adrenal hyperplasia," J Clin Endocrinol Metab., Mar. 2000, 85(3):1114-1120.
Merke et al., "Management of adolescents with congenital adrenal hyperplasia," Lancet Diabetes Endocrinol., Dec. 2013, 1(4):341-352.
Merke et al., "New ideas for medical treatment of congenital adrenal hyperplasia," Endocrinol. Metab. Clin. North. Am., 2001, 30(1):121-135.
Merke et al., "NIH conference: Future directions in the study and management of congenital adrenal hyperplasia due to 21-hydroxylase deficiency," Ann. Intern. Med., 2002, 136:320-334.
Merke et al., "Congenital Adrenal Hyperplasia Due to 21-Hydroxylase Deficiency," N Engl J Med., Sep. 24, 2020, 383(13):1248-1261.
Meslamani et al., "Computational profiling of bioactive compounds using a target-dependent composite workflow," J. Chem. Inf. Model., 2013, 2322-2333.
Migeon et al., "Congenital Adrenal Hyperplasia Owing to 21-Hydroxylase Deficiency," Endocrinology and Metabolism Clinics of North America, 2001, 30(1):193-206.
Million et al., "The newly developed CRF1-receptor antagonists, NGD 98-2 and NGD 9002, suppress acute stress-induced stimulation of colonic motor function and visceral hypersensitivity in rats," PLOS One, 2013, 8(9):e73749.
Million M, et al., "A novel water-soluble selective CRF1 receptor antagonist, NBI 35965, blunts stress-induced visceral hyperalgesia and colonic motor function in rats," Brain Research, 2003, 985(1): 32-42.
Mims et al., "Plasma ACTH in Rats Following Medical Adrenalectomy," Journal of the National Medical Association 69(3):145-147, 1977.
Morikawa S, et al., "Results from 28 years of Newborn Screening for Congenital Adrenal Hyperplasia in Sapporo," Clin Pediatr Endocrinol., 2014, 23(2):35-43.
Muthusamy et al., "Clinical review: Adult height in patients with congenital adrenal hyperplasia: a systematic review and metaanalysis," J Clin Endocrinol Metab., Sep. 2010, 95(9):4161-4172.
Nebesio TD, et al., "Growth and Reproductive Outcomes in Congenital Adrenal Hyperplasia," Int J Pediatr Endocrinol., 2010, Article ID 298937, 1-10.
Nermoen et al., "Subjective health status in men and women with congenital adrenal hyperplasia: a population-based survey in Norway," Eur J Endocrinol., Sep. 2010, 163(3):453-459.
Newfield R.S., "Acth receptor blockade: A novel approach to treat congenital adrenal hyperplasia, or Cushing's disease," Medical Hypotheses, 2010, 74:705-706.
No Author, "Neurocrine Biosciences Reports Positive Phase II Data for Crinecerfont in Adults with Congenital Adrenal Hyperplasia at ENDO Online 2020," Neurocrine Biosciences Inc., Jun. 8, 2020, 3 pages.
Okuyama et al., "Receptor Binding, Behavioral, and Electrophysiological Profiles of Nonpeptide Corticotropin-Releasing Factor Subtype 1 Receptor Antagonists CRA1000 and CRA 1001," Journal of Pharmacology and Experimental Therapeutics, 1999, 289(2):926-935.
Oray et al., "Long-term effect of glucocorticoids," Expert Opinion on Drug Safety, 2016, 30 pages.
Overstreet et al., "Antidepressant-like effects of $CRF_1$ receptor antagonist SSR125543 in an animal model of depression," European Journal of Pharmacology, 2004, 497:49-53.
Owens et al., "Physiology and pharmacology of corticotropin-releasing factor," Pharmacol Rev., Dec. 1991, 43(4):425-473.
Pang et al., "Worldwide Experience in Newborn Screening for Classical Congenital Adrenal Hyperplasia due to 21-Hydroxylase Deficiency," Pediatrics, 1988, 81(6):866-874.
Pang S, et al., "Congenital adrenal hyperplasia due to 21-hydroxylase deficiency: newborn screening and its relationship to the diagnosis and treatment of the disorder," Screening, 1993, 2:105-139.
Pelleymounter MA, et al., "Role of Corticotropin-Releasing Factor (CRF) Receptors in the Anorexic Syndrome Induced by CRF," Journal of Pharmacology and Experimental Therapeutics, 2000, 293(3): 799-806.
Perry SJ, et al., "Distinct Conformations of the Corticotropin Releasing Factor Type 1 Receptor Adopted following Agonist and Antagonist Binding Are Differentially Regulated," J. Biol. Chem., 2005, 280(12): 11560 -11568.
Philbert et al., "The $CRF_1$ Receptor Antagonist SSR125543 Attenuates Long-Term Cognitive Deficit Induced by Acute Inescapable Stress in Mice, Independently From the Hypothalamic Pituitary Adrenal Axis," Pharmacology, Biochemistry, and Behavior, 2012, 10:415-422.
Philbert et al., "The $CRF_1$ Receptor Antagonist SSR125543 Prevents Stress-Induced Cognitive Deficit Associated With Hippocampal Dysfunction: Comparison With Paroxetine and D-cycloserine," Psychopharmacology, 2013, 228:97-107.
Ramos et al., "Drug-induced suppression of ACTH secretion does not promote anti-depressive or anxiolytic effects," Behavioral Brain Research, 2014, 265:69-75.

(56) References Cited

OTHER PUBLICATIONS

Rivier CL, et al., "Role of Corticotropin-Releasing Factor Receptors Type 1 and 2 in Modulating the Rat Adrenocorticotropin Response to Stressors," Endocrinology, 2003, 144(6): 2396-2403.
Rivier JE, et al., "Constrained Corticotropin Releasing Factor Antagonists (Astressin Analogues) with Long Duration of Action in the Rat," J. Med. Chem. 1999, 42(16):3175-3182.
Rose & Hurst, "Plasma Cortisol and Growth Hormone Responses to Intravenous Catheterization, " J Hum Stress., Mar. 1975, 1(1):22-36.
Russian Office Action in Russian Application No. 2016133972/15(052775), dated Sep. 26, 2018, 10 pages.
Sarafoglou K, et al., "Impact of Hydrocortisone on Adult Height in Congenital Adrenal Hyperplasia—The Minnesota Cohort," J Pediatr., 2014, 164(5):1141-1146.
Seymour et al., "The pharmacology of CP-154,526, a non-peptide antagonist of the CRH1 receptor: a review," CNS Drug Reviews, 2003, 9(1):57-96.
Shargel et al., "Multiple-Dosage Regiments," Applied Biopharmaceutics & Pharmacokinetics, 2012, 6th Edition, 31 pages.
Shargel et al., "Multiple-Dosage Regiments," Applied Biopharmaceutics & Pharmacokinetics, 2016, 7th Edition, 33 pages.
Silva IN, et al., "Randomised controlled trial of growth effect of hydrocortisone in congenital adrenal hyperplasia," Archives of Disease in Childhood, 1997, 77:214-218.
Smith et al., "The role of the hypothalamic-pituitary-adrenal axis in neuroendocrine responses to stress," Dialogues Clin Neurosci., 2006, 8:383-395.
Soliman et al., "Congenital adrenal hyperplasia complicated by central precocious puberty: linear growth during infancy and treatment with gonadotropin-releasing hormone analog," Metabolism., May 1997, 46(5):513-517.
Somajni et al., "Neuropsychological assessment in prepubertal patients with congenital adrenal hyperplasia: preliminary study," Minerva Pediatr., Feb. 2011, 63(1):1-9.
Speiser et al., "Congenital adrenal hyperplasia due to steroid 21-hydroxylase deficiency: an Endocrine Society clinical practice guideline," J Clin Endocrinol Metab., Sep. 2010, 95(9):4133-4160.
Speiser et al., "A Summary of the Endocrine Society Clinical Practice Guidelines on Congenital Adrenal Hyperplasia due to Steroid 21-Hydroxylase Deficiency," International Journal of Pediatric Endocrinology 2010, 2010:494173.
Speiser et al., "Congenital Adrenal Hyperplasia Due to Steroid 21-Hydroxylase Deficiency: An Endocrine Society Clinical Practice Guideline," J Clin Endocrinol Metab., 2018, 103(11):4043-4088.
Spierling et al., "Don't stress about CRF: assessing the translational failures of $CRF_1$ antagonists," Psychopharmacology, 2017, 234(9-10):1467-1481.
Steckler, "Developing small molecule nonpeptidergic drugs for the treatment of anxiety disorders: is the challenge still ahead?" Curr. Topics in Behav. Neurosciences, 2009, 415-428.
Stewart et al., "Development of a Biorelevant, Material-Sparing Membrane Flux Test for Rapid Screening of Bioavailability-Enhancing Drug Product Formulations," Mol Pharm., 2017, 14(6):2032-2046.
Stikkelbroeck et al., "High prevalence of testicular adrenal rest tumors, impaired spermatogenesis, and Leydig cell failure in adolescent and adult males with congenital adrenal hyperplasia," J Clin Endocrinol Metab., Dec. 2001, 86(12):5721-5728.
Surget et al., "Corticolimbic transcriptome changes are state-dependent and region-specific in a rodent model of depression and of antidepressant reversal," Neuropsychopharmacology, 2009, 34:1363-1380.
Surget et al., "Drug-dependent requirement of hippocampal neurogenesis in a model of depression and of antidepressant reversal," Biol. Psychiatry, 2008, 64:293-301.
Teitelbaum, "Chronic peripheral administration of corticotropin-releasing factor causes colonic barrier dysfunction similar to psychological stress," Am J Physiol Gastrointest Liver Physiol, 2008, 295: G452-G459.
Tellew et al., "Discovery ofNBI-77860/GSK561679, a potent corticotropin-releasing factor ($CRF_1$) receptor antagonist with improved pharmacokinetic properties," Bioorganic & Medicinal Chemistry Letters, 2010, 20(24):7259-7264.
TheFreeDictionary.com, "Baseline," available on or before Nov. 7, 2016, via Internet Archive: Wayback Machine URL <https://web.archive.org/web/20161107132345/http:/medical-dictionary.thefreedictionary.com/baseline>, 3 pages.
Therrell BL, et al., "Newborn Screening for Congenital Adrenal Hyperplasia," Endocrinol Metab Clin North Am., 2001, 30(1):15-30.
Trakakis et al., "An update to 21-hydroxylase deficient congenital adrenal hyperplasia," Gynecol Endocrinol., Jan. 2010, 26(1):63-71.
Trapp CM, et al. "Recommendations for Treatment of Nonclassic Congenital Adrenal Hyperplasia (NCCAH): an Update," Steroids, 2012, 77(4):342-346.
Trapp et al., "Congenital adrenal hyperplasia: an update in children," Curr Opin Endocrinol Diabetes Obes., 2011, 18(3):166-170.
Turcu et al., "Novel treatment strategies in congenital adrenal hyperplasia," Curr Opin Endocrinol Diabetes Obes., 2016, 23(3):225-232.
Turcu et al., "Single-Dose Study of a Corticotropin-Releasing Factor Receptor-1 Antagonist in Women With 21-Hydroxylase Deficiency," J Clin Endocrinol Metab., Mar. 2016, 101(3):1174-1180.
Turcu et al., "The Next 150 Years of Congenital Adrenal Hyperplasia," J Steroid Biochem Mol Biol., Sep. 2015, 153:63-71.
U.S. Appl. No. 62/545,406, Howerton et al., "Corticotropin Releasing Factor Receptor Antagonists," filed Aug. 14, 2017, 65 pages.
Urani et al., "The Corticotropin-Releasing Factor 1 Receptor Antagonist, SSR125543, and the Vasopressin 1b Receptor Antagonist, SSR149415, Prevent Stress-Induced Cognitive Impairment in Mice," Pharmacology, Biochemistry, and Behavior, 2011, 98:425-431.
Vale et al., "Chemical and biological characterization of corticotropin releasing factor," Recent Prog Horm Res., 1983, 39:245-270.
Vale et al., "Characterization of a 41-Residue Ovine Hypothalamic Peptide That Stimulates Secretion of Corticotropin and β-Endorphin," Science, 1981, 213:1394-1397.
Vickers et al., "Why Use Placebos in Clinical Trials? A Narrative Review of the Methodological Literature," Journal of Clinical Epidemiology, 2000, 53(2):157-161.
Vokl TMK, et al., "Adrenarche and Puberty in Children with Classic Congenital Adrenal Hyperplasia due to 21-Hydroxylase Deficiency," Horm Res Paediatr., 2011, 76(6):400-410.
Vokl TMK, et al., "Obesity Among Children and Adolescents with Classic Congenital Adrenal Hyperplasia due to 21-Hydroxylase Deficiency," Pediatrics, 2006, 117(1):e98-e105.
Webb et al., "Current and Novel Approaches to Children and Young People with Congenital Adrenal Hyperplasia and Adrenal Insufficiency," Best Pract Res Clin Endocrinol Metab., 2015, 29:449-468.
Webb TR, et al., "Synthesis of benzoylpyrimidines as antagonists of the corticotropin-releasing factor-1 receptor," Bioorganic & Medicinal Chemistry Letters, 2004, 14(15): 3869-3873.
Webster et al., "In Vivo and In Vitro Characterization of Antalarmin, a Nonpeptide Corticotropin-Releasing Hormone (CRH) Receptor Antagonist: Suppression of Pituitary ACTH Release and Peripheral Inflammation ," Endocrinology, Jan. 1, 1996, 137(12):5747-5750.
White PC, et al., "Congenital Adrenal Hyperplasia due to 21-Hydroxylase Deficiency," Endocr Rev., 2000, 21(3):245-291.
White PC, et al., "Optimizing Newborn Screening for Congenital Adrenal Hyperplasia ," J. Pediatr., 2013, 163:10-12.
Whitten JP, et al., "Rapid Microscale Synthesis, a New Method for Lead Optimization Using Robotics and Solution Phase Chemistry: Application to the Synthesis and Optimization of Corticotropin-Releasing Factor1 Receptor Antagonists," J. Med. Chem., 1996, 39(22): 4354-4357.
Wilcoxen K, et al., "Synthesis of 3-phenylpyrazolo[4,3-b]pyridines via a convenient synthesis of 4-amino-3-arylpyrazoles and SAR of corticotropin-Releasing factor receptor type-1 antagonists," Bioorganic & Medicinal Chemistry Letters, 2003, 13(19): 3367-3370.
Williams, "Corticotropin-releasing factor 1 receptor antagonists: a patent review," Expert Opin. Ther. Patents, 2013, 23(8):1057-1068.

(56) References Cited

OTHER PUBLICATIONS

Witchel et al., "Congenital Adrenal Hyperplasia," J. Pediatr. Adolesc. Gynecol., 2011, 24:116-126.
Witchel et al., "Congenital Adrenal Hyperplasia," J. Pediatr. Adolesc. Gynecol., 2017, 30(5):520-534.
Wong et al., "Increased hepatobiliary clearance of unconjugated thyroxine determines DMP 904-induced alterations in thyroid hormone homeostasis in rats," Toxicological Sciences, 2005, 84(2):232-242.
Wood S, et al., "Depressive and cardiovascular disease comorbidity in a rat model of social stress: a putative role for corticotropin-releasing factor," Psychopharmacology, 2012, 222(2): 325-336.
Wustrow DJ, et al., "Pyrazolo[1,5-a]pyrimidine CRF-1 receptor antagonists," Bioorganic & Medicinal Chemistry Letters, 1998, 8(16): 2067-2070.
Yuan J, et al., "3-Aryl pyrazolo[4,3-d]pyrimidine derivatives: nonpeptide CRF-1 antagonists," Bioorganic & Medicinal Chemistry Letters, 2002, 12(16): 2133-2136.
Zorrilla et al., "Behavioral, biological, and chemical perspectives on targeting CRF(1) receptor antagonists to treat alcoholism," Drug and Alcohol Dependence, (2013), 128(3):175-186.
Zorrilla et al., "The therapeutic potential of CRF1 antagonists for anxiety," Expert Opin. Investig. Drugs, 2004, 13(7):799-828.
Zorrilla, "Progress in corticotropin-releasing factor-1 antagonist development," Drug Discov Today, 2010, 15:371-383.
Zoumakis et al., "Corticotropin-releasing hormone receptor antagonists," European Journal of Endocrinology, 2006, 155(1):S85-S91.
Zoumakis et al., "Corticotropin-releasing hormone receptor antagonists: an update," Pediatric Neuroendocrinology Endocr Dev., 2010, 17:36-43.
Alejandro et al., "Behavioral, Adrenal, and Sympathetic Responses to Long-Term Administration of an Oral Corticotropin-Releasing Hormone Receptor Antagonist in a Primate Stress Paradigm," The Journal of Clinical Endocrinology & Metabolism, Nov. 1, 2004, 89(11):5729-5737.
Heike et al., "Treatment of depression with the CRH-1-receptor antagonist R121919: endocrine changes and side effects", J Psych Res., Nov. 1, 2003, 37(8):525-533.
[No Author Listed], "Assessing the Effects of Food on Drugs in INDs and NDAs—Clinical Pharmacology Considerations: Guidance for Industry," posted by the U.S. Department of Health and Human Services: Food and Drug Administration on www.fda.gov, dated Feb. 2019, 17 pages.
[No Author Listed], "Emergency Instructions—Treatment for Congenital Adrenal Hyperplasia in times of stress," posted by CARES Foundation on www.caresfoundation.org, posted in Aug. 2014, 2 pages.
[No Author Listed], "FDA, Center for Drug Evaluation and Research, 218808Orig1s000, 218820Orig1s000, Product Quality Review(s)," posted by the U.S. Department of Health and Human Services: Food and Drug Administration on www.fda.gov, posted on Oct. 7, 2024, 90 pages.
[No Author Listed], "Form 8-K: Current Report," filed by Neurocrine Biosciences, Inc. with the U.S. Securities and Exchange Commission, dated Apr. 5, 2000, 4 pages.
[No Author Listed], "Gelucire® 44/14," posted by Gattefossé on www.gattefosse.com, posted on or before Nov. 30, 2023, 6 pages.
[No Author Listed], "InterQuartile Range (IQR)," posted by Boston University on www.bu.edu, posted on or before Oct. 31, 2013, 4 pages.
[No Author Listed], "Labrafac™ Lipophile WL 1349," posted by Gattefossé on www.gattefosse.com, posted on or before Nov. 30, 2023, 6 pages.
[No Author Listed], "Labrafac™ PG," posted by Gattefossé on www.gattefosse.com, posted on or before Nov. 30, 2023, 5 pages.
[No Author Listed], "Medium-chain triglyceride," posted by Wikipedia on www.wikipedia.org, last updated on Dec. 28, 2024, 4 pages.
[No Author Listed], "Medium-Chain Triglycerides," posted by the US Pharmacopeial Convention on www.uspnf.com, posted on Nov. 1, 2020, 4 pages.
[No Author Listed], "Molecular mass," posted by Wikipedia on www.wikipedia.org, last updated on Nov. 2, 2024, 4 pages.
[No Author Listed], "Neurocrine announces top-line results of corticotropin releasing factor antagonist GSK561679 for treatment of major depressive disorder," Press Release, posted by Neurocrine Biosciences on www.neurocrine.com, dated Sep. 14, 2010, 1 page.
[No Author Listed], "Pediatric Endocrinology Training Program: Patient Handouts and Support Groups," posted by the U.S. Department of Health and Human Services: National Institutes of Health on www.nih.gov, posted on or before Oct. 20, 2011, 3 pages.
[No Author Listed], "Propylene Glycol Dicaprylate/Dicaprate," posted by the US Pharmacopeial Convention on www.uspnf.com, posted on May 1, 2020, 2 pages.
[No Author Listed], "Safety, Tolerability, Pharmacokinetics, and Pharmacodynamics of NBI-74788 in Pediatric Subjects With Congenital Adrenal Hyperplasia," posted by Neurocrine Biosciences on www.ClinicalTrials.gov, Identifier No. NCT04045145, posted on Aug. 5, 2019, 7 pages.
[No Author Listed], "Sanofi-Aventis: strong performance of growth platforms in Q1 2011," Press Release, posted by Sanofi-Aventis on www.sanofi.us, dated Apr. 28, 2011, 13 pages.
[No Author Listed], "Neurocrine Biosciences to Present New Data Analyses for Crinecerfont in Adults with Classical Congenital Adrenal Hyperplasia at ENDO 2021," Press Release, posted by Neurocrine Biosciences on www.neurocrine.com, dated Mar. 20, 2021, 5 pages.
[No Author Listed], "Search Results for CAS No. 121548-04-7," American Chemical Society CAS SciFinder, search performed on Apr. 7, 2025 at www.cas.org, 2 pages.
[No Author Listed], "Spruce Biosciences Presents Phase 1 and 2 Data for Tildacerfont in Adults with Congenital Adrenal Hyperplasia from Endocrine Society's 2021 Annual Meeting," Press Release, posted by Spruce Biosciences on www.sprucebio.com, dated Mar. 17, 2021, 2 pages.
Ceramella et al., "A Look at the Importance of Chirality in Drug Activity: Some Significative Examples," Applied Sciences, Oct. 27, 2022, 12:10909, 22 pages.
Claahsen-van der Grinten et al., "Challenges in Adolescent and Adult Males With Classic Congenital Adrenal Hyperplasia Due to 21-Hydroxylase Deficiency," J Clinical Endocrinology & Metabolism, Feb. 2025, 110 (Supplement_1):S25-36.
Do Thi et al., "Formulate-ability of ten compounds with different physicochemical profiles in SMEDDS," European journal of pharmaceutical sciences, Dec. 8, 2009, 38(5):479-88.
Dwivedi et al., "Evergreening: a deceptive device in patent rights," Technology in Society, Nov. 1, 2010, 32(4):324-30.
Eitel et al., "Barriers to the Management of Classic Congenital Adrenal Hyperplasia Due to 21-Hydroxylase Deficiency," J Clinical Endocrinology & Metabolism, Feb. 2025, 110 (Supplement 1):S67-73.
Engberg et al., "Clinical Manifestations and Challenges in Adolescent and Adult Females With Classic Congenital Adrenal Hyperplasia Due to 21-Hydroxylase Deficiency," J Clinical Endocrinology & Metabolism, Feb. 2025, 110(Supplement_1):S37-45.
Feldman, "Understanding 'Evergreening': Making Minor Modifications of Existing Medications To Extend Protections," Health Affairs, Jun. 1, 2022, 41(6):801-4.
Foster, "Deuterium isotope effects in the metabolism of drugs and xenobiotics: implications for drug design," Advances in Drug Research, 1985, 14:1-40.
Gupta et al., "Salts of therapeutic agents: chemical, physicochemical, and biological considerations, " Molecules, Jul. 14, 2018, 23(7):1719.
Kamrath et al., "CRH receptor antagonist crinecerfont—a promising new treatment option for patients with congenital adrenal hyperplasia due to 21-hydroxylase deficiency," Journal of Pediatric Endocrinology and Metabolism, Nov. 25, 2024, 38(1):16-21.
Kushner et al., "Pharmacological uses and perspectives of heavy water and deuterated compounds," Canadian journal of physiology and pharmacology, Feb. 1, 1999, 77(2):79-88.
Nokoff et al., "Clinical Manifestations and Treatment Challenges in Infants and Children With Classic Congenital Adrenal Hyperplasia

(56) References Cited

OTHER PUBLICATIONS

Due to 21-Hydroxylase Deficiency," J Clinical Endocrinology & Metabolism, Feb. 2025, 110(Supplement_1):S13-24.
Peter, "Congenital adrenal hyperplasia: 11β-hydroxylase deficiency," Seminars in reproductive medicine, Aug. 2002, 20(3):249-254, abstract.
Pouton, "Lipid formulations for oral administration of drugs: non-emulsifying, self-emulsifying and 'self-microemulsifying' drug delivery systems," European journal of pharmaceutical sciences, Oct. 1, 2000, 11:S93-8.
Sandberg et al., "Mental Health Issues Associated With Classic Congenital Adrenal Hyperplasia Due to 21-Hydroxylase Deficiency," J Clinical Endocrinology & Metabolism, Feb. 2025, 110 (Supplement_1):S46-55.
Sarafoglou et al., "Future Directions in the Management of Classic Congenital Adrenal Hyperplasia Due to 21-Hydroxylase Deficiency," J Clinical Endocrinology & Metabolism, Feb. 2025, 110 (Supplement_1):S74-87.
Sarafoglou et al., "Phase 3 Trial of Crinecerfont in Pediatric Congenital Adrenal Hyperplasia," New England Journal of Medicine, Jun. 2, 2024, 1-11.
Spernath et al., "Microemulsions as carriers for drugs and nutraceuticals," Advances in colloid and interface science, Dec. 21, 2006, 128:47-64.
Vijayan et al., "Metabolic profile, cardiovascular risk factors and health-related quality of life in children, adolescents and young adults with congenital adrenal hyperplasia," Journal of Pediatric Endocrinology and Metabolism, Jul. 4, 2019, 32(8):871-877.
Witchel et al., "Life With Classic Congenital Adrenal Hyperplasia Due to 21-Hydroxylase Deficiency: Challenges and Burdens," J Clinical Endocrinology & Metabolism, Feb. 2025, 110 (Supplement_1):S56-66.
Yang et al., "Genetics and Pathophysiology of Classic Congenital Adrenal Hyperplasia Due to 21-Hydroxylase Deficiency," J Clinical Endocrinology & Metabolism, Feb. 2025, 110 (Supplement_1):S1-2.
[No Author Listed], "CAS Registry®," posted by the American Chemical Society on www.cas.org, posted on or before Apr. 30, 2021, 10 pages.
[No Author Listed], "Handbook of Pharmaceutical Excipients—9th Edition," posted by PharmaExcipients on www.pharmaexcipients.com, posted on or before Jan. 16, 2021, 3 pages.
[No Author Listed], "Highlights of Prescribing Information: Crenessity," Neurocrine Biosciences Inc., Dec. 2024, 24 pages.
[No Author Listed], "Labrafac™ PG," posted by Gattefossé on www.gattefosse.com, posted on or before Nov. 30, 2023, 4 pages.
[No Author Listed], "Labrafil® M 1944 CS," posted by Gattefossé on www.gattefosse.com, posted on or before Dec. 5, 2023, 4 pages.
[No Author Listed], "Labrafil® M 2125 CS," posted by Gattefossé on www.gattefosse.com, posted on or before Nov. 30, 2023, 4 pages.
[No Author Listed], "Medium-chain Triglycerides," Handbook of Pharmaceutical Excipients, 6th ed., Rowe et al. (ed.), 2009, pp. 429-431.
[No Author Listed], "Regulatory data sheet (RDS)—Pharmaceutical market (human and veterinary medicines): Labrafac Lipophile WL 1349 (Code: 3139)," Gattefossé SAS, Mar. 19, 2025, 8 pages.
[No Author Listed], "USP Reference Standards," posted by the U.S. Pharmacopeia on www.USP.org, posted on or before Feb. 5, 2012, 7 pages.
CAS Registry No. 57107-95-6, "Poly(oxy-1,2-ethanediyl), α,α',α"-1,2,3-propanetriyltris[ω-hydroxy-, dodecanoate (9Cl, ACl)," SciFinder, retrieved on Aug. 4, 2025, 3 pages.
CAS Registry No. 61789-25-1, "Corn oil, ethoxylated (13C, 14C)," SciFinder, retrieved on Aug. 4, 2025, 2 pages.
CAS Registry No. 68583-51-7, "Decanoic acid, mixed diesters with octanoic acid and propylene glycol," SciFinder, retrieved on Aug. 4, 2025, 4 pages.
CAS Registry No. 69071-70-1, "Ethoxylated apricot kernel oil (16C)," SciFinder, retrieved on Aug. 4, 2025, 2 pages.
CAS Registry No. 73398-61-5, "Glycerides, mixed decanoyl and octanoyl (10C)," SciFinder, retrieved on Aug. 4, 2025, 3 pages.
Claahsen-van der Grinten et al., "Congenital Adrenal Hyperplasia-Current Insights in Pathophysiology, Diagnostics, and Management," Endocr Rev, Jan. 12, 2022, 43(1):91-159.
Ghadi et al., "BCS class IV drugs: Highly notorious candidates for formulation development," Journal of Controlled Release, Feb. 28, 2017, 248;71-95 (abstract only).
Kageyama et al., "Hypothalamic Regulation of Corticotropin-Releasing Factor under Stress and Stress Resilience," Int J Mol Sci, Nov. 12, 2021, 22(22):12242.
Nahm et al., "N-Methoxy-N-methylamides as effective acylating agents," Tetrahedron Letters, Jan. 1, 1981, 22(39):3815-8.
Newfield et al., "Crinecerfont, a CRF1 Receptor Antagonist, Lowers Adrenal Androgens in Adolescents With Congenital Adrenal Hyperplasia," J Clin Endocrinol Metab, Oct. 18, 2023, 108(11):2871-2878.
Nicolaides et al., "Glucocorticoid Therapy and Adrenal Suppression," Endotext, Oct. 19, 2018, retrieved on Aug. 27, 2025, retrieved from URL<https://www.ncbi.nlm.nih.gov/books/NBK279156/>, 28 pages.
Prete et al., "Clinical advances in the pharmacotherapy of congenital adrenal hyperplasia," Eur J Endocrinol, Nov. 30, 2021, 186(1):R1-R14.
Sharma et al., "Congenital Adrenal Hyperplasia," StatPearls Publishing, Jan. 27, 2025, retrieved on Aug. 27, 2025, retrieved from URL<https://www.ncbi.nlm.nih.gov/books/NBK448098/>, 16 pages.
[No Author Listed], "EU/3/19/2194—orphan designation for treatment of congenital adrenal hyperplasia," European Medicines Agency, Aug. 21, 2019, 4 pages.
[No Author Listed], "Highlights of Prescribing Information: RAYOS," Horizon Therapeutics, Mar. 2024, 22 pages.
[No Author Listed], "Proposed INN: List 119," WHO Drug Information, Jul. 2018, 32(2):369-370.
[No Author Listed], "Public summary of opinion on orphan designation: Verucerfont for the treatment of congenital adrenal hyperplasia," European Medicines Agency, Sep. 30, 2015, 5 pages.
[No Author Listed], "Recommended INN: List 81," WHO Drug Information, Apr. 2019, 33(1):122.
[No Author Listed], "Regulation (EC) No. 141/2000 of the European Parliament and of the Council of Dec. 16, 1999 on orphan medicinal products," Official Journal of the European Communities, Jan. 22, 2000, L18/1-L18/5.
Al-Kasmi et al., "Mechanical microencapsulation: The best technique in taste masking for the manufacturing scale—Effect of polymer encapsulation on drug targeting," Journal of Controlled Release, Aug. 28, 2017, 260:134-41.
Application to Amend Claims of EP 3784233 B1 in Claim No. HP-2025-000005 against EP Patent No. 378423, filed on Nov. 11, 2025, 8 pages.
Application to Stay Proceedings in UPC Proceeding No. 34386/2025, filed on Sep. 18, 2025, 18 pages.
Auchus et al., "Phase 3 Trial of Crinecerfont in Adult Congenital Adrenal Hyperplasia," N. Engl. J. Med., Aug. 8, 2024, 391(6):504-514.
Auchus et al., "Phase 3 Trial of Crinecerfont in Adult Congenital Adrenal Hyperplasia," N. Engl. J. Med., Aug. 8, 2024, 391(6):504-514; Supplementary Appendix, 30 pages.
Auchus, "Clinical Study Protocol: A Phase 2, Multiple-Dose, Dose-Escalation Study to Evaluate the Safety and Efficacy of SPR001 in Adults with Classic Congenital Adrenal Hyperplasia (CAH)," Spruce Biosciences, Inc., Aug. 23, 2018, 80 pages.
Auchus, "Management considerations for the adult with congenital adrenal hyperplasia," Mol. Cell Endocrinol., Jun. 15, 2015, 408:190-197.
Avila et al., "Testicular adrenal rest tissue in congenital adrenal hyperplasia: serial sonographic and clinical findings," Am. J. Roentgenol., May 1999, 172(5):1235-1238.
Aycan et al., "Prevalence and long-term follow-up outcomes of testicular adrenal rest tumours in children and adolescent males with congenital adrenal hyperplasia," Clin. Endocrinol., May 2013, 78(5):667-672.

(56) References Cited

OTHER PUBLICATIONS

Bacon et al., "Effect of Cortisol Treatment on Hormonal Relationships in Congenital Adrenal Hyperplasia," Clin. Endocrinol., Feb. 1977, 6(2):113-126.
Benvenga et al., "Testicular adrenal rests: evidence for luteinizing hormone receptors and for distinct types of testicular nodules differing for their autonomization," Eur. J. Endocrinol., Sep. 1999, 141(3):231-237.
Bhatt et al., "A Controlled Trial of Renal Denervation for Resistant Hypertension," N. Engl. J. Med., Apr. 10, 2014, 370(15):1393-1401.
Brief Communication of Opposition Proceedings against European Patent No. 3784233, filed on Dec. 12, 2025, 18 pages.
Brown et al., "Medication Adherence: WHO Cares?," Mayo Clin. Proc., Apr. 2011, 86(4):304-314.
Cakir et al., "Testicular Adrenal Rest Tumors in Patients with Congenital Adrenal Hyperplasia," J. Clin. Res. Pediatr. Endocrinol., Jun. 2012, 4(2):94-100.
Campinos, "G 1/24 ("Heated aerosol"): Comments by the President of the EPO," European Patent Office, dated Nov. 7, 2024, 50 pages.
Cano et al., "Direct asymmetric alkylation of ketones: still unconquered," Angewandte Chemie International Edition, May 12, 2017, 56(32):9278-90.
Chen et al., "Ovarian Adrenal Rest Tumors Undetected by Imaging Studies and Identified at Surgery in Three Females with Congenital Adrenal Hyperplasia Unresponsive to Increased Hormone Therapy Dosage," Endocr. Pathol., Dec. 28, 2016, 28(2):146-151.
Claahsen-van der Grinten et al., "Repeated successful induction of fertility after replacing hydrocortisone with dexamethasone in a patient with congenital adrenal hyperplasia and testicular adrenal rest tumors," Fertil. Steril., Sep. 2007, 88(3):705.e5-e8.
Claahsen-van der Grinten et al., "Testicular adrenal rest tumours in congenital adrenal hyperplasia," Int. J. Pediatr. Endocrinol., Feb. 2009, 2009:624823, 8 pages.
Claahsen-van der Grinten et al., "Testicular Tumors in Patients with Congenital Adrenal Hyperplasia due to 21-Hydroxylase Deficiency Show Functional Features of Adrenocortical Tissue," J. Clin. Endocrinol. Metab., Jun. 26, 2007, 92(9):3674-3680.
Claim Form in Claim No. HP-2025-000005 against EP Patent No. 3784233, filed on Jan. 30, 2025, 5 pages.
Claimant's Initial Disclosure List in Claim No. HP-2025-000005 against EP Patent No. 378423, filed on Jan. 31, 2025, 2 pages.
Communication of Notices of Opposition against European Patent No. 3784233, mailed on Mar. 18, 2025, 2 pages.
Communication of Opposition against European Patent No. 3784233, mailed on Nov. 19, 2025, 3 pages.
Congenital Adrenal Hyperplasia, 1st ed., Hindmarsh et al. (eds)., May 2017, pp. 263-264 and 319-320.
Congenital Adrenal Hyperplasia, 1st ed., Hindmarsh et al. (eds)., May 2017, pp. 24, 42, 165, 170, 171, 212, 264, 319, 320, 413 and 417.
Curriculum Vitae of Associate Professor Dr. Henrik Falhammar, produced Nov. 17, 2025, 2 pages.
Curriculum Vitae of Associate Professor Dr. Henrik Falhammar, produced Dec. 16, 2026, 29 pages.
Curriculum Vitae of Vivian H Lin, MD, produced Dec. 17, 2025, 8 pages.
Curriculum Vitae of Vivian H Lin, MD, produced Nov. 14, 2025, 2 pages.
Decision of the Enlarged Board of Appeal in Case No. G 0001/24, dated Jun. 18, 2025, 12 pages.
Decision of the Enlarged Board of Appeal in Case No. G 0002/21, dated Mar. 23, 2023, 75 pages.
Decision of the Technical Board of Appeal in Case No. T 0184/16-3.3.02, dated Dec. 12, 2019, 33 pages.
Decision of the Technical Board of Appeal in Case No. T 0429/96-3.3.4, dated May 31, 2001, 23 pages.
Decision of the Technical Board of Appeal in Case No. T 0609/02-3.3.8, dated Oct. 27, 2004, 18 pages.
Decision of the Technical Board of Appeal in Case No. T 0728/21-3.3.07, dated Nov. 16, 2023, 25 pages.
Decision of the Technical Board of Appeal in Case No. T 0799/16-3.3.01, dated Sep. 4, 2019, 42 pages.
Decision of the Technical Board of Appeal in Case No. T 0816/22-3.3.04, dated Nov. 19, 2024, 17 pages.
Decision of the Technical Board of Appeal in Case No. T 0852/09-3.3.04, dated Sep. 6, 2013, 10 pages.
Decision of the Technical Board of Appeal in Case No. T 0979/23-3.3.04, dated Oct. 1, 2024, 26 pages.
Decision of the Technical Board of Appeal in Case No. T 1045/13-3.3.01, dated Oct. 23, 2017, 13 pages.
Decision of the Technical Board of Appeal in Case No. T 1229/03-3.3.02, dated Nov. 23, 2006, 21 pages.
Decision of the Technical Board of Appeal in Case No. T 1437/07-3.3.04, dated Oct. 26, 2009, 42 pages.
Decision of the Technical Board of Appeal in Case No. T 1863/21-3.3.09, dated Apr. 29, 2024, 29 pages.
Decision of the Technical Board of Appeal in Case No. T 19/90-3.3.2, dated Oct. 3, 1990 (with correction dated Oct. 22, 1990), 26 pages.
Decision of the Technical Board of Appeal in Case No. T 1959/15-3.3.01, dated Apr. 2, 2020, 14 pages.
Decision of the Technical Board of Appeal in Case No. T 2443/18-3.3.01, dated Apr. 9, 2021, 14 pages.
Declaration of Associate Professor Dr. Henrik Falhammar in Opposition against European Patent No. 3784233, dated Nov. 17, 2025, 9 pages.
Declaration of Associate Professor Dr. Henrik Falhammar in proceedings of *Neurocrine Biosciences, Inc.* v *Spruce Biosciences, Inc.* for revocation of European Patent No. 3784233, dated Dec. 11, 2025, 13 pages.
Declaration of Dr. Chris N. Barnes under 37 C.F.R. § 1.132 in U.S. Appl. No. 17/081,694, filed Dec. 13, 2021, 4 pages.
Declaration of Professor Peter Hindmarsh in Opposition against European Patent No. 3784233, dated Oct. 23, 2025, 5 pages.
Declaration of Vivian H Lin, MD, in Opposition against European Patent No. 3784233, dated Nov. 14, 2025, 7 pages.
Defendant's Defence in Claim No. HP-2025-000005 against EP Patent No. 378423, filed on Mar. 13, 2025, 3 pages.
Delfino et al., "Testicular adrenal rest tumors in patients with congenital adrenal hyperplasia: prevalence and sonographic, hormonal, and seminal characteristics, " J. Ultrasound Med., Mar. 2012, 31(3):383-388.
Ekbom et al., "Assessment of medication adherence in children and adults with congenital adrenal hyperplasia and the impact of knowledge and self-management," Clinical Endocrinology, May 2021, 94(5):753-64.
Engels et al., "Testicular Adrenal Rest Tumors: Current Insights on Prevalence, Characteristics, Origin, and Treatment," Endocr. Rev., Aug. 2019, 40(4):973-987.
EP Patent Application No. 19793181.9 as filed on Apr. 26, 2019, 134 pages.
Essentials of Cell Biology, 1st ed., O'Connor (ed.), 2010, Units 4.2 and 4.4, 7 pages.
Fedorova et al., "What is the need for adrenalectomy in patients with congenital adrenal hyperplasia in the era of CRF1/ACTH inhibitors?," Front Endocrinol (Lausanne), Nov. 5, 2025, 16(1693063):1-10.
Gjerstad et al., "Role of glucocorticoid negative feedback in the regulation of HPA axis pulsatility," Stress, May 15, 2018, 21(5):403-416.
Greenspan's Basic & Clinical Endocrinology, 10th ed., Gardner et al. (eds)., Sep. 19, 2017, pp. 413 and 440-441.
Greenspan's Basic & Clinical Endocrinology, 10th ed., Gardner et al. (eds)., Sep. 19, 2017, excerpt from Chapter 9, 4 pages.
Grounds for the Decision of Opposition against European Patent No. 3784233, filed on Dec. 12, 2025, 26 pages.
Grounds of Invalidity in Claim No. HP-2025-000005 against EP Patent No. 378423, filed on Jan. 31, 2025, 10 pages.
Gupta et al., "Corticosteroid Physiology and Principles of Therapy," Indian J. Pediatr., Oct. 2008, 75(10):1039-1044.
Gwathmey et al., "Glucocorticoid-Induced Fetal Programming Alters the Functional Complement of Angiotensin Receptor Subtypes Within the Kidney," Hypertension, Mar. 2011, 57(3):620-626.

(56) References Cited

OTHER PUBLICATIONS

Hillhouse et al., "The Molecular Mechanisms Underlying the Regulation of the Biological Activity of Corticotropin-Releasing Hormone Receptors: Implications for Physiology and Pathophysiology," Endocr. Rev., Feb. 16, 2006, 27(3):260-286.
Information about results of the Oral Proceedings against European Patent No. 3784233, mailed on Nov. 26, 2025, 2 pages.
Joseph et al., "Stress and the HPA Axis: Balancing Homeostasis and Fertility," Int. J. Mol. Sci., Oct. 24, 2017, 18(10):2224, 15 pages.
Koziolek et al., "Intragastric pH and pressure profiles after intake of the high-caloric, high-fat meal as used for food effect studies," J. Controlled Release, 2015, 220:71-78.
Letter to the European Patent Office in European Appln. No. 19793181.9, filed on Jul. 21, 2021, 2 pages.
Leung, "Polyethylene Glycol," Encyclopedia of Toxicology, Apr. 14, 2014, Third edition, pp. 1043-1044.
Ma et al., "Sonographic features of the testicular adrenal rests tumors in patients with congenital adrenal hyperplasia: a single-center experience and literature review," Orphanet J. Rare Dis., Nov. 6, 2019, 14(1):242, 8 pages.
Manu et al., "Spray Drying in pharmaceutical industry: A Review," Research Journal Pharmaceutical Dosage Forms Technology, Mar. 1, 2012, 4(2):74-79.
Matsubara, "Pathophysiological Role of Angiotensin II Type 2 Receptor in Cardiovascular and Renal Diseases," Circ. Res., Dec. 14, 1998, 83(12):1182- 1191.
Meena et al., "Growth Pattern and Clinical Profile of Indian Children with Classical 21-Hydroxylase Deficiency Congenital Adrenal Hyperplasia on Treatment," Indian J. Pediatr., Jan. 30, 2019, 86(6):496-502.
Memorandum in United States District Court Case No. 1:25-cv-00059-JDW, issued on Jun. 9, 2025, 10 pages.
Mendes-dos-Santos et al., "Prevalence of Testicular Adrenal Rest Tumor and Factors Associated with Its Development in Congenital Adrenal Hyperplasia," Horm. Res. Paediatr., Aug. 27, 2018, 90(3):161-168.
Mesa et al., "Immunophenotypic differences between neoplastic and non-neoplastic androgen-producing cells containing and lacking Reinke crystals," Virchows Arch., Oct. 1, 2016, 469:679-686.
Nagurney et al., "The Accuracy and Completeness of Data Collected by Prospective and Retrospective Methods," Acad. Emerg. Med., Sep. 2005, 12(9):884-895.
Neurocrine Biosciences, Inc., "Form 10-Q: Quarterly Report Pursuant To Section 13 OR 15(d) of the Securities Exchange Act of 1934 for the quarterly period ended Jun. 30, 2025," United States Securities and Exchange Commission, filed Jul. 30, 2025, 63 pages.
Nissen et al., "The clinical case report: a review of its merits and limitations, " BMC Research Notes, Apr. 23, 2014, 7(1):264, 7 pages.
Notice of Opposition against European Patent No. 3096756, filed on Mar. 7, 2025, 17 pages.
Notice of Opposition against European Patent No. 3784233, filed on Feb. 28, 2025, 36 pages.
Notice of Opposition against European Patent No. 3784233, filed on Dec. 10, 2024, 3 pages.
Opinion of the Enlarged Board of Appeal in Case No. G 10/91, dated Mar. 31, 1993, 17 pages.
Opponents Response to Patentees Submissions under Rule 116 EPC in Opposition against European Patent No. 3784233, filed on Nov. 17, 2025, 10 pages.
Opponents Submission under Rule 116 EPC in Opposition against European Patent No. 3784233, filed on Oct. 24, 2025, 7 pages.
Paragliola, "Treatment with Synthetic Glucocorticoids and the Hypothalamus-Pituitary-Adrenal Axis," Int. J. Mol. Sci., Oct. 20, 2017, 18(10):2201, 18 pages.
Particulars of Claim in Claim No. HP-2025-000005 against EP Patent No. 378423, filed on Jan. 31, 2025, 2 pages.
Patentees Response to Opponents Submission under Rule 116 EPC in Opposition against European Patent No. 3784233, filed on Nov. 14, 2025, 14 pages.
Patentees Submission under Rule 116 EPC in Opposition against European Patent No. 3784233, filed on Oct. 24, 2025, 48 pages.
Poyrazoglu et al., "Prevalence of Testicular Microlithiasis in Males with Congenital Adrenal Hyperplasia and Its Association with Testicular Adrenal Rest Tumors," Horm. Res. Paediatr., Apr. 20, 2010, 73:443-448.
Preliminary Order in UPC Proceeding No. 34386/2025, issued on Sep. 25, 2025, 2 pages.
Preliminary Order in UPC Proceeding No. 34386/2025, issued on Sep. 30, 2025, 4 pages.
Reisch et al., "High prevalence of reduced fecundity in men with congenital adrenal hyperplasia," J. Clin. Endocrinol. Metab., Mar. 3, 2009, 94(5):1665-1670.
Reisch et al., "Testicular adrenal rest tumors develop independently of long-term disease control: a longitudinal analysis of 50 adult men with congenital adrenal hyperplasia due to classic 21-hydroxylase deficiency," J. Clin. Endocrinol. Metab., Aug. 22, 2013, 98(11):E1820-E1826.
Rentsch, "The importance of stereoselective determination of drugs in the clinical laboratory," Journal of Biochemical and Biophysical Methods, Nov. 15, 2002, 54(1-3):1-9.
Reply to Defence to Revocation and Defence to the Application to Amend the Patent with regard to patent EP 3784233 B1, filed on Dec. 16, 2025, 61 pages.
Reply to Response to Notice of Opposition against European Patent No. 3784233, filed on Jul. 18, 2025, 7 pages.
Reply to the Notice of Opposition against European Patent No. 3096756, filed on Jul. 24, 2025, 36 pages.
Response to Application to Stay Proceedings in UPC Proceeding No. 34386/2025, filed on Sep. 26, 2025, 26 pages.
Response to Notice of Opposition against European Patent No. 3784233, filed on Jun. 18, 2025, 123 pages.
Response to the Reply to the Notice of Opposition against European Patent No. 3096756, filed on Oct. 24, 2025, 9 pages.
Rivkees, "Dexamethasone therapy of congenital adrenal hyperplasia and the myth of the" growth toxic" glucocorticoid," International journal of pediatric endocrinology, Mar. 28, 2010, 2010(569680):1-7.
Smeets et al., "Molecular Characterization of Testicular Adrenal Rest Tumors in Congenital Adrenal Hyperplasia: Lesions With Both Adrenocortical and Leydig Cell Features," J. Clin. Endocrinol. Metab., Mar. 2015, 100(3):E524-E530.
Sowers et al., "Effect of dexamethasone on gonadotropin responsiveness to luteinizing hormone-releasing hormone and clomiphene in women with secondary amenorrhea," Am. J. Obstet. Gynecol., Jun. 1979, 134(3):325-328.
Spruce Biosciences, Inc., "Form 10-Q: Quarterly Report Pursuant To Section 13 OR 15(d) of the Securities Exchange Act of 1934 for the quarterly period ended Mar. 31, 2025," United States Securities and Exchange Commission, filed May 6, 2025, pp. 19 and 34-35.
Statement for Revocation of Patent EP 3784233 B1 in UPC Proceeding No. 34386/2025, filed on Aug. 8, 2025, 45 pages.
Statement of Defence and Application to Amend in UPC Proceeding No. 34386/2025, filed on Oct. 15, 2025, 168 pages.
Statement of Grounds for Amendment of EP 3784233 in Claim No. HP-2025-000005 against EP Patent No. 378423, filed on Nov. 11, 2025, 4 pages.
Summons to Attend Oral Proceedings in Opposition against European Patent No. 3784233, mailed on Aug. 5, 2025, 21 pages.
Transmission of the certificate for a European patent with unitary effect for European Patent No. 3784233, mailed on Jul. 8, 2024, 2 pages.
Turcu et al., "Adrenal steroidogenesis and congenital adrenal hyperplasia," Endocrinol. Metab. Clin. North Am., Jun. 2015, 44(2):275-296.
U.S. Appl. No. 62/663,951, filed Apr. 27, 2018, 153 pages.
U.S. Appl. No. 62/822,815, filed Mar. 23, 2019, 25 pages.
Wang et al., "Diagnosis of Testicular Adrenal Rest Tumors on Ultrasound: A retrospective Study of 15 Cases Report," Medicine, Sep. 2015, 94(36):e1471, 6 pages.
Williams Textbook of Endocrinology, 13th ed., Melmed et al. (eds.), Oct. 2016, pp. 497 and 507-510.

(56) References Cited

OTHER PUBLICATIONS

Withdrawal of an opt-out pursuant to RoP5.9 from the exclusive competence of the Unified Patent Court in UPC Proceeding No. 38945/2024, dated Jun. 29, 2024, 4 pages.
Xavier et al., "Gene Expression Control by Glucocorticoid Receptors during Innate Immune Responses," Front. Endocrinol., Apr. 19, 2016, 7:31, 8 pages.
Xue et al., "Glucocorticoid Modulates Angiotensin II Receptor Expression Patterns and Protects the Heart from Ischemia and Reperfusion Injury," PLOS One, Sep. 2014, 9(9):e106827, 10 pages.
Yamada et al., "New class of corticotropin-releasing factor (CRF) antagonists: small peptides having high binding affinity for CRF receptor," J. Med. Chem., Feb. 26, 2004, 47(5):1075-1078.
Yasir et al., "Corticosteroid Adverse Effects," StatPearls, Jul. 3, 2023, 14 pages.
Yu et al., "Clinical manifestations of testicular adrenal rest tumor in males with congenital adrenal hyperplasia," Ann. Pediatr. Endocrinol. Metab., Sep. 30, 2015, 20(3):155-161.
Zaarour et al., "Bilateral ovary adrenal rest tumor in a congenital adrenal hyperplasia following adrenalectomy," Endocr. Pract., Jan. 21, 2014, 20(4):e69-e74.
[No Author Listed], CAS Registry No. 68583-51-7, "Propylene Glycol Dicaprylate/Dicaprate," Jan. 28, 2026, posted by www.alfa-chemical.com, 6 pages.
[No Author Listed], "A Ph2b to Evaluate Clinical Efficacy and Safety of Tildacerfont in Adult CAH," NCT04457336, Jun. 10, 2024, posted by www.clinicaltrials.gov, 14 pages.
[No Author Listed], "FDA Approves New Treatment for Congenital Adrenal Hyperplasia," Dec 13, 2024, posted by www.fda.gov, 2 pages.
[No Author Listed], "Spruce saws off only drug after 2nd hyperplasia fail, leaving biotech's direction in doubt," Dec 11, 2024, posted on www.fiercebiotech.com, 2 pages.
[No Author Listed], "Technical Data Sheet Miglyol 812 N (Excipient)," IOI Oleochemical, Apr. 2017, posted on marcordev.com, 5 pages.
[No Author Listed], Cat#: 522656, Nov. 22, 2025, posted on www.medkoo.com, 2 pages.
[No Author Listed], Order in Claim No. HP-2025-000005 against EP Patent No. 378423, May 2, 2025, 6 pages.
[No Author Listed], "JCEM Author Guidelines," Jan. 27, 2017, posted on www.academicoup.com, 1 page.
[No Author Listed], CAS Registry No. 68583-51-7, "Decanoic acid, mixed diesters with octanoic acid and propylene glycol," Jan. 28, 2026, posted on www.pharmaffiliates.com, 5 pages.
[No Author Listed], "Definition of Body Surface Area," Jan. 21, 2021, posted on www.rxlist.com/body_surface_area/definition.htm>, 1 page.
[No Author Listed], "Investors/Media," Jul. 24, 2025, posted on www.investors.sprucebio.com, 2 pages.
[No Author Listed], "Spruce Biosciences announces topline results from CAHMELIA-203 in adult classic CAH and CAHPTAIN-205 in pediatric classic CAH," Mar. 13, 2024, posted on www.investors.sprucebio.com, 7 pages.
[No Author Listed], "Spruce Biosciences announces topline results from CAHMELIA-204 in adult CAH and CAHPTAIN-205 in adult and pediatric CAH," Dec 10, 2024, posted on www.investors.sprucebio.com, 4 pages.
[No Author Listed], "SpruceBio: About US," Jul. 24, 2023 posted on www.sprucebio.com, 5 pages.
[No Author Listed], "Weight charts for Girls and Boys 5 to 10 years old," World Health Organization, 2007, posted on www.cdn.who.int, 2 pages.
[No Author Listed], "Average Sizes of Man and Woman," Nov. 2025, posted on www.worlddata.info, 9 pages.

* cited by examiner a SDD=Compound of Formula (I) spray dried dispersion (suspension or capsule formulation).
b Reference formulation=Compound of Formula (I) encapsulated, lipid semi-solid.

a Visit on Days 21 (+3 days), 28 (+3 days), and 35 (+3 days); final study visit on Day 49 (+7 days) or early termination.
PD = pharmacodynamic.

* Can be contained in hydro-alcoholic solution ready for manufacturing use

CRF1 RECEPTOR ANTAGONIST, PHARMACEUTICAL FORMULATIONS AND SOLID FORMS THEREOF FOR THE TREATMENT OF CONGENITAL ADRENAL HYPERPLASIA

CROSS-REFERENCE TO RELATED APPLICATION

This application is a National Stage Application under 35 U.S.C. § 371 and claims the benefit of International Application No. PCT/IB2019/001325, filed Dec. 6, 2019, which claims priority to U.S. Application No. 62/816,674, filed Mar. 11, 2019 and U.S. Application No. 62/776,763, filed Dec. 7, 2018. The disclosures of the foregoing applications are hereby incorporated by reference in their entireties.

TECHNICAL FIELD

The present disclosure relates to 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for the treatment of congenital adrenal hyperplasia (CAH). The present disclosure further relates to pharmaceutical formulations and solid forms of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, and their use in the treatment of congenital adrenal hyperplasia (CAH).

BACKGROUND

Classic congenital adrenal hyperplasia (CAH) is a disease that includes a group of autosomal recessive disorders that result in an enzyme deficiency that alters the production of adrenal steroids due to 21-hydroxylase deficiency, a condition that results in little or no cortisol biosynthesis. One clinical manifestation of the absence of cortisol is the lack of feedback inhibition of pituitary adrenocorticotropic hormone (ACTH) secretion. Increased ACTH levels cause adrenal hyperplasia and the enzyme mutation causes a shunting of cortisol precursor steroids to alternate pathways. Most notably, the shunting of androgens leads to virilization and other developmental complications in females and the over-accumulation of ACTH is associated with the formation of testicular adrenal rest tumors in males. In addition, since the same enzyme (21-hydroxylase) is used in the pathway for the biosynthesis of the mineralocorticoids, a number of these patients suffer from aldosterone deficiency which can result in dehydration and death due to salt-wasting. The prevalence of classic 21-hydroxylase deficiency CAH in the US general population, based on newborn screening, has been documented as 1:10,000 to 1:20,800 (Trakakis et al., "An update to 21-hydroxylase deficient congenital adrenal hyperplasia," *Gynecol. Endocrinol.* (2010) 26(1):63-71; Hertzberg et al., "Birth prevalence rates of newborn screening disorders in relation to screening practices in the United States," *J. Pediatr.* (2011) 159(4): 555-560).

Pediatric patients from birth through adolescence, and females in particular, appear to be the most vulnerable population of CAH sufferers and represent the subgroup of patients with the greatest unmet medical need (Cheng and Speiser, "Treatment outcomes in congenital adrenal hyperplasia," *Adv. Pediatr.* (2012) 59(1):269-281; Merke and Poppas, "Management of adolescents with congenital adrenal hyperplasia," *Lancet Diabetes Endocrinol.* (2013) 1(4): 341-352). Excessive androgen production in these younger patients results in early onset puberty and adrenarche, changes in skeletal maturation patterns, short stature caused by premature growth plate fusion, as well as significant hirsutism and acne problems. While survival is properly ensured through steroid replacement strategies based on physiologic dosing of glucocorticoids (e.g., hydrocortisone) and mineralocorticoids (e.g., fludrocortisone), these doses are often inadequate to suppress the accumulating ACTH and overproduction of progestogens and androgens (e.g., 17-hydroxyprogesterone [17-OHP], androstenedione, and testosterone). The uncontrolled symptoms of androgen excess, indeed, have a substantial impact on the day-to-day functioning and development of these patients.

Currently, exogenous corticosteroids are the standard of care for treating patients with classic CAH. This treatment is used to correct the cortisol deficiency and reduce the excessive ACTH levels and androgen excess. However, the dose and duration of steroid use required to suppress ACTH are typically well above the normal physiological level used for cortisol replacement alone (as in patients with Addison's disease). This increased exposure to glucocorticoids can lead to iatrogenic Cushing's syndrome, increased cardiovascular risk factors, glucose intolerance, reduced growth velocity, and decreased bone mineral density in CAH patients (Elnecave et al., "Bone mineral density in girls with classical congenital adrenal hyperplasia due to CYP21 deficiency," *J. Pediatr. Endocrinol. Metab.* (2008) 21(12):1155-1162; King et al., "Long-term corticosteroid replacement and bone mineral density in adult women with classical congenital adrenal hyperplasia," *J. Clin. Endocrinol. Metab.* (2006) 91(3):865-869; Migeon and Wisniewski, "Congenital adrenal hyperplasia owing to 21-hydroxylase deficiency. Growth, development, and therapeutic considerations," *Endocrinol. Metab. Clin. North Am.* (2001) 30(1):193-206).

Corticotropin releasing factor (CRF) is a hypothalamic hormone released directly into the hypophyseal portal vasculature and acts on specific corticotropin releasing factor 1 (CRF1) receptors on corticotropes in the anterior pituitary to stimulate the release of ACTH. Blockade of these receptors has been shown to decrease the release of ACTH in both animals and humans. Therefore, compounds that block CRF1 receptors have the potential to directly inhibit the excessive ACTH release that occurs in CAH and thereby allow for normalization of androgen production while using lower, more physiologic doses of hydrocortisone.

The compound of Formula (I)

(I)

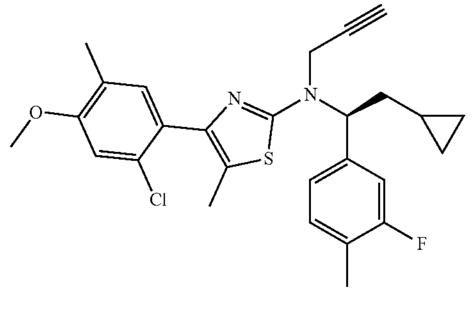

4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, is a selective CRF1 receptor antagonist. The compound of Formula (I) can be prepared according to the methods described in U.S. Pat. Nos. 6,586,456 and 8,314,249, each of which is hereby incorporated by reference in its entirety. The compound of Formula (I) is a low solubility compound with low bioavailability. Partially due to its low solubility, attempts at formulating the compound of Formula (I) have proven to be difficult, particularly for formulations suitable for pediatric administration.

Thus, there is a need for a treatment for CAH that avoids the severe complications associated with corticosteroid therapy. There is also a need for a formulation of the compound of Formula (I) with increased bioavailability and a need for a formulation of the compound of Formula (I) that is suitable for pediatric administration. The formulations and methods of the present invention help address these and other needs.

SUMMARY

Provided herein is a pharmaceutical composition comprising:

(a) a compound of Formula (I):

(I)

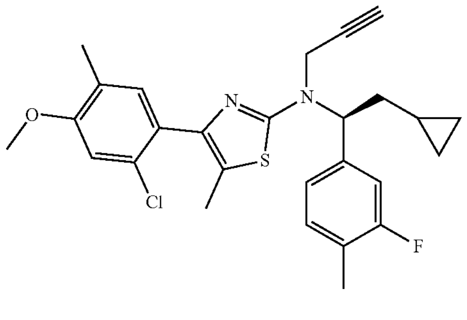

or a pharmaceutically acceptable salt thereof; and (b) one or more of an oily phase vehicle, an emulsifying agent, a nonionic surfactant, and a solubilizing agent.

Provided herein is a pharmaceutical composition in oral solution dosage form comprising:

(a) a compound of Formula (I):

(I)

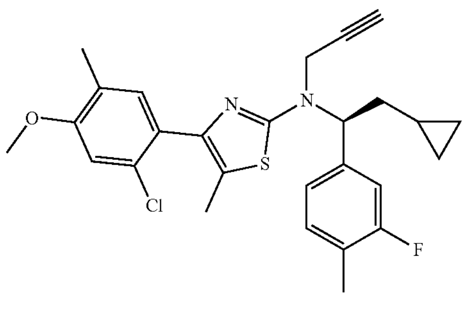

or a pharmaceutically acceptable salt thereof;

(b) one or more of a sweetener, an anti-oxidant, and a flavor; and (c) a liquid vehicle.

Also provided herein is a pharmaceutical composition of the present disclosure (e.g., a pharmaceutical composition in oral solution dosage form of the present disclosure) for use in therapy, for example, for use in any of the methods disclosed herein.

Provided herein is a method for treating congenital adrenal hyperplasia (CAH) comprising administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine having the Formula (I):

(I)

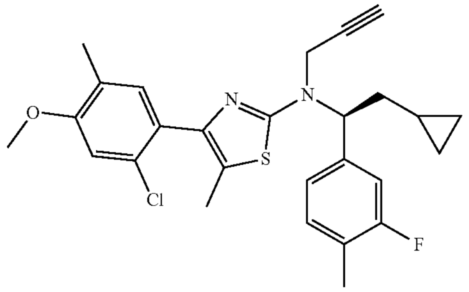

or a pharmaceutically acceptable salt thereof.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of treating congenital adrenal hyperplasia in a subject.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of treating congenital adrenal hyperplasia in a subject.

Provided herein is a method of treating congenital adrenal hyperplasia in a subject in need thereof comprising administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in an amount sufficient to reduce the level of one or more biomarkers selected from (a) 17-hydroxyprogesterone (17-OHP); (b) adrenocorticotropic hormone (ACTH); and (c) androstenedione in the subject.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of treating congenital adrenal hyperplasia in a subject, wherein the compound, or pharmaceutically acceptable salt thereof, is administered in an amount sufficient to reduce the level of one or more biomarkers selected from (a) 17-hydroxyprogesterone (17-OHP); (b) adrenocorticotropic hormone (ACTH); and (c) androstenedione in the subject.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of treating congenital adrenal hyperplasia in a subject, wherein the compound, or pharmaceutically acceptable salt thereof, is administered in an amount sufficient to reduce the level of one or more biomarkers selected from (a) 17-hydroxyprogesterone (17-OHP); (b) adrenocorticotropic hormone (ACTH); and (c) androstenedione in the subject.

In some embodiments, the reduction in level of any of biomarkers is determined by comparing the level of the biomarker as measured during the circadian release on a day prior to administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof and the level of the biomarker as measured during the circadian release on the day after administering the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof. In some embodiments, the circadian release occurs between the hours of 2 a.m. and 10 a.m.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered three to eight hours prior to the circadian release of the biomarker.

In some embodiments, the level of 17-hydroxyprogesterone is reduced by at least 25%. In some embodiments, the level of 17-hydroxyprogesterone is reduced by at least 50%.

In some embodiments, the level of adrenocorticotropic hormone is reduced by at least 25%. In some embodiments, the level of adrenocorticotropic hormone is reduced by at least 40%. In some embodiments, the level of adrenocorticotropic hormone is reduced by at least 50%.

In some embodiments, the level of androstenedione is reduced by at least 25%. In some embodiments, the level of androstenedione is reduced by at least 30%. In some embodiments, the level of androstenedione is reduced by at least 50%.

In some embodiments, the level of 17-hydroxyprogesterone is reduced by at least 50% and the level of androstenedione is reduced by at least 50%.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered once daily at an amount equivalent to about 50 mg or about 100 mg of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine free base.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is administered in the free base form.

Provided herein is a method for reducing the severity of one or more symptoms selected from hirsutism, precocious puberty, fertility problems, acne, and growth impairment in a subject having classic congenital adrenal hyperplasia, comprising administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in an amount sufficient to reduce the level of androstenedione in the subject. In some embodiments, the growth impairment is selected from one or more of accelerated height velocity, accelerated weight velocity, or accelerated bone age.

Also provided herein is a compound which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of reducing the severity of one or more symptoms selected from hirsutism, precocious puberty, fertility problems, acne, and growth impairment in a subject having classic congenital adrenal hyperplasia, wherein the compound, or pharmaceutically acceptable salt thereof, is administered in an amount sufficient to reduce the level of androstenedione in the subject.

Also provided herein is use of a compound which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of reducing the severity of one or more symptoms selected from hirsutism, precocious puberty, fertility problems, acne, and growth impairment in a subject having classic congenital adrenal hyperplasia, wherein the compound, or pharmaceutically acceptable salt thereof, is administered in an amount sufficient to reduce the level of androstenedione in the subject.

In some embodiments, the level of androstenedione is reduced by at least 25%. In some embodiments, the level of androstenedione is reduced by at least 30%. In some embodiments, the level of androstenedione is reduced by at least 50%.

Provided herein is a method of reducing the level of one or more biomarkers of congenital adrenal hyperplasia in a subject having congenital adrenal hyperplasia comprising administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of reducing the level of one or more biomarkers of congenital adrenal hyperplasia in a subject having congenital adrenal hyperplasia.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of reducing the level of one or more biomarkers of congenital adrenal hyperplasia in a subject having congenital adrenal hyperplasia.

In some embodiments, the one or more biomarkers of congenital adrenal hyperplasia are selected from (a) 17-hydroxyprogesterone (17-OHP); (b) adrenocorticotropic hormone (ACTH); and (c) androstenedione.

Provided herein is a method of reducing the dosage of corticosteroid administered to a subject having congenital adrenal hyperplasia for controlling congenital adrenal hyperplasia comprising administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof. In some embodiments, the corticosteroid is a glucocorticoid.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of reducing the dosage of corticosteroid administered to a subject having congenital adrenal hyperplasia.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of reducing the dosage of corticosteroid administered to a subject having congenital adrenal hyperplasia.

Provided herein is a method of reducing the severity of one or more side effects of glucocorticoid treatment in a subject having congenital adrenal hyperplasia comprising administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, and reactivation of latent infections.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of reducing the severity of one or more side effects of glucocorticoid treatment in a subject having congenital adrenal hyperplasia, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, and reactivation of latent infections.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of reducing the severity of one or more side effects of glucocorticoid treatment in a subject having congenital adrenal hyperplasia, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, and reactivation of latent infections.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof is administered at an amount sufficient to reduce the level of 17-hydroxyprogesterone (17-OHP) by at least 50% as compared to the level prior to administration.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof is administered at an amount sufficient to reduce the level of androstenedione by at least 30% as compared to the level prior to administration.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof is administered at an amount sufficient to (a) reduce the level of 17-hydroxyprogesterone (17-OHP) by at least 50% as compared to the level prior to administration; and (b) reduce the level of androstenedione by at least 30% as compared to the level prior to administration.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered once daily at an amount equivalent to from about 25 mg to about 150 mg 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine free base.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered once daily at an amount equivalent to about 50 mg or about 100 mg of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine free base.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is administered in the free base form.

Provided herein is a method of treating congenital adrenal hyperplasia in a subject comprising (i) measuring the level of one or more biomarkers selected from (a) 17-hydroxyprogesterone (17-OHP); (b) adrenocorticotropic hormone (ACTH); and (c) androstenedione in a biological sample obtained from the subject;

(ii) analyzing the level of the one or more biomarkers to determine if the level of the one or more biomarkers is elevated compared to a healthy subject not having congenital adrenal hyperplasia; and (iii) administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof if the subject is determined to have elevated levels of the one or more biomarkers.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of treating congenital adrenal hyperplasia in a subject comprising (i) measuring the level of one or more biomarkers selected from (a) 17-hydroxyprogesterone (17-OHP); (b) adrenocorticotropic hormone (ACTH); and (c) androstenedione in a biological sample obtained from the subject;

(ii) analyzing the level of the one or more biomarkers to determine if the level of the one or more biomarkers is elevated compared to a healthy subject not having congenital adrenal hyperplasia; and (iii) administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof if the subject is determined to have elevated levels of the one or more biomarkers.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of treating congenital adrenal hyperplasia in a subject, wherein the method comprises:

(i) measuring the level of one or more biomarkers selected from (a) 17-hydroxyprogesterone (17-OHP); (b) adrenocorticotropic hormone (ACTH); and (c) androstenedione in a biological sample obtained from the subject;

(ii) analyzing the level of the one or more biomarkers to determine if the level of the one or more biomarkers is elevated compared to a healthy subject not having congenital adrenal hyperplasia; and (iii) administering to the subject 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof if the subject is determined to have elevated levels of the one or more biomarkers.

In some embodiments, the method further comprises (iv) measuring the level of the one or more biomarkers after administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in a biological sample obtained from the subject to determine whether the subject has reduced levels of the one or more biomarkers as compared with the measurement of step (i). In some embodiments, the method further comprises (v) continuing the administration of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof if the subject has reduced levels of the one or more biomarkers.

In some embodiments, steps (i) and (iv) are performed on biological samples taken from the subject in a similar manner and within a same time of day window. In some embodiments, steps (i) and (iv) are performed on biological samples taken from the subject within the time of day window from 2 a.m. to 10 a.m. In some embodiments, steps (i) and (iv) are performed on biological samples taken from the subject within the time of day window from 6 a.m. to 10 a.m.

In some embodiments, steps (i) and (iv) comprise measuring the levels of at least two biomarkers selected from (a) 17-hydroxyprogesterone (17-OHP); (b) adrenocorticotropic hormone (ACTH); and (c) androstenedione.

In some embodiments, steps (i) and (iv) comprise measuring the levels of (a) 17-hydroxyprogesterone (17-OHP); (b) adrenocorticotropic hormone (ACTH); and (c) androstenedione.

In some embodiments, step (i) comprises measuring the level of 17-hydroxyprogesterone (17-OHP), wherein the level of 17-hydroxyprogesterone (17-OHP) is elevated when it is greater than or equal to 1,000 ng/dL.

In some embodiments, step (i) comprises measuring the level of androstenedione, wherein the level of androstenedione is elevated when it is greater than 200 ng/dL.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered once daily at an amount equivalent to from about 25 mg to about 150 mg of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine free base. In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered once daily at an amount equivalent to about 50 mg or about 100 mg of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine free base. In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is administered in the free base form.

Provided herein is a method of treating congenital adrenal hyperplasia (CAH), in a subject in need thereof, comprising administering to the subject a therapeutically effective amount of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, where in the subject is in a fed state.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of treating congenital adrenal hyperplasia (CAH) in a subject, wherein the subject is in a fed state.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of treating congenital adrenal hyperplasia (CAH) in a subject, wherein the subject is in a fed state.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered to the subject with a nutritional composition. In some embodiments, the nutritional composition is a liquid dietary supplement comprising about 1500 calories per liter with a caloric distribution of about 14.7% protein, about 32% fat and about 53.3% carbohydrate. In some embodiments, the nutritional composition is administered in an amount of about 8 fluid ounces. In some embodiments, the nutritional composition is administered within 30 minutes of administration of the 4-(2-chloro-4-methoxy-5-methylphenyl)-N-[(1S)-2-cyclopropyl-1-(3-fluoro-4-methylphenyl) ethyl]-5-methyl-N-prop-2-ynyl-1,3-thiazol-2-amine, or a pharmaceutically acceptable salt thereof.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered to the subject with a nutritional composition. In some embodiments, the nutritional composition is a liquid dietary supplement comprising 1500 calories per liter with a caloric distribution of 1$^{4}$0.7% protein, 32% fat and 53.3% carbohydrate. In some embodiments, the nutritional composition is administered in an amount of about 8 fluid ounces. In some embodiments, the nutritional composition is administered within 30 minutes of administration of the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof.

In some embodiments, administering the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, exhibits a positive food effect. In some embodiments, the positive food effect is measured in terms of $C_{max}$, area under the curve (AUC), or combinations thereof when comparing oral administration of the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the fed and fasting states.

In some embodiments, the ratio of the AUC in the fed state to the AUC in the fasted state is about 5 to about 10. In some embodiments, the ratio of the $C_{max}$ in the fed state to the $C_{max}$ in the fasted state is about 5 to about 10.

Provided herein is a method of reducing glucocorticoid burden in a subject as measured after a time period of administration of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, wherein the decrease in glucocorticoid burden is relative to the glucocorticoid burden prior to administration of the compound, or pharmaceutically acceptable salt thereof.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of reducing glucocorticoid burden in a subject, wherein the decrease in glucocorticoid burden is relative to the glucocorticoid burden prior to administration of the compound, or pharmaceutically acceptable salt thereof.

Also provided herein is use of a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of reducing glucocorticoid burden in a subject, wherein the decrease in glucocorticoid burden is relative to the glucocorticoid burden prior to administration of the compound, or pharmaceutically acceptable salt thereof.

Provided herein is a method of improving one or more symptoms selected from quality of life, fatigue, sleep, insulin resistance, glucose tolerance, glucose control, dyslipidemia, hyperlipidemia, bone mineral density, bone turnover, fat mass, weight, central obesity, blood pressure, hirsutism severity, menstrual cyclicity, control of testicular adrenal rest tumor and fertility in a subject having classic congenital adrenal hyperplasia, comprising administering 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, wherein the symptom is improved after a time period of administration of the compound, or pharmaceutically acceptable salt thereof, wherein the improvement in the one or more symptoms is relative to the status of the one or more symptoms prior to administration of the compound, or pharmaceutically acceptable salt thereof.

Also provided herein is a compound which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in a method of improving one or more symptoms selected from quality of life, fatigue, sleep, insulin resistance, glucose tolerance, glucose control, dyslipidemia, hyperlipidemia, bone mineral density, bone turnover, fat mass, weight, central obesity, blood pressure, hirsutism severity, menstrual cyclicity, control of testicular adrenal rest tumor and fertility in a subject having classic congenital adrenal hyperplasia, wherein the symptom is improved after a time period of administration of the compound, or pharmaceutically acceptable salt thereof, wherein the improvement in the one or more symptoms is relative to the status of the one or more symptoms prior to administration of the compound, or pharmaceutically acceptable salt thereof.

Also provided herein is use of a compound which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, in the manufacture of a medicament for use in a method of improving one or more symptoms selected from quality of life, fatigue, sleep, insulin resistance, glucose tolerance, glucose control, dyslipidemia, hyperlipidemia, bone mineral density, bone turnover, fat mass, weight, central obesity, blood pressure, hirsutism severity, menstrual cyclicity, control of testicular adrenal rest tumor and fertility in a subject having classic congenital adrenal hyperplasia, wherein the symptom is improved after a time period of administration of the compound, or pharmaceutically acceptable salt thereof, wherein the improvement in the one or more symptoms is relative to the status of the one or more symptoms prior to administration of the compound, or pharmaceutically acceptable salt thereof.

Also provided herein is a compound, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof for use in therapy, for example, for use in any of the methods disclosed herein.

Also provided herein is use of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for manufacture of a medicament for use in any of the methods disclosed herein.

Also provided herein is a spray-dried dispersion containing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine having the Formula (I):

(I)

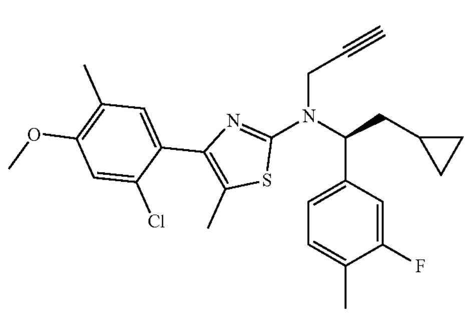

or a pharmaceutically acceptable salt thereof, and a polymer. In some embodiments, the polymer is selected from a neutral polymer, an enteric polymer, and a pyrrolidone polymer. In some embodiments, the weight ratio of the compound of Formula (I) to the polymer is from about 1:9 to about 1:1.

In some embodiments, the polymer is a neutral polymer. In some embodiment, the neutral polymer is selected from hydroxypropyl methylcellulose (HPMC) and hydroxyethyl cellulose (HEC).

In some embodiments, the polymer is an enteric polymer. In some embodiments, the enteric polymer is selected from hydroxypropyl methyl cellulose acetate succinate (HPMCAS), cellulose acetate phthalate (CAP), hydroxypropyl methyl cellulose phthalate (HPMCP), an amino methacrylate copolymer, an ammonioalkyl methacrylate copolymer, and a methacrylic copolymer.

In some embodiments, the polymer is a pyrrolidone polymer. In some embodiments, the pyrrolidone polymer is selected from polyvinyl pyrrolidone (PVP) and a polyvinyl pyrrolidone vinyl acetate (PVP/VA). In some embodiments, the pyrrolidone polymer is PVP/VA. In some embodiments, the copolymer comprises 1-vinyl-2-pyrrolidone and vinyl acetate at a ratio of about 40:60 to about 60:40 by weight. In some embodiments, the copolymer comprises 1-vinyl-2-pyrrolidone and vinyl acetate at a ratio of about 60:40 by weight. In some embodiments, the copolymer has the structure:

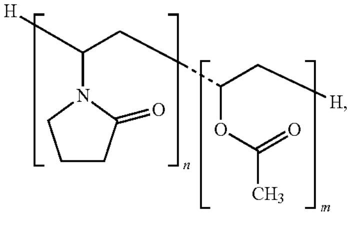

wherein the value of n is about 1 to about 2 times the value of m. In some embodiments, the copolymer is copovidone, wherein the value of n is about 1.16 times the value of m. In some embodiments, the copolymer is copovidone having an average molecular weight of about 45,000 to about 70,000.

Provided herein is a spray-dried dispersion comprising 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine having the Formula (I):

(I)

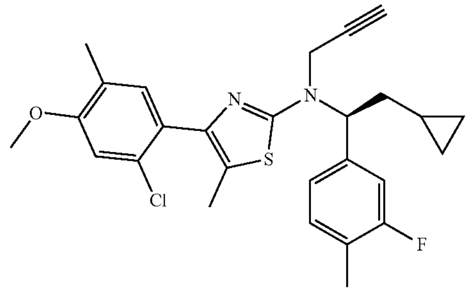

or a pharmaceutically acceptable salt thereof, and a polymer that is a copolymer of 1-vinyl-2-pyrrolidone and vinyl acetate having the structure:

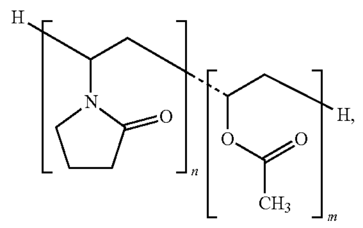

wherein the value of n is about 1 to about 2 times the value of m and the copolymer comprises 1-vinyl-2-pyrrolidone and vinyl acetate at a ratio of about 60:40 by weight; and wherein the weight ratio of the compound of Formula (I) to the copolymer is from about 1:1 to about 1:9.

In some embodiments of the spray-dried dispersions of the present disclosure, the compound of Formula (I) and the polymer together form homogeneous particles. In some embodiments, the particles have a particle size distribution $D_{50}$ of about 5 μm to about 100 μm. In some embodiments, the particles have a particle size distribution $D_{50}$ of about 10 μm to about 50 μm. In some embodiments, the particles have a particle size distribution $D_{50}$ of about 15 μm to about 30 μm.

In some embodiments, the weight ratio of the compound of Formula (I) to the polymer is from about 1:1.5 to about 1:9. In some embodiments, the weight ratio of the compound of Formula (I) to the polymer is from about 1:2.5 to about 1:4. In some embodiments, the weight ratio of the compound of Formula (I) to the polymer is about 1:3.

In some embodiments, the particles have a residual solvent content less than about 2 wt %. In some embodiments, the particles have a residual solvent content less than about 1 wt %. In some embodiments, the particles have a residual solvent content of about 0.5 wt % or less.

In some embodiments, the compound of Formula (I) in the dispersion is substantially amorphous.

Also provided herein is a method for preparing a spray-dried dispersion of the present disclosure, comprising: dissolving the compound of Formula (I), or a pharmaceutically acceptable salt thereof, and the polymer in an organic solvent to form a solution; and spray-drying the solution to produce the spray-dried dispersion, wherein the spray-drying forms homogeneous particles of the compound of Formula (I) and the polymer.

In some embodiments, the method comprises removing the organic solvent after formation of the spray-dried dispersion by drying the spray-dried dispersion. In some embodiments, the spray-dried dispersion is dried with a convection tray dryer. In some embodiments, the organic solvent is acetone.

In some embodiments, the spray dryer inlet temperature is about 60° C. to about 80° C. In some embodiments, the spray dryer inlet temperature is about 72° C.

In some embodiments, the spray dryer outlet temperature is about 25° C. to about 45° C. In some embodiments, the spray dryer outlet temperature is about 35° C.

In some embodiments, the homogeneous particles comprise a bulk density of less than about 0.2 g/mL. In some embodiments, the homogeneous particles comprise a bulk density of less than about 0.15 g/mL.

In some embodiments, the homogeneous particles comprise a tapped density of less than about 0.3 g/mL. In some embodiments, the homogeneous particles comprise a tapped density of less than about 0.25 g/mL.

Also provided herein is a pharmaceutical composition comprising the spray-dried dispersion of the present disclosure and one or more pharmaceutically acceptable excipients. In some embodiments, the spray-dried dispersion is present in an amount of about 20% to about 90% w/w of the composition. In some embodiments, the spray-dried dispersion is present in an amount of about 40% to 80% w/w of the composition.

In some embodiments, the pharmaceutical excipients are selected from the group consisting of a filler, a lubricant, and combinations thereof. In some embodiments, the filler is selected from the group consisting of a binder, a diluent, a disintegrant, a glidant, a surfactant, and combinations thereof.

In some embodiments, the pharmaceutical composition is formulated in unit dosage form, wherein the compound of Formula (I), or a pharmaceutically acceptable salt thereof, is present in an amount of about 5 mg to about 200 mg. In some embodiments, the compound of Formula (I), or a pharmaceutically acceptable salt thereof, is present in an amount of about 75 mg to about 150 mg. In some embodiments, the compound of Formula (I), or a pharmaceutically acceptable salt thereof, is present in an amount of about 50 mg. In some embodiments, the compound of Formula (I), or a pharmaceutically acceptable salt thereof, is present in an amount of about 100 mg.

In some embodiments, the pharmaceutical composition is formulated as a tablet, capsule, sachet, powder, granules, coated particle, coated tablet, enterocoated tablet, enterocoated capsule, melting strip, or melting film. In some embodiments, the pharmaceutical composition is in tablet form. In some embodiments, the pharmaceutical composition is in capsule form. In some embodiments, the pharmaceutical composition is coated.

In some embodiments, the spray-dried dispersion is formulated for oral administration and exhibits a positive food effect when administered orally. In some embodiments, the spray-dried dispersion has a ratio of the AUC in the fed state to the AUC in the fasted state of about 5 to about 10. In some embodiments, wherein the spray-dried dispersion has a ratio of the $C_{max}$ in the fed state to the $C_{max}$ in the fasted state of about 5 to about 10.

Also provided herein is a method for preparing a pharmaceutical composition, comprising combining the spray-dried dispersion of the present disclosure with one or more pharmaceutically acceptable excipients.

Also provided herein is a method of treating congenital adrenal hyperplasia (CAH), in a subject in need thereof, comprising administering to the subject a therapeutically effective amount of a spray-dried dispersion of the present disclosure or a pharmaceutical composition comprising a spray-dried dispersion of the present disclosure.

Also provided herein is a spray-dried dispersion of the present disclosure or a pharmaceutical composition comprising a spray-dried dispersion of the present disclosure for use in a method of treating congenital adrenal hyperplasia (CAH) in a subject.

Also provided herein is use of a spray-dried dispersion of the present disclosure in the manufacture of a medicament for use in a method of treating congenital adrenal hyperplasia (CAH) in a subject.

In some embodiments, the spray-dried dispersion or the pharmaceutical composition is administered to the subject in a fed state. In some embodiments, the spray-dried dispersion or the pharmaceutical composition is administered to the subject with a nutritional composition. In some embodiments, the nutritional composition is a liquid dietary supplement comprising about 1000 to about 2000 calories per liter with a fat content greater than 30%. In some embodiments, the nutritional composition is a liquid dietary supplement comprising 1500 calories per liter with a caloric distribution of 14.7% protein, 32% fat and 53.3% carbohydrate. In some embodiments, the nutritional composition is administered in an amount of about 8 fluid ounces. In some embodiments, the nutritional composition is administered within 30 minutes of administration of the spray-dried dispersion or the pharmaceutical composition.

In some embodiments, administering the spray-dried dispersion or the pharmaceutical composition exhibits a positive food effect. In some embodiments, the positive food effect is measured in terms of $C_{max}$, AUC, or combinations thereof when comparing oral administration of the spray-dried dispersion or pharmaceutical composition in the fed and fasting states. In some embodiments, the ratio of the AUC in the fed state to the AUC in the fasted state is about 5 to about 10. In some embodiments, the ratio of the $C_{max}$ in the fed state to the $C_{max}$ in the fasted state is about 5 to about 10. In some embodiments, the ratio of the AUC in the fed state to the AUC in the fasted state is about 10 to about 20. In some embodiments, the ratio of the $C_{max}$ in the fed state to the $C_{max}$ in the fasted state is about 10 to about 20.

In some embodiments of the disclosed methods, the subject is a pediatric subject.

Also provided herein is a spray-dried dispersion of the present disclosure or a pharmaceutical composition comprising a spray-dried dispersion of the present disclosure, for use in therapy, for example, for use in any of the methods disclosed herein.

Also provided herein is use of a spray-dried dispersion of the present disclosure for manufacture of a medicament for use in any of the methods disclosed herein.

Also provided herein is a method of treating congenital adrenal hyperplasia (CAH), in a subject in need thereof, comprising administering to the subject a pharmaceutical composition of the present disclosure, wherein the pharmaceutical composition comprises a therapeutically effective amount of the compound of Formula (I), or a pharmaceutically acceptable salt thereof.

Also provided herein is a pharmaceutical composition of the present disclosure, wherein the pharmaceutical composition comprises a therapeutically effective amount of the compound of Formula (I), or a pharmaceutically acceptable salt thereof, for use in a method of treating congenital adrenal hyperplasia (CAH) in a subject.

Also provided herein is use of pharmaceutical composition of the present disclosure, wherein the pharmaceutical composition comprises a therapeutically effective amount of the compound of Formula (I), or a pharmaceutically acceptable salt thereof, in the manufacture of a medicament for use in a method of treating congenital adrenal hyperplasia (CAH) in a subject.

Also provided herein is pharmaceutical composition of the present disclosure, wherein the pharmaceutical composition comprises a therapeutically effective amount of the compound of Formula (I), or a pharmaceutically acceptable salt thereof, for use in therapy, for example, for use in any of the methods disclosed herein.

Also provided herein is use of pharmaceutical composition of the present disclosure, wherein the pharmaceutical composition comprises a therapeutically effective amount of the compound of Formula (I), or a pharmaceutically acceptable salt thereof, for manufacture of a medicament for use in any of the methods disclosed herein.

Also provided herein is a method of improving gastrointestinal absorption of a compound of Formula (I) in a subject, comprising orally administering to the subject a therapeutically effective amount of a spray-dried dispersion of the present disclosure or a pharmaceutical composition comprising a spray-dried dispersion of the present disclosure, wherein the improvement is relative to oral administration of the compound of Formula (I) which has not been prepared as a spray-dried dispersion.

Also provided herein is a spray-dried dispersion of the present disclosure or a pharmaceutical composition comprising a spray-dried dispersion of the present disclosure, for use in a method of improving gastrointestinal absorption of a compound of Formula (I) in a subject, wherein the improvement is relative to oral administration of the compound of Formula (I) which has not been prepared as a spray-dried dispersion.

Also provided herein is use of a spray-dried dispersion of the present disclosure in the manufacture of a medicament for use in a method of improving gastrointestinal absorption of a compound of Formula (I) in a subject, wherein the improvement is relative to oral administration of the compound of Formula (I) which has not been prepared as a spray-dried dispersion.

In some embodiments, the subject is a pediatric subject.

Also provided herein is a method of improving oral bioavailability of a compound of Formula (I) in a subject, comprising orally administering to the subject a therapeutically effective amount of a spray-dried dispersion of the present disclosure or a pharmaceutical composition comprising a spray-dried dispersion of the present disclosure, wherein the improvement is relative to oral administration of the compound of Formula (I) which has not been prepared as a spray-dried dispersion.

Also provided herein is a spray-dried dispersion of the present disclosure or a pharmaceutical composition comprising a spray-dried dispersion of the present disclosure, for use in a method of improving oral bioavailability of a compound of Formula (I) in a subject, wherein the improvement is relative to oral administration of the compound of Formula (I) which has not been prepared as a spray-dried dispersion.

Also provided herein is use of a spray-dried dispersion of the present disclosure in the manufacture of a medicament for use in a method of improving oral bioavailability of a compound of Formula (I) in a subject, wherein the improvement is relative to oral administration of the compound of Formula (I) which has not been prepared as a spray-dried dispersion.

In some embodiments, the subject is a pediatric subject.

Also provided herein is a crystalline salt, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, p-toluenesulfonic acid salt.

Also provided herein is a crystalline salt, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, p-toluenesulfonic acid salt, for use in therapy, for example, for use in any of the methods disclosed herein.

Also provided herein is use of a crystalline salt, which is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, p-toluenesulfonic acid salt, for manufacture of a medicament for use in any of the methods disclosed herein.

Other features and advantages of the methods, processes, formulations, and uses provided herein will be apparent from the following detailed description and figures, and from the claims.

DESCRIPTION OF DRAWINGS

FIG. 6A shows the results from Cohort 1 and FIG. 6B shows the results from Cohort 2.

FIG. 9A shows the $AUC_{0\text{-}tlast}$ values.

FIG. 9B shows the $AUC_{0\text{-}\infty}$ values. FIG. 9C shows the $C_{max}$ values.

FIG. 14A shows the values for each time point as compared to baseline. FIG. 14B shows the mean values across all three timepoints.

FIG. 15A shows the values for each time point as compared to baseline. FIG. 15B shows the mean values across all three timepoints.

FIG. 16A shows the values for each time point as compared to baseline. FIG. 16B shows the mean values across all three timepoints.

DETAILED DESCRIPTION

Figure 1:
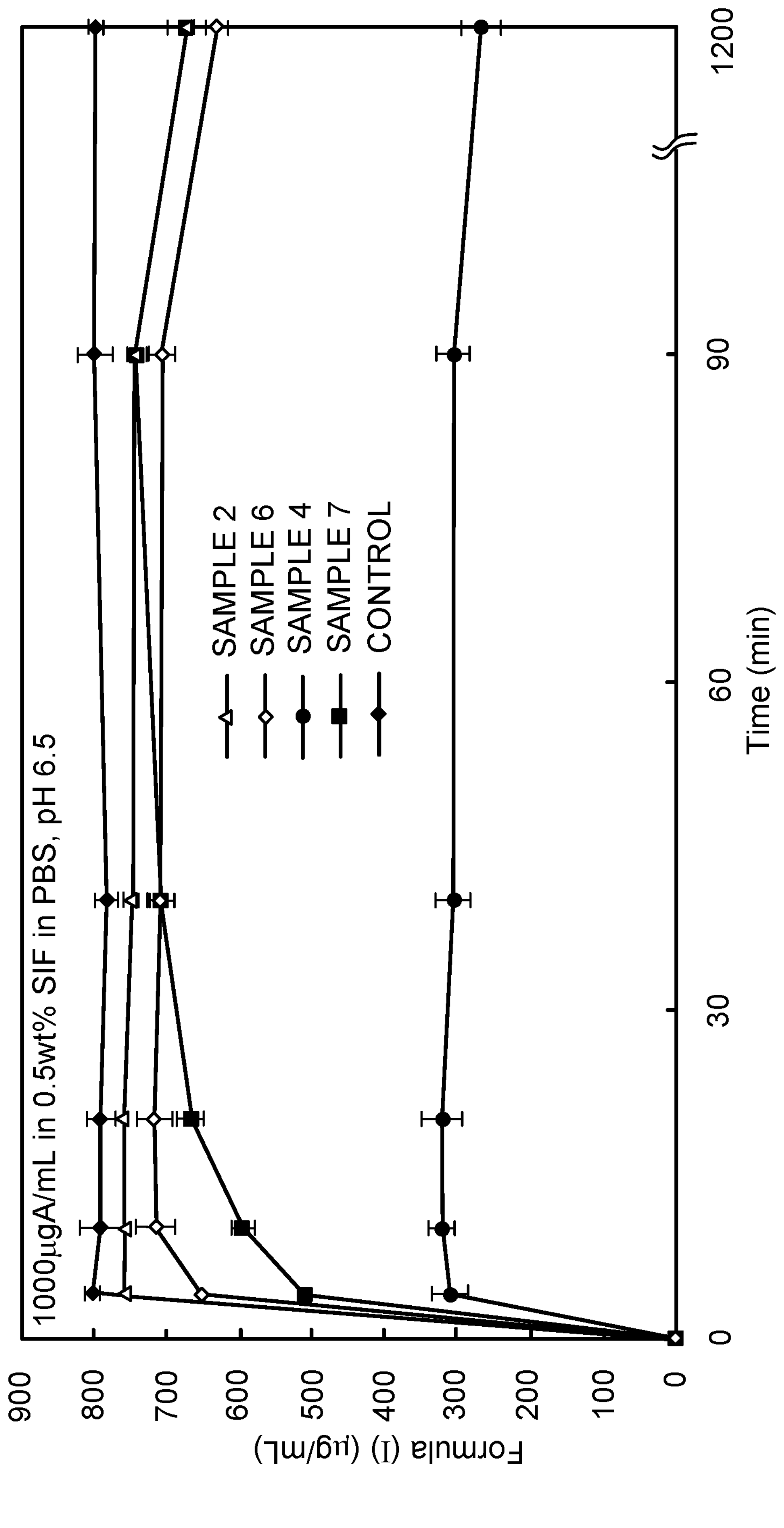
FIG. 1 shows the dissolution performance of several spray-dried dispersion formulations in 0.5 wt % simulated intestinal fluid (SIF) in phosphate buffered saline (PBS), pH 6.5.

As described herein, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine having the Formula (I):

(I)

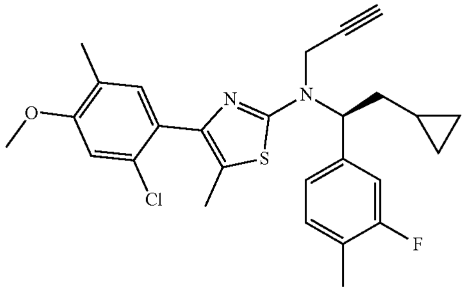

or a pharmaceutically acceptable salt thereof, is a selective CRF1 receptor antagonist that has been found to be effective treating congenital adrenal hyperplasia. Specifically, the compound of Formula (I) has been found to effectively reduce several biomarkers associated with congenital adrenal hyperplasia.

Newborn screening for CAH is performed by immunoassay to measure 17-OHP levels in heel-stick capillary blood specimens obtained within the first 72 hours of life. The blood sample is analyzed for 17-OHP by commercially available dissociation-enhanced lanthanide fluoroimmunoassay (DELFIA; PerkinElmer, Waltham Massachusetts) (White et al., *J. Pediatr.* 163:10-12 (2013)). Second-tier screening tests utilizing biochemical and molecular genetic testing methods, performed between 8 and 14 days of life, are employed by nine states in the United States and strongly recommended by an additional 5 states. The biochemical method includes immunoassay with organic solvent extraction or liquid chromatography followed by tandem mass spectrometry to measure steroid ratios of 17-OHP, androstenedione, and 21-deoxycortisol to cortisol (see, e.g., Speiser et al., *Int. J. Pediatr. Endocrinol.* 2010:494173, 2010). The genetic screen looks for CYP21A2 mutations that are associated with CAH. While not widely employed in the U.S., the addition of a second screening could potentially improve the sensitivity of the overall screening process, where sensitivity of the first screen alone is approximately 72%.

In absence of results from the newborn screening, female infants with classical CAH are typically identified due to the presence of ambiguous genitalia. Males have normal genitalia at birth and therefore are not diagnosed unless newborn screening is conducted or other medical complications come to attention. Infants who are not initially diagnosed with CAH and suffer from the salt-wasting form of the disease are later diagnosed in the setting of poor weight gain, vomiting, hyperkalemia and hyponatremia within the first few weeks of life.

Treatment of CAH is based on normalization of hormone and steroid levels using a variety of medications from diagnosis in infancy through adulthood. Glucocorticoids are the current standard treatment in CAH and are used both to correct the endogenous cortisol deficiency and for reducing the elevated ACTH levels from the pituitary, which drives increased androgen production. Unlike the treatment of Addison's disease (adrenal insufficiency), in which cortisol replacement is sufficient, the treatment of CAH must also reduce ACTH production, to control the subsequent androgen excess as well. Thus, the goals of glucocorticoid treatment include cortisol replacement and suppression of ACTH to prevent virilization and menstrual disturbances in women and to inhibit testicular adrenal rest tumors in men. Mineralocorticoid replacement is needed to achieve normal plasma renin activity for maintenance of regular blood pressure, electrolyte balance, and volume status in those patients with the salt-wasting form of CAH.

The regimen of glucocorticoid treatment must support normal physiology and also ensure that sufficient cortisol is available during events that may elicit a strong stress response (e.g., intercurrent illness, exercise, hypotension). Careful monitoring is also necessary to avoid the development of iatrogenic Cushing's syndrome due to glucocorticoid overtreatment in an effort to adequately suppress androgen production, or Addisonian syndrome due to under-treatment.

Overtreatment with mineralocorticoids may cause hypertension while under-treatment may lead to low blood pressure, salt loss, fatigue and increased requirements for glucocorticoids. Typical laboratory tests for monitoring treatment efficacy include measurement of plasma concentrations of 17-OHP, androstenedione, testosterone, renin activity, and electrolytes. Adult patients with CAH have an increased prevalence of risk factors for cardiovascular disease including obesity, hypertension, and insulin resistance (see, e.g., Kim et al., *Semin. Reprod. Med.* 27(4):316-21 (2009)). A study of a large cohort of pediatric and adult CAH patients (n=244) demonstrated that patients are prescribed a variety of glucocorticoid treatment regimens yet frequently suffer from poor hormonal control and the aforementioned adverse outcomes (see, e.g., Finkielstain et al., *J. Clin. Endocrinol Metab.* 97(12):4429-38 (2012)).

Treatment of CAH includes efforts to normalize the cortisol deficiency with glucocorticoids (usually hydrocortisone in children but often more potent agents with narrow therapeutic indices, such as dexamethasone, in adults) and, if necessary for salt-wasting, mineralocorticoids (usually fludrocortisone). The glucocorticoid doses required to achieve sufficient suppression of excess androgens, however, are usually well above the normal physiologic dose used for cortisol replacement alone as in patients with Addison's disease. This increased exposure to glucocorticoids can lead to iatrogenic Cushing's syndrome, increased cardiovascular risk factors, glucose intolerance, and decreased bone mineral density in CAH patients (see, e.g., Elnecave et al., *J. Pediatr. Endocrinol. Metab.* 21:1155-62 (2008); King et al., *J. Clin. Endocrinol. Metab.* 91(3):8656-59 (2006); Migeon et al., *Endocrinol. Metab. Clin. North Am.* 30:193-206 (2001)). Recently, best practices for the clinical management of congenital adrenal hyperplasia were published in the Journal of Clinical Endocrinology and Metabolism (Speiser, P. W., et al. *J. Clin. Endocrinol. Metab.* November 2018, 103(11): 1-46). This article is incorporated by reference in its entirety.

Corticotropin-releasing factor (CRF) was isolated from ovine hypothalami and identified as a 41-amino acid peptide. CRF has been found to produce profound alterations in endocrine, nervous, and immune system function. CRF is believed to be the major physiological regulator of the basal and stress-induced release of adrenocorticotropic hormone ("ACTH"), β-endorphin, and other pro-opiomelanocortin ("POMC")-derived peptides from the anterior pituitary (see, e.g., Vale et al., *Science* 213:1394-1397, 1981). Secretion of CRF causes release of ACTH from corticotrophs in the anterior pituitary via binding to the $CRF_1$ receptor, a member of the class B family of G-protein coupled receptors.

Due to the physiological significance of CRF, the development of biologically-active small molecules having significant $CRF_1$ receptor binding activity and which are capable of antagonizing the $CRF_1$ receptor remains a desirable goal and has been the subject of ongoing research and development for the treatment of anxiety, depression, irritable bowel syndrome, post-traumatic stress disorder, and substance abuse.

The pituitary hormone ACTH, under the control of hypothalamic corticotropin-releasing factor (CRF), stimulates uptake of cholesterol and drives the synthesis of pregnenolone initiating steroidogenesis in the adrenal gland. The adrenal cortex is comprised of three zones, which produce distinct classes of hormones many of which are driven by ACTH mobilizing cholesterol through this pathway. Deficiencies in these enzymes as a result of mutation or deletion cause the substrate concentrations to increase. In the most common form of CAH resulting from mutations or deletions in the 21-hydroxylase gene (CYP21A2), potent androgens are produced by the adrenal because of the accumulation of the steroid precursors, progesterone and 17-hydroxyprogesterone (17-01HP). Plasma levels of 17-OHP can reach 10-1000 times the normal concentration in these cases. These increases result in the overproduction of androgens, specifically androstenedione, testosterone, and dihydroxytestosterone causing virilization in females. In addition, 21-hydroxylase deficiency in CAH causes insufficient biosynthesis of glucocorticoids and mineralocorticoids, specifically cortisol and aldosterone. Cortisol is a critical negative feedback regulator of hypothalamic CRY secretion and pituitary ACTH release. The lack of glucocorticoid synthesis and release eliminates the restraint on the hypothalamus and pituitary, which causes ACTH levels to increase. The excessive ACTH stimulation causes hypertrophy of the zona *fasciculata* and zona *reticularis* resulting in adrenal hyperplasia.

Definitions

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "about" preceding a value for DSC, TGA, or $T_g$, which are reported as degrees Celsius, have an allowable variability of 5° C. In all other instances, unless otherwise specified, the term "about" preceding a stated value includes the stated value and also includes ±20% of the stated value, and includes more specifically values of ±10%, ±5%, ±2%, and ±1% of the stated value.

To provide a more concise description, some of the quantitative expressions herein are recited as a range from about amount X to about amount Y. It is understood that when a range is recited, the range is not limited to the recited upper and lower bounds, but rather includes the full range from about amount X through about amount Y, or any range therein.

"Room temperature" or "RT" refers to the ambient temperature of a typical laboratory, which is typically around 25° C.

"Spray-drying" refers to the method of producing a dry powder from a solution or slurry. The solution or slurry is atomized or rapidly dried with a hot gas, e.g., air or nitrogen, that causes the solvent to evaporate quickly and uniformly. A "spray-dried dispersion" refers to the powder obtained from the spray-drying process.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various excipients, such as are commonly used in the art, can be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

"Subject," as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, the subject is a human.

In some embodiments, the subject has experienced and/or exhibited at least one symptom of the disease or disorder to be treated and/or prevented. In some embodiments, the subject has been identified or diagnosed as having congenital adrenal hyperplasia (CAH). In some embodiments, the subject is suspected of having CAH. In some embodiments, the subject has a clinical record indicating that the subject has CAH (and optionally the clinical record indicates that the subject should be treated with any of the compositions provided herein). In some embodiments, the subject is a pediatric subject.

The term "pediatric subject" as used herein refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman et al., *Textbook of Pediatrics,* 15th Ed. Philadelphia: W.B. Saunders Company, 1996; Rudolph et al., *Rudolph's Pediatrics,* 21st Ed. New York: McGraw-Hill, 2002; and Avery et al., *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

As used herein, the terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

The term "preventing," as used herein, means the prevention of the onset, recurrence or spread, in whole or in part, of the disease or condition as described herein, or a symptom thereof.

The term "administration" or "administering" refers to a method of giving a dosage of a compound or pharmaceutical formulation to a vertebrate or invertebrate, including a mammal, a bird, a fish, or an amphibian. The preferred method of administration can vary depending on various factors, e.g., the components of the pharmaceutical formulation, the site of the disease, and the severity of the disease.

As used herein, "therapeutically effective amount" is an amount of the compound of Formula (I), or a pharmaceutically acceptable salt thereof, or an amount of a pharmaceutical composition comprising the compound of Formula (I), which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

The term "amorphous" means a solid in a solid state that is a non-crystalline state. Amorphous solids are disordered arrangements of molecules and therefore possess no distinguishable crystal lattice or unit cell and consequently have no definable long range ordering. The solid state form of a solid may be determined by polarized light microscopy, X-ray powder diffraction (XRPD), differential scanning calorimetry (DSC), or other standard techniques known to those of skill in the art.

As used herein, "time of day window" refers to a period of time defined by a window start time and a window stop time. These times all refer to local times where a sample was taken. The phrase "same time of day window" when referring to samples taken from the subject mean, e.g., that a sample taken at 8:15 a.m. and a sample taken at 9:15 a.m. are considered to be taken in the same time of day window of, e.g., 2 a.m. to 10 a.m. or 6 a.m. to 10 a.m.

Methods

The present disclosure relates to methods of treating congenital adrenal hyperplasia (CAH). The methods include administering to a subject a therapeutically effective amount of a compound of Formula (I), or pharmaceutically acceptable salt thereof. In some embodiments, the method includes administering to a subject a therapeutically effective amount of a SDD of the present disclosure that includes a polymer and a compound of Formula (I), or a pharmaceutically acceptable salt thereof. In some embodiments, the method includes administering to a subject a therapeutically effective amount of pharmaceutical composition of the present disclosure that contains a SDD that includes a polymer and a compound of Formula (I), or a pharmaceutically acceptable salt thereof.

Provided herein is a method of treating congenital adrenal hyperplasia (CAH) comprising administering a compound of Formula (I), or a pharmaceutically acceptable salt thereof to normalize or partially normalize levels of biomarkers associated with congenital adrenal hyperplasia. In some embodiments, normalizing or partially normalizing levels of biomarkers comprises reducing levels of elevated biomarkers or increasing levels of depressed biomarkers as compared to subject without CAH.

Provided herein is a method of treating congenital adrenal hyperplasia in a subject in need thereof comprising administering a compound of Formula (I), or a pharmaceutically acceptable salt thereof, in an amount sufficient to reduce the level of one or more biomarkers associated with congenital adrenal hyperplasia. In some embodiments, the biomarkers are selected from (a) 17-hydroxyprogesterone (17-OHP); (b) adrenocorticotropic hormone (ACTH); and (c) androstenedione in the subject.

In some embodiments, the reduction in level of any of the biomarkers (e.g., any of 17-OHP, ACTH, and androstenedione) is determined by comparing the level of the biomarker as measured during the circadian release on a day prior to administering the compound of Formula (I), or a pharmaceutically acceptable salt thereof and the level of the biomarker as measured during the circadian release on the day after administering the compound of Formula (I), or a pharmaceutically acceptable salt thereof. A day prior to administering the compound of Formula (I) applies to a subject that has not previously been administered the compound of Formula (I) within at least the past 24 hours.

In some embodiments, the circadian release of biomarkers associated with CAH occurs between the hours of 2 a.m. and 10 a.m. In other embodiments, the circadian release of biomarkers associated with CAH occurs between the hours of 6 a.m. and 10 a.m.

In some embodiments of any of the methods disclosed herein, the compound of Formula (I), or a pharmaceutically acceptable salt, is administered to the subject at nighttime or administration prior to sleep (i.e., bedtime administration). In some embodiments, the compound of Formula (I), or a pharmaceutically acceptable salt thereof, is administered three to eight hours prior to the circadian release of the biomarker. In some embodiments, the compound of Formula (I), or a pharmaceutically acceptable salt thereof, is administered six to eight hours prior to the circadian release of the biomarker. Administration prior to the circadian release may be adapted for shift workers (e.g., those who work at night and sleep during the day), in which case administration will not necessarily occur at nighttime. Administration is therefore dependent upon the expected circadian release of the biomarker, and can vary depending upon the individual's (i.e., subject, patient) particular work and sleep patterns.

In some embodiments of the methods provided herein, the level of 17-hydroxyprogesterone is reduced by at least 10%, at least 15%, at least 20%, at least 25%, at least 30%, at lease 35%, at least 40%, at least 50%, at least 55% or at least 60% from pre-administration levels. In some embodiments, the level of 17-hydroxyprogesterone is reduced by at least 25%. In some embodiments, the level of 17-hydroxyprogesterone is reduced by at least 50%. In some embodiments of the methods provided herein, the level of 17-hydroxyprogesterone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of 17-hydroxyprogesterone is reduced to a level within the range of 17-hydroxyprogesterone expected for a subject without CAH, i.e., less than 1,000 ng/dL or less than 200 ng/dL.

In some embodiments of the methods provided herein, the level of adrenocorticotropic hormone is reduced by at least 10%, at least 15%, at least 20%, at least 25%, at least 30%, at lease 35%, at least 40%, at least 50%, at least 55% or at least 60% from pre-administration levels. In some embodiments, the level of adrenocorticotropic hormone is reduced by at least 25%. In some embodiments, the level of adrenocorticotropic hormone is reduced by at least 40%. In some embodiments, the level of adrenocorticotropic hormone is reduced by at least 50%.

In some embodiments of the methods provided herein, the level of adrenocorticotropic hormone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of adrenocorticotropic hormone is reduced to a level within the range of adrenocorticotropic hormone expected for a subject without CAH.

In some embodiments of the methods provided herein, the level of androstenedione is reduced by at least 10%, at least 15%, at least 20%, at least 25%, at least 30%, at lease 35%, at least 40%, at least 50%, at least 55% or at least 60% from pre-administration levels. In some embodiments, the level of androstenedione is reduced by at least 25%. In some embodiments, the level of androstenedione is reduced by at least 30%. In some embodiments, the level of androstenedione is reduced by at least 50%.

In some embodiments of the methods provided herein, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of androstenedione is reduced to a level within the range of androstenedione expected for a subject without CAH, i.e., less than 200 ng/dL.

Also provided herein is a method for reducing the severity of one or more symptoms selected from hirsutism, precocious puberty, fertility problems, acne, and growth impairment in a subject having classic congenital adrenal hyperplasia, comprising administering a compound of Formula (I), or a pharmaceutically acceptable salt thereof, in an amount sufficient to reduce one or more biomarker of CAH in a subject, e.g. reduce the androstenedione in the subject. Growth impairment can refer to, e.g., accelerated height velocity, accelerated weight velocity, and/or accelerated bone age.

Provided herein is a method for reducing the level of one or more biomarkers of congenital adrenal hyperplasia in a subject having congenital adrenal hyperplasia comprising administering to the subject a compound of Formula (I), or a pharmaceutically acceptable salt thereof. In some embodiments, the one or more biomarkers of congenital adrenal hyperplasia are selected from (a) 17-hydroxyprogesterone (17-OHP); (b) adrenocorticotropic hormone (ACTH); and (c) androstenedione.

Provided herein is a method for reducing the dosage of corticosteroid administered to a subject having congenital adrenal hyperplasia for controlling congenital adrenal hyperplasia comprising administering to the subject a compound of Formula (I), or a pharmaceutically acceptable salt thereof. In some embodiments, the corticosteroid is a glucocorticoid.

Also provided herein is a method of reducing the severity of one or more side effects of glucocorticoid treatment in a subject having congenital adrenal hyperplasia comprising administering to the subject a compound of Formula (I), or a pharmaceutically acceptable salt thereof. The long-term effects of glucocorticoid treatment are well documented in the art (see, e.g., Oray, M. et al. (2016): Long-term effect of glucocorticoids, *Expert Opinion on Drug Safety*. DOI: 10.1517/14740338.2016.1140743). Such side effects are associated with every biological system, e.g., musculoskeletal (e.g., osteoporosis, avascular necrosis of bone, and myopathy), endocrine and metabolic (e.g., hyperglycemia, diabetes mellitus, dyslipidemia, weight gain, Cushing syndrome, Cushingoid features, growth suppression, adrenal suppression), gastrointestinal (e.g., gastritis, peptic ulcer, gastrointestinal bleeding, visceral perforation, hepatic steatosis, pancreatitis), cardiovascular (e.g., hypertension, coronary heart disease, ischemic heart disease, heart failure), dermatologic (e.g., dermatoprosis, skin atrophy, ecchymosis, purpura, erosions, striae, delayed wound healing, easy bruising, acne, hirsutism, and hair loss), neuropsychiatric (e.g., mood changes, depression, euphoria, mood lability, irritability, akathisia, anxiety, cognitive impairment, psychosis, dementia, and delirium), ophthalmologic (e.g., cataract, glaucoma, ptosis, mydriasis, opportunistic ocular infections, and central serous chorioretinopathy), and immunologic (e.g., suppression of cell-mediated immunity, predisposition to infections, and reactivation of latent infections).

Accordingly, in some embodiments, the side effects of glucocorticoid treatment are selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections, and any combination thereof.

Provided herein is a method of treating congenital adrenal hyperplasia in a subject comprising (i) measuring the level of one or more biomarkers selected from (a) 17-hydroxyprogesterone (17-OUP); (b) adrenocorticotropic hormone (ACTH); and (c) androstenedione in a biological sample obtained from the subject;

(ii) analyzing the level of the one or more biomarkers to determine if the level of the one or more biomarkers is elevated compared to a healthy subject not having congenital adrenal hyperplasia; and (iii) administering to the subject a compound of Formula (I), or a pharmaceutically acceptable salt thereof if the subject is determined to have elevated levels of the one or more biomarkers.

In some embodiments, the method further comprises (iv) measuring the level of the one or more biomarkers after administering a compound of Formula (I), or a pharmaceutically acceptable salt thereof, in a biological sample obtained from the subject to determine whether the subject has reduced levels of the one or more biomarkers as compared with the measurement of step (i). In some embodiments, the method further comprises (v) continuing the administration of the compound of Formula (I), or a pharmaceutically acceptable salt thereof if the subject has reduced levels of the one or more biomarkers.

In some embodiments, steps (i) and (iv) are performed on biological samples taken from the subject in a similar manner and within a same time of day window. In some embodiments, steps (i) and (iv) are performed on biological samples taken from the subject within the time of day window from 2 a.m. to 10 a.m. In some embodiments, steps (i) and (iv) are performed on biological samples taken from the subject within the time of day window from 6 a.m. to 10 a.m.

In some embodiments, steps (i) and (iv) comprise measuring the levels of at least two biomarkers selected from (a) 17-hydroxyprogesterone (17-OHP); (b) adrenocorticotropic hormone (ACTH); and (c) androstenedione.

In some embodiments, steps (i) and (iv) comprise measuring the levels of (a) 17-hydroxyprogesterone (17-OHP); (b) adrenocorticotropic hormone (ACTH); and (c) androstenedione.

In some embodiments, step (i) comprises measuring the level of 17-hydroxyprogesterone (17-OHP), wherein the level of 17-hydroxyprogesterone (17-OHP) is elevated when it is greater than or equal to 1,000 ng/dL.

In some embodiments, step (i) comprises measuring the level of androstenedione, wherein the level of androstenedione is elevated when it is greater than 200 ng/dL.

In some embodiments of the methods of the present disclosure, the compound of Formula (I) is administered at an amount equivalent to from about 25 mg to about 150 mg of the compound of Formula (I) free base. In some embodiments, compound of Formula (I), or a pharmaceutically acceptable salt thereof, is administered at an amount equivalent to about 50 mg or about 100 mg of the compound of Formula (I) free base.

In some embodiments of the methods disclosed herein, compound of Formula (I) is administered in the free base form.

In some embodiments of the methods disclosed herein, the compound of Formula (I) is administered once daily.

Also provided herein is a method of treating CAH in a pediatric subject. The methods include administering to a pediatric subject a therapeutically effective amount of a compound of Formula (I), or pharmaceutically acceptable salt thereof. In some embodiments, the method includes administering to a pediatric subject a therapeutically effective amount of a SDD of the present disclosure that includes a polymer and a compound of Formula (I), or a pharmaceutically acceptable salt thereof. In some embodiments, the method includes administering to a pediatric subject a therapeutically effective amount of pharmaceutical composition of the present disclosure that contains a SDD that includes a polymer and a compound of Formula (I), or a pharmaceutically acceptable salt thereof. In some embodiments, the pediatric subject is a neonate. In some embodiments, the pediatric subject is an infant. In some embodiments, the pediatric subject is a child. In some embodiments, the pediatric subject is an adolescent.

In some embodiments of the methods of the present disclosure, the compound of Formula (I), or a pharmaceutically acceptable salt thereof, is administered to the subject in a fed state. The term "fed state," as used herein, refers to administration of the compound of Formula (I), or a pharmaceutically acceptable salt thereof from about 1 hour before consumption of food or a nutritional composition to about 1 hour after consumption of food or a nutritional composition. The term "fasted state," as used herein, refers to a gap of at least two hours between consumption of food or a nutritional composition and administration of the compound of Formula (I), or a pharmaceutically acceptable salt thereof. In some embodiments, the compound of Formula (I), or a pharmaceutically acceptable salt thereof is administered to the subject with food or a nutritional composition, such as a nutritional supplement or formula, a meal replacement beverage, a liquid dietary supplement, or a high caloric liquid meal. In some embodiments, the compound of Formula (I), or a pharmaceutically acceptable salt thereof is administered to the subject within about 1 hour before the subject has consumed food or a nutritional composition. In some embodiments, the compound of Formula (I), or a pharmaceutically acceptable salt thereof is administered to the subject within about 1 hour after the subject has consumed food or a nutritional composition. Examples of suitable nutritional compositions include, but are not limited to, infant formulas, dietary supplements, dietary substitutes, and rehydration compositions. In some embodiments, the food is a product containing concentrated calories and protein. In some embodiments, the nutritional composition is a composition utilized for enteral and parenteral supplementation for infants, specialty infant formulas, supplements for the elderly, and supplements for those with gastrointestinal difficulties and/or malabsorption. Adult and pediatric nutritional formulas are well known in the art and are commercially available (e.g., the nutritional compositions sold under the trademarks SIMILAC®, ENSURE®, JEVITY® and ALIMENTUM® from Ross Products Division, Abbott Laboratories, Columbus, Ohio).

In some embodiments, the nutritional composition is in liquid form. The energy density of the nutritional compositions, when in liquid form, can range from about 0.6 Kcal to about 3 Kcal per mL. In some embodiments, the nutritional composition is in solid or powdered form. When in solid or powdered form, the nutritional supplements can contain from about 1.2 to more than 9 Kcals per gram, such as about 3 to 7 Kcals per gram.

In some embodiments, the nutritional composition is a meal replacement bar. Examples include the meal replacement bars sold under the trademarks POWERBAR®, GLUCERNA® bars, CHOICE DM® bars, ENSURE® bars, and BOOST® bars. In some embodiments, the nutritional composition is a nutrition shake or meal replacement beverage. Commercially available examples include the nutritional compositions sold under the trademarks ENSURE® branded adult products (such as ENSURE® ORIGINAL, ENSURE® PLUS, ENSURE® ENLIVE, ENSURE® HIGH PROTEIN, ENSURE® CLEAR, AND ENSURE® LIGHT), GLUCERNA®, CHOICE DM®, SLIM FAST®, PEDIASURE®, GLYTROL®, AND RESOURCE®. In some embodiments, the nutritional composition is the nutritional composition sold under the trademark ENSURE® PLUS. In some embodiments, the nutritional composition is vanilla-flavored nutritional composition sold under the trademark ENSURE® PLUS. The nutritional composition sold under the trademark ENSURE PLUS® is a high calorie liquid dietary supplement that contains 1500 calories per liter with a caloric distribution of 14.7% protein, 32% fat and 53.3% carbohydrate.

In some embodiments of the disclosed methods, the compound of Formula (I), or a pharmaceutically acceptable salt thereof is administered to the subject with 8 fluid ounces (237 mL) of the nutritional composition sold under the trademark ENSURE® PLUS. In some embodiments, the nutritional composition sold under the trademark ENSURE® PLUS is vanilla-flavored.

In some embodiments of the methods, the compound of Formula (I), or a pharmaceutically acceptable salt thereof is administered to the subject after administration of the nutritional composition. In some embodiments, the compound of Formula (I), or a pharmaceutically acceptable salt thereof is administered to the subject before administration of the nutritional composition. In some embodiments, the compound of Formula (I), or a pharmaceutically acceptable salt thereof, is administered to the subject at the same time as administration of the nutritional composition.

In some embodiments, the compound of Formula (I), or a pharmaceutically acceptable salt thereof is administered to the subject, followed by administration of the nutritional composition. In some embodiments, the nutritional composition is administered about 1 minute, about 5 minutes, about 10 minutes, about 15 minutes, about 20 minutes, about 25 minutes, about 30 minutes, about 35 minutes, about 40 minutes, about 45 minutes, or about 60 minutes, or within a range defined by any of the preceding values after administration of the compound of Formula (I), or a pharmaceutically acceptable salt thereof. In some embodiments, the nutritional composition is administered 1 minute, 5 minutes, 10 minutes, 15 minutes, 20 minutes, 25 minutes, 30 minutes, 35 minutes, 40 minutes, 45 minutes, or 60 minutes, or within a range defined by any of the preceding values after administration of the compound of Formula (I), or a pharmaceutically acceptable salt thereof. In some embodiments, the nutritional composition is administered within 30 minutes of administering the compound of Formula (I), or a pharmaceutically acceptable salt thereof. In some embodiments of the disclosed methods, the compound of Formula (I), or a pharmaceutically acceptable salt thereof, is administered to the subject with 8 fluid ounces (237 mL) of the nutritional composition sold under the trademark ENSURE® PLUS. In some embodiments, the nutritional composition sold under the trademark ENSURE® PLUS is vanilla-flavored.

In some embodiments, the nutritional composition is administered to the subject, followed by administration of the compound of Formula (I), or a pharmaceutically acceptable salt thereof. In some embodiments, compound of Formula (I), or a pharmaceutically acceptable salt thereof is administered about 1 minute, about 5 minutes, about 10 minutes, about 15 minutes, about 20 minutes, about 25 minutes, about 30 minutes, about 35 minutes, about 40 minutes, about 45 minutes, or about 60 minutes, or within a range defined by any of the preceding values after administration of the nutritional composition. In some embodiments, the compound of Formula (I), or a pharmaceutically acceptable salt thereof, is administered 1 minute, 5 minutes, 10 minutes, 15 minutes, 20 minutes, 25 minutes, 30 minutes, 35 minutes, 40 minutes, 45 minutes, or 60 minutes, or within a range defined by any of the preceding values after administration of the nutritional composition. In some embodiments, the compound of Formula (I), or a pharmaceutically acceptable salt thereof, is administered within 30 minutes of administering the nutritional composition. In some embodiments of the disclosed methods, the compound of Formula (I), or a pharmaceutically acceptable salt thereof, is administered to the subject with 8 fluid ounces (237 mL) of the nutritional composition sold under the trademark ENSURE® PLUS. In some embodiments, the nutritional composition sold under the trademark ENSURE® PLUS is vanilla-flavored.

In some embodiments of the methods, a food effect is observed between administration of the compound of Formula (I), or a pharmaceutically acceptable salt thereof in a fed state versus a fasted state. The term "food effect," as used herein, refers to the relative difference in AUC (area under the curve $AUC_{(0-t)}$ and/or $AUC_{(0-\infty)}$ or $C_{max}$ (maximum plasma concentration or peak plasma concentration) of an active substance, when the compound of Formula (I), or a pharmaceutically acceptable salt thereof, is administered orally to a subject, concomitantly with food or in a fed state as compared to the same values when the same compound of Formula (I), or a pharmaceutically acceptable salt thereof is administered in a fasted state. The food effect (F) is calculated as:

$$F\,\% = \left[(X_{fasted} - X_{fed})/X_{fasted}\right] \times 100$$

where $X_{fed}$ and $X_{fasted}$ are the values of AUC ($AUC_{(0-t)}$ and/or $AUC_{(0-\infty)}$ or $C_{max}$ in the fed and fasted state, respectively. In some embodiments, an increased, or positive, food effect is observed when the compound of Formula (I), or a pharmaceutically acceptable salt thereof is administered to a subject in a fed state. In some embodiments, administration of the compound of Formula (I), or a pharmaceutically acceptable salt thereof, results in an increased, or positive, food effect, whereby an increased $C_{max}$ and/or AUC are observed when administered orally in the fed state as compared to the fasting state.

In some embodiments of the methods, the ratio of the AUC in the fed state to the AUC in the fasted state is about 5 to about 10, such as about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 8 to about 10. In some embodiments, the ratio of the AUC in the fed state to the AUC in the fasted state is about 5, about 6, about 7, about 8, about 9, or about 10, or within a range defined by any of the preceding values. In some embodiments of the methods, the ratio of the AUC in the fed state to the AUC in the fasted state is about 10 to about 20.

In some embodiments of the methods, the ratio of the AUC in the fed state to the AUC in the fasted state is 5 to 10, such as 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, or 8 to 10. In some embodiments, the ratio of the AUC in the fed state to the AUC in the fasted state is 5, 6, 7, 8, 9, or 10, or within a range defined by any of the preceding values.

In some embodiments of the methods, the ratio of the $C_{max}$ in the fed state to the $C_{max}$ in the fasted state is about 5 to about 10, such as about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 8 to about 10. In some embodiments, the ratio of the $C_{max}$ in the fed state to the $C_{max}$ in the fasted state is about 5, about 6, about 7, about 8, about 9, or about 10, or within a range defined by any of the preceding values. In some embodiments, the mean $C_{max}$ of the compound of Formula (I), or pharmaceutically acceptable salt thereof, is about 1.5 to about 3 times higher in the fed stated compared to the fasted state. In some embodiments of the methods, the ratio of the $C_{max}$ in the fed state to the $C_{max}$ in the fasted state is 5 to 10, such as 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, or 8 to 10. In some embodiments, the ratio of the $C_{max}$ in the fed state to the $C_{max}$ in the fasted state is 5, 6, 7, 8, 9, or 10, or within a range defined by any of the preceding values. In some embodiments, the mean $C_{max}$ of the compound of Formula (I), or pharmaceutically acceptable salt thereof, is 1.5 to 3 times higher in the fed stated compared to the fasted state. In some embodiments, the mean $C_{max}$ of the compound of Formula (I), or pharmaceutically acceptable salt thereof, is about 2 times higher in the fed stated compared to the fasted state. In some embodiments of the methods, the ratio of the $C_{max}$ in the fed state to the $C_{max}$ in the fasted state is about 10 to about 20.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered to the subject with a meal. In some embodiments, the meal is a high fat, high caloric meal. In some embodiments, the meal is a low fat, low caloric meal. In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, is administered within approximately 5 minutes after the start of the meal. In some embodiments, the meal is an evening meal. In some embodiments, the meal is a morning meal.

In some embodiments, the fed state is with a high fat meal. In some embodiments, the fed state is with a low fat meal. The FDA has provided draft guidelines regarding high fat and low fat meals ("Assessing the Effects of Food on Drugs in INDs and NDAs—Clinical Pharmacology Considerations Guidance for Industry," U.S. Department of Health and Human Services, Food and Drug Administration, Center for Drug Evaluation and Research (CDER), February 2019, Clinical Pharmacology). Table 1 shows test meal definitions provided by the FDA guidance.

TABLE 1

| | | Fat | | |
|---|---|---|---|---|
| Meal Type | Total Kcal | Kcal | Grams | Percent |
| High-Fat | 800-1000 | 500-600 | 55-65 | 50 |
| Low-Fat | 400-500 | 100-125 | 11-14 | 25 |

The composition of a high fat meal provided by the FDA guidance is depicted in Table 2.

TABLE 2

| Composition of a High Fat Meal* | |
|---|---|
| Total Calories | 800-1000 |
| Calories from Protein | 150 |
| Calories from Carbohydrates | 250 |
| Calories from Fat | 500-600 |
| An Example of a High Fat Breakfast | Two eggs fried in butter<br>Two strips of bacon<br>Two slices of toast with butter<br>Four ounces of hash brown potatoes<br>Eight ounces of whole milk |

*50 percent of calories are derived from fat. Substitutions can be made to this meal, if the content, volume, and viscosity are maintained.

The composition of a low fat meal provided by the FDA guidance is depicted in Table 3.

TABLE 3

| Composition of a Low Fat Meal | |
|---|---|
| Total Calories | 400-500 |
| Fat (g) | 250 |
| Percent Calories from Fat | 25 |
| An Example of a Low Fat Breakfast* | Eight ounces milk (1 percent fat)<br>One boiled egg<br>One packet flavored instant oatmeal made with water |

*This low-fat breakfast contains 387 calories and has 10 grams of fat.

In some embodiments, a high fat meal contains 800-1000 total Kcal and 500-600 fat Kcal. In some embodiments, a low fat meal contains 400-500 total Kcal and 100-125 fat Kcal.

Also provided herein is a method of improving gastrointestinal absorption of a compound of Formula (I), or pharmaceutically acceptable salt thereof, in a subject. The method includes orally administering to the subject a pharmaceutical composition of the present disclosure, wherein the improvement is relative to oral administration of the compound of Formula (I), or pharmaceutically acceptable salt thereof, which has not been prepared as a spray-dried dispersion. In some embodiments, the subject is a pediatric subject.

Also provided herein is a method of improving oral bioavailability of a compound of Formula (I), or pharmaceutically acceptable salt thereof, in a subject. The method includes orally administering to the subject a pharmaceutical composition of the present disclosure, wherein the improvement is relative to oral administration of the compound of Formula (I), or pharmaceutically acceptable salt thereof, which has not been prepared as a spray-dried dispersion.

In some embodiments of the methods provided herein, the subject is a pediatric subject.

Also provided herein is a method of treating congenital adrenal hyperplasia (CAH), in a subject in need thereof, comprising administering to the subject a pharmaceutical composition of the present disclosure, wherein the pharmaceutical composition comprises a therapeutically effective amount of the compound of Formula (I), or a pharmaceutically acceptable salt thereof. In some embodiments, the pharmaceutical composition is a lipidic semi-solid formulation. In some embodiments, the pharmaceutical composition is a liquid formulation. In some embodiments, the pharmaceutical composition is administered to the subject in a fed state.

Also provided herein is a pharmaceutical composition of the present disclosure for use in a method of treating congenital adrenal hyperplasia (CAH) in a subject. In some embodiments, the subject is in a fed state.

In some embodiments, the pharmaceutical composition is administered to the subject with a nutritional composition. In some embodiments, the nutritional composition is a liquid dietary supplement comprising about 1000 to about 2000 calories per liter with a fat content greater than about 30%. In some embodiments, the nutritional composition is a liquid dietary supplement comprising 1500 calories per liter with a caloric distribution of 14.7% protein, 32% fat and 53.3% carbohydrate. In some embodiments, the nutritional composition is administered in an amount of about 6 to about 12 fluid ounces. In some embodiments, the nutritional composition is administered in an amount of about 8 fluid ounces. In some embodiments, the nutritional composition is administered within 30 minutes of administration of the pharmaceutical composition.

In some embodiments, the pharmaceutical composition exhibits a positive food effect. In some embodiments, the positive food effect is measured in terms of $C_{max}$, AUC, or a combination thereof of a compound of Formula (I) when comparing oral administration of the pharmaceutical composition in the fed and fasting states. In some embodiments, the ratio of the AUC of the compound of Formula (I) in the fed state to the AUC of the compound of Formula (I) in the fasted state is about 5 to about 10. In some embodiments, the ratio of the $C_{max}$ of the compound of Formula (I) in the fed state to the $C_{max}$ of the compound of Formula (I) in the fasted state is about 5 to about 10. In some embodiments, the ratio of the AUC of the compound of Formula (I) in the fed state to the AUC of the compound of Formula (I) in the fasted state is about 10 to about 20. In some embodiments, the ratio of the $C_{max}$ of the compound of Formula (I) in the fed state to the $C_{max}$ of the compound of Formula (I) in the fasted state is about 10 to about 20. In some embodiments, the ratio of the AUC of the compound of Formula (I) in the fed state to the AUC of the compound of Formula (I) in the fasted state is about 1 to about 4 or about 5 to about 10. In some embodiments, the ratio of the $C_{max}$ of the compound of Formula (I) in the fed state to the $C_{max}$ of the compound of Formula (I) in the fasted state is about 1 to about 4 or about 5 to about 10. In some embodiments, the ratio of the AUC of the compound of Formula (I) in the fed state to the AUC of the compound of Formula (I) in the fasted state is about 1 to about 4. In some embodiments, the ratio of the $C_{max}$ of the compound of Formula (I) in the fed state to the $C_{max}$ of the compound of Formula (I) in the fasted state is about 1 to about 4. In some embodiments, the ratio of the AUC of the compound of Formula (I) in the fed state to the AUC of the compound of Formula (I) in the fasted state is about 1.5 to about 3. In some embodiments, the ratio of the $C_{max}$ of the compound of Formula (I) in the fed state to the $C_{max}$ of the compound of Formula (I) in the fasted state is about 1.5 to about 3. In some embodiments, the ratio of the AUC of the compound of Formula (I) in the fed state to the AUC of the compound of Formula (I) in the fasted state is 1 to 4 or 5 to 10. In some embodiments, the ratio of the $C_{max}$ of the compound of Formula (I) in the fed state to the $C_{max}$ of the compound of Formula (I) in the fasted state is 1 to 4 or 5 to 10. In some embodiments, the ratio of the AUC of the compound of Formula (I) in the fed state to the AUC of the compound of Formula (I) in the fasted state is 1 to 4. In some embodiments, the ratio of the $C_{max}$ of the compound of Formula (I) in the fed state to the $C_{max}$ of the compound of Formula (I) in the fasted state is 1 to 4. In some embodiments, the ratio of the AUC of the compound of Formula (I) in the fed state to the AUC of the compound of Formula (I) in the fasted state is 1.5 to 3. In some embodiments, the ratio of the $C_{max}$ of the compound of Formula (I) in the fed state to the $C_{max}$ of the compound of Formula (I) in the fasted state is 1.5 to 3.

In some embodiments, the subject is a pediatric subject.

In some embodiments, the pharmaceutical composition is formulated for oral administration and exhibits a positive food effect when administered orally. In some embodiments, the compound of Formula (I) has a ratio of the AUC in the fed state to the AUC in the fasted state of about 5 to about 10. In some embodiments, the compound of Formula (I) has a ratio of the $C_{max}$ in the fed state to the $C_{max}$ in the fasted state of about 5 to about 10. In some embodiments, the compound of Formula (I) has a ratio of the AUC in the fed state to the AUC in the fasted state of about 10 to about 20. In some embodiments, the compound of Formula (I) has a ratio of the $C_{max}$ in the fed state to the $C_{max}$ in the fasted state of about 10 to about 20. In some embodiments, the compound of Formula (I) has a ratio of the AUC in the fed state to the AUC in the fasted state of about 1 to about 4 or about 5 to about 10. In some embodiments, the compound of Formula (I) has a ratio of the $C_{max}$ in the fed state to the $C_{max}$ in the fasted state of about 1 to about 4 or about 5 to about 10. In some embodiments, the compound of Formula (I) has a ratio of the AUC in the fed state to the AUC in the fasted state of about 1 to about 4. In some embodiments, the compound of Formula (I) has a ratio of the $C_{max}$ in the fed state to the $C_{max}$ in the fasted state of about 1 to about 4. In some embodiments, the compound of Formula (I) has a ratio of the AUC in the fed state to the AUC in the fasted state of about 1.5 to about 3. In some embodiments, the compound of Formula (I) has a ratio of the $C_{max}$ in the fed state to the $C_{max}$ in the fasted state of about 1.5 to about 3. In some embodiments, the compound of Formula (I) has a ratio of the AUC in the fed state to the AUC in the fasted state of 1 to 4 or 5 to 10. In some embodiments, the compound of Formula (I) has a ratio of the $C_{max}$ in the fed state to the $C_{max}$ in the fasted state of 1 to 4 or 5 to 10. In some embodiments, the compound of Formula (I) has a ratio of the AUC in the fed state to the AUC in the fasted state of 1 to 4. In some embodiments, the compound of Formula (I) has a ratio of the $C_{max}$ in the fed state to the $C_{max}$ in the fasted state of 1 to 4. In some embodiments, the compound of Formula (I) has a ratio of the AUC in the fed state to the AUC in the fasted state of 1.5 to 3. In some embodiments, the compound of Formula (I) has a ratio of the $C_{max}$ in the fed state to the $C_{max}$ in the fasted state of 1.5 to 3.

In some embodiments, the pharmaceutical composition is administered to the subject with a meal. In some embodiments, the meal is a high fat meal. In some embodiments, the meal is a low fat meal. In some embodiments, the pharmaceutical composition is administered within about 5 minutes after the start of the meal. In some embodiments, the meal is an evening meal. In some embodiments, the meal is a morning meal.

In some embodiments, administering the pharmaceutical composition exhibits a positive food effect. In some embodiments, the positive food effect is measured in terms of $C_{max}$, AUC, or combinations thereof of the compound of Formula (I) when comparing oral administration of the pharmaceutical composition in the fed and fasting states. In some embodiments, the ratio of the AUC of the compound of Formula (I) in the fed state to the AUC of the compound of Formula (I) in the fasted state is about 5 to about 10. In some embodiments, the ratio of the $C_{max}$ of the compound of Formula (I) in the fed state to the $C_{max}$ of the compound of Formula (I) in the fasted state is about 5 to about 10. In some embodiments, the ratio of the AUC of the compound of Formula (I) in the fed state to the AUC of the compound of Formula (I) in the fasted state is about 10 to about 20. In some embodiments, the ratio of the $C_{max}$ of the compound of Formula (I) in the fed state to the $C_{max}$ of the compound of Formula (I) in the fasted state is about 10 to about 20. In some embodiments, the ratio of the AUC of the compound of Formula (I) in the fed state to the AUC of the compound of Formula (I) in the fasted state is about 1 to about 4 or about 5 to about 10. In some embodiments, the ratio of the $C_{max}$ of the compound of Formula (I) in the fed state to the $C_{max}$ of the compound of Formula (I) in the fasted state is about 1 to about 4 or about 5 to about 10. In some embodiments, the ratio of the AUC of the compound of Formula (I) in the fed state to the AUC of the compound of Formula (I) in the fasted state is about 1 to about 4. In some embodiments, the ratio of the $C_{max}$ of the compound of Formula (I) in the fed state to the $C_{max}$ of the compound of Formula (I) in the fasted state is about 1 to about 4. In some embodiments, the ratio of the AUC of the compound of Formula (I) in the fed state to the AUC of the compound of Formula (I) in the fasted state is about 1.5 to about 3. In some embodiments, the ratio of the $C_{max}$ of the compound of Formula (I) in the fed state to the $C_{max}$ of the compound of Formula (I) in the fasted state is about 1.5 to about 3. In some embodiments, the ratio of the AUC of the compound of Formula (I) in the fed state to the AUC of the compound of Formula (I) in the fasted state is 1 to 4 or 5 to 10. In some embodiments, the ratio of the $C_{max}$ of the compound of Formula (I) in the fed state to the $C_{max}$ of the compound of Formula (I) in the fasted state is 1 to 4 or 5 to 10. In some embodiments, the ratio of the AUC of the compound of Formula (I) in the fed state to the AUC of the compound of Formula (I) in the fasted state is 1 to 4. In some embodiments, the ratio of the $C_{max}$ of the compound of Formula (I) in the fed state to the $C_{max}$ of the compound of Formula (I) in the fasted state is 1 to 4. In some embodiments, the ratio of the AUC of the compound of Formula (I) in the fed state to the AUC of the compound of Formula (I) in the fasted state is 1.5 to 3. In some embodiments, the ratio of the $C_{max}$ of the compound of Formula (I) in the fed state to the $C_{max}$ of the compound of Formula (I) in the fasted state is 1.5 to 3.

For the avoidance of doubt, also provided herein is the corresponding compound of Formula (I), or a pharmaceutically acceptable salt thereof, or corresponding pharmaceutical composition comprising a compound of Formula (I), or a pharmaceutically acceptable salt thereof, for use in the corresponding methods, as described herein.

For the avoidance of doubt, also provided herein is use of the corresponding compound of Formula (I), or a pharmaceutically acceptable salt thereof, in the manufacture of a medicament for use in the corresponding methods, as described herein.

For the avoidance of doubt, also provided herein is use of the corresponding pharmaceutical composition comprising a compound of Formula (I), or a pharmaceutically acceptable salt thereof, in the manufacture of a medicament for use in the corresponding methods, as described herein.

Reduction in Glucocorticoid Burden, Adrenal Androgens and Precursors

Glucocorticoids are a class of corticosteroids, which are a class of steroid hormones. Glucocorticoids are corticosteroids that bind to the glucocorticoid receptor that is present in almost every vertebrate animal cell. In some embodiments, the subject is concurrently receiving a dose of a glucocorticoid. In some embodiments, the glucocorticoid is selected from cortisol (hydrocortisone), cortisone, prednisone, prednisolone, methylprednisolone, dexamethasone, betamethasone, triamcinolone, fludrocortisone acetate, and deoxycorticosterone acetate. In some embodiments, the glucocorticoid is cortisol (hydrocortisone). In some embodiments, the glucocorticoid is cortisone. In some embodiments, the glucocorticoid is prednisone. In some embodiments, the glucocorticoid is dexamethasone.

In some embodiments, the glucocorticoid dose is measured in hydrocortisone equivalents. In some embodiments, the glucocorticoid dose is measured as a multiple of the upper limit of normal of physiologic dosing in hydrocortisone equivalents. Any glucocorticoid can be given in a dose that provides approximately the same glucocorticoid effects as normal cortisol production; this is referred to as physiologic, replacement, or maintenance dosing.

In some embodiments, the glucocorticoid dose is a physiologic dose as measured after a time period of administration of the compound of Formula (I), or a pharmaceutically acceptable salt thereof. In some embodiments, the glucocorticoid dose is a physiologic dose of about 4 to about 12 $mg/m^2$/day as measured after a time period of administration of the compound of Formula (I), or a pharmaceutically acceptable salt thereof. In some embodiments, the glucocorticoid dose is a physiologic dose of about 4 to about 9 $mg/m^2$/day as measured after a time period of administration of the compound of Formula (I), or a pharmaceutically acceptable salt thereof. In some embodiments, the glucocorticoid dose is a physiologic dose that is less than about 8 $mg/m^2$/day as measured after a time period of administration of the compound of Formula (I), or a pharmaceutically acceptable salt thereof.

In some embodiments, the glucocorticoid dose is a physiologic dose as measured after a time period of administration of the pharmaceutical composition comprising the compound of Formula (I), or a pharmaceutically acceptable salt thereof. In some embodiments, the glucocorticoid dose is a physiologic dose of about 4 to about 12 $mg/m^2$/day as measured after a time period of administration of the pharmaceutical composition comprising the compound of Formula (I), or a pharmaceutically acceptable salt thereof. In some embodiments, the glucocorticoid dose is a physiologic dose of about 4 to about 9 $mg/m^2$/day as measured after a time period of administration of the pharmaceutical composition comprising the compound of Formula (I), or a pharmaceutically acceptable salt thereof. In some embodiments, the glucocorticoid dose is a physiologic dose that is less than about 8 $mg/m^2$/day as measured after a time period of administration of the pharmaceutical composition comprising the compound of Formula (I), or a pharmaceutically acceptable salt thereof.

In some embodiments, the glucocorticoid dose concurrently given to the subject is a normal physiological dose of hydrocortisone equivalents. In some embodiments, the glucocorticoid dose concurrently given to the subject is determined after a time period of administration of the compound of Formula (I), or a pharmaceutically acceptable salt thereof. In some embodiments, the glucocorticoid dose concurrently given to the subject is determined after a time period of administration of the pharmaceutical composition comprising the compound of Formula (I), or a pharmaceutically acceptable salt thereof. In some embodiments, a normal physiological dose of hydrocortisone equivalents is about 2 to about 16 $mg/m^2$/day. In some embodiments, a normal physiological dose of hydrocortisone equivalents is about 4 to about 12 $mg/m^2$/day. In some embodiments, a normal physiological dose of hydrocortisone equivalents is about 5 to about 11 $mg/m^2$/day. In some embodiments, a normal physiological dose of hydrocortisone equivalents is about 6 to about 10 $mg/m^2$/day. In some embodiments, a normal physiological dose of hydrocortisone equivalents is about 7 to about 9 $mg/m^2$/day. In some embodiments, a normal physiological dose of hydrocortisone equivalents is about 4 to about 9 $mg/m^2$/day. In some embodiments, a normal physiological dose of hydrocortisone equivalents is about 8 $mg/m^2$/day. In some embodiments, a normal physiological dose of hydrocortisone equivalents is about 12 $mg/m^2$/day. In some embodiments, a normal physiological dose of hydrocortisone equivalents is less than about 8 $mg/m^2$/day. In some embodiments, a normal physiological dose of hydrocortisone equivalents is about 2, about 3, about 4, about 5, about 6, about 7, about 8, about 9, about 10, about 11, about 12, about 13, about 14, about 15 or about 16 $mg/m^2$/day, or within a range defined by any of the preceding values.

In some embodiments, the glucocorticoid dose concurrently given to the subject is at the upper limit of normal of a normal physiological dose of hydrocortisone equivalents. In some embodiments, the glucocorticoid dose concurrently given to the subject is determined after a time period of administration of the compound of Formula (I), or a pharmaceutically acceptable salt thereof. In some embodiments, the glucocorticoid dose concurrently given to the subject is determined after a time period of administration of the pharmaceutical composition comprising the compound of Formula (I), or a pharmaceutically acceptable salt thereof. In some embodiments, the upper limit of normal is 1.5 times the normal physiological dose. In some embodiments, the upper limit of normal is about 1.5 times the normal physiological dose. In some embodiments, the upper limit of normal is about 2 times the normal physiological dose. In some embodiments, the upper limit of normal is about 2.5 times the normal physiological dose. In some embodiments, the upper limit of normal is about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 times the normal physiological dose, or within a range defined by any of the preceding values.

In some embodiments, the glucocorticoid dose of the subject is reduced by about 10% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 20% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 30% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 40% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 50% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 60% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 70% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by less than about 20% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by about 20% to about 50% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof. In some embodiments, the glucocorticoid dose of the subject is reduced by greater than about 50% after a time period of administration of the compound of Formula (I), or a pharmaceutically acceptable salt thereof, wherein the reduction of the glucocorticoid dose is relative to the glucocorticoid dose prior to administration of the compound of Formula (I), or a pharmaceutically acceptable salt thereof.

In some embodiments, the glucocorticoid dose of the subject is reduced by about 10% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 20% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 30% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 40% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 50% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 60% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 70% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by less than about 20% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by about 20% to about 50% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof. In some embodiments, the glucocorticoid dose of the subject is reduced by greater than about 50% after a time period of administration of the pharmaceutical composition comprising the compound of Formula (I), or a pharmaceutically acceptable salt thereof, wherein the reduction of the glucocorticoid dose is relative to the glucocorticoid dose prior to administration of the pharmaceutical composition comprising the compound of Formula (I), or a pharmaceutically acceptable salt thereof.

In some embodiments, the glucocorticoid dose of the subject is reduced within a range defined by any of the preceding values.

In some embodiments, the level of 17-hydroxyprogesterone is reduced by at least 25% after a time period of administration of the compound of Formula (I), or a pharmaceutically acceptable salt thereof, wherein the reduction of the level of 17-hydroxyprogesterone is relative to the level of 17-hydroxyprogesterone prior to administration of the compound of Formula (I), or a pharmaceutically acceptable salt thereof. In some embodiments, the level of 17-hydroxyprogesterone is reduced by at least 50% after a time period of administration of the compound of Formula (I), or a pharmaceutically acceptable salt thereof, wherein the reduction of the level of 17-hydroxyprogesterone is relative to the level of 17-hydroxyprogesterone prior to administration of the compound of Formula (I), or a pharmaceutically acceptable salt thereof. In some embodiments, the level of 17-hydroxyprogesterone is less than 1.5 times the upper limit of normal after a time period of administration of the compound of Formula (I), or a pharmaceutically acceptable salt thereof. In some embodiments, the level of 17-hydroxyprogesterone is within normal limits after a time period of administration of the compound of Formula (I), or a pharmaceutically acceptable salt thereof.

In some embodiments, the level of 17-hydroxyprogesterone is reduced by at least about 25% after a time period of administration of the pharmaceutical composition comprising the compound of Formula (I), or a pharmaceutically acceptable salt thereof, wherein the reduction of the level of 17-hydroxyprogesterone is relative to the level of 17-hydroxyprogesterone prior to administration of the pharmaceutical composition comprising the compound of Formula (I), or a pharmaceutically acceptable salt thereof. In some embodiments, the level of 17-hydroxyprogesterone is reduced by at least about 50% after a time period of administration of the pharmaceutical composition comprising the compound of Formula (I), or a pharmaceutically acceptable salt thereof, wherein the reduction of the level of 17-hydroxyprogesterone is relative to the level of 17-hydroxyprogesterone prior to administration of the pharmaceutical composition comprising the compound of Formula (I), or a pharmaceutically acceptable salt thereof. In some embodiments, the level of 17-hydroxyprogesterone is less than about 1.5 times the upper limit of normal after a time period of administration of the pharmaceutical composition comprising the compound of Formula (I), or a pharmaceutically acceptable salt thereof. In some embodiments, the level of 17-hydroxyprogesterone is within normal limits after a time period of administration of the pharmaceutical composition comprising the compound of Formula (I), or a pharmaceutically acceptable salt thereof.

In some embodiments, the level of 17-hydroxyprogesterone of the subject is reduced within a range defined by any of the preceding values.

In some embodiments, the level of adrenocorticotropic hormone is reduced by at least 25% after a time period of administration of the compound of Formula (I), or a pharmaceutically acceptable salt thereof, wherein the reduction of the level of adrenocorticotropic hormone is relative to the level of adrenocorticotropic hormone prior to administration of the compound of Formula (I), or a pharmaceutically acceptable salt thereof. In some embodiments, the level of adrenocorticotropic hormone is reduced by at least 40% after a time period of administration of the compound of Formula (I), or a pharmaceutically acceptable salt thereof, wherein the reduction of the level of adrenocorticotropic hormone is relative to the level of adrenocorticotropic hormone prior to administration of the compound of Formula (I), or a pharmaceutically acceptable salt thereof. In some embodiments, the level of adrenocorticotropic hormone is reduced by at least 50% after a time period of administration of the compound of Formula (I), or a pharmaceutically acceptable salt thereof, wherein the reduction of the level of adrenocorticotropic hormone is relative to the level of adrenocorticotropic hormone prior to administration of the compound of Formula (I), or a pharmaceutically acceptable salt thereof. In some embodiments, the level of adrenocorticotropic hormone is less than 1.5 times the upper limit of normal after a time period of administration of the compound of Formula (I), or a pharmaceutically acceptable salt thereof. In some embodiments, the level of adrenocorticotropic hormone is within normal limits after a time period of administration of the compound of Formula (I), or a pharmaceutically acceptable salt thereof.

In some embodiments, the level of adrenocorticotropic hormone is reduced by at least about 25% after a time period of administration of the pharmaceutical composition comprising the compound of Formula (I), or a pharmaceutically acceptable salt thereof, wherein the reduction of the level of adrenocorticotropic hormone is relative to the level of adrenocorticotropic hormone prior to administration of the pharmaceutical composition comprising the compound of Formula (I), or a pharmaceutically acceptable salt thereof. In some embodiments, the level of adrenocorticotropic hormone is reduced by at least about 40% after a time period of administration of the pharmaceutical composition comprising the compound of Formula (I), or a pharmaceutically acceptable salt thereof, wherein the reduction of the level of adrenocorticotropic hormone is relative to the level of adrenocorticotropic hormone prior to administration of the pharmaceutical composition comprising the compound of Formula (I), or a pharmaceutically acceptable salt thereof. In some embodiments, the level of adrenocorticotropic hormone is reduced by at least about 50% after a time period of administration of the pharmaceutical composition comprising the compound of Formula (I), or a pharmaceutically acceptable salt thereof, wherein the reduction of the level of adrenocorticotropic hormone is relative to the level of adrenocorticotropic hormone prior to administration of the pharmaceutical composition comprising the compound of Formula (I), or a pharmaceutically acceptable salt thereof. In some embodiments, the level of adrenocorticotropic hormone is less than about 1.5 times the upper limit of normal after a time period of administration of the pharmaceutical composition comprising the compound of Formula (I), or a pharmaceutically acceptable salt thereof. In some embodiments, the level of adrenocorticotropic hormone is within normal limits after a time period of administration of the pharmaceutical composition comprising the compound of Formula (I), or a pharmaceutically acceptable salt thereof.

In some embodiments, the level of adrenocorticotropic hormone of the subject is reduced within a range defined by any of the preceding values.

In some embodiments, the level of androstenedione is reduced by at least 25% after a time period of administration of the compound of Formula (I), or a pharmaceutically acceptable salt thereof, wherein the reduction of the level of androstenedione is relative to the level of androstenedione prior to administration of the compound of Formula (I), or a pharmaceutically acceptable salt thereof. In some embodiments, the level of androstenedione is reduced by at least 30% after a time period of administration of the compound of Formula (I), or a pharmaceutically acceptable salt thereof, wherein the reduction of the level of androstenedione is relative to the level of androstenedione prior to administration of the compound of Formula (I), or a pharmaceutically acceptable salt thereof. In some embodiments, the level of androstenedione is reduced by at least 50% after a time period of administration of the compound of Formula (I), or a pharmaceutically acceptable salt thereof, wherein the reduction of the level of androstenedione is relative to the level of androstenedione prior to administration of the compound of Formula (I), or a pharmaceutically acceptable salt thereof. In some embodiments, the level of androstenedione is less than 1.5 times the upper limit of normal after a time period of administration of the compound of Formula (I), or a pharmaceutically acceptable salt thereof. In some embodiments, the level of androstenedione is within normal limits after a time period of administration of the compound of Formula (I), or a pharmaceutically acceptable salt thereof.

In some embodiments, the level of androstenedione is reduced by at least about 25% after a time period of administration of the pharmaceutical composition comprising the compound of Formula (I), or a pharmaceutically acceptable salt thereof, wherein the reduction of the level of androstenedione is relative to the level of androstenedione prior to administration of the pharmaceutical composition comprising the compound of Formula (I), or a pharmaceutically acceptable salt thereof. In some embodiments, the level of androstenedione is reduced by at least about 30% after a time period of administration of the pharmaceutical composition comprising the compound of Formula (I), or a pharmaceutically acceptable salt thereof, wherein the reduction of the level of androstenedione is relative to the level of androstenedione prior to administration of the pharmaceutical composition comprising the compound of Formula (I), or a pharmaceutically acceptable salt thereof. In some embodiments, the level of androstenedione is reduced by at least about 50% after a time period of administration of the pharmaceutical composition comprising the compound of Formula (I), or a pharmaceutically acceptable salt thereof, wherein the reduction of the level of androstenedione is relative to the level of androstenedione prior to administration of the pharmaceutical composition comprising the compound of Formula (I), or a pharmaceutically acceptable salt thereof. In some embodiments, the level of androstenedione is less than about 1.5 times the upper limit of normal after a time period of administration of the pharmaceutical composition comprising the compound of Formula (I), or a pharmaceutically acceptable salt thereof. In some embodiments, the level of androstenedione is within normal limits after a time period of administration of the pharmaceutical composition comprising the compound of Formula (I), or a pharmaceutically acceptable salt thereof.

In some embodiments, the level of androstenedione of the subject is reduced within a range defined by any of the preceding values.

In some embodiments, the level of testosterone is reduced by at least 25% after a time period of administration of the compound of Formula (I), or a pharmaceutically acceptable salt thereof, wherein the reduction of the level of testosterone is relative to the level of testosterone prior to administration of the compound of Formula (I), or a pharmaceutically acceptable salt thereof. In some embodiments, the level of testosterone is reduced by at least 30% after a time period of administration of the compound of Formula (I), or a pharmaceutically acceptable salt thereof, wherein the reduction of the level of testosterone is relative to the level of testosterone prior to administration of the compound of Formula (I), or a pharmaceutically acceptable salt thereof. In some embodiments, the level of testosterone is reduced by at least 50% after a time period of administration of the compound of Formula (I), or a pharmaceutically acceptable salt thereof, wherein the reduction of the level of testosterone is relative to the level of testosterone prior to administration of the compound of Formula (I), or a pharmaceutically acceptable salt thereof. In some embodiments, the level of testosterone is less than 1.5 times the upper limit of normal after a time period of administration of the compound of Formula (I), or a pharmaceutically acceptable salt thereof. In some embodiments, the level of testosterone is within normal limits after a time period of administration of the compound of Formula (I), or a pharmaceutically acceptable salt thereof.

In some embodiments, the level of testosterone is reduced by at least about 25% after a time period of administration of the pharmaceutical composition comprising the compound of Formula (I), or a pharmaceutically acceptable salt thereof, wherein the reduction of the level of testosterone is relative to the level of testosterone prior to administration of the pharmaceutical composition comprising the compound of Formula (I), or a pharmaceutically acceptable salt thereof. In some embodiments, the level of testosterone is reduced by at least about 30% after a time period of administration of the pharmaceutical composition comprising the compound of Formula (I), or a pharmaceutically acceptable salt thereof, wherein the reduction of the level of testosterone is relative to the level of testosterone prior to administration of the pharmaceutical composition comprising the compound of Formula (I), or a pharmaceutically acceptable salt thereof. In some embodiments, the level of testosterone is reduced by at least about 50% after a time period of administration of the pharmaceutical composition comprising the compound of Formula (I), or a pharmaceutically acceptable salt thereof, wherein the reduction of the level of testosterone is relative to the level of testosterone prior to administration of the pharmaceutical composition comprising the compound of Formula (I), or a pharmaceutically acceptable salt thereof. In some embodiments, the level of testosterone is less than about 1.5 times the upper limit of normal after a time period of administration of the pharmaceutical composition comprising the compound of Formula (I), or a pharmaceutically acceptable salt thereof. In some embodiments, the level of testosterone is within normal limits after a time period of administration of the pharmaceutical composition comprising the compound of Formula (I), or a pharmaceutically acceptable salt thereof.

In some embodiments, the level of testosterone of the subject is reduced within a range defined by any of the preceding values.

In some embodiments, the level of 17-hydroxyprogesterone is reduced by at least 50% and the level of androstenedione is reduced by at least 50% after a time period of administration of the compound of Formula (I), or a pharmaceutically acceptable salt thereof, wherein the reduction of the level of 17-hydroxyprogesterone and the level of androstenedione is relative to the level of 17-hydroxyprogesterone and the level of androstenedione prior to administration of the compound of Formula (I), or a pharmaceutically acceptable salt thereof. In some embodiments, the level of 17-hydroxyprogesterone is less than 1.5 times the upper limit of normal and the level of androstenedione is less than 1.5 times the upper limit of normal after a time period of administration of the compound of Formula (I), or a pharmaceutically acceptable salt thereof. In some embodiments, the level of 17-hydroxyprogesterone is within normal limits and the level of androstenedione is within normal limits after a time period of administration of the compound of Formula (I), or a pharmaceutically acceptable salt thereof.

In some embodiments, the level of 17-hydroxyprogesterone is reduced by at least about 50% and the level of androstenedione is reduced by at least about 50% after a time period of administration of the pharmaceutical composition comprising the compound of Formula (I), or a pharmaceutically acceptable salt thereof, wherein the reduction of the level of 17-hydroxyprogesterone and the level of androstenedione is relative to the level of 17-hydroxyprogesterone and the level of androstenedione prior to administration of the pharmaceutical composition comprising the compound of Formula (I), or a pharmaceutically acceptable salt thereof. In some embodiments, the level of 17-hydroxyprogesterone is less than about 1.5 times the upper limit of normal and the level of androstenedione is less than about 1.5 times the upper limit of normal after a time period of administration of the pharmaceutical composition comprising the compound of Formula (I), or a pharmaceutically acceptable salt thereof. In some embodiments, the level of 17-hydroxyprogesterone is within normal limits and the level of androstenedione is within normal limits after a time period of administration of the pharmaceutical composition comprising the compound of Formula (I), or a pharmaceutically acceptable salt thereof.

In some embodiments, the level of 17-hydroxyprogesterone and androstenedione of the subject is reduced within a range defined by any of the preceding values.

In some embodiments, the subject exhibits a decrease in glucocorticoid burden after a time period of administration of the compound of Formula (I), or a pharmaceutically acceptable salt thereof, wherein the decrease in glucocorticoid burden is relative to the glucocorticoid burden prior to administration of the compound of Formula (I), or a pharmaceutically acceptable salt thereof. In some embodiments, one or more symptoms selected from quality of life, fatigue, sleep, insulin resistance, glucose tolerance, glucose control, dyslipidemia, hyperlipidemia, bone mineral density, bone turnover, fat mass, weight, central obesity, blood pressure, hirsutism severity, menstrual cyclicity, control of testicular adrenal rest tumor and fertility, is improved after a time period of administration of the compound of Formula (I), or a pharmaceutically acceptable salt thereof, wherein the improvement in the one or more symptoms is relative to the status of the one or more symptoms prior to administration of the compound of Formula (I), or a pharmaceutically acceptable salt thereof.

In some embodiments, the subject exhibits a decrease in glucocorticoid burden after a time period of administration of the pharmaceutical composition comprising the compound of Formula (I), or a pharmaceutically acceptable salt thereof, wherein the decrease in glucocorticoid burden is relative to the glucocorticoid burden prior to administration of the pharmaceutical composition comprising the compound of Formula (I), or a pharmaceutically acceptable salt thereof. In some embodiments, one or more symptoms of glucocorticoid burden selected from quality of life, fatigue, sleep, insulin resistance, glucose tolerance, glucose control, dyslipidemia, hyperlipidemia, bone mineral density, bone turnover, fat mass, weight, central obesity, blood pressure, hirsutism severity, menstrual cyclicity, control of testicular adrenal rest tumor and fertility, is improved after a time period of administration of the pharmaceutical composition comprising the compound of Formula (I), or a pharmaceutically acceptable salt thereof, wherein the improvement in the one or more symptoms is relative to the status of the one or more symptoms prior to administration of the pharmaceutical composition comprising the compound of Formula (I), or a pharmaceutically acceptable salt thereof.

In some embodiments, the quality of life as measured by the EuroQol 5 Dimensions 5 Levels (EQ-5D-5L) in the subject is improved after a time period of administration of the compound of Formula (I), or a pharmaceutically acceptable salt thereof, wherein the improvement in the EuroQol 5 Dimensions 5 Levels (EQ-5D-5L) is relative to the EuroQol 5 Dimensions 5 Levels (EQ-5D-5L) results prior to administration of the compound of Formula (I), or a pharmaceutically acceptable salt thereof.

In some embodiments, fatigue is reduced in the subject after a time period of administration of the compound of Formula (I), or a pharmaceutically acceptable salt thereof, wherein the reduction in fatigue is relative to the fatigue prior to administration of the compound of Formula (I), or a pharmaceutically acceptable salt thereof.

In some embodiments, sleep is increased in the subject after a time period of administration of the compound of Formula (I), or a pharmaceutically acceptable salt thereof, wherein the increase in sleep is relative to the sleep prior to administration of the compound of Formula (I), or a pharmaceutically acceptable salt thereof.

In some embodiments, insulin resistance is reduced in the subject after a time period of administration of the compound of Formula (I), or a pharmaceutically acceptable salt thereof, wherein the reduction of insulin resistance is relative to the insulin resistance prior to administration of the compound of Formula (I), or a pharmaceutically acceptable salt thereof.

In some embodiments, glucose tolerance is reduced in the subject after a time period of administration of the compound of Formula (I), or a pharmaceutically acceptable salt thereof, wherein the reduction in glucose tolerance is relative to the glucose tolerance prior to administration of the compound of Formula (I), or a pharmaceutically acceptable salt thereof.

In some embodiments, glucose control is increased in the subject after a time period of administration of the compound of Formula (I), or a pharmaceutically acceptable salt thereof, wherein the increase in glucose control is relative to the glucose control prior to administration of the compound of Formula (I), or a pharmaceutically acceptable salt thereof.

In some embodiments, lipid levels reflecting dyslipidemia are reduced in the subject after a time period of administration of the compound of Formula (I), or a pharmaceutically acceptable salt thereof, wherein the reduction in lipid levels is relative to the lipid levels prior to administration of the compound of Formula (I), or a pharmaceutically acceptable salt thereof.

In some embodiments, lipid levels reflecting hyperlipidemia are reduced in the subject after a time period of administration of the compound of Formula (I), or a pharmaceutically acceptable salt thereof, wherein the reduction in lipid levels is relative to the lipid levels prior to administration of the compound of Formula (I), or a pharmaceutically acceptable salt thereof.

In some embodiments, bone mineral density is increased in the subject after a time period of administration of the compound of Formula (I), or a pharmaceutically acceptable salt thereof, wherein the increase in bone mineral density is relative to the bone mineral density prior to administration of the compound of Formula (I), or a pharmaceutically acceptable salt thereof.

In some embodiments, bone turnover is increased in the subject after a time period of administration of the compound of Formula (I), or a pharmaceutically acceptable salt thereof, wherein the increase in bone turnover is relative to the bone turnover prior to administration of the compound of Formula (I), or a pharmaceutically acceptable salt thereof.

In some embodiments, fat mass is decreased in the subject after a time period of administration of the compound of Formula (I), or a pharmaceutically acceptable salt thereof, wherein the decrease in fat mass is relative to the fat mass prior to administration of the compound of Formula (I), or a pharmaceutically acceptable salt thereof.

In some embodiments, body weight is decreased in the subject after a time period of administration of the compound of Formula (I), or a pharmaceutically acceptable salt thereof, wherein the decrease in body weight is relative to the body weight prior to administration of the compound of Formula (I), or a pharmaceutically acceptable salt thereof.

In some embodiments, central obesity is decreased in the subject after a time period of administration of the compound of Formula (I), or a pharmaceutically acceptable salt thereof, wherein the decrease in central obesity is relative to the central obesity prior to administration of the compound of Formula (I), or a pharmaceutically acceptable salt thereof.

In some embodiments, blood pressure is increased in the subject after a time period of administration of the compound of Formula (I), or a pharmaceutically acceptable salt thereof, wherein the increase in blood pressure is relative to the blood pressure prior to administration of the compound of Formula (I), or a pharmaceutically acceptable salt thereof.

In some embodiments, the severity of hirsutism is decreased in the subject after a time period of administration of the compound of Formula (I), or a pharmaceutically acceptable salt thereof, wherein the decrease in the severity of hirsutism is relative to the severity of hirsutism prior to administration of the compound of Formula (I), or a pharmaceutically acceptable salt thereof.

In some embodiments, menstrual cyclicity is increased in the subject after a time period of administration of the compound of Formula (I), or a pharmaceutically acceptable salt thereof, wherein the increase in menstrual cyclicity is relative to the menstrual cyclicity prior to administration of the compound of Formula (I), or a pharmaceutically acceptable salt thereof.

In some embodiments, control of testicular adrenal rest tumor is increased in the subject after a time period of administration of the compound of Formula (I), or a pharmaceutically acceptable salt thereof, wherein the increase in control of testicular adrenal rest tumor is relative to the control of testicular adrenal rest tumor prior to administration of the compound of Formula (I), or a pharmaceutically acceptable salt thereof.

In some embodiments, fertility is increased in the subject after a time period of administration of the compound of Formula (I), or a pharmaceutically acceptable salt thereof, wherein the increase in fertility is relative to the fertility prior to administration of the compound of Formula (I), or a pharmaceutically acceptable salt thereof.

In some embodiments, gonadotropin levels are increased in the subject after a time period of administration of the compound of Formula (I), or a pharmaceutically acceptable salt thereof, wherein the increase in gonadotropin levels is relative to the gonadotropin levels prior to administration of the compound of Formula (I), or a pharmaceutically acceptable salt thereof.

In some embodiments, progesterone levels are increased in the subject after a time period of administration of the compound of Formula (I), or a pharmaceutically acceptable salt thereof, wherein the increase in progesterone levels is relative to the progesterone levels prior to administration of the compound of Formula (I), or a pharmaceutically acceptable salt thereof.

In some embodiments, semen levels are increased in the subject after a time period of administration of the compound of Formula (I), or a pharmaceutically acceptable salt thereof, wherein the increase in semen levels is relative to the semen levels prior to administration of the compound of Formula (I), or a pharmaceutically acceptable salt thereof.

In some embodiments, LH (luteinizing hormone) levels are increased in the subject after a time period of administration of the compound of Formula (I), or a pharmaceutically acceptable salt thereof, wherein the increase in LH levels are relative to the LH levels prior to administration of the compound of Formula (I), or a pharmaceutically acceptable salt thereof.

In some embodiments, the time period of administration is at least about 4 weeks. In some embodiments, the time period of administration is at least about 24 weeks. In some embodiments, the time period of administration is at least about one year. In some embodiments, the time period of administration is at least 4 weeks. In some embodiments, the time period of administration is at least 24 weeks. In some embodiments, the time period of administration is at least one year. In some embodiments, the time period of administration is less than about 1 day. In some embodiments, the time period of administration is about 1, 2, 3, 4, 5, 6 or 7 days, or within a range of any of the preceding values. In some embodiments, the time period of administration is about 1, 2, 3, 4, 5, 6, 7, 8, 9, 10, 11, 12, 13, 14, 15, 16, 17, 18, 19, 20, 21, 22, 23 or 24 weeks, or within a range of any of the preceding values. In some embodiments, the time period of administration is about 1, 2, 3, 4, 5, 6, 7, 8, 9, 10, 11, or 12 months, or within a range of any of the preceding values. It is understood that comparative measurements occur preferably during the morning.

In some embodiments, the subject is a pediatric subject. In some embodiments, the pediatric subject is less than or equal to six years old. In some embodiments, the pediatric subject is greater than six years old and less than eleven years old. In some embodiments, the pediatric subject is greater than ten years old and less than fifteen years old. In some embodiments, the pediatric subject is greater than fourteen years old and less than nineteen years old.

In some embodiments, the subject is an adult subject. In some embodiments, the subject is over eighteen years old. In some embodiments, the subject is female. In some embodiments, the subject is male.

In some embodiments, the compound of Formula (I), or a pharmaceutically acceptable salt thereof, is administered as a pharmaceutical composition described herein. In some embodiments, the compound of Formula (I), or a pharmaceutically acceptable salt thereof, is administered as a pharmaceutical composition described in Example 9. In some embodiments, the compound of Formula (I), or a pharmaceutically acceptable salt thereof, is administered as a pharmaceutical composition described in Example 11. In some embodiments, the compound of Formula (I), or a pharmaceutically acceptable salt thereof, is administered as a pharmaceutical composition described in Example 12. In some embodiments, the compound of Formula (I), or a pharmaceutically acceptable salt thereof, is administered as a pharmaceutical composition described in Example 13. In some embodiments, the compound of Formula (I), or a pharmaceutically acceptable salt thereof, is administered as a hydrochloric acid salt or p-toluenesulfonic acid salt.

In some embodiments, the compound of Formula (I), or a pharmaceutically acceptable salt thereof, is administered as a p-toluenesulfonic acid salt described herein.

For the avoidance of doubt, also provided herein is the corresponding compound of Formula (I), or a pharmaceutically acceptable salt thereof, or corresponding pharmaceutical composition comprising a compound of Formula (I), or a pharmaceutically acceptable salt thereof, for use in the corresponding methods, as described herein.

For the avoidance of doubt, also provided herein is use of the corresponding compound of Formula (I), or a pharmaceutically acceptable salt thereof, in the manufacture of a medicament for use in the corresponding methods, as described herein.

For the avoidance of doubt, also provided herein is use of the corresponding pharmaceutical composition comprising a compound of Formula (I), or a pharmaceutically acceptable salt thereof, in the manufacture of a medicament for use in the corresponding methods, as described herein.

p-Toluenesulfonic Acid Salt

In some embodiments, the compound of Formula (I) or a pharmaceutically acceptable salt thereof is 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, p-toluenesulfonic acid salt.

In some embodiments, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, p-toluenesulfonic acid salt is a crystalline salt. In some embodiments, the p-toluenesulfonic acid crystalline salt has Form 1.

Figure 27:
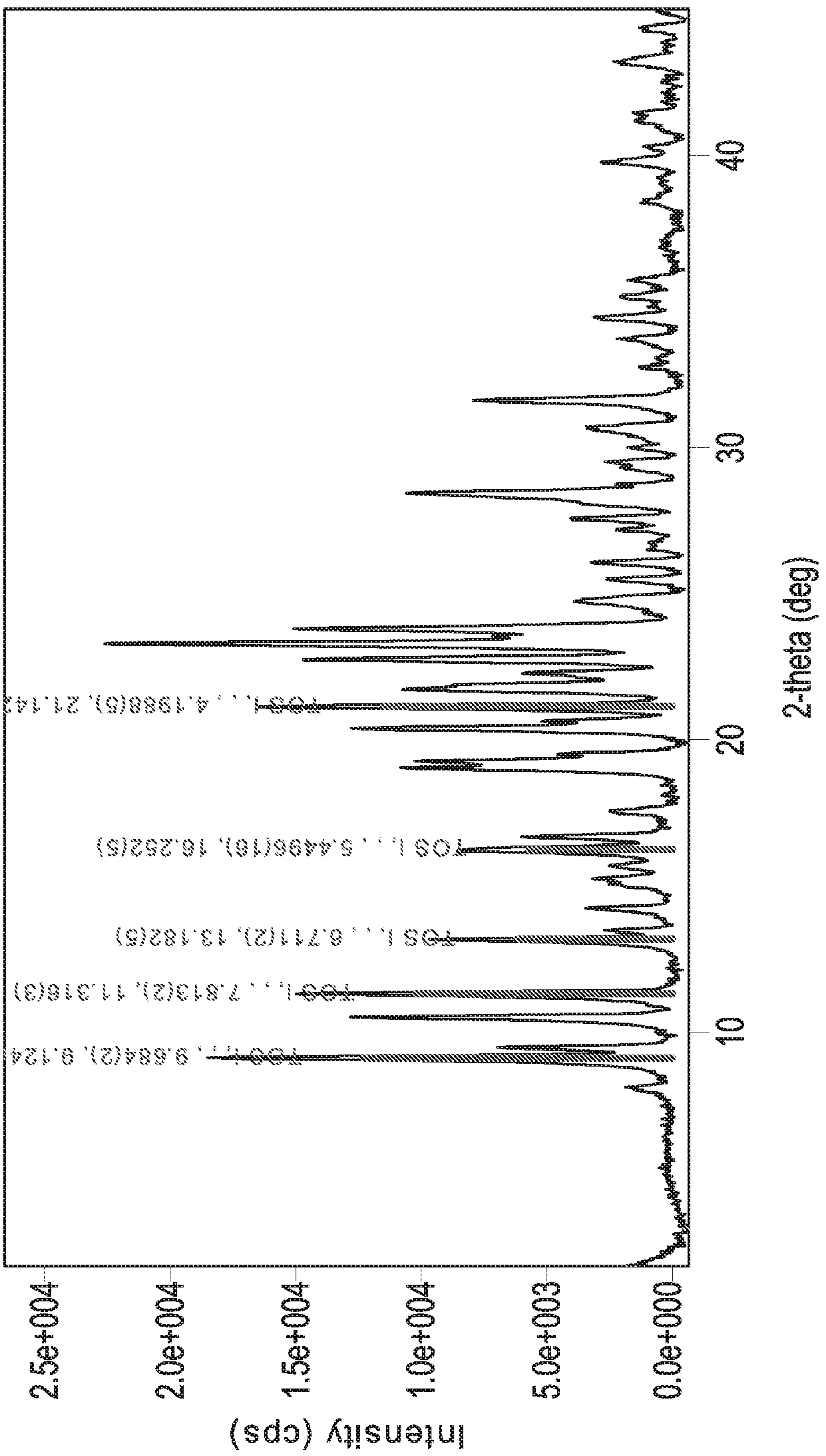
FIG. 27 is an XRPD spectrum of the compound of Formula (I) tosylate crystalline form 1.
Figure 28:
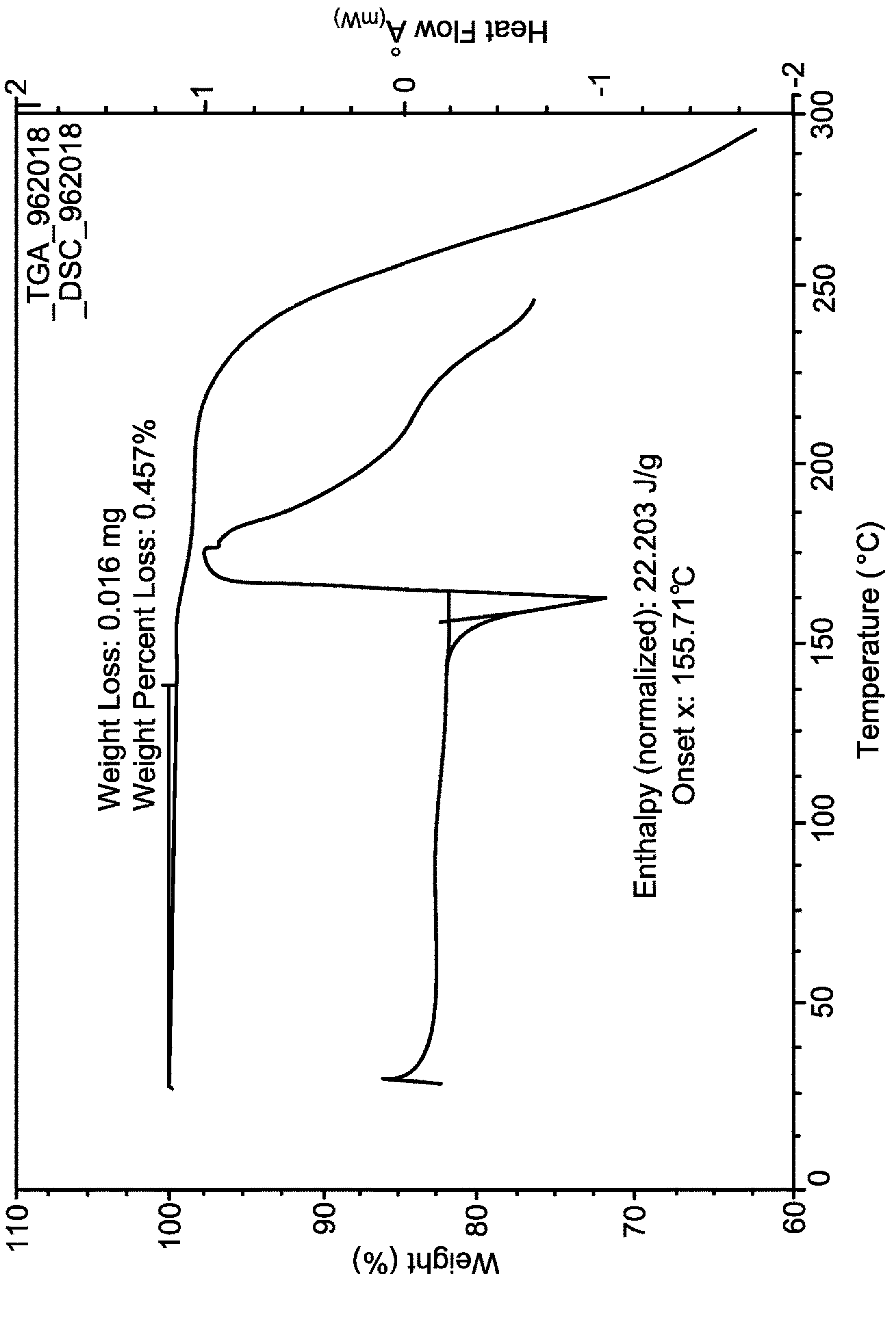
FIG. 28 is a DSC and TGA spectrum of the compound of Formula (I) tosylate crystalline form 1.

In some embodiments, the p-toluenesulfonic acid crystalline salt has an X-ray powder diffraction pattern as substantially shown in FIG. 27. In some embodiments, the p-toluenesulfonic acid crystalline salt has a DSC thermogram substantially as depicted in FIG. 28. In some embodiments, the p-toluenesulfonic acid crystalline salt has a thermogravimetric analysis (TGA) thermogram substantially as depicted in FIG. 28.

In some embodiments, the p-toluenesulfonic acid crystalline salt has at least one X-ray powder diffraction (XRPD) peak, in terms of 2-theta (±0.2 degrees), selected 9.1, 11.3, 13.2, 16.3 and 21.1 degrees. In some embodiments, the p-toluenesulfonic acid crystalline salt has at least two X-ray powder diffraction (XRPD) peaks, in terms of 2-theta (±0.2 degrees), selected from 9.1, 11.3, 13.2, 16.3 and 21.1 degrees. In some embodiments, the p-toluenesulfonic acid crystalline salt has at least three X-ray powder diffraction (XRPD) peaks, in terms of 2-theta (±0.2 degrees), selected from 9.1, 11.3, 13.2, 16.3 and 21.1 degrees. In some embodiments, the p-toluenesulfonic acid crystalline salt has at least four X-ray powder diffraction (XRPD) peaks, in terms of 2-theta (0.2 degrees), selected from 9.1, 11.3, 13.2, 16.3 and 21.1 degrees. In some embodiments, the p-toluenesulfonic acid crystalline salt has characteristic X-ray powder diffraction (XRPD) peaks, in terms of 2-theta (±0.2 degrees), at 9.1, 11.3, 13.2, 16.3 and 21.1 degrees. In some embodiments, the p-toluenesulfonic acid crystalline salt has an endothermic peak having an onset of melt at about 156° C. (22.2 J/g) in a differential scanning calorimetry (DSC) thermogram.

Lipidic Semi-Solid Formulation

Provided herein is a lipidic semi-solid formulation, which is a pharmaceutical composition comprising:

(a) a compound of Formula (I):

(I)

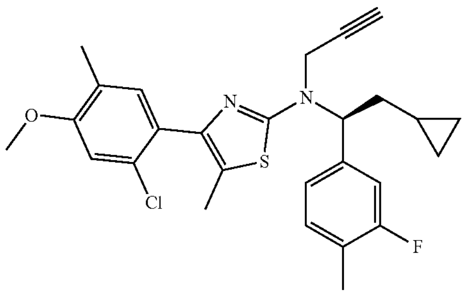

or a pharmaceutically acceptable salt thereof; and (b) one or more of an oily phase vehicle, an emulsifying agent, a nonionic surfactant, and a solubilizing agent.

In some embodiments, the pharmaceutical composition comprises about 1 wt % to about 20 wt % of the compound of Formula (I), or a pharmaceutically acceptable salt thereof, based on the weight of the free base. In some embodiments, the pharmaceutical composition comprises about 5 wt % to about 15 wt % of the compound of Formula (I), or a pharmaceutically acceptable salt thereof, based on the weight of the free base. In some embodiments, the pharmaceutical composition comprises about 10 wt % of the compound of Formula (I), or a pharmaceutically acceptable salt thereof, based on the weight of the free base. In some embodiments, the pharmaceutical composition comprises about 1, 2, 3, 4, 5, 6, 7, 8, 9, 10, 11, 12, 13, 14, 15, 16, 17, 18, 19, or 20 wt % of the compound of Formula (I), or a pharmaceutically acceptable salt thereof, based on the weight of the free base, or within a range of any of the preceding values.

In some embodiments, the pharmaceutical composition comprises an oily phase vehicle. An oily phase vehicle is a solvent that is poorly miscible with water. In some embodiments, the pharmaceutical composition comprises about 1 wt % to about 50 wt % of the oily phase vehicle. In some embodiments, the pharmaceutical composition comprises about 20 wt % to about 50 wt % of the oily phase vehicle. In some embodiments, the pharmaceutical composition comprises about 35 wt % to about 45 wt % of the oily phase vehicle. In some embodiments, the pharmaceutical composition comprises about 39 wt % of the oily phase vehicle. In some embodiments, the pharmaceutical composition comprises about 35, 36, 37, 38, 39, 40, 41, 42, 43, 44, or 45 wt % of the oily phase vehicle, or within a range of any of the preceding values.

In some embodiments, the oily phase vehicle is selected from medium-chain triglycerides, glycerin, propylene glycol, polyethylene glycol, olive oil, soybean oil, corn oil, and transcutol. In some embodiments, the oily phase vehicle is medium-chain triglycerides. In some embodiments, the medium-chain triglycerides are medium-chain triglycerides sold under the trademark LABRAFAC™ LIPOPHILE WL1349. In some embodiments, the medium-chain triglycerides are medium-chain triglycerides sold under the trademark MIGLYOL 812N.

In some embodiments, the pharmaceutical composition comprises an emulsifying agent. An emulsifying agent is a compound or substance that acts as a stabilizer for emulsions. In some embodiments, the pharmaceutical composition comprises about 5 wt % to about 50 wt % of the emulsifying agent. In some embodiments, the pharmaceutical composition comprises about 10 wt % to about 30 wt % of the emulsifying agent. In some embodiments, the pharmaceutical composition comprises about 15 wt % to about 25 wt % of the emulsifying agent. In some embodiments, the pharmaceutical composition comprises about 20 wt % of the emulsifying agent. In some embodiments, the pharmaceutical composition comprises about 10, 11, 12, 13, 14, 15, 16, 17, 18, 19, 20, 21, 22, 23, 24, 25, 26, 27, 28, 29 or 30 wt % of the emulsifying agent, or within a range of any of the preceding values.

In some embodiments, the emulsifying agent is selected from medium-chain triglycerides, propylene glycol dicaprylate/dicaprate, glycerin, propylene glycol, polyethylene glycol, olive oil, soybean oil, corn oil, and transcutol. In some embodiments, the emulsifying agent is propylene glycol dicaprylate/dicaprate. In some embodiments, the propylene glycol dicaprylate/dicaprate is a propylene glycol dicaprylate/dicaprate sold under the trademark LABRAFAC™ PG.

In some embodiments, the pharmaceutical composition comprises a nonionic surfactant. A nonionic surfactant is a substance with a hydrophilic head and a hydrophobic tail that has no charge that is a formulation component added to improve solubility or emulsion properties. In some embodiments, the pharmaceutical composition comprises about 5 wt % to about 50 wt % of the nonionic surfactant. In some embodiments, the pharmaceutical composition comprises about 10 wt % to about 30 wt % of the nonionic surfactant. In some embodiments, the pharmaceutical composition comprises about 15 wt % to about 25 wt % of the nonionic surfactant. In some embodiments, the pharmaceutical composition comprises about 19 wt % of the nonionic surfactant. In some embodiments, the pharmaceutical composition comprises about 10, 11, 12, 13, 14, 15, 16, 17, 18, 19, 20, 21, 22, 23, 24, 25, 26, 27, 28, 29 or 30 wt % of the nonionic surfactant, or within a range of any of the preceding values.

In some embodiments, the nonionic surfactant is selected from oleoyl polyoxyl-6 glycerides, linoleoyl polyoxyl-6 glycerides, polysorbate 80, polysorbate 20, Gelucire, lauroyl polyoxyl-32 glycerides, poloxamer, PEG-32 stearate, and PEG-32 hydrogenated palm glycerides. In some embodiments, the nonionic surfactant is lauroyl polyoxyl-32 glycerides. In some embodiments, the lauroyl polyoxyl-32 glycerides are lauroyl polyoxyl triglycerides sold under the trademark GELUCIRE® 44/14.

In some embodiments, the pharmaceutical composition comprises a solubilizing agent. A solubilizing agent is a solvent that assists with solubilizing the compound of Formula (I), or a pharmaceutically acceptable salt thereof. In some embodiments, the pharmaceutical composition comprises about 1 wt % to about 50 wt % of the solubilizing agent. In some embodiments, the pharmaceutical composition comprises about 1 wt % to about 20 wt % of the solubilizing agent. In some embodiments, the pharmaceutical composition comprises about 5 wt % to about 15 wt % of the solubilizing agent. In some embodiments, the pharmaceutical composition comprises about 11 wt % of the solubilizing agent. In some embodiments, the pharmaceutical composition comprises about 1, 2, 3, 4, 5, 6, 7, 8, 9, 10, 11, 12, 13, 14, 15, 16, 17, 18, 19, or 20 wt % of the solubilizing agent, or within a range of any of the preceding values.

In some embodiments, the solubilizing agent is selected from oleoyl polyoxyl-6 glycerides, linoleoyl polyoxyl-6 glycerides, polysorbate 80, polysorbate 20, vitamin E polyethylene glycol succinate, Gelucire, lauroyl polyoxyl-32 glycerides, and poloxamer. In some embodiments, the solubilizing agent is vitamin E polyethylene glycol succinate. In some embodiments, the vitamin E polyethylene glycol succinate is vitamin E polyethylene glycol succinate sold under the trademark KOLLIPHOR® TPGS. In some embodiments, the vitamin E polyethylene glycol succinate is Vitamin E/TPGS 260.

In some embodiments, the pharmaceutical composition comprises:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof;
(b) an oily phase vehicle;
(c) an emulsifying agent;
(d) a nonionic surfactant; and
(e) a solubilizing agent.

In some embodiments, the pharmaceutical composition comprises:

(a) about 5 wt % to about 15 wt % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 35 wt % to about 45 wt % of an oily phase vehicle;
(c) about 15 wt % to about 25 wt % of an emulsifying agent;
(d) about 15 wt % to about 25 wt % of a nonionic surfactant; and
(e) about 5 wt % to about 15 wt % of a solubilizing agent.

In some embodiments, the pharmaceutical composition comprises:

(a) about 10 wt % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 39 wt % of an oily phase vehicle;
(c) about 20 wt % of an emulsifying agent;
(d) about 19 wt % of a nonionic surfactant; and
(e) about 11 wt % of a solubilizing agent.

In some embodiments, the pharmaceutical composition comprises:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine;
(b) a medium-chain triglycerides component;

(c) a propylene glycol dicaprylate/dicaprate component;
(d) a lauroyl polyoxyl-32 glycerides component; and
(e) a vitamin E polyethylene glycol succinate component.

In some embodiments, the pharmaceutical composition comprises:

(a) about 5 wt % to about 15 wt % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine;
(b) about 35 wt % to about 45 wt % of medium-chain triglycerides;
(c) about 15 wt % to about 25 wt % of propylene glycol dicaprylate/dicaprate;
(d) about 15 wt % to about 25 wt % of lauroyl polyoxyl-32 glycerides; and
(e) about 5 wt % to about 15 wt % of vitamin E polyethylene glycol succinate.

In some embodiments, the pharmaceutical composition comprises:

(a) about 10 wt % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine;
(b) about 39 wt % of medium-chain triglycerides;
(c) about 20 wt % of propylene glycol dicaprylate/dicaprate;
(d) about 19 wt % of lauroyl polyoxyl-32 glycerides; and
(e) about 11 wt % of vitamin E polyethylene glycol succinate.

In some embodiments, the lipidic semi-solid pharmaceutical composition has a viscosity between about 15 to about 40 centipoise at about 45° C. In some embodiments, the lipidic semi-solid pharmaceutical composition has a viscosity between about 26 to about 30 centipoise at about 45° C. In some embodiments, the lipidic semi-solid pharmaceutical composition has a viscosity between about 5 to about 25 centipoise at about 60° C. In some embodiments, the lipidic semi-solid pharmaceutical composition has a viscosity between about 14 to about 18 centipoise at about 60° C.

In some embodiments, the pharmaceutical composition does not comprise a combination of mannitol, croscarmellose sodium, maize starch, hydroxypropyl methylcellulose, and magnesium stearate.

In some embodiments, the pharmaceutical composition does not comprise at least one of mannitol, croscarmellose sodium, maize starch, hydroxypropyl methylcellulose, and magnesium stearate.

In some embodiments, the pharmaceutical composition comprises a compound of Formula (I), or pharmaceutically acceptable salt thereof, in crystalline form. In some embodiments, the pharmaceutical composition comprises a compound of Formula (I), or pharmaceutically acceptable salt thereof, in amorphous form. In some embodiments, the pharmaceutical composition comprises a compound of Formula (I) as a free base. In some embodiments, the crystalline form of the compound of Formula (I) is of Form I.

In some embodiments, the pharmaceutical composition is formulated in unit dosage form, wherein the compound of Formula (I), or a pharmaceutically acceptable salt thereof, is present in an amount of about 5 mg to about 200 mg, based on the weight of the free base. In some embodiments, the compound of Formula (I), or a pharmaceutically acceptable salt thereof, is present in the unit dosage form in an amount of about 75 mg to about 150 mg, based on the weight of the free base. In some embodiments, the compound of Formula (I), or a pharmaceutically acceptable salt thereof, is present in the unit dosage form in an amount of about 50 mg, based on the weight of the free base. In some embodiments, the compound of Formula (I), or a pharmaceutically acceptable salt thereof, is present in the unit dosage form in an amount of about 100 mg, based on the weight of the free base. In some embodiments, the compound of Formula (I), or a pharmaceutically acceptable salt thereof, is present in the unit dosage form in an amount of about 25 mg, based on the weight of the free base.

In some embodiments, the pharmaceutical composition is in the form of a tablet, capsule, sachet, powder, granules, coated particle, coated tablet, enterocoated tablet, enterocoated capsule, melting strip, or melting film. In some embodiments, the pharmaceutical composition is in tablet form. In some embodiments, the pharmaceutical composition is in capsule form. In some embodiments, the dosage form is coated.

Some embodiments provide a method for preparing the pharmaceutical composition, comprising:

(a) heating a mixture of an oily phase vehicle, an emulsifying agent, a nonionic surfactant, and a solubilizing agent;
(b) mixing the mixture of step (a) until a homogeneous mixture is achieved; and
(c) mixing the compound of Formula (I), or a pharmaceutically acceptable salt thereof, with the homogeneous mixture of step (b) until the compound of Formula (I), or a pharmaceutically acceptable salt thereof, is dissolved, forming a composition.

In some embodiments, the method further comprises:

(d) encapsulating the composition of step (c) in a capsule shell to form a capsule; and
(e) banding the capsule of step (d) in a mixture of banding agent and banding solvent.

Liquid Formulations

Provided herein is a pharmaceutical composition in oral solution dosage form comprising:

(a) a compound of Formula (I):

(I)

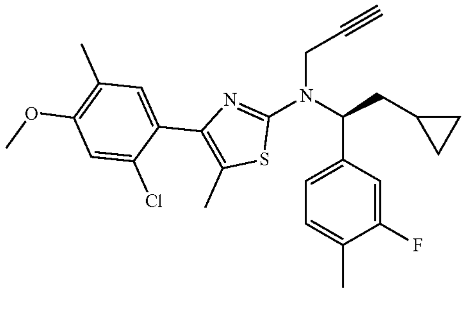

or a pharmaceutically acceptable salt thereof;
(b) one or more of a sweetener, an anti-oxidant, and a flavor; and
(c) a liquid vehicle.

In some embodiments, the pharmaceutical composition comprises about 1 w/v % to about 50 w/v % of the compound of Formula (I), or a pharmaceutically acceptable salt thereof, based on the weight of the free base. In some embodiments, the pharmaceutical composition comprises about 1 w/v % to about 10 w/v % of the compound of Formula (I), or a pharmaceutically acceptable salt thereof, based on the weight of the free base. In some embodiments, the pharmaceutical composition comprises about 5 w/v % of the compound of Formula (I), or a pharmaceutically acceptable salt thereof, based on the weight of the free base. In some embodiments, the pharmaceutical composition comprises about 1, 2, 3, 4, 5, 6, 7, 8, 9, or 10 w/v % of the compound of Formula (I), or a pharmaceutically acceptable salt thereof, based on the weight of the free base, or within a range of any of the preceding values.

In some embodiments, the pharmaceutical composition comprises a sweetener. A sweetener is a formulation component added to improve taste. In some embodiments, the pharmaceutical composition comprises about 0.01 w/v % to about 1.5 w/v % of the sweetener. In some embodiments, the pharmaceutical composition comprises about 0.1 w/v % to about 0.5 w/v % of the sweetener. In some embodiments, the pharmaceutical composition comprises about 0.15 w/v % of the sweetener. In some embodiments, the pharmaceutical composition comprises about 0.1, 0.2, 0.3, 0.4, or 0.5 w/v % of the sweetener, or within a range of any of the preceding values.

In some embodiments, the sweetener is selected from saccharin, sucrose, sucralose, aspartame, dextrose, fructose, maltitol, mannitol, sorbitol, and avantame. In some embodiments, the sweetener is saccharin.

In some embodiments, the pharmaceutical composition comprises an anti-oxidant. An anti-oxidant is a formulation component included to improve stability by preventing oxidation. In some embodiments, the pharmaceutical composition comprises about 0.01 w/v % to about 1.5 w/v % of the anti-oxidant. In some embodiments, the pharmaceutical composition comprises about 0.1 w/v % to about 0.5 w/v % of the anti-oxidant. In some embodiments, the pharmaceutical composition comprises about 0.17 w/v % of the anti-oxidant. In some embodiments, the pharmaceutical composition comprises about 0.1, 0.2, 0.3, 0.4, or 0.5 w/v % of the anti-oxidant, or within a range of any of the preceding values.

In some embodiments, the anti-oxidant is selected from butylated hydroxytoluene, vitamin E TPGS, butylated hydroxyanisole, ascorbic acid, lecithin, tert-butylhydroquinone, and citric acid. In some embodiments, the anti-oxidant is butylated hydroxytoluene.

In some embodiments, the pharmaceutical composition comprises a flavor. A flavor is a formulation component added to mask taste through aromatics. In some embodiments, the pharmaceutical composition comprises about 0.01 w/v % to about 0.5 w/v % of the flavor. In some embodiments, the pharmaceutical composition comprises about 0.05 w/v % to about 0.2 w/v % of the flavor. In some embodiments, the pharmaceutical composition comprises about 0.10 w/v % of the flavor. In some embodiments, the pharmaceutical composition comprises about 0.05, 0.06, 0.07, 0.08, 0.09, 0.10, 0.11, 0.12, 0.13, 0.14, 0.15, 0.16, 0.17, 0.18, 0.19 or 0.2 w/v % of the flavor, or within a range of any of the preceding values.

In some embodiments, the flavor is selected from FONA International (FONA) orange flavor, FONA Juicy Flavor, FONA Grape Flavor, Firmenich SA Lemon Flavor, Firmenich Tetrarome Orange Flavor, IFF Cherry Flavor, and IFF Grape Flavor. In some embodiments, the flavor is FONA orange flavor.

A liquid vehicle is a solvent capable of dissolving or partially dissolving the compound of Formula (I), or a pharmaceutically acceptable salt thereof, for the purposes of delivery as an oral dosing solution. In some embodiments, the pharmaceutical composition comprises about 50 w/v % to about 99.9 w/v % of the liquid vehicle. In some embodiments, the pharmaceutical composition comprises about 90 w/v % to about 99 w/v % of the liquid vehicle. In some embodiments, the pharmaceutical composition comprises about 92 w/v % to about 97 w/v % of the liquid vehicle. In some embodiments, the pharmaceutical composition comprises about 94.6 w/v % of the liquid vehicle. In some embodiments, the pharmaceutical composition comprises about 90, 91, 92, 93, 94, 95, 96, 97, 98 or 99 w/v % of the liquid vehicle, or within a range of any of the preceding values.

In some embodiments, the liquid vehicle is selected from medium-chain triglycerides, propylene glycol dicaprylate/dicaprate, glycerin, propylene glycol, polyethylene glycol, olive oil, soybean oil, corn oil, and transcutol. In some embodiments, the liquid vehicle is medium-chain triglycerides. In some embodiments, the medium-chain triglycerides is medium-chain triglycerides sold under the trademark LABRAFAC LIPOPHILE WL1349.

In some embodiments, the pharmaceutical composition further comprises a surfactant. A surfactant is a formulation component added to improve solubility or emulsion properties. In some embodiments, the pharmaceutical composition comprises about 1 w/v % to about 50 w/v % of the surfactant. In some embodiments, the pharmaceutical composition comprises about 10 w/v % to about 30 w/v % of the surfactant. In some embodiments, the pharmaceutical composition comprises about 20 w/v % of the surfactant. In some embodiments, the pharmaceutical composition comprises about 10, 11, 12, 13, 14, 15, 16, 17, 18, 19, 20, 21, 22, 23, 24, 25, 26, 27, 28, 29 or 30 w/v % of the surfactant, or within a range of any of the preceding values.

In some embodiments, the surfactant is selected from oleoyl polyoxyl-6 glycerides, linoleoyl polyoxyl-6 glycerides, polysorbate 80, polysorbate 20, vitamin E polyethylene glycol succinate, Gelucire, lauroyl polyoxyl-32 glycerides, sodium lauryl sulfate, poloxamer, corn oil PEG-6 esters, and hydrogenated palm/palm kernel oil PEG-6 esters. In some embodiments, the surfactant is oleoyl polyoxyl-6 glycerides. In some embodiments, the oleoyl polyoxyl-6 glycerides is oleoyl polyoxyl-6-glycerides sold under the trademark LABRAFIL M 1944 CS.

In some embodiments, the pharmaceutical composition comprises about 50 w/v % to about 90 w/v % of the liquid vehicle. In some embodiments, the pharmaceutical composition comprises about 70 w/v % to about 80 w/v % of the liquid vehicle. In some embodiments, the pharmaceutical composition comprises about 75 w/v % of the liquid vehicle. In some embodiments, the pharmaceutical composition comprises about 74.6 w/v % of the liquid vehicle. In some embodiments, the pharmaceutical composition comprises about 70, 71, 72, 73, 74, 75, 76, 77, 78, 79, or 80 w/v % of the liquid vehicle, or within a range of any of the preceding values.

In some embodiments, the liquid vehicle is selected from medium-chain triglycerides, propylene glycol dicaprylate/dicaprate, glycerin, propylene glycol, polyethylene glycol, olive oil, soybean oil, corn oil, and transcutol. In some embodiments, the liquid vehicle is medium-chain triglycerides. In some embodiments, the medium-chain triglycerides is medium-chain triglycerides sold under the trademark LABRAFAC LIPOPHILE WL1349.

In some embodiments, the pharmaceutical composition comprises:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof;

(b) a sweetener;

(c) an anti-oxidant;

(d) a flavor; and
(e) a liquid vehicle.

In some embodiments, the pharmaceutical composition further comprises a surfactant.

In some embodiments, the pharmaceutical composition comprises:

(a) about 4 w/v % to about 6 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.1 w/v % to about 0.2 w/v % of a sweetener;
(c) about 0.1 w/v % to about 0.2 w/v % of an anti-oxidant;
(d) about 0.05 w/v % to about 0.2 w/v % of a flavor; and
(e) about 92 w/v % to about 97 w/v % of a liquid vehicle.

In some embodiments, the pharmaceutical composition comprises:

(a) about 5 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.15 w/v % of a sweetener;
(c) about 0.17 w/v % of an anti-oxidant;
(d) about 0.1 w/v % of a flavor; and
(e) about 94.6 w/v % of a liquid vehicle.

In some embodiments, the pharmaceutical composition comprises:

(a) about 4 w/v % to about 6 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.1 w/v % to about 0.2 w/v % of a sweetener;
(c) about 0.1 w/v % to about 0.2 w/v % of an anti-oxidant;
(d) about 0.05 w/v % to about 0.2 w/v % of a flavor;
(e) about 15 w/v % to about 25 w/v % of a surfactant; and
(f) about 70 w/v % to about 80 w/v % of a liquid vehicle.

In some embodiments, the pharmaceutical composition comprises:

(a) about 5 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.15 w/v % of a sweetener;
(c) about 0.17 w/v % of an anti-oxidant;
(d) about 0.1 w/v % of a flavor;
(e) about 20 w/v % of a surfactant; and
(f) about 75 w/v % of a liquid vehicle.

In some embodiments, the pharmaceutical composition comprises:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof;
(b) saccharin;
(c) butylated hydroxytoluene;
(d) FONA orange flavor; and
(e) medium-chain triglycerides.

In some embodiments, the pharmaceutical composition further comprises oleoyl polyoxyl-6 glycerides.

In some embodiments, the pharmaceutical composition comprises:

(a) about 4 w/v % to about 6 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.1 w/v % to about 0.2 w/v % of saccharin;
(c) about 0.1 w/v % to about 0.2 w/v % of butylated hydroxytoluene;
(d) about 0.05 w/v % to about 0.2 w/v % of FONA orange flavor; and
(e) about 92 w/v % to about 97 w/v % of medium-chain triglycerides.

In some embodiments, the pharmaceutical composition comprises:

(a) about 5 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.15 w/v % of saccharin;
(c) about 0.17 w/v % of butylated hydroxytoluene;
(d) about 0.1 w/v % of FONA orange flavor; and
(e) about 94.6 w/v % of medium-chain triglycerides.

In some embodiments, the pharmaceutical composition comprises:

(a) about 4 w/v % to about 6 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.1 w/v % to about 0.2 w/v % of saccharin;
(c) about 0.1 w/v % to about 0.2 w/v % of butylated hydroxytoluene;
(d) about 0.05 w/v % to about 0.2 w/v % of FONA orange flavor;
(e) about 15 w/v % to about 25 w/v % of oleoyl polyoxyl-6 glycerides; and
(f) about 70 w/v % to about 80 w/v % of medium-chain triglycerides.

In some embodiments, the pharmaceutical composition comprises:

(a) about 5 w/v % of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, based on the weight of the free base;
(b) about 0.15 w/v % of saccharin;
(c) about 0.17 w/v % of butylated hydroxytoluene;
(d) about 0.1 w/v % of FONA orange flavor;
(e) about 20 w/v % of oleoyl polyoxyl-6 glycerides; and
(f) about 75 w/v % of medium-chain triglycerides.

In some embodiments, the pharmaceutical composition comprises the compound of Formula (I) as a free base.

In some embodiments, the pharmaceutical composition is formulated in unit dosage form, wherein the compound of Formula (I), or a pharmaceutically acceptable salt thereof, is present in an amount of about 5 mg/mL to about 200 mg/mL, based on the weight of the free base. In some embodiments, the compound of Formula (I), or a pharmaceutically acceptable salt thereof, is present in the unit dosage form in an amount of about 75 mg/mL to about 150 mg/mL, based on the weight of the free base. In some embodiments, the compound of Formula (I), or a pharmaceutically acceptable salt thereof, is present in the unit dosage form in an amount of about 50 mg/mL, based on the weight of the free base. In some embodiments, the compound of Formula (I), or a pharmaceutically acceptable salt thereof, is present in the unit dosage form in an amount of about 100 mg/mL, based on the weight of the free base.

In some embodiments, the liquid pharmaceutical composition has a viscosity between about 1 to about 50 centipoise at about 25° C.

Some embodiments provide a method for preparing a pharmaceutical composition comprising:

(a) mixing a liquid vehicle with a sweetener;
(b) mixing the mixture of step (a) with an anti-oxidant and a flavor;
(c) mixing the compound of Formula (I), or a pharmaceutically acceptable salt thereof, with the mixture of step (b); and
(d) mixing the mixture of step (c) with an additional portion of the liquid vehicle.

In some embodiments, step (a) of the method comprises mixing a liquid vehicle with sweetener and a surfactant.

Spray-Dried Dispersions

The methods and uses of the present disclosure may comprise administering a spray-dried dispersion (SDDs) of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, and to the use of the SDDs in the treatment of congenital adrenal hyperplasia (CAH).

In some embodiments, concentration and bioavailability enhancement in an aqueous environment of a low-solubility drug in a spray-dried dispersion is achieved if the SDD exhibits one or more properties, including, for example: (1) the solid dispersion is substantially homogeneous; (2) the drug is substantially amorphous; (3) the SDD has a relatively high drug loading; and (4) the SDD has a low residual solvent content. In some embodiments, the dispersion, when administered to an aqueous environment, provides at least a temporary dissolved drug concentration in the aqueous environment that is greater than the solubility of the crystalline form of the drug in the same environment. The aqueous environment can be, for example, an in vitro environment, such as a dissolution test media (e.g., phosphate buffered saline (PBS) solution), or an in vivo environment, such as the gastrointestinal (GI) tract of an animal, for example, a human. In some embodiments, the aqueous environment is the lower GI tract, such as the small intestine and large intestine.

Provided in the present disclosure is a spray-dried dispersion that contains a polymer and a compound having the structure of Formula (I):

(I)

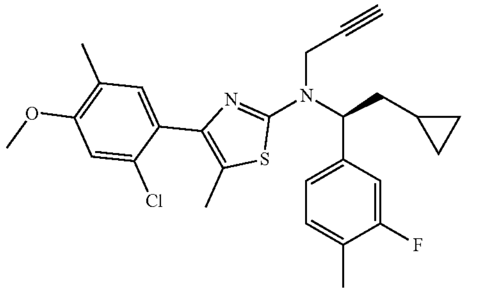

or a pharmaceutically acceptable salt thereof. In some embodiments, the SDD includes a polymer selected from a neutral polymer, an enteric polymer, and a pyrrolidone polymer. In some embodiments, the weight ratio of the compound of Formula (I), or a pharmaceutically acceptable salt thereof, to the polymer is from about 1:1 to about 1:9.

In some embodiments, the polymer is a neutral polymer. For example, the polymer does not contain any charged functional groups. In some embodiments, the neutral polymer is a cellulosic polymer. For example, the cellulosic polymer can be a polymer with at least one ester- and/or ether-linked substituent in which the polymer has a degree of substitution of at least 0.05 for each substituent. Examples of suitable neutral polymers include, but are not limited to, hydroxypropyl methylcellulose (HPMC) and hydroxyethyl cellulose (HEC).

In some embodiments, the polymer is an enteric polymer. An "enteric polymer," as used herein, is a polymeric substance that is substantially insoluble and/or substantially stable under acidic conditions exhibiting a pH of less than about 7 and which is substantially soluble or can decompose under conditions exhibiting a pH of about 7 or more. Examples of suitable enteric polymers include, but are not limited to, carboxymethyl ethyl cellulose (CMEC), cellulose acetate phthalate (CAP), cellulose acetate succinate (CAS), methylcellulose phthalate, hydroxymethyl ethyl cellulose phthalate, hydroxypropyl methyl cellulose phthalate (HPMCP), hydroxypropyl methyl cellulose acetate succinate (HPMCAS), polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, an amino methacrylate copolymer, an ammonioalkyl methacrylate copolymer, a methacrylic copolymer, and mixtures thereof. In some embodiments, the enteric polymer is selected from hydroxypropyl methyl cellulose acetate succinate (HPMCAS), cellulose acetate phthalate (CAP), hydroxypropyl methyl cellulose phthalate (HPMCP), an amino methacrylate copolymer, an ammonioalkyl methacrylate copolymer, and a methacrylic copolymer. In some embodiments, the enteric polymer is an enteric polymer sold under the trademark EUDRAGIT® by Evonik Industries (Essen, Germany). In some embodiments, the enteric polymer is an amino methacrylate copolymer. In some embodiments, the amino methacrylate copolymer is an amino methacrylate polymer sold under the trademark EUDRAGIT® E PO/100. In some embodiments, the enteric polymer is an ammonioalkyl methacrylate copolymer. In some embodiments, the ammonioalkyl methacrylate copolymer is an ammonioalkyl methacrylate polymer sold under the trademark EUDRAGIT® RLPO. In some embodiments, the enteric polymer is a methacrylic copolymer. In some embodiments, the methacrylic copolymer is a methacrylic copolymer sold under the trademarks EUDRAGIT® L100 or EUDRAGIT® S100.

In some embodiments, the polymer is a pyrrolidone polymer. For example, the pyrrolidone polymer can be a vinyl pyrrolidone polymer, such as polyvinyl pyrrolidone (PVP) or polyvinyl pyrrolidone vinyl acetate (PVP/VA), including homopolymers and copolymers of PVP and homopolymers and copolymers of N-vinyl pyrrolidone. In some embodiments, the pyrrolidone polymer is PVP/VA. In some embodiments, the PVP/VA is a copolymer of 1-vinyl-2-pyrrolidone and vinyl acetate. In some embodiments, the copolymer contains 1-vinyl-2-pyrrolidone and vinyl acetate at a ratio of about 30:70 to about 70:30 by weight, such as about 40:60 to about 60:40 by weight, or about 45:55 to about 55:45 by weight. In some embodiments, the copolymer contains 1-vinyl-2-pyrrolidone and vinyl acetate at a ratio of about 30:70, about 35:65, about 40:60, about 45:55, about 50:50, about 55:45, about 60:40, about 65:35, or about 70:30 by weight. In some embodiments, the copolymer contains 1-vinyl-2-pyrrolidone and vinyl acetate at a ratio of about 60:40 by weight.

In some embodiments, the pyrrolidone polymer has the structure:

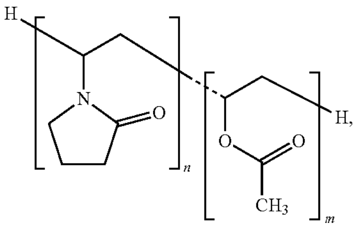

where the value of n is about 1 to about 2 times the value of m. For example, the value of n can be about 1, about 1.05, about 1.1, about 1.15, about 1.16, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, or about 2 times the value of m, or a value within a range defined by any of the preceding values. In some embodiments, the value of n is about 1.16 times the value of m. In some embodiments, the copolymer is copovidone, and the value of n is about 1.16 times the value of m.

In some embodiments, the pyrrolidone polymer has the structure:

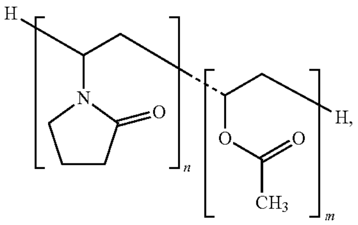

where the value of n is 1 to 2 times the value of m. For example, the value of n can be 1, 1.05, 1.1, 1.15, 1.16, 1.2, 1.25, 1.3, 1.35, 1.4, 1.45, 1.5, 1.55, 1.6, 1.65, 1.7, 1.75, 1.8, 1.85, 1.9, 1.95, or 2 times the value of m, or a value within a range defined by any of the preceding values. In some embodiments, the value of n is 1.16 times the value of m. In some embodiments, the copolymer is copovidone, and the value of n is 1.16 times the value of m.

In some embodiments, the polymer used in the disclosed SDDs is present in an amount sufficient to increase the maximum drug concentration of the amorphous form of the compound of Formula (I), or a pharmaceutically acceptable salt thereof, in the environment of use (e.g., aqueous environment) relative to a control composition that contains an equivalent amount of a crystalline form of the compound of Formula (I), or a pharmaceutically acceptable salt thereof, but without polymer. In some embodiments, once the SDD is introduced into an environment of use (e.g., aqueous environment), the polymer increases the aqueous concentration of the compound of Formula (I), or a pharmaceutically acceptable salt thereof, relative to the control composition. It is to be understood that the control composition is free from solubilizers or other components that would materially affect the solubility of the compound of Formula (I), or a pharmaceutically acceptable salt thereof, and that the compound of Formula (I), or a pharmaceutically acceptable salt thereof, is in solid form in the control composition.

In some embodiments of the SDDs, the weight ratio of the compound of Formula (I), or a pharmaceutically acceptable salt thereof, to the polymer is from about 1:1 to about 1:9. For example, the weight ratio of the compound of Formula (I), or a pharmaceutically acceptable salt thereof, to the polymer can be about 1:1 to about 1:8, about 1:1 to about 1:7, about 1:1 to about 1:6, about 1:1 to about 1:5, about 1:1 to about 1:4, about 1:1 to about 1:3, about 1:1 to about 1:2, about 1:1 to about 1:1.5, about 1:1.5 to about 1:9, or about 1:2.5 to about 1:4. In some embodiments, the weight ratio of the compound of Formula (I), or a pharmaceutically acceptable salt thereof, to the polymer is about 1:9, about 1:8, about 1:7.5, about 1:7, about 1:6, about 1:5, about 1:4, about 1:3, about 1:2.5, about 1:2, about 1:1.5, or about 1:1, or a weight ratio within a range defined by any of the preceding values. In some embodiments, the weight ratio of the compound of Formula (I), or a pharmaceutically acceptable salt thereof, to the polymer is about 1:9. In some embodiments, the weight ratio of the compound of Formula (I), or a pharmaceutically acceptable salt thereof, to the polymer is about 1:1.5. In some embodiments, the weight ratio of the compound of Formula (I), or a pharmaceutically acceptable salt thereof, to the polymer is about 1:1.

In some embodiments of the SDDs, the weight ratio of the compound of Formula (I), or a pharmaceutically acceptable salt thereof, to the polymer is from 1:1 to 1:9. For example, the weight ratio of the compound of Formula (I), or a pharmaceutically acceptable salt thereof, to the polymer can be 1:1 to 1:8, 1:1 to 1:7, 1:1 to 1:6, 1:1 to 1:5, 1:1 to 1:4, 1:1 to 1:3, 1:1 to 1:2, 1:1 to 1:1.5, 1:1.5 to 1:9, or 1:2.5 to 1:4. In some embodiments, the weight ratio of the compound of Formula (I), or a pharmaceutically acceptable salt thereof, to the polymer is 1:9, 1:8, 1:7.5, 1:7, 1:6, 1:5, 1:4, 1:3, 1:2.5, 1:2, 1:1.5, or 1:1, or a weight ratio within a range defined by any of the preceding values. In some embodiments, the weight ratio of the compound of Formula (I), or a pharmaceutically acceptable salt thereof, to the polymer is 1:9. In some embodiments, the weight ratio of the compound of Formula (I), or a pharmaceutically acceptable salt thereof, to the polymer is 1:1.5. In some embodiments, the weight ratio of the compound of Formula (I), or a pharmaceutically acceptable salt thereof, to the polymer is 1:1.

In some embodiments, the spray dried dispersion includes a compound of Formula (I), or a pharmaceutically acceptable salt thereof, and a polymer that is a copolymer of 1-vinyl-2-pyrrolidone and vinyl acetate having the structure:

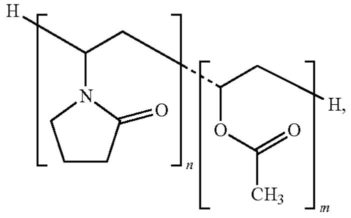

where the value of n is about 1 to about 2 times the value of m and the copolymer contains 1-vinyl-2-pyrrolidone and vinyl acetate at a ratio of about 60:40 by weight, and the weight ratio of the compound of Formula (I), or a pharmaceutically acceptable salt thereof, to the copolymer is from about 1:1 to about 1:9.

In some embodiments, the spray dried dispersion includes a compound of Formula (I), or a pharmaceutically acceptable salt thereof, and a polymer that is a copolymer of 1-vinyl-2-pyrrolidone and vinyl acetate having the structure:

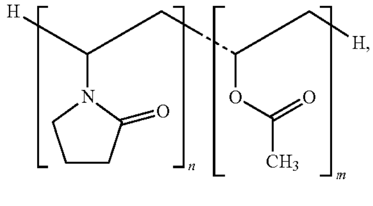

where the value of n is 1 to 2 times the value of m and the copolymer contains 1-vinyl-2-pyrrolidone and vinyl acetate at a ratio of 60:40 by weight, and the weight ratio of the compound of Formula (I), or a pharmaceutically acceptable salt thereof, to the copolymer is from 1:1 to 1:9.

In some embodiments of the SDDs, the compound of Formula (I), or a pharmaceutically acceptable salt thereof, and the polymer together form homogeneous particles. In some embodiments, the particles are a substantially homogeneous composition that includes the compound of Formula (I), or a pharmaceutically acceptable salt thereof, and the polymer. As used herein, "substantially homogeneous" means that the compound of Formula (I), or a pharmaceutically acceptable salt thereof, is dispersed as homogeneously as possible throughout the polymer and can be thought of as a solid solution of the compound of Formula (I), or a pharmaceutically acceptable salt thereof, dispersed in the polymer. While the dispersion can have some concentrated domains of the compound of Formula (I), or a pharmaceutically acceptable salt thereof, the dispersion itself has a single glass transition temperature ($T_g$) which demonstrates that the dispersion is substantially homogeneous. This contrasts with a simple physical mixture of pure amorphous particles of the compound of Formula (I), or a pharmaceutically acceptable salt thereof, and pure amorphous polymer particles, which generally displays two distinct $T_g$s, one of the compound of Formula (I), or a pharmaceutically acceptable salt thereof, and one of the polymer. "$T_g$," as used herein, is the characteristic temperature where a glassy material, upon gradual heating, undergoes a relatively rapid (e.g., 10 to 100 seconds) physical change from a glass state to a rubber state.

In some embodiments, the particles have a particle size distribution (D-value, $D_{50}$), of about 5 μm to about 100 μm, such as about 5 μm to about 95 μm, about 5 μm to about 90 μm, about 5 μm to about 85 μm, about 5 μm to about 80 μm, about 5 μm to about 75 μm, about 5 μm to about 70 μm, about 5 μm to about 65 μm, about 5 μm to about 60 μm, about 5 μm to about 55 μm, about 5 μm to about 50 μm, about 5 μm to about 45 μm, about 5 μm to about 40 μm, about 5 μm to about 35 μm, about 5 μm to about 30 μm, about 5 μm to about 25 μm, about 5 μm to about 20 μm, about 5 μm to about 15 μm, about 5 μm to about 10 μm, about 10 μm to about 100 μm, about 10 μm to about 95 μm, about 10 μm to about 90 μm, about 10 μm to about 85 μm, about 10 μm to about 80 μm, about 10 μm to about 75 μm, about 10 μm to about 70 μm, about 10 μm to about 65 μm, about 10 μm to about 60 μm, about 10 μm to about 55 μm, about 10 μm to about 50 μm, about 10 μm to about 45 μm, about 10 μm to about 40 μm, about 10 μm to about 35 μm, about 10 μm to about 30 μm, about 10 μm to about 25 μm, about 10 μm to about 20 μm, about 10 μm to about 15 μm, about 15 μm to about 100 μm, about 15 μm to about 95 μm, about 15 μm to about 90 μm, about 15 μm to about 85 μm, about 15 μm to about 80 μm, about 15 μm to about 75 μm, about 15 μm to about 70 μm, about 15 μm to about 65 μm, about 15 μm to about 60 μm, about 15 μm to about 55 μm, about 15 μm to about 50 μm, about 15 μm to about 45 μm, about 15 μm to about 40 μm, about 15 μm to about 35 μm, about 15 μm to about 30 μm, about 15 μm to about 25 μm, about 15 μm to about 20 μm, about 20 μm to about 100 μm, about 20 μm to about 95 μm, about 20 μm to about 90 μm, about 20 μm to about 85 μm, about 20 μm to about 80 μm, about 20 μm to about 75 μm, about 20 μm to about 70 μm, about 20 μm to about 65 μm, about 20 μm to about 60 μm, about 20 μm to about 55 μm, about 20 μm to about 50 μm, about 20 μm to about 45 μm, about 20 μm to about 40 μm, about 20 μm to about 35 μm, about 20 μm to about 30 μm, about 20 μm to about 25 μm, about 25 μm to about 100 μm, about 25 μm to about 95 μm, about 25 μm to about 90 μm, about 25 μm to about 85 μm, about 25 μm to about 80 μm, about 25 μm to about 75 μm, about 25 μm to about 70 μm, about 25 μm to about 65 μm, about 25 μm to about 60 μm, about 25 μm to about 55 μm, about 25 μm to about 50 μm, about 25 μm to about 45 μm, about 25 μm to about 40 μm, about 25 μm to about 35 μm, about 25 μm to about 30 μm, about 30 μm to about 100 μm, about 30 μm to about 95 μm, about 30 μm to about 90 μm, about 30 μm to about 85 μm, about 30 μm to about 80 μm, about 30 μm to about 75 μm, about 30 μm to about 70 μm, about 30 μm to about 65 μm, about 30 μm to about 60 μm, about 30 μm to about 55 μm, about 30 μm to about 50 μm, about 30 μm to about 45 μm, about 30 μm to about 40 μm, about 30 μm to about 35 μm, about 35 μm to about 100 μm, about 35 μm to about 95 μm, about 35 μm to about 90 μm, about 35 μm to about 85 μm, about 35 μm to about 80 μm, about 35 μm to about 75 μm, about 35 μm to about 70 μm, about 35 μm to about 65 μm, about 35 μm to about 60 μm, about 35 μm to about 55 μm, about 35 μm to about 50 μm, about 35 μm to about 45 μm, about 35 μm to about 40 μm, about 40 μm to about 100 μm, about 40 μm to about 95 μm, about 40 μm to about 90 μm, about 40 μm to about 85 μm, about 40 μm to about 80 μm, about 40 μm to about 75 μm, about 40 μm to about 70 μm, about 40 μm to about 65 μm, about 40 μm to about 60 μm, about 40 μm to about 55 μm, about 40 μm to about 50 μm, about 40 μm to about 45 μm, about 45 μm to about 100 μm, about 45 μm to about 95 μm, about 45 μm to about 90 μm, about 45 μm to about 85 μm, about 45 μm to about 80 μm, about 45 μm to about 75 μm, about 45 μm to about 70 μm, about 45 μm to about 65 μm, about 45 μm to about 60 μm, about 45 μm to about 55 μm, about 45 μm to about 50 μm, about 50 μm to about 100 μm, about 50 μm to about 95 μm, about 50 μm to about 90 μm, about 50 μm to about 85 μm, about 50 μm to about 80 μm, about 50 μm to about 75 μm, about 50 μm to about 70 μm, about 50 μm to about 65 μm, about 50 μm to about 60 μm, about 50 μm to about 55 μm, about 55 μm to about 100 μm, about 55 μm to about 95 μm, about 55 μm to about 90 μm, about 55 μm to about 85 μm, about 55 μm to about 80 μm, about 55 μm to about 75 μm, about 55 μm to about 70 μm, about 55 μm to about 65 μm, about 55 μm to about 60 μm, about 60 μm to about 100 μm, about 60 μm to about 95 μm, about 60 μm to about 90 μm, about 60 μm to about 85 μm, about 60 μm to about 80 μm, about 60 μm to about 75 μm, about 60 μm to about 70 μm, about 60 μm to about 65 μm, about 65 μm to about 100 μm, about 65 μm to about 95 μm, about 65 μm to about 90 μm, about 65 μm to about 85 μm, about 65 μm to about 80 μm, about 65 μm to about 75 μm, about 65 μm to about 70 μm, about 70 μm to about 100 μm, about 70 μm to about 95 μm, about 70 μm to about 90 μm, about 70 μm to about 85 μm, about 70 μm to about 80 μm, about 70 μm to about 75 μm, about 75 μm to about 100 μm, about 75 μm to about 95 μm, about 75 μm to about 90 μm, about 75 μm to about 85 μm, about 75 μm to about 80 μm, about 80 μm to about 100 μm, about 80 μm to about 95 μm, about 80 μm to about 90 μm, about 80 μm to about 85 μm, about 85 μm to about 100 μm, about 85 μm to about 95 μm, about 85 μm to about 90 μm, about 90 μm to about 100 μm, about 90 μm to about 95 μm, or about 95 μm to about 100 μm. In some embodiments, the $D_{50}$ is about 5 μm, about 10 μm, about 15 μm, about 16 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, or about 100 μm. In some embodiments, the $D_{50}$ is about 10 μm, about 11 μm, about 12 μm, about 13 μm, about 14 μm, about 15 μm, about 16 μm, about 17 μm, about 18 μm, about 19 μm, or about 20 μm, or a value within a range defined by any of the preceding values. In some embodiments, the $D_{50}$ value is about 16 μm. The $D_{50}$ value can be measured by conventional particle size measuring techniques well known to those skilled in the art. Such techniques include, for example, sedimentation field flow fractionation, photon correlation spectroscopy, light scattering, laser diffraction and disc centrifugation.

In some embodiments, the particles have a particle size distribution (D-value, $D_{50}$), of 5 μm to 100 μm, such as 5 μm to 95 μm, 5 μm to 90 μm, 5 μm to 85 μm, 5 μm to 80 μm, 5 μm to 75 μm, 5 μm to 70 μm, 5 μm to 65 μm, 5 μm to 60 μm, 5 μm to 55 μm, 5 μm to 50 μm, 5 μm to 45 μm, 5 μm to 40 μm, 5 μm to 35 μm, 5 μm to 30 μm, 5 μm to 25 μm, 5 μm to 20 μm, 5 μm to 15 μm, 5 μm to 10 μm, 10 μm to 100 μm, 10 μm to 95 μm, 10 μm to 90 μm, 10 μm to 85 μm, 10 μm to 80 μm, 10 μm to 75 μm, 10 μm to 70 μm, 10 μm to 65 μm, 10 μm to 60 μm, 10 μm to 55 μm, 10 μm to 50 μm, 10 μm to 45 μm, 10 μm to 40 μm, 10 μm to 35 μm, 10 μm to 30 μm, 10 μm to 25 μm, 10 μm to 20 μm, 10 μm to 15 μm, 15 μm to 100 μm, 15 μm to 95 μm, 15 μm to 90 μm, 15 μm to 85 μm, 15 μm to 80 μm, 15 μm to 75 μm, 15 μm to 70 μm, 15 μm to 65 μm, 15 μm to 60 μm, 15 μm to 55 μm, 15 μm to 50 μm, 15 μm to 45 μm, 15 μm to 40 μm, 15 μm to 35 μm, 15 μm to 30 μm, 15 μm to 25 μm, 15 μm to 20 μm, 20 μm to 100 μm, 20 μm to 95 μm, 20 μm to 90 μm, 20 μm to 85 μm, 20 μm to 80 μm, 20 μm to 75 μm, 20 μm to 70 μm, 20 μm to 65 μm, 20 μm to 60 μm, 20 μm to 55 μm, 20 μm to 50 μm, 20 μm to 45 μm, 20 μm to 40 μm, 20 μm to 35 μm, 20 μm to 30 μm, 20 μm to 25 μm, 25 μm to 100 μm, 25 μm to 95 μm, 25 μm to 90 μm, 25 μm to 85 μm, 25 μm to 80 μm, 25 μm to 75 μm, 25 μm to 70 μm, 25 μm to 65 μm, 25 μm to 60 μm, 25 μm to 55 μm, 25 μm to 50 μm, 25 μm to 45 μm, 25 μm to 40 μm, 25 μm to 35 μm, 25 μm to 30 μm, 30 μm to 100 μm, 30 μm to 95 μm, 30 μm to 90 μm, 30 μm to 85 μm, 30 μm to 80 μm, 30 μm to 75 μm, 30 μm to 70 μm, 30 μm to 65 μm, 30 μm to 60 μm, 30 μm to 55 μm, 30 μm to 50 μm, 30 μm to 45 μm, 30 μm to 40 μm, 30 μm to 35 μm, 35 μm to 100 μm, 35 μm to 95 μm, 35 μm to 90 μm, 35 μm to 85 μm, 35 μm to 80 μm, 35 μm to 75 μm, 35 μm to 70 μm, 35 μm to 65 μm, 35 μm to 60 μm, 35 μm to 55 μm, 35 μm to 50 μm, 35 μm to 45 μm, 35 μm to 40 μm, 40 μm to 100 μm, 40 μm to 95 μm, 40 μm to 90 μm, 40 μm to 85 μm, 40 μm to 80 μm, 40 μm to 75 μm, 40 μm to 70 μm, 40 μm to 65 μm, 40 μm to 60 μm, 40 μm to 55 μm, 40 μm to 50 μm, 40 μm to 45 μm, 45 μm to 100 μm, 45 μm to 95 μm, 45 μm to 90 μm, 45 μm to 85 μm, 45 μm to 80 μm, 45 μm to 75 μm, 45 μm to 70 μm, 45 μm to 65 μm, 45 μm to 60 μm, 45 μm to 55 μm, 45 μm to 50 μm, 50 μm to 100 μm, 50 μm to 95 μm, 50 μm to 90 μm, 50 μm to 85 μm, 50 μm to 80 μm, 50 μm to 75 μm, 50 μm to 70 μm, 50 μm to 65 μm, 50 μm to 60 μm, 50 μm to 55 μm, 55 μm to 100 μm, 55 μm to 95 μm, 55 μm to 90 μm, 55 μm to 85 μm, 55 μm to 80 μm, 55 μm to 75 μm, 55 μm to 70 μm, 55 μm to 65 μm, 55 μm to 60 μm, 60 μm to 100 μm, 60 μm to 95 μm, 60 μm to 90 μm, 60 μm to 85 μm, 60 μm to 80 μm, 60 μm to 75 μm, 60 μm to 70 μm, 60 μm to 65 μm, 65 μm to 100 μm, 65 μm to 95 μm, 65 μm to 90 μm, 65 μm to 85 μm, 65 μm to 80 μm, 65 μm to 75 μm, 65 μm to 70 μm, 70 μm to 100 μm, 70 μm to 95 μm, 70 μm to 90 μm, 70 μm to 85 μm, 70 μm to 80 μm, 70 μm to 75 μm, 75 μm to 100 μm, 75 μm to 95 μm, 75 μm to 90 μm, 75 μm to 85 μm, 75 μm to 80 μm, 80 μm to 100 μm, 80 μm to 95 μm, 80 μm to 90 μm, 80 μm to 85 μm, 85 μm to 100 μm, 85 μm to 95 μm, 85 μm to 90 μm, 90 μm to 100 μm, 90 μm to 95 μm, or 95 μm to 100 μm. In some embodiments, the $D_{50}$ is 5 μm, 10 μm, 15 μm, 16 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm. In some embodiments, the $D_{50}$ is 10 μm, 11 μm, 12 μm, 13 μm, 14 μm, 15 μm, 16 μm, 17 μm, 18 μm, 19 μm, or 20 μm, or a value within a range defined by any of the preceding values. In some embodiments, the $D_{50}$ value is 16 μm. The $D_{50}$ value can be measured by conventional particle size measuring techniques well known to those skilled in the art. Such techniques include, for example, sedimentation field flow fractionation, photon correlation spectroscopy, light scattering, laser diffraction and disc centrifugation.

The SDDs of the present disclosure have a low residual solvent content. "Residual solvent content," as used herein, refers to the amount of solvent present in the SDD following spray drying, immediately upon exit from the spray dryer. The presence of solvent in the SDD lowers the glass transition temperature ($T_g$) of the dispersion. In some embodiments, mobility of the compound of Formula (I), or a pharmaceutically acceptable salt thereof, in the SDD and its propensity to phase separate and crystallize decreases as the amount of residual solvent in the SDD decreases. In some embodiments, the SDDs have a residual solvent content of not more than about 10 wt %, such as not more than about 5 wt %, or not more than about 1 wt %. For example, the SDDs have a residual solvent content of about 2 wt %, about 1.9 wt %, about 1.8 wt %, about 1.7 wt %, about 1.6 wt %, about 1.5 wt %, about 1.4 wt %, about 1.3 wt %, about 1.2 wt %, about 1.1 wt %, about 1 wt %, about 0.9 wt %, about 0.8 wt %, about 0.7 wt %, about 0.6 wt %, about 0.5 wt %, or less. In some embodiments, the SDDs have a residual solvent content of less than about 2 wt %. In some embodiments, the SDDs have a residual solvent content of less than about 1 wt %. In some embodiments, the SDDs have a residual solvent content of about 0.5 wt % or less. In some embodiments, the SDDs have a residual solvent content of not more than 10 wt %, such as not more than 5 wt %, or not more than 1 wt %. For example, the SDDs may have a residual solvent content of 2 wt %, 1.9 wt %, 1.8 wt %, 1.7 wt %, 1.6 wt %, 1.5 wt %, 1.4 wt %, 1.3 wt %, 1.2 wt %, 1.1 wt %, 1 wt %, 0.9 wt %, 0.8 wt %, 0.7 wt %, 0.6 wt %, 0.5 wt %, or less. In some embodiments, the SDDs have a residual solvent content of less than 2 wt %. In some embodiments, the SDDs have a residual solvent content of less than 1 wt %. In some embodiments, the SDDs have a residual solvent content of 0.5 wt % or less.

In some embodiments, the compound of Formula (I), or a pharmaceutically acceptable salt thereof, in the spray-dried dispersion is substantially amorphous. As used herein, "substantially amorphous" means that the amount of the compound of Formula (I), or a pharmaceutically acceptable salt thereof, in amorphous form is at least 60 wt % and that the amount of crystalline form present does not exceed 20 wt %. In some embodiments, the compound of Formula (I), or a pharmaceutically acceptable salt thereof, in the dispersion is "almost completely amorphous," meaning that at least 90 wt % of the drug is amorphous, or that the amount of the compound of Formula (I), or a pharmaceutically acceptable salt thereof, in the crystalline form does not exceed 10 wt %. Amounts of crystalline drug can be measured by powder X-ray diffraction (PXRD), scanning electron microscope (SEM) analysis, differential scanning calorimetry (DSC), polarized light microscopy (PLM), or any other standard quantitative or qualitative measurement used to detect crystalline material. Without wishing to be bound by any theory, it is believed that the amorphous, or non-crystalline form, in combination with the polymer, leads to greater ease of dissolution and absorption in the desired location, for example, the intestines, resulting in enhanced bioavailability as compared to a crystalline form of the compound of Formula (I) without polymer.

Process for Preparing Spray-Dried Dispersions

Provided in the present disclosure are methods for preparing a spray-dried dispersion containing a polymer and the compound of Formula (I), or a pharmaceutically acceptable salt thereof, such as the SDDs described herein. In some embodiments, the method includes dissolving the compound of Formula (I), or a pharmaceutically acceptable salt thereof, and the polymer in an organic solvent to form a solution; and spray-drying the solution to produce the spray-dried dispersion, wherein the spray-drying forms homogeneous particles of the compound of Formula (I) and the polymer. In some embodiments, the product obtained by spray-drying is dried to remove the solvent or solvent mixture. In some embodiments, the organic solvent is acetone.

The SDDs disclosed herein can be obtained by spray-drying a mixture comprising the compound of Formula (I), or a pharmaceutically acceptable salt thereof, one or more polymer(s), and an appropriate solvent or solvent mixture. Spray-drying involves atomization of a liquid mixture containing, for example, a solid and a solvent or solvent mixture, and removal of the solvent or solvent mixture. Atomization can be done, for example, through a two-fluid or pressure or electrosonic nozzle, or on a rotating disk.

Spray-drying converts a liquid feed to a dried particulate form. In some embodiments, spray-drying involves the atomization of a liquid feed solution into a spray of droplets and contacting the droplets with hot air or gas in a drying chamber. The composition to be spray-dried can be any solution, coarse suspension, slurry, colloidal dispersion, or paste that can be atomized using the selected spray-drying apparatus. In some embodiments, the composition is a solution that is clear and free of undissolved solids. In some embodiments, the sprays are produced by either rotary (wheel) or nozzle atomizers. Evaporation of moisture from the droplets and formation of dry particles proceed under controlled temperature and airflow conditions. Commercially available types of apparatus can be used to conduct the spray-drying. For example, commercial spray dryers are manufactured by Buchi Ltd. and Niro (e.g., the PSD line of spray driers manufactured by Niro). Techniques and methods for spray-drying can also be found in *Perry's Chemical Engineering Handbook*, 6th Ed., R. H. Perry, D. W. Green & J. O. Maloney, eds., McGraw-Hill Book Co. (1984); and Marshall, "Atomization and Spray-Drying" 50, Chem. Eng. Prog. Monogr. Series 2 (1954).

In some embodiments, the spray-drying is conducted with an inlet temperature of from about 40° C. to about 100° C., for example, from about 60° C. to about 80° C., or from about 70° C. to about 75° C. In some embodiments, the spray-drying is conducted with an inlet temperature of about 40° C., about 45° C., about 50° C., about 55° C., about 60° C., about 70° C., about 72° C., about 75° C., about 80° C., about 85° C., about 90° C., about 95° C., or about 100° C., or within a range defined by any of the preceding values. In some embodiments, the inlet temperature is about 60° C. to about 80° C. In some embodiments, the spray-drying is conducted with an inlet temperature of about 61° C., about 63° C., about 65° C., about 67° C., about 69° C., about 71° C., about 73° C., about 75° C., about 77° C., about 79° C., about 81° C., about 83° C., or about 85° C., or within a range defined by any of the preceding values. In some embodiments, the inlet temperature is about 72° C.

In some embodiments, the spray-drying is conducted with an inlet temperature of from 40° C. to 100° C., for example, from 60° C. to 80° C., or from 70° C. to 75° C. In some embodiments, the spray-drying is conducted with an inlet temperature of 40° C., 45° C., 50° C., 55° C., 60° C., 70° C., 72° C., 75° C., 80° C., 85° C., 90° C., 95° C., or 100° C., or within a range defined by any of the preceding values. In some embodiments, the inlet temperature is 60° C. to 80° C. In some embodiments, the spray-drying is conducted with an inlet temperature of 61° C., 63° C., 65° C., 67° C., 69° C., 71° C., 73° C., 75° C., 77° C., 79° C., 81° C., 83° C., or 85° C., or within a range defined by any of the preceding values. In some embodiments, the inlet temperature is 72° C.

In some embodiments, the spray-drying is conducted with an outlet temperature of from about 20° C. to about 75° C., for example, from about 25° C. to about 50° C., or from about 30° C. to about 40° C. In some embodiments, the spray-drying is conducted with an outlet temperature of about 20° C., about 25° C., about 30° C., about 35° C., about 40° C., about 45° C., about 50° C., about 55° C., about 60° C., about 65° C., about 70° C., or about 75° C., or within a range defined by any of the preceding values. In some embodiments, the outlet temperature is about 25° C. to about 45° C. In some embodiments, the spray-drying is conducted with an outlet temperature of about 24° C., about 26° C., about 28° C., about 30° C., about 32° C., about 34° C., about 36° C., about 38° C., about 40° C., about 42° C., about 44° C., or about 46° C., or within a range defined by any of the preceding values. In some embodiments, the outlet temperature is about 35° C.

In some embodiments, the spray-drying is conducted with an outlet temperature of from 20° C. to 75° C., for example, from 25° C. to 50° C., or from 30° C. to 40° C. In some embodiments, the spray-drying is conducted with an outlet temperature of 20° C., 25° C., 30° C., 35° C., 40° C., 45° C., 50° C., 55° C., 60° C., 65° C., 70° C., or 75° C., or within a range defined by any of the preceding values.

In some embodiments, the outlet temperature is 25° C. to 45° C. In some embodiments, the spray-drying is conducted with an outlet temperature of 24° C., 26° C., 28° C., 30° C., 32° C., 34° C., 36° C., 38° C., 40° C., 42° C., 44° C., or 46° C., or within a range defined by any of the preceding values. In some embodiments, the outlet temperature is 35° C.

In some embodiments, the method involves removing the organic solvent after formation of the spray-dried dispersion. In some embodiments, the organic solvent is removed by drying the SDD. In some embodiments, a secondary drying process, such as fluidized bed drying, vacuum drying, tray drying, microwave drying, rotary drum drying or biconical vacuum drying is used to remove or reduce residual solvents, such as the organic solvent, to pharmaceutically acceptable levels. In some embodiments, the SDD is dried with a convection tray dryer.

In some embodiments, the homogeneous particles produced by the methods of the present disclosure have a bulk density of less than about 0.2 g/mL, or less than about 0.15 g/mL. In some embodiments, the homogeneous particles produced by the methods of the present disclosure have a bulk density of about 0.19 g/mL, about 0.18 g/mL, about 0.17 g/mL, about 0.16 g/mL, about 0.15 g/mL, about 0.14 g/mL, about 0.13 g/mL, about 0.12 g/mL, about 0.11 g/mL, about 0.1 g/mL, about 0.09 g/mL, about 0.08 g/mL, about 0.07 g/mL, about 0.06 g/mL or about 0.05 g/mL, or within a range defined by any of the preceding values. In some embodiments, the homogeneous particles produced by the methods of the present disclosure have a bulk density of less than 0.2 g/mL, or less than 0.15 g/mL. In some embodiments, the homogeneous particles produced by the methods of the present disclosure have a bulk density of 0.19 g/mL, 0.18 g/mL, 0.17 g/mL, 0.16 g/mL, 0.15 g/mL, 0.14 g/mL, 0.13 g/mL, 0.12 g/mL, 0.11 g/mL, 0.1 g/mL, 0.09 g/mL, 0.08 g/mL, 0.07 g/mL, 0.06 g/mL or 0.05 g/mL, or within a range defined by any of the preceding values. The term "bulk density," as used herein, refers to a property of powders and is defined as the mass of many particles of the material divided by the total volume they occupy. The total volume includes particle volume, inter-particle void volume and internal pore volume.

In some embodiments, the homogeneous particles produced by the methods of the present disclosure have a tapped density of less than about 0.3 g/mL, or less than about 0.25 g/mL. In some embodiments, the homogeneous particles produced by the methods of the present disclosure have a tapped density of about 0.29 g/mL, about 0.28 g/mL, about 0.27 g/mL, about 0.26 g/mL, about 0.25 g/mL, about 0.24 g/mL, about 0.23 g/mL, about 0.22 g/mL, about 0.21 g/mL, about 0.2 g/mL, or about 0.19 g/mL, or within a range defined by any of the preceding values. In some embodiments, the homogeneous particles produced by the methods of the present disclosure have a tapped density of less than 0.3 g/mL, or less than 0.25 g/mL. In some embodiments, the homogeneous particles produced by the methods of the present disclosure have a tapped density of 0.29 g/mL, 0.28 g/mL, 0.27 g/mL, 0.26 g/mL, 0.25 g/mL, 0.24 g/mL, 0.23 g/mL, 0.22 g/mL, 0.21 g/mL, 0.2 g/mL, or 0.19 g/mL, or within a range defined by any of the preceding values. The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

Deuterated Compounds

Also disclosed herein are compounds having the structure of the following formula (II):

(II)

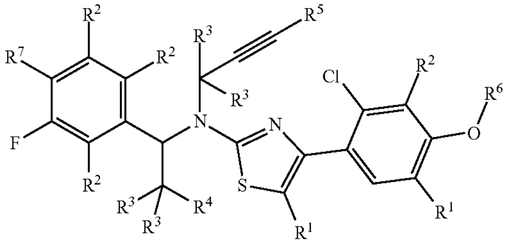

or a pharmaceutically acceptable salt thereof, wherein:

each $R^1$ is independently $C(R^A)_3$;

each $R^A$ is independently hydrogen or deuterium;

each $R^2$ is independently hydrogen or deuterium;

each $R^3$ is independently hydrogen or deuterium;

$R^4$ is

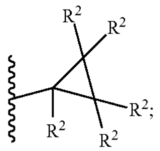

$R^5$ is hydrogen or deuterium;

$R^6$ is $C(R^A)_3$; and $R^7$ is $C(R^B)_3$, wherein at least one of $R^A$, $R^B$, $R^2$, $R^3$ and $R^5$ is deuterium.

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

In some embodiments, the compound of Formula (II) may be one of the following, or a pharmaceutically acceptable salt thereof:

1

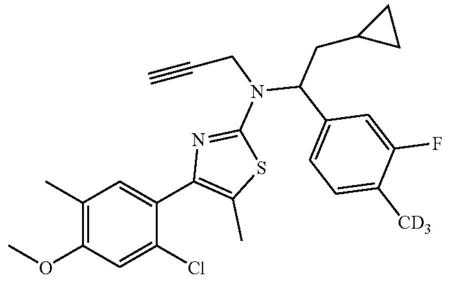

-continued

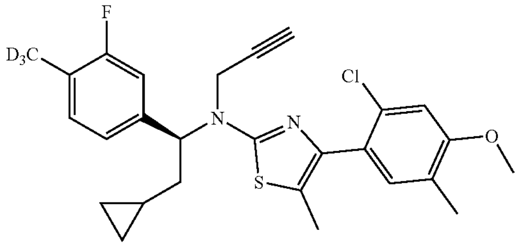

2

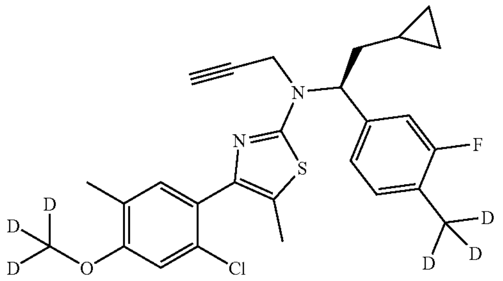

3

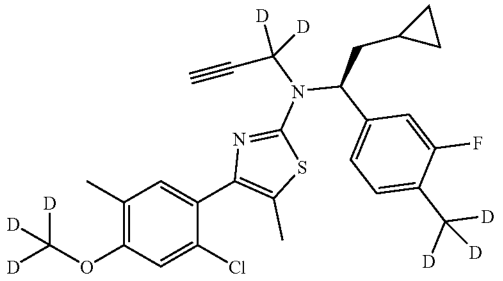

4

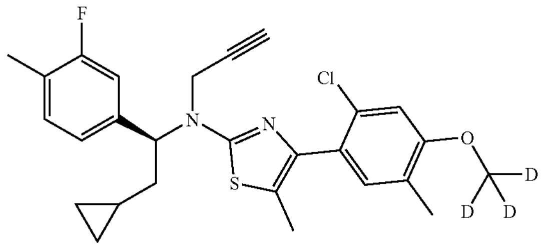

5

Pharmaceutical Compositions

The methods and uses disclosed herein can comprise administering the compound of Formula (I) as a pharmaceutical composition.

In some embodiments of the methods described herein, the 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof is administered in a pharmaceutical composition further comprising one or more pharmaceutically acceptable excipients.

Also provided herein is a pharmaceutical composition comprising 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, for use in any of the methods described herein.

In some embodiments, the methods and uses described herein comprise administering a pharmaceutical composition that does not comprise a spray-dried dispersion of the compound of Formula (I), as specified, e.g., in Example 1.

Accordingly, in some embodiments, the pharmaceutical composition does not comprise any of the following polymers: hydroxypropylmethylcellulose acetate succinate-L (HPMCAS-L); polyvinyl pyrrolidone vinyl acetate 64 (PVP/VA 64); HPMCAS-M; and methyl methacrylate copolymer (1:1) (Eudragit® L100).

In some embodiments, the methods and uses described herein comprise administering a pharmaceutical composition that is not the reference formulation described in Example 9. Accordingly, in some embodiments, the pharmaceutical composition does not comprise at least three of the excipients selected from caprylic/capric triglyceride (caprylic/capric triglyceride sold under the trademark LABRAFAC® LIPOPHILE, Gattefosse, France); propylene glycol dicrapolate/dicaprate (propylene glycol dicrapolate/dicaprate sold under the trademark LABRAFAC® PG, Gattefosse, France); oleoyl polyoxyl-6 glycerides (oleoyl polyoxyl-6 glycerides sold under the trademark LABRAFIL® M 1944 CS, Gattefosse, France); polysorbate 20; polyoxyl castor oil (polyoxyl castor oil sold under the trademark KOLLIPHOR® RH 40, BASF, Germany); polyoxyl 15 hydroxystearate (polyoxyl 15 hydroxystearate sold under the trademark KOLLIPHOR® HS 15, BASF, Germany); lauroyl polyoxyl-32 glycerides (lauroyl polyoxyl-32 glycerides sold under the trademark GELUCIRE® 44/14, Gattefosse, France); d-α-tocopheryl polyethylene glycol 1000 succinate (TPGS); and diethylene glycol monoethyl ether (diethylene glycol monoethyl ether sold under the trademark TRANSCUTOL®, Gattefosse, France).

In some embodiments, the methods and uses described herein comprise administering a pharmaceutical composition that is the formulation described in Example 9. In some embodiments, the methods and uses described herein comprise administering a pharmaceutical composition that is the formulation described in Example 11. In some embodiments, the methods and uses described herein comprise administering a pharmaceutical composition that is the formulation described in Example 12. In some embodiments, the methods and uses described herein comprise administering a pharmaceutical composition that is the formulation described in Example 13.

In some embodiments, the pharmaceutical compositions include a spray-dried dispersion containing a polymer and the compound of Formula (I), or a pharmaceutically acceptable salt thereof.

In some embodiments, the pharmaceutical composition includes the SDD comprising a compound of Formula (I) and one or more pharmaceutically acceptable excipients. In some embodiments, the SDD is present in the pharmaceutical composition in an amount of about 20% to about 90% w/w of the composition, such as about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, or about 85% to about 90% w/w of the composition. In some embodiments, the SDD is present in an amount of about 40% to about 90% w/w of the composition. In some embodiments, the SDD is present in an amount of about 40% to about 80% w/w of the composition. In some embodiments, the SDD is present in the pharmaceutical composition in an amount of about 60% to about 80% w/w of the composition. In some embodiments, the SDD is present in an amount of about 80% w/w of the composition. In some embodiments, the SDD is present in the pharmaceutical composition in an amount of about 1% to about 20% w/w of the composition, such as about 13% w/w of the composition.

In some embodiments, the pharmaceutical composition includes the SDD comprising a compound of Formula (I) and one or more pharmaceutically acceptable excipients. In some embodiments, the SDD is present in the pharmaceutical composition in an amount of 20% to 90% w/w of the composition, such as 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 90%, 35% to 85%, 35% to 80%, 35% to 75%, 35% to 70%, 35% to 65%, 35% to about 60%, 35% to 55%, 35% to 50%, 35% to 45%, 35% to 40%, 40% to 90%, 40% to 85%, 40% to 80%, 40% to 75%, 40% to 70%, 40% to 65%, 40% to 60%, 40% to 55%, 40% to 50%, 40% to 45%, 45% to 90%, 45% to 85%, 45% to 80%, 45% to 75%, 45% to 70%, 45% to 65%, 45% to 60%, 45% to 55%, 45% to 50%, 50% to 90%, 50% to 85%, 50% to 80%, 50% to 75%, 50% to 70%, 50% to 65%, 50% to 60%, 50% to 55%, 55% to 90%, 55% to 85%, 55% to 80%, 55% to 75%, 55% to 70%, 55% to 65%, 55% to 60%, 60% to 90%, 60% to 85%, 60% to 80%, 60% to 75%, 60% to 70%, 60% to 65%, 65% to 90%, 65% to 85%, 65% to 80%, 65% to 75%, 65% to 70%, 70% to 90%, 70% to 85%, 70% to 80%, 70% to 75%, 75% to 90%, 75% to 85%, 75% to 80%, 80% to 90%, 80% to 85%, or about 85% to 90% w/w of the composition. In some embodiments, the SDD is present in an amount of 40% to 90% w/w of the composition. In some embodiments, the SDD is present in an amount of 40% to 80% w/w of the composition. In some embodiments, the SDD is present in the pharmaceutical composition in an amount of 60% to 80% w/w of the composition. In some embodiments, the SDD is present in an amount of 80% w/w of the composition. In some embodiments, the SDD is present in the pharmaceutical composition in an amount of about 1% to about 20% w/w of the composition, such as about 13% w/w of the composition.

In some embodiments of the pharmaceutical compositions disclosed herein (e.g., a composition including an SDD), the pharmaceutically acceptable excipient is selected from the group consisting of a filler, a lubricant, and combinations thereof. In some embodiments, the pharmaceutical excipients are selected from the group consisting of a glidant, a filler, a disintegrant, a lubricant, and a combination thereof.

In some embodiments, the pharmaceutical composition includes a filler. In some embodiments, the filler is selected from among binders, diluents, disintegrants, glidants, surfactants, and combinations thereof.

In some embodiments, the filler include saccharides (e.g., sugars, starch, and cellulose), gelatin, calcium carbonate, and synthetic polymers (e.g., polyvinylpyrrolidone, polyethylene glycol, and poloxamers (e.g., poloxamer 188, a copolymer of polyoxyethylene and polyoxypropylene)). Exemplary fillers include, but are not limited to, glucose, sucrose, lactose, a starch, including modified starches such as sodium starch glycolate (e.g., sodium starch glycolate sold under the trademark EXPLOTAB®), xylitol, dextrin, saccharose, sorbitol, mannitol (e.g., mannitol sold under the trademark PARTECK® M 200 (mannitol with an average particle size of about 50 μm to about 500 μm) or mannitol sold under the trademark PARTECK® M 100 (mannitol with an average particle size of less than 212 μm)), a cellulose, a polyvinylpyrrolidone, a polyethylene glycol, a polyvinyl alcohol, a polymethacrylate, dibasic calcium phosphate, magnesium stearate, calcium stearate, sodium stearate, stearic acid, hydrogenated vegetable oils, a mineral oil, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, aliginic acid, alginates (e.g., sodium alginate), calcium silicate, and ion exchange resins. Exemplary cellulose fillers include microcrystalline cellulose (e.g., microcrystalline cellulose sold under the trademark AVICEL® PH-101 (microcrystalline cellulose with an average particle size of approximately 50 μm) or microcrystalline cellulose sold under the trademark AVICEL® PH 200 (microcrystalline cellulose with an average particle size of approximately 180 μm)), methyl cellulose, ethyl cellulose, hydroxypropyl cellulose, and hydroxypropylmethylcellulose. Exemplary fillers include cross-linked polyvinylpyrrolidone such as with an average particle size of 90 μm to 130 μm) or with an average particle size of 10 μm to 30 μm). Other fillers known to those of skill in the art are also contemplated as being useful when formulated in the pharmaceutical compositions described herein.

In some embodiments, the filler is a binder. Binders include agents that hold the active pharmaceutical ingredient (e.g., spray-dried dispersion containing a polymer and the compound of Formula (I), or a pharmaceutically acceptable salt thereof) and inactive ingredients together in a cohesive mix. Exemplary binders include, but are not limited to, glucose, sucrose, lactose, a starch, including modified starches such as sodium starch glycolate (sodium starch glycolate sold under the trademark EXPLOTAB®), xylitol, dextrin, saccharose, sorbitol, mannitol (e.g., mannitol sold under the trademark PARTECK® M 200 (mannitol with an average particle size of about 50 μm to about 500 μm), mannitol sold under the trademark PARTECK® M 100 (mannitol with an average particle size of less than 212 μm)), gelatin, gum tragacanth, acacia mucilage, a cellulose, a polyvinylpyrrolidone, a polyethylene glycol, a polyvinyl alcohol, a polymethacrylate, and sodium starch glycolate. Exemplary cellulose fillers include microcrystalline cellulose (e.g., microcrystalline cellulose sold under the trademark AVICEL® PH-101 (microcrystalline cellulose with an average particle size of approximately 50 μm) or microcrystalline cellulose sold under the trademark AVICEL® PH 200 (microcrystalline cellulose with an average particle size of approximately 180 μm)), cellulose ethers, methyl cellulose, ethyl cellulose, croscarmellose sodium, sodium carboxy methyl cellulose starches, hydroxypropyl cellulose, and hydroxypropyl methyl cellulose. Exemplary polyvinylpyrrolidone fillers include cross-linked polyvinylpyrrolidone such as cross-linked polyvinylpyrrolidone sold under the trademark KOLLIDON® CL (crospovidone with an average particle size of 90 μm to 130 μm) or cross-linked polyvinylpyrrolidone sold under the trademark KOLLIDON® CL-SF (crospovidone with an average particle size of 10 μm to 30 μm). Other binders known to those of skill in the art are also contemplated as being useful when formulated in the compositions described herein.

In some embodiments, the filler is a diluent. Suitable diluents include, but are not limited to, lactose, mannitol, isomalt, sucrose, dextrose, and sorbitol.

In some embodiments, the filler is a disintegrant. Disintegrants include any agent that promotes breakup of the formulation in an aqueous environment, for example, to promote more rapid release of the active pharmaceutical ingredient (e.g., the compound of Formula (I), or a pharmaceutically acceptable salt thereof). Exemplary disintegrants include, but are not limited to, starch and modified starches, such as corn starch, potato starch, sodium starch glycolate or croscarmellose sodium, alginic acid, alginates, such as sodium alginate, polyvinylpyrrolidone, bentonite, methylcellulose, agar, carboxymethylcellulose, crospovidone, acid-carbonate effervescent systems, such as citric acid with bicarbonate salts, and ion exchange resins. Other disintegrants known to those of skill in the art are also contemplated as being useful when formulated in the compositions described herein.

In some embodiments, the pharmaceutical composition comprises a disintegrant. In some embodiments, the pharmaceutical composition comprises about 1 w/w % to about 30 w/w % of the disintegrant. In some embodiments, the pharmaceutical composition comprises about 5 w/w % to about 15 w/w % of the disintegrant. In some embodiments, the pharmaceutical composition comprises about 10 w/w % of the disintegrant. In some embodiments, the disintegrant is selected from croscarmellose sodium, sodium starch glycolate, crospovidone, and sodium bicarbonate. In some embodiments, the disintegrant is croscarmellose sodium.

In some embodiments, the filler is a glidant. Glidants can be used to improve the flowability of a powder or granules or both. Glidants include, but are not limited to, silicone dioxide, such as colloidal silicon dioxide or hydrated silicon dioxide, magnesium silicate, magnesium aluminometasilicate, talc, starch, calcium silicate, light anhydrous silicic acid, and silicon dioxide aerogels.

In some embodiments, the pharmaceutical composition comprises a glidant. In some embodiments, the pharmaceutical composition comprises about 0.1 w/w % to about 5 w/w % of the glidant. In some embodiments, the pharmaceutical composition comprises about 0.1 w/w % to about 1 w/w % of the glidant. In some embodiments, the pharmaceutical composition comprises about 0.67 w/w % of the glidant. In some embodiments, the glidant is selected from calcium silicate, silicon dioxide, and talc. In some embodiments, the glidant is calcium silicate.

In some embodiments, the filler is a surfactant, wetting agent, solubilizer, or combination thereof. Examples include, but are not limited to, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., polyoxyethylene sorbitan fatty acid esters sold under the trademark TWEEN®), polyoxyethylene stearates, sodium dodecylsulfate, tyloxapol (a nonionic liquid polymer of the alkyl aryl polyether alcohol type, also known as superinone or triton). Other examples include, but are not limited to, poloxamers such as poloxamers sold under the trademarks PLURONIC® F68, F127, and F108, which are block copolymers of ethylene oxide and propylene oxide, and polyxamines such as a poloxamer sold under the trademark TETRONIC® 908 (also known as a poloxamer sold under the trademark POLOXAMINE® 908), which is a tetrafunctional block copolymer derived from sequential addition of propylene oxide and ethylene oxide to ethylenediamine (available from BASF), dextran, lecithin, dialkylesters of sodium sulfosuccinic acid, such as dialkylesters of sodium sulfosuccinic acid sold under the trademark AEROSOL® OT, which is a dioctyl ester of sodium sulfosuccinic acid (available from American Cyanimid), sodium lauryl sulfate sold under the trademark DUPONOL® P, which is a sodium lauryl sulfate (available from DuPont), alkyl aryl polyether sulfonate sold under the trademark TRITON® X-200, which is an alkyl aryl polyether sulfonate (available from Rohm and Haas), polyoxyethylene sorbitan fatty acid esters sold under the trademarks TWEEN® 20 and TWEEN® 80, which are polyoxyethylene sorbitan fatty acid esters (available from ICI Specialty Chemicals), polyethylene glycols sold under the trademarks CARBOWAX™ 3550 and 934, which are polyethylene glycols (available from Union Carbide), mixtures of sucrose stearate and sucrose distearate sold under the trademarks CRODESTA™ F-110, which is a mixture of sucrose stearate and sucrose distearate, and CRODESTA™ SL-40 (both available from Croda Inc.), and SA90HCO, which has the chemical formula $C_{18}H_{37}$—$CH_2(CON(CH_3)CH_2(CHOH)_4CH_2OH)_2$.

In some embodiments, the pharmaceutical composition comprises a filler. In some embodiments, the pharmaceutical composition comprises about 30 w/w % to about 99 w/w % of the filler. In some embodiments, the pharmaceutical composition comprises about 50 w/w % to about 90 w/w % of the filler. In some embodiments, the pharmaceutical composition comprises about 75.5 w/w % of the filler. In some embodiments, the filler is selected from mannitol, microcrystalline cellulose, lactose, starch, isomalt, silicified microcrystalline cellulose, dicalcium phosphate, maltodextrin, and a combination thereof. In some embodiments, the filler is a combination of mannitol and microcrystalline cellulose. In some embodiments, the pharmaceutical composition comprises about 30 w/w % to about 80 w/w % of mannitol. In some embodiments, the pharmaceutical composition comprises about 50 w/w % to about 60 w/w % of mannitol. In some embodiments, the pharmaceutical composition comprises about 56 w/w % of mannitol. In some embodiments, the pharmaceutical composition comprises about 1 w/w % to about 50 w/w % of microcrystalline cellulose. In some embodiments, the pharmaceutical composition comprises about 10 w/w % to about 30 w/w % of microcrystalline cellulose. In some embodiments, the pharmaceutical composition comprises about 20 w/w % of microcrystalline cellulose. In some embodiments, the pharmaceutical composition comprises about 56 w/w % of mannitol and about 20 w/w % of microcrystalline cellulose.

In some embodiments, the pharmaceutical composition includes a lubricant. Lubricants are agents added to pharmaceutical formulations to reduce friction during processing and prevent ingredients from clumping together. Exemplary lubricants include, but are not limited to, talc, starch, magnesium stearate, calcium stearate, sodium stearate, zinc stearate, stearic acid, vegetable stearin, adipic acid, waxy fatty acids, such as glyceryl behenate, a hydrogenated vegetable oil, a mineral oil, a polyethylene glycol, lycopodium, sodium lauryl sulfate, magnesium lauryl sulfate, glyceryl palmitostearate, sodium benzoate, sodium chloride, sterotex, glycerol monostearate, sodium stearyl fumarate, colloidal silicon dioxide, sodium benzoate, sodium oleate, and sodium acetate. Other lubricants known to those of skill in the art are also contemplated as being useful when formulated in the compositions described herein.

In some embodiments, the pharmaceutical composition comprises a lubricant. In some embodiments, the pharmaceutical composition comprises about 0.1 w/w % to about 10 w/w % of the lubricant. In some embodiments, the pharmaceutical composition comprises about 0.1 w/w % to about 1 w/w % of the lubricant. In some embodiments, the pharmaceutical composition comprises about 0.5 w/w % of the lubricant. In some embodiments, the pharmaceutical lubricant is selected from sodium stearyl fumarate, magnesium stearate, stearic acid sodium lauryl sulfate, sodium oleate, glyceryl behenate, and talc. In some embodiments, the lubricant is sodium stearyl fumarate.

In some embodiments, the pharmaceutical composition comprises:

(a) the spray-dried dispersion comprising the compound of Formula (I), or a pharmaceutically acceptable salt thereof, and a polymer;
(b) a glidant;
(c) a filler; and
(d) a disintegrant.

In some embodiments, the pharmaceutical composition comprises:

(a) about 1 w/w % to about 20 w/w % of the spray-dried dispersion comprising the compound of Formula (I), or a pharmaceutically acceptable salt thereof, and a polymer;
(b) about 0.1 w/w % to about 1 w/w % of a glidant;
(c) about 50 w/w % to about 90 w/w % of a filler; and
(d) about 5 w/w % to about 0.2 w/w % of a disintegrant.

In some embodiments, the pharmaceutical composition comprises:

(a) about 13 w/w % of the spray-dried dispersion comprising the compound of Formula (I), or a pharmaceutically acceptable salt thereof, and a polymer;
(b) about 0.67 w/w % of a glidant;
(c) about 75.5 w/w % of a filler; and
(d) about 10 w/w % of a disintegrant.

In some embodiments, the pharmaceutical composition comprises:

(a) the spray-dried dispersion of Example 3;
(b) calcium silicate;
(c) a combination of mannitol and microcrystalline cellulose; and
(d) croscarmellose sodium.

In some embodiments, the pharmaceutical composition comprises:

(a) about 1 w/w % to about 20 w/w % of the spray-dried dispersion of Example 3;
(b) about 0.1 w/w % to about 1 w/w % of calcium silicate;
(c) about 50 w/w % to about 60 w/w % of mannitol and about 10 w/w % to about 30 w/w % of microcrystalline cellulose; and
(d) about 5 w/w % to about 0.2 w/w % of croscarmellose sodium.

In some embodiments, the pharmaceutical composition comprises:

(a) about 13 w/w % of the spray-dried dispersion of Example 3;
(b) about 0.67 w/w % of calcium silicate;
(c) about 56 w/w % of mannitol and about 20 w/w % of microcrystalline cellulose; and
(d) about 10 w/w % of croscarmellose sodium.

Additional excipients can be included in the pharmaceutical formulations of the present disclosure. Further examples of excipients include, but are not limited to, pigments, colorants, flavoring agents, preservatives, and sweeteners. Flavors and colors can be added to improve the taste or appearance of a formulation. Examples of preservatives used in pharmaceutical compositions are aromatic alcohols, such as benzyl or phenol alcohol, antioxidants such as vitamin A, vitamin E, vitamin C, and selenium, amino acids such as cysteine and methionine, citric acid and sodium citrate, or synthetic preservatives such as methyl paraben and propyl paraben. Sweeteners can be added to make the ingredients more palatable, especially in chewable tablets or liquids like syrups.

Also provided are methods for preparing a pharmaceutical composition, such as a pharmaceutical composition of the present disclosure. In some embodiments, the method includes combining the spray-dried dispersion described herein with one or more pharmaceutically acceptable excipients, e.g., a pharmaceutically acceptable excipient described herein.

In some embodiments, the method for preparing the pharmaceutical composition comprises:

(a) blending the spray-dried dispersion described herein, with a glidant;
(b) further blending the blend of step (a) with a filler and a disintegrant;
(c) screening the blend of step (b) to break up aggregates and assist with blend uniformity;
(d) further blending the intragranular blend of step (c);
(e) compaction of the intragranular blend of step (d) via roller compaction to form granules; and
(f) milling of ribbon from roller compaction into granules of step (e).

In some embodiments, the spray-dried dispersion is the spray-dried dispersion described in Example 3.

The pharmaceutical compositions of the present disclosure are formulated for oral administration. In preparing the compositions in oral dosage form, any of the usual pharmaceutical media can be employed. For solid oral preparations such as, for example, powders, capsules, caplets, gelcaps, and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral pharmaceutical dosage forms can be solid, gel, or liquid. In some embodiments, the dosage form is a solid dosage form. In some embodiments, the solid dosage form is a pill, tablet, capsule, caplet, gelcaps, granules, powder, sachet, melting strip, or melting film. In some embodiments, the solid dosage form is coated. In some embodiments, the coating is an enteric coating, a sugar coating, or a film coating. In some embodiments, the solid dosage form is a coated particle, coated tablet, enterocoated tablet, or enterocoated capsule. In some embodiments, the solid dosage form is a pill or tablet. Types of oral tablets include compressed, chewable lozenges and tablets which may be enteric coated, sugar coated or film coated. In some embodiments, the pharmaceutical composition is formulated as a capsule. In some embodiments, the pharmaceutical composition is formulated as a powder, solution, or suspension (e.g., in propylene carbonate, vegetable oils, PEG's, poloxamer 124 or triglycerides), or is encapsulated in a capsule (gelatin or cellulose base capsule). Capsules can be hard or soft gelatin capsules, while granules and powders can be provided in non-effervescent or effervescent form with a combination of other ingredients known to those skilled in the art.

The pharmaceutical compositions of the present disclosure can contain, per dosage unit, e.g., tablet, capsule, powder, and the like, an amount of the active ingredient necessary to deliver an effective dose as described above.

In some embodiments, the pharmaceutical compositions of the present disclosure are formulated in unit dosage form. In some embodiments, the compound of Formula (I), or pharmaceutically acceptable salt thereof, is present in an amount of about 5 mg to about 200 mg in the unit dosage form. For example, about 5 mg to about 175 mg, about 5 mg to about 150 mg, about 5 mg to about 125 mg, about 5 mg to about 100 mg, about 5 mg to about 75 mg, about 5 mg to about 50 mg, about 5 mg to about 25 mg, about 25 mg to about 200 mg, about 25 mg to about 175 mg, about 25 mg to about 150 mg, about 25 mg to about 125 mg, about 25 mg to about 100 mg, about 25 mg to about 75 mg, about 25 mg to about 50 mg, about 50 mg to about 200 mg, about 50 mg to about 175 mg, about 50 mg to about 150 mg, about 50 mg to about 125 mg, about 50 mg to about 100 mg, about 50 mg to about 75 mg, about 75 mg to about 200 mg, about 75 mg to about 175 mg, about 75 mg to about 150 mg, about 75 mg to about 125 mg, about 75 mg to about 100 mg, about 100 mg to about 200 mg, about 100 mg to about 175 mg, about 100 mg to about 150 mg, about 100 mg to about 125 mg, about 125 mg to about 200 mg, about 125 mg to about 175 mg, about 125 mg to about 150 mg, about 150 mg to about 200 mg, about 150 mg to about 175 mg, or about 175 mg to about 200 mg in the unit dosage form. In some embodiments, the compound of Formula (I), or pharmaceutically acceptable salt thereof, is present in an amount of about 25 mg to about 125 mg in the unit dosage form. In some embodiments, the compound of Formula (I), or pharmaceutically acceptable salt thereof, is present in an amount of about 75 mg to about 150 mg in the unit dosage form. In some embodiments, the compound of Formula (I), or pharmaceutically acceptable salt thereof, is present in an amount of about 5 mg, about 10 mg, about 25 mg, about 35 mg, about 50 mg, about 65 mg, about 75 mg, about 90 mg, about 100 mg, about 125 mg, about 150 mg, about 175 mg, or about 200 mg in the unit dosage form, or within a range defined by any of the preceding values. In some embodiments, the compound of Formula (I), or pharmaceutically acceptable salt thereof, is present in an amount of about 50 mg in the unit dosage form. In some embodiments, the compound of Formula (I), or pharmaceutically acceptable salt thereof, is present in an amount of about 100 mg in the unit dosage form. In some embodiments, the compound of Formula (I), or pharmaceutically acceptable salt thereof, is present in an amount of about 25 mg in the unit dosage form. In some embodiments, the compound of Formula (I), or pharmaceutically acceptable salt thereof, is present in an amount of 5 mg to 250 mg in the unit dosage form. For example, 5 mg to 175 mg, 5 mg to 150 mg, 5 mg to 125 mg, 5 mg to 100 mg, 5 mg to 75 mg, 5 mg to 50 mg, 5 mg to 25 mg, 25 mg to 200 mg, 25 mg to 175 mg, 25 mg to 150 mg, 25 mg to 125 mg, 25 mg to 100 mg, 25 mg to 75 mg, 25 mg to 50 mg, 50 mg to 200 mg, 50 mg to 175 mg, 50 mg to 150 mg, 50 mg to 125 mg, 50 mg to 100 mg, 50 mg to 75 mg, 75 mg to 200 mg, 75 mg to 175 mg, 75 mg to 150 mg, 75 mg to 125 mg, 75 mg to 100 mg, 100 mg to 200 mg, 100 mg to 175 mg, 100 mg to 150 mg, 100 mg to 125 mg, 125 mg to 200 mg, 125 mg to 175 mg, 125 mg to 150 mg, 150 mg to 200 mg, 150 mg to 175 mg, or 175 mg to 200 mg in the unit dosage form. In some embodiments, the compound of Formula (I), or pharmaceutically acceptable salt thereof, is present in an amount of 25 mg to 125 mg in the unit dosage form. In some embodiments, the compound of Formula (I), or pharmaceutically acceptable salt thereof, is present in an amount of 75 mg to 150 mg in the unit dosage form. In some embodiments, the compound of Formula (I), or pharmaceutically acceptable salt thereof, is present in an amount of 5 mg, 10 mg, 25 mg, 35 mg, 50 mg, 65 mg, 75 mg, 90 mg, 100 mg, 125 mg, 150 mg, 175 mg, or 200 mg in the unit dosage form, or within a range defined by any of the preceding values. In some embodiments, the compound of Formula (I), or pharmaceutically acceptable salt thereof, is present in an amount of 50 mg in the unit dosage form. In some embodiments, the compound of Formula (I), or pharmaceutically acceptable salt thereof, is present in an amount of 100 mg in the unit dosage form. In some embodiments, the pharmaceutical compositions of the present disclosure are formulated as a tablet. In some embodiments, the tablet is coated. In some embodiments, the pharmaceutical compositions of the present disclosure are formulated as capsules. In some embodiments, the pharmaceutical compositions are in sachet form. In some embodiments, the pharmaceutical compositions are in granule form.

In some embodiments, the compound of Formula (I), or a pharmaceutically acceptable salt thereof, is administered in a dose of about 25 mg, based on the weight of the free base. In some embodiments, the compound of Formula (I), or a pharmaceutically acceptable salt thereof, is administered in a dose of about 50 mg, based on the weight of the free base. In some embodiments, the compound of Formula (I), or a pharmaceutically acceptable salt thereof, is administered in a dose of about 75 mg, based on the weight of the free base. In some embodiments, the compound of Formula (I), or a pharmaceutically acceptable salt thereof, is administered in a dose of about 100 mg, based on the weight of the free base.

In some embodiments, the pharmaceutical composition is administered in a dose of about 25 mg of the compound of Formula (I), or a pharmaceutically acceptable salt thereof, based on the weight of the free base. In some embodiments, the pharmaceutical composition is administered in a dose of about 50 mg of the compound of Formula (I), or a pharmaceutically acceptable salt thereof, based on the weight of the free base. In some embodiments, the pharmaceutical composition is administered in a dose of about 75 mg of the compound of Formula (I), or a pharmaceutically acceptable salt thereof, based on the weight of the free base. In some embodiments, the pharmaceutical composition is administered in a dose of about 100 mg of the compound of Formula (I), or a pharmaceutically acceptable salt thereof, based on the weight of the free base.

In some embodiments, the pharmaceutical composition comprises about 25 mg of the compound of Formula (I), or a pharmaceutically acceptable salt thereof, based on the weight of the free base. In some embodiments, the pharmaceutical composition comprises about 50 mg of the compound of Formula (I), or a pharmaceutically acceptable salt thereof, based on the weight of the free base. In some embodiments, the pharmaceutical composition comprises about 75 mg of the compound of Formula (I), or a pharmaceutically acceptable salt thereof, based on the weight of the free base. In some embodiments, the pharmaceutical composition comprises about 100 mg of the compound of Formula (I), or a pharmaceutically acceptable salt thereof, based on the weight of the free base.

The daily dosage of the compound of Formula (I), or a pharmaceutically acceptable salt thereof, in a pharmaceutical composition as described in the present disclosure can be varied over a wide range from about 1.0 mg to about 10,000 mg per adult human per day, or higher, or any range therein. For oral administration, the compositions can be provided in the form of tablets containing, for example, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 75.0 mg, about 100 mg, about 150 mg, about 200 mg, about 250 or about 500 milligrams of the compound of Formula (I), or pharmaceutically acceptable salt thereof, for the symptomatic adjustment of the dosage to the subject to be treated. In some embodiments, an effective amount of the compound of Formula (I), or pharmaceutically acceptable salt thereof, can be supplied at a dosage level of from about 0.1 mg/kg to about 1000 mg/kg of body weight per day, or any range therein, for example, the range can be from about 0.5 mg/kg to about 500 mg/kg, about 1.0 mg/kg to about 250 mg/kg, about 0.1 mg/kg to about 100 mg/kg, about 0.1 mg/kg to about 50.0 mg/kg of body weight per day, about 0.1 mg/kg to about 15.0 mg/kg of body weight per day, about 0.5 mg/kg to about 7.5 mg/kg of body weight per day, or any amount to range therein. In some embodiments, an effective amount of the compound of Formula (I), or pharmaceutically acceptable salt thereof, can be supplied at a dosage level of from 0.1 mg/kg to 1000 mg/kg of body weight per day, or any range therein, for example, the range can be from 0.5 mg/kg to 500 mg/kg, 1.0 mg/kg to 250 mg/kg, 0.1 mg/kg to 100 mg/kg, 0.1 mg/kg to 50.0 mg/kg of body weight per day, 0.1 mg/kg to 15.0 mg/kg of body weight per day, 0.5 mg/kg to 7.5 mg/kg of body weight per day, or any amount to range therein. A pharmaceutical composition as provided herein can be administered on a regimen of 1 to 4 times per day or in a single daily dose.

In some embodiments, the daily dose of the compound of Formula (I), or a pharmaceutically acceptable salt thereof, is about 25 mg, based on the weight of the free base. In some embodiments, the daily dose of the compound of Formula (I), or a pharmaceutically acceptable salt thereof, is about 50 mg, based on the weight of the free base. In some embodiments, the daily dose of the compound of Formula (I), or a pharmaceutically acceptable salt thereof, is about 75 mg, based on the weight of the free base. In some embodiments, the daily dose of the compound of Formula (I), or a pharmaceutically acceptable salt thereof, is about 100 mg, based on the weight of the free base. In some embodiments, the daily dose of the compound of Formula (I), or a pharmaceutically acceptable salt thereof, is about 150 mg, based on the weight of the free base. In some embodiments, the daily dose of the compound of Formula (I), or a pharmaceutically acceptable salt thereof, is about 200 mg, based on the weight of the free base.

In some embodiments, the compound of Formula (I), or a pharmaceutically acceptable salt thereof, is administered twice daily in a dose of about 25 mg, based on the weight of the free base. In some embodiments, the compound of Formula (I), or a pharmaceutically acceptable salt thereof, is administered twice daily in a dose of about 50 mg, based on the weight of the free base. In some embodiments, the compound of Formula (I), or a pharmaceutically acceptable salt thereof, is administered twice daily in a dose of about 75 mg, based on the weight of the free base. In some embodiments, the compound of Formula (I), or a pharmaceutically acceptable salt thereof, is administered twice daily in a dose of about 100 mg, based on the weight of the free base.

In some embodiments, the daily dose of the pharmaceutical composition is about 25 mg of the compound of Formula (I), or a pharmaceutically acceptable salt thereof, based on the weight of the free base. In some embodiments, the daily dose of the pharmaceutical composition is about 50 mg of the compound of Formula (I), or a pharmaceutically acceptable salt thereof, based on the weight of the free base. In some embodiments, the daily dose of the pharmaceutical composition is about 75 mg of the compound of Formula (I), or a pharmaceutically acceptable salt thereof, based on the weight of the free base. In some embodiments, the daily dose of the pharmaceutical composition is about 100 mg of the compound of Formula (I), or a pharmaceutically acceptable salt thereof, based on the weight of the free base. In some embodiments, the daily dose of the pharmaceutical composition is about 150 mg of the compound of Formula (I), or a pharmaceutically acceptable salt thereof, based on the weight of the free base. In some embodiments, the daily dose of the pharmaceutical composition is about 200 mg of the compound of Formula (I), or a pharmaceutically acceptable salt thereof, based on the weight of the free base.

In some embodiments, the pharmaceutical composition is administered twice daily in a dose of about 25 mg of the compound of Formula (I), or a pharmaceutically acceptable salt thereof, based on the weight of the free base. In some embodiments, the pharmaceutical composition is administered twice daily in a dose of about 50 mg of the compound of Formula (I), or a pharmaceutically acceptable salt thereof, based on the weight of the free base. In some embodiments, the compound of Formula (I), or a pharmaceutically acceptable salt thereof, is administered twice daily in a dose of about 75 mg of the compound of Formula (I), or a pharmaceutically acceptable salt thereof, based on the weight of the free base. In some embodiments, the pharmaceutical composition is administered twice daily in a dose of about 100 mg of the compound of Formula (I), or a pharmaceutically acceptable salt thereof, based on the weight of the free base.

In some embodiments, the method comprises administering a daily dose of the pharmaceutical composition comprising about 25 mg of the compound of Formula (I), or a pharmaceutically acceptable salt thereof, based on the weight of the free base. In some embodiments, the method comprises administering a daily dose of the pharmaceutical composition comprising about 50 mg of the compound of Formula (I), or a pharmaceutically acceptable salt thereof, based on the weight of the free base. In some embodiments, the method comprises administering a daily dose of the pharmaceutical composition comprising about 75 mg of the compound of Formula (I), or a pharmaceutically acceptable salt thereof, based on the weight of the free base. In some embodiments, the method comprises administering a daily dose of the pharmaceutical composition comprising about 100 mg of the compound of Formula (I), or a pharmaceutically acceptable salt thereof, based on the weight of the free base. In some embodiments, the method comprises administering a daily dose of the pharmaceutical composition comprising about 150 mg of the compound of Formula (I), or a pharmaceutically acceptable salt thereof, based on the weight of the free base. In some embodiments, the method comprises administering a daily dose of the pharmaceutical composition comprising about 200 mg of the compound of Formula (I), or a pharmaceutically acceptable salt thereof, based on the weight of the free base.

In some embodiments, the method comprises administering the pharmaceutical composition twice daily in a dose of about 25 mg of the compound of Formula (I), or a pharmaceutically acceptable salt thereof, based on the weight of the free base. In some embodiments, the method comprises administering the pharmaceutical composition twice daily in a dose of about 50 mg of the compound of Formula (I), or a pharmaceutically acceptable salt thereof, based on the weight of the free base. In some embodiments, the method comprises administering the compound of Formula (I), or a pharmaceutically acceptable salt thereof, twice daily in a dose of about 75 mg of the compound of Formula (I), or a pharmaceutically acceptable salt thereof, based on the weight of the free base. In some embodiments, the method comprises administering the pharmaceutical composition twice daily in a dose of about 100 mg of the compound of Formula (I), or a pharmaceutically acceptable salt thereof, based on the weight of the free base.

Factors associated with the particular subject being treated, including subject age, weight, diet, and time of administration, can result in the need to adjust dosages. In some embodiments, the subject is a human adult. In some embodiments, the subject is a pediatric subject.

One skilled in the art will recognize that both in vivo and in vitro trials using suitable, known, and generally accepted cell and/or animal models are predictive of the ability of a test compound to treat or prevent a given disorder. One skilled in the art will further recognize that human clinical trials including first-in-human, dose ranging and efficacy trials, in healthy subjects and/or those suffering from a given disorder, can be completed according to methods well known in the clinical and medical arts. For example, determining proper dosages for pediatric subjects can be determined using known methods, including weight, age, and models such as a simulation model sold under the trademark SIMCYP® PEDIATRIC SIMULATION modeling (CERTARA, Princeton, N.J.) which can be used to establish a pharmacokinetic approach for dosing that takes into account subject age, ontogeny of the clearance pathways that a compound of Formula (I), or a pharmaceutically acceptable salt thereof, and body surface area (BSA).

In some embodiments, the pharmaceutical compositions of the present disclosure are stable for at least 3 months. In some embodiments, the pharmaceutical compositions are stable for at least 6 months. In some embodiments, the pharmaceutical compositions are stable for at least 9 months. In some embodiments, the pharmaceutical compositions are stable for at least 12 months. For example, the compositions do not exhibit a change (e.g., greater than 5%) in appearance, pH, percent impurities, activity (as measured by in vitro assays), or osmolarity over time, e.g., at least 3 months, 6 months, 9 months, or at least 12 months as compared to the original composition after manufacturing. In some embodiments, the pharmaceutical compositions do not exhibit a significant change, as defined by the International Conference on Harmonisation of Technical Requirements for Registration of Pharmaceuticals for Human Use (ICH), in one or more of appearance, pH, percent impurities, activity (as measured by in vitro assays), or osmolarity over time, e.g., at least 12 months as compared to the original pharmaceutical composition after manufacturing.

Kits

Also provided are kits. Typically, a kit includes one or more pharmaceutical compositions as described herein, e.g., a pharmaceutical composition containing, e.g., a spray-dried dispersion as described in Examples 1-4, or the formulation described in Example 9. In certain embodiments, a kit can include one or more delivery systems, e.g., for delivering or administering the pharmaceutical composition as provided herein, and directions for use of the kit (e.g., instructions for treating a subject). In some embodiments, the kit can include a pharmaceutical composition as described herein and a label that indicates that the contents are to be administered to a subject with congenital adrenal hyperplasia. The actual dose of the compound of Formula (I), or pharmaceutically acceptable salt thereof, provided herein depends on the specific formulation, the weight of the patient, and on the condition to be treated.

EXAMPLES

Example 1: Spray-Dried Dispersion Formulations Containing the Compound of Formula (I) and Various Polymers Spray-Dried Dispersion Formulations A series of spray-dried dispersion (SDD) formulations containing the compound of Formula (I) and a polymer were prepared. The SDD formulations included: (1) 10% compound of Formula (I)/90% hydroxypropylmethylcellulose acetate succinate-L (HPMCAS-L); (2) 25% compound of Formula (I)/75% HPMCAS-L; (3) 40% compound of Formula (I)/60% HPMCAS-L; (4) 25% compound of Formula (I)/75% polyvinyl pyrrolidone vinyl acetate 64 (PVP/VA 64); (5) 25% compound of Formula (I)/60% Cabosil (fumed silica)/15% HPMCAS-L; (6) 25% compound of Formula (I)/75% HPMCAS-M; and (7) 25% compound of Formula (I)/75% methyl methacrylate copolymer (1:1) (methyl methacrylate copolymer sold under the trademark EUDRAGIT® L 100).

The PVP/VA polymer was a copolymer of 1-vinyl-2-pyrrolidone and vinyl acetate with a ratio of 60:40 by weight 1-vinyl-2-pyrrolidone:vinyl acetate with an average molecular weight of 45,000-70,000 (copovidone, sold under the trademark KOLLIDON® VA 64, BASF, Florham Park, NJ). The HPMCAS was a mixture of acetic acid and monosuccinic acid esters of hydroxypropylmethyl cellulose that was either grade L (HPMCAS-L), with an acetyl content of 5-9%, a succinoyl content of 14-18%, a methoxyl content of 20-24%, and a hydroxypropoxy content of 5-9% (sold by Shin-Etsu, Japan); or grade M (HPMCAS-M), with an acetyl content of 7-11%, a succinoyl content of 10-14%, a methoxyl content of 21-25%, and a hydroxypropoxy content of 5-9% (sold by Shin-Etsu, Japan).

Dissolution Performance

Dissolution performance of several of the SDD formulations described above was tested (see FIG. 1). 1000 μgA/mL of each SDD was tested in 0.5 wt % simulated intestinal fluid (SIF) in PBS, pH 6.5. Samples were tested at 5, 10, 20, 45, 90, and 1200 minutes. A lipid formulation containing 10% of the compound of Formula (I) was used as a control. The results are shown in Table 4, below.

TABLE 4

Dissolution data of various SDDs

| Sample | $C_{max90}$ (μg/mL) | $AUC_{90}$ (min * μg/mL) | $C_{max90}$ (μg/mL) | $Ultra_{90}$ (μg/mL) | $C_{1200}$ (μg/mL) | $Ultra_{1200}$ (μg/mL) |
|---|---|---|---|---|---|---|
| 2 | 762 | 66,080 | 743 | 210 | 671 | 166 |
| 4 | 322 | 27,330 | 306 | 109* | 268 | 199 |
| 6 | 718 | 62,240 | 708 | 202 | 632 | 217 |
| 7 | 742 | 60,600 | 742 | 113* | 674 | 194 |
| Control | 802 | 69,580 | 800 | 253 | 799 | 270 |

*Large variability between replicates, high value discarded

Non-Sink Dissolution

A membrane flux assay was performed (see, e.g., Stewart et al., Mol. Pharm. (2017) 14:2032-2046) and non-sink dissolution data was collected for several of the SDD formulations described above and compared to the compound of Formula (I) and several reference formulations, including a semi-solid lipidic formulation (Reference Formulation 1) and two self-emulsifying drug delivery system (SEDDS) formulations (Reference Formulations 2 and 3). The components of the Reference Formulations are shown in Table 5, below, and include, in addition to the compound of Formula (I), caprylic/capric triglyceride (sold under the trademark LABRAFAC® LIPOPHILE, Gattefosse, France); propylene glycol dicrapolate/dicaprate (sold under the trademark LABRAFAC® PG, Gattefosse, France); oleoyl polyoxyl-6 glycerides (sold under the trademark LABRAFIL® M 1944 CS, Gattefosse, France); polysorbate 20; polyoxyl castor oil (sold under the trademark KOLLIPHOR® RH 40, BASF, Germany); polyoxyl 15 hydroxystearate (sold under the trademark KOLLIPHOR® HS 15, BASF, Germany); lauroyl polyoxyl-32 glycerides (sold under the trademark GELUCIRE® 44/14, Gattefosse, France); d-α-tocopheryl polyethylene glycol 1000 succinate (TPGS); and diethylene glycol monoethyl ether (sold under the trademark TRANSCUTOL®, Gattefosse, France).

TABLE 5

Reference formulations (capsules)

| Formulation (mg/caps) | Ref. Formulation 1 | Ref. Formulation 2 | Ref. Formulation 3 |
|---|---|---|---|
| Formula (I) | 50.0 | 50.0 | 50.0 |
| LABRAFAC ® LIPOPHILE | 196.0 | 100.0 | 100.0 |
| LABRAFAC ® PG | 102.0 | — | — |
| LABRAFIL ® M 1944 CS | — | 135.0 | 46.0 |
| Polysorbate 20 | — | — | 89.9 |
| KOLLIPHOR ® RH 40 | — | — | 100.0 |
| KOLLIPHOR ® HS 15 | — | 165.0 | — |
| GELUCIRE ® 44/14 | 95.0 | — | — |
| TPGS | 57.0 | — | 65.0 |
| TRANSCUTOL ® | — | 50.0 | 50.0 |
| Total | 500.0 | 500.0 | 500.0 |

Figure 2:
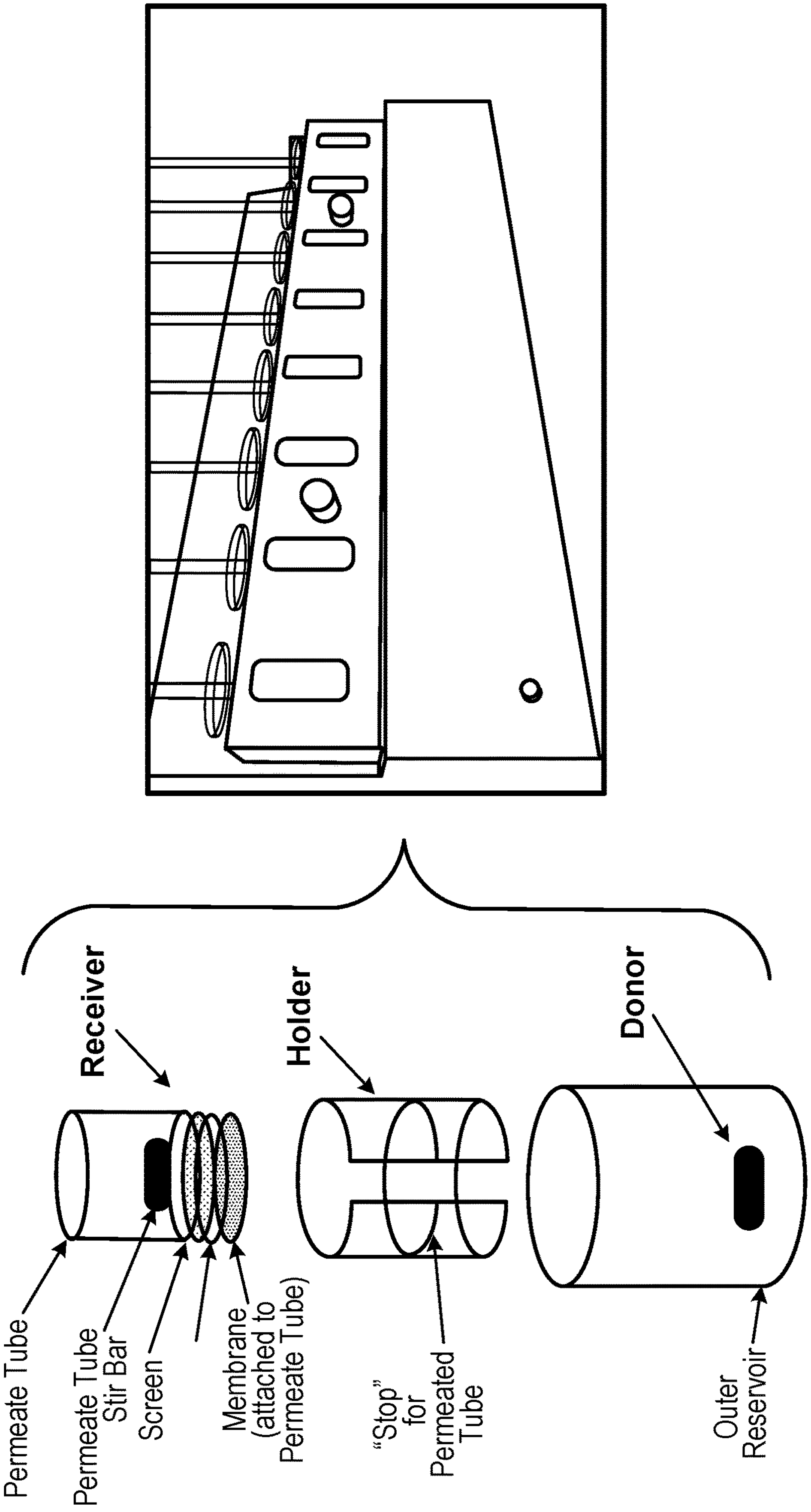
FIG. 2 shows the vertical membrane flux cell integrated in the UV monitoring system sold under the trademark pDISS PROFILER™ used for the membrane flux assay.
Figure 3:
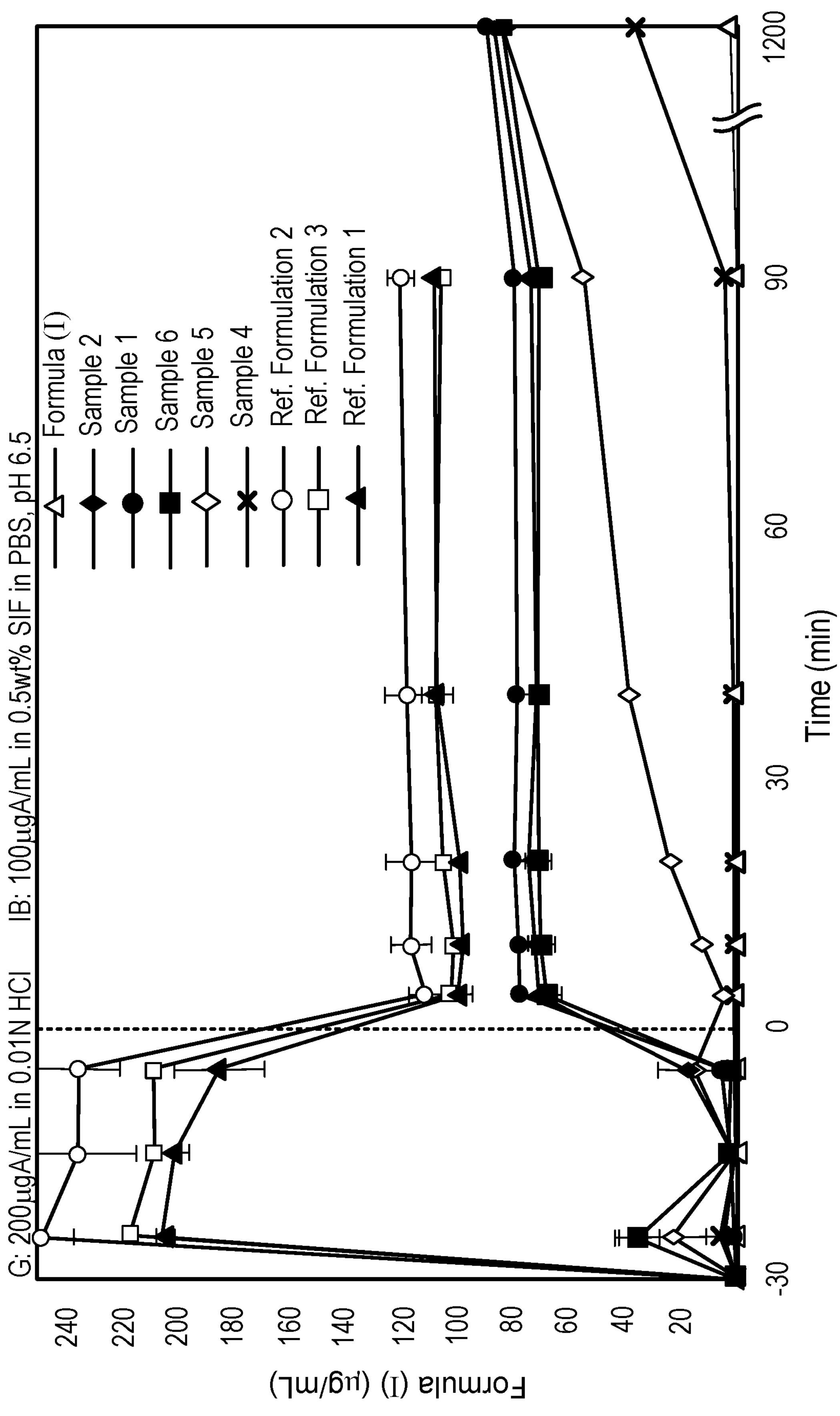
FIG. 3 shows non-sink dissolution data for several spray-dried dispersion formulations and the compound of Formula (I) in 0.5 wt % SIF in PBS, pH 6.5.

The assay measured the flux across simulated gastric and intestinal walls via UV spectroscopy (sold under the trademark DISS PROFILER™, Pion Inc., Billerica, MA). Briefly, the assay was performed as follows. A vertical membrane flux cell consisting of a donor compartment and a receiver compartment, and separated by an Accurel PP IE (5500 porous, 100 μm thickness) polypropylene membrane (3M, Maplewood, MN) (FIG. 2), was impregnated with 50 μL of Pion GIT-0 lipid solution consisting of 20% w/w phospholipid dissolved into dodecane (Pion Inc., Billerica, MA) and attached to the receiver vessel. Both the donor and receiver compartments were agitated by magnetic stirring. The receiver compartment contained a plastic spacer and grating to elevate the stir bar above the membrane. Samples were introduced to the donor vessel by pre-weighing directly into the donor vessel and subsequently adding dissolution medium. Once the dissolution medium was added to the donor vessel, the receiver vessel was inserted into the donor vessel and suspended vertically 5 mm above the donor compartment by a plastic sleeve. For this assay, the simulated gastric (feed) media was 0.1 N HCl, pH 2 and included 200 μgA/mL of each SDD, and the simulated intestinal (receiver) media was 0.5 wt % SIF in PBS, pH 6.5 and included 100 μgA/mL of each SDD. The temperature for the assay was maintained at 44.5° C. UV probes (10 mm path length) connected to a Rainbow UV spectrometer (Pion Inc.) system were used to determine the apparent drug concentration in the receiver vessels. Samples of the donor compartment were removed with a disposable pipet for centrifugation followed by HPLC and DLS analysis of the supernatant. The results are shown in FIG. 3 and Table 6, below.

TABLE 6

Non-sink dissolution data

| Sample | $C_{maxGB}$ (μg/mL) | $C_{max90IB}$ (μg/mL) | $AUC_{4-90IB}$ (min * μg/mL) | $C_{90}$ (μg/mL) | $Ultra_{90}$ (μg/mL) | $C_{1200}$ (μg/mL) |
|---|---|---|---|---|---|---|
| Formula (I) | 0 | 1 | 10 | 0 | 0 | 3 |
| 1 | 6 | 80 | 6,800 | 80 | 79 | 90 |
| 2 | 17 | 74 | 6,240 | 73 | 73 | 86 |
| 4 | 6 | 4 | 200 | 4 | 5 | 36 |
| 5 | 23 | 55 | 3,180 | 55 | 54 | 83 |
| 6 | 35 | 71 | 6,070 | 71 | 77 | 83 |
| Ref. Formulation 1 | 205 | 109 | 9,050 | 109 | — | — |
| Ref. Formulation 2 | 249 | 120 | 10,160 | 120 | — | — |
| Ref. Formulation 3 | 218 | 107 | 9,100 | 107 | — | — |

Figure 4:
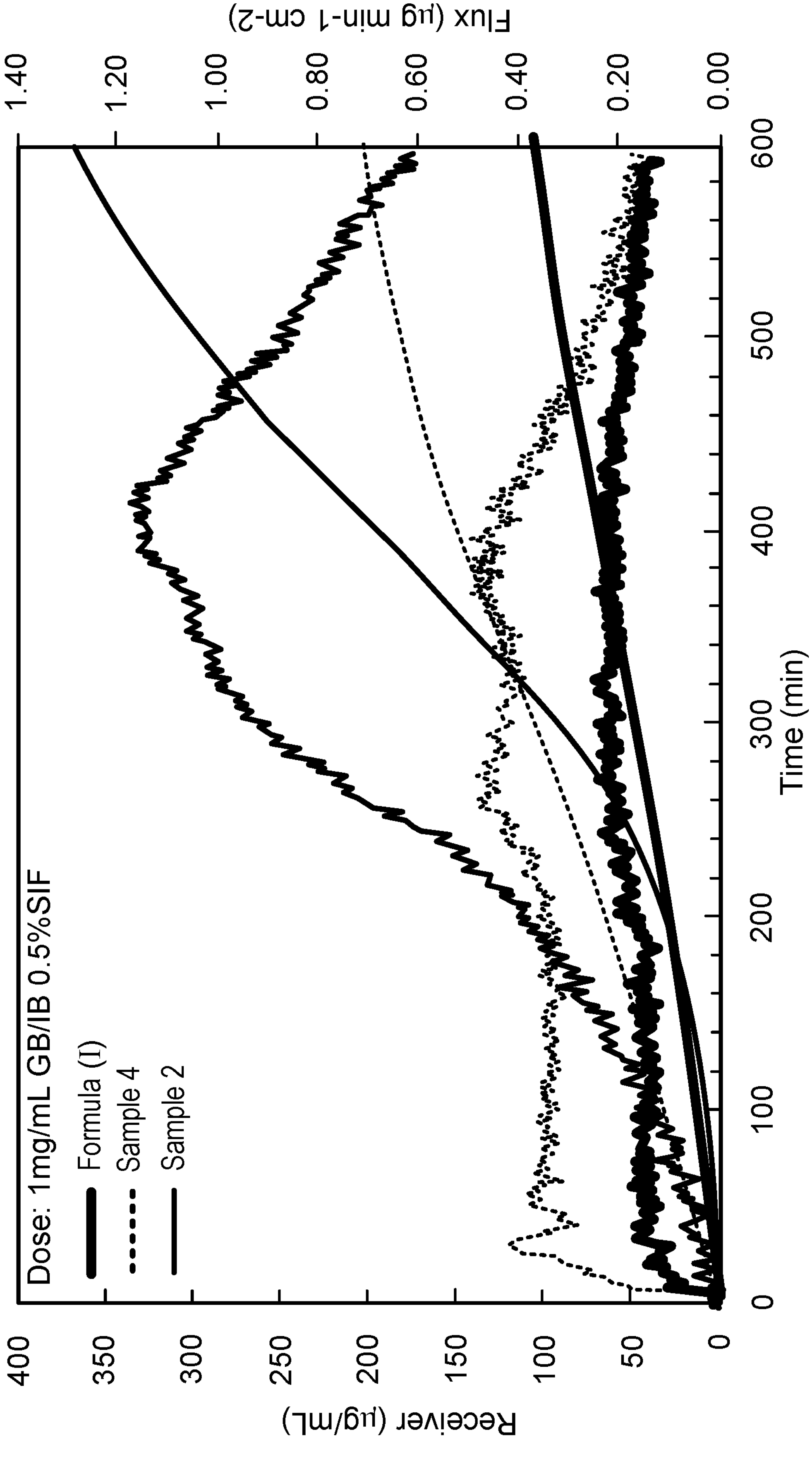
FIG. 4 is a graph showing membrane flux of 1 mg/mL GB/IB 0.5 wt % SIF doses of the compound of Formula (I) and various spray-dried dispersion formulations over time. The solid lines indicate flux (μg $min^{-1}$ $cm^{-2}$) and the broken lines indicate concentration (μg/mL) in 0.5% SIF.

The membrane flux of 1 mg/mL gastric barrier/intestinal barrier (GB/IB) 0.5 wt % SIF doses of the compound of Formula (I) and spray-dried dispersions (2) 25% compound of Formula (I)/75% HPMCAS-L and (4) 25% compound of Formula (I)/75% PVP/VA 64 were also determined. The results are shown in FIG. 4 as receiver concentration vs. time and flux vs. time (smoothed derivative of receiver concentration×volume/surface area).

Example 2: Characterization of a Spray-Dried Dispersion Containing 25% of the Compound of Formula (I) and 75% of a Polyvinyl Pyrrolidone Vinyl Acetate (PVP/VA) Polymer SDD Stability Screening Several of the SDDs described in Example 1 were tested for chemical and physical stability. Wet SDD stability studies were performed, with samples stored at both 5° C. and 25° C. Measurements were taken after 1 week and 2 weeks of storage. The results are shown in Table 7 below. The column with a retention time of 32.36 min correlates with the compound of Formula (I).

TABLE 7

| Wet SDD stability data | | | | | | | | | | |
|---|---|---|---|---|---|---|---|---|---|---|
| Retention time (min) | | | 11.04 | 16.79 | 17.26 | 30.94 | 32.26 | | | |
| Relative retention time | | | 0.34 | 0.52 | 0.53 | 0.96 | 1.00 | | | |
| | Storage temp | Timepoint | | | | | | Total impurities | Potency (mgA/g) | Std Dev |
| Ref. Std. | | | | | | 0.37 | 99.63 | 0.37 | | |
| Formula (I) | | | | | | 0.26 | 99.74 | 0.26 | | |
| Sample 1 | | initial | | 0.13 | 0.16 | 0.25 | 99.46 | 0.54 | 100 | 1.3 |
| | 5 °C | 1 week | | 0.03 | 0.03 | 0.26 | 99.69 | 0.31 | 99 | 0.0 |
| | | 2 weeks | | 0.12 | 0.16 | 0.28 | 99.45 | 0.55 | 99 | 0.5 |
| | 25 °C | 1 week | | 0.03 | 0.04 | 0.26 | 99.67 | 0.33 | 99 | 0.3 |
| | | 2 weeks | | 0.21 | 0.27 | 0.28 | 99.24 | 0.76 | 98 | 0.8 |
| Sample 2 | | initial | <LOQ | 0.07 | 0.08 | 0.26 | 99.59 | 0.41 | 247 | 0.3 |
| | 5 °C | 1 week | <LOQ | 0.02 | 0.03 | 0.26 | 99.70 | 0.30 | 248 | 1.3 |
| | | 2 weeks | <LOQ | 0.22 | 0.27 | 0.27 | 99.24 | 0.76 | 246 | 0.3 |
| | 25 °C | 1 week | <LOQ | 0.02 | 0.03 | 0.26 | 99.69 | 0.31 | 248 | 0.9 |
| | | 2 weeks | <LOQ | 0.23 | 0.28 | 0.26 | 99.23 | 0.77 | 246 | 1.4 |

LOQ = limit of quantification

Solution stability studies were also performed, with samples stored at both 5° C. and 25° C. Measurements were taken after 1 week and 2 weeks of storage. The results are shown in Table 8 below. The column with a retention time of 32.36 min correlates with the compound of Formula (I).

TABLE 8

| SDD solution stability data | | | | | |
|---|---|---|---|---|---|
| Retention time (min) | | | 31.51 | 32.26 | |
| Relative retention time | | | 0.97 | 1.00 | |
| | Storage temp | Timepoint | | | Total impurities |
| Ref. Std. | | | 0.74 | 99.26 | 0.74 |
| Formula (I) | | | 0.26 | 99.74 | 0.26 |
| Sample 1 | | initial | 0.33 | 99.67 | 0.33 |
| | 5° C. | 2 weeks | 0.29 | 99.71 | 0.29 |
| | 25° C. | 2 weeks | 0.38 | 99.62 | 0.38 |
| Sample 2 | | initial | 0.25 | 99.75 | 0.25 |
| | 5° C. | 2 weeks | 0.26 | 99.74 | 0.26 |
| | 25° C. | 2 weeks | 0.33 | 99.67 | 0.33 |

Stability studies were also performed for the SDD containing 25% of the compound of Formula (I) and 7500 PVP/VA 64, with samples stored at both 5° C. (closed with desiccant), 25° C. (6000 relative humidity (RH), closed with desiccant), and 30° C. (65% RH, closed with desiccant). Measurements were taken after storage for 1 month, 2 months, 3 months, 6 months, and 12 months. No change in purity was observed after 12 months of storage. The results are shown in Table 9 below. The column with a retention time of 30.2 min correlates with the compound of Formula (I).

TABLE 9

| SDD stability data | | | | | | |
|---|---|---|---|---|---|---|
| Retention time (min) | | | 28.7 | 30.2 | | |
| Relative retention time | | | 0.95 | 1.00 | | |
| | Storage conditions | Timepoint | | | Total impurities | Potency (mgA/g) |
| Crystalline Formula (I) | | | 0.26 | 99.74 | 0.26 | 1001 |
| Sample 4 (25% Formula (I):75% PVP/VA 64) | | initial | 0.26 | 99.74 | 0.26 | 245 |
| | 5 °C (closed w/ desiccant) | 1 month | 0.25 | 99.75 | 0.25 | 247 |
| | | 2 months | 0.25 | 99.75 | 0.25 | 244 |
| | | 3 months | 0.26 | 99.74 | 0.26 | 246 |
| | | 6 months | 0.25 | 99.75 | 0.25 | 245 |
| | | 12 months | 0.25 | 99.75 | 0.25 | 248 |
| | 25 °C/60% RH (closed with desiccant) | 1 month | 0.25 | 99.75 | 0.25 | 245 |
| | | 2 months | 0.25 | 99.75 | 0.25 | 247 |
| | | 3 months | 0.25 | 99.75 | 0.25 | 246 |
| | | 6 months | 0.25 | 99.75 | 0.25 | 242 |
| | | 12 months | 0.25 | 99.75 | 0.25 | 245 |
| | 30 °C/65% RH (closed with desiccant) | 1 month | 0.25 | 99.75 | 0.25 | 249 |
| | | 2 months | 0.25 | 99.75 | 0.25 | 242 |
| | | 3 months | 0.25 | 99.75 | 0.25 | 246 |

TABLE 9-continued

| SDD stability data | | | | |
|---|---|---|---|---|
| 6 months | 0.25 | 99.73 | 0.25 | 243 |
| 12 months | 0.25 | 99.75 | 0.25 | 242 |

While Samples 1 and 2 showed degradation after about 2 weeks of storage, the SDD containing 2500 of the compound of Formula (I) and 7500 PVP/VA 64 (Sample 4) was found to be both chemically and physically stable and was further screened and characterized as described below.

25% Formula (I)/75% PVP/VA 64 SDD Process Parameter Screening Manufacture Round 1

The 25% Formula (I)/75% PVP/VA 64 SDD was prepared on a Pharmaceutical Spray Dryer with 100 kg/hr drying gas capacity (PSD-1). The manufacturing summary is shown in Table 10, below.

TABLE 10

Manufacturing summary of process parameters

| | |
|---|---|
| Formulation | 25% Formula (I):75% PVP/VA 64 |
| Solids Loading (wt %) | 10 |
| Batch Size (kg) | 1.5 |
| Solvent | Acetone |
| Atomizer (Pressure Swirl) | SK 80-16 |
| Solution Flow-rate (g/min) | 160 |
| Atomization Pressure (psig) | 480 |
| Inlet Temperature (° C.) | 94 |
| Outlet Temperature (° C.) | 40 |
| Calculated Outlet Acetone Saturation (% relative saturation (RS)) | 6.2 |
| Dry Yield (%) | 73 |

Based on the 73% yield observed in the first round of process screening, three sprays were performed to investigate the effect of reducing solution throughput and outlet temperature on product yield. All sprays were conducted at a reduced flow-rate of 110 g/min. The outlet temperature was varied at 40° C. (Lot A), 35° C. (Lot B), and 30° C. (Lot C). The outlet temperature was decreased while maintaining a low outlet acetone saturation to increase the difference between the chamber outlet temperature and the wet SDD $T_g$, thus improving product yields. The spray dryer chamber and outlet ductwork were cleaned between all manufactures. A manufacturing summary is shown in Table 11.

TABLE 11

Manufacturing summary for process parameters (1.5 kg batch size)

| Description | Low Flow-Rate | Low Flow-Rate/Low Outlet Temperature | Low Flow-Rate/Lower Outlet Temperature |
|---|---|---|---|
| Lot | A | B | C |
| Solids Loading (wt %) | 10 | 10 | 10 |
| Batch Size (kg) | 1.5 | 1.5 | 1.5 |
| Solvent | Acetone | Acetone | Acetone |
| Atomizer (Pressure Swirl) | Steinen A75 | Steinen A75 | Steinen A75 |
| Solution Flow-Rate (g/min) | no | 110 | 110 |
| Atomization Pressure (psig) | 275 | 285 | 285 |
| Inlet Temperature (° C.) | 79 | 79 | 63 |
| Outlet Temperature (° C.) | 40 | 35 | 30 |
| Calculated Outlet Acetone Saturation (% RS) | 4.3 | 5.2 | 6.4 |
| Calculated wet SDD $T_g$ (° C.) | 72 | 71 | 69 |
| Dry Yield (%) | 55 | 80 | 43 |

The conditions used for Lot B were found to give the highest yield. One additional spray was then performed at the same processing conditions as Lot B while increasing the batch size from 1.5 kg to 3.5 kg to evaluate process consistency and to determine if product yield would continue to improve over time. The averaged process conditions for this lot are shown in Table 12.

TABLE 12

Manufacturing summary of process parameters (1.5 kg and 3.5 kg batch sizes)

| Description | Low Flow-Rate/Low Outlet Temperature | Low Flow-Rate/Low Outlet Temperature/Larger Batch Size |
|---|---|---|
| Lot | B | D |
| Solids Loading (wt %) | 10 | 10 |
| Batch Size (kg) | 1.5 | 3.5 |
| Solvent | Acetone | Acetone |
| Atomizer (Pressure Swirl) | Steinen A75 | Steinen A75 |
| Solution Flow-Rate (g/min) | 110 | 110 |
| Atomization Pressure (psig) | 285 | 2.85 |
| Inlet Temperature (° C.) | 72 | 72 |
| Outlet Temperature (° C.) | 35 | 35 |
| Calculated Outlet Acetone Saturation (% RS) | 5.2 | 5.2 |
| Calculated wet SDD $T_g$ (° C.) | 71 | 71 |
| Dry Yield (%) | 80 | 84 |

The 1.5 kg batch size (Lot D) was sprayed with an 8400 yield compared to the 800% yield of the 3.5 kg batch (Lot B).

25% Formula (I)/75% PVP/VA 64 SDD Process Parameter Screening Characterization

The 250% Formula (I)/75% PVP/VA 64 SDDs manufactured to evaluate processing parameters were characterized for powder properties, performance, and physical and chemical properties. Testing included particle size distribution by Malverm, determination of bulk and tapped density, microcentrifuge dissolution, modulated differential scanning calorimetry (mDSC), powder x-ray diffraction (PXRD), scanning electron microscope (SEM), and assay and related substances. The results did not show any significant differences between the lots.

The particle size distribution (PSD) and tabulated powder properties data of the 250% Formula (J)/75% PVP/VA 64

SDDs are shown in Table 13. All 25% Formula (J)/75% PVP/VA 64 SDDs were observed to have a very similar PSD with a $D_{50}$ of approximately 16 am. All 250% Formula (I)/75% PVP/VA 64 SDDs were observed to have low bulk and tapped densities.

TABLE 13

Powder properties of process parameter screening PVP/VA-64 SDDs

| Sample | Lot | $D_{10}$ (μm) | $D_{50}$ (μm) | $D_{90}$ (μm) | $D_{(3,2)}$ (μm) | $D_{(4,3)}$ (μm) | Span | Bulk density (g/mL) | Tapped density (g/mL) |
|---|---|---|---|---|---|---|---|---|---|
| 40 °C Outlet | A | 5 | 15 | 34 | 8 | 17 | 1.93 | 0.12 | 0.25 |
| 35 °C Outlet | B | 5 | 16 | 36 | 9 | 19 | 1.97 | 0.11 | 0.23 |
| 30 °C Outlet | C | 5 | 15 | 32 | 7 | 17 | 1.86 | 0.12 | 0.27 |
| 35 °C Outlet, 3.5 kg batch | D | 5 | 16 | 38 | 9 | 19 | 1.98 | 0.12 | 0.24 |

The 3.5 kg batch size lot was analyzed and compared to process parameter Lot A. Dissolution performance was similar for each of these lots. Dissolution was rapid to $C_{max}$ and high free drug was sustained through 90 minutes. These data are shown in Table 14.

TABLE 14

Dissolution performance of Lot A (1.5 kg batch size) vs. Lot D (3.5 kg batch size)

| Sample | $C_{max}90$ (μg/mL) | $AUC_{90}$ (min * μg/mL) | $C_{90}$ (μg/mL) | $Ultra_{90}$ (μg/mL) |
|---|---|---|---|---|
| Lot A | 447 | 37,740 | 437 | 319 |
| Lot D | 437 | 37,120 | 433 | 301 |

The 25% Formula (I)/75% PVP/VA 64 SDDs were also evaluated by DSC, PXRD, and SEM. The DSC thermograms showed a single $T_g$ at 84° C., indicating homogeneous dispersions. PXRD diffractograms showed no evidence of crystals in the SDDs. SEM images showed inflated sphere morphology with some broken particles and some very small particles.

Additional testing on Lot B was carried out, which included assessing the chemical/physical stability of both spray solution and SDD prior to secondary drying (wet SDD) to establish maximum in-process hold times. Residual acetone concentration as a function of secondary drying time in a convection tray dryer was also evaluated to nominate tray drying conditions to ensure the SDD is dried below International Council for Harmonization of Technical Requirements for Pharmaceuticals for Human Use (ICH) guidelines for acetone.

Residual acetone content as a function of drying time was assessed by drying wet SDD in a tray dryer and collecting samples over a 24-hour period. Wet SDD was dried at 40° C./15% relative humidity (RH) and was observed to dry below ICH acetone guidelines (0.5 wt %, 5000 ppm) by four hours.

Spray solution hold time was determined by making up a representative solution that contained 2.5 wt % compound of Formula (I), 7.5 wt % PVP/VA 64, and 90 wt % acetone. These solutions were analyzed initially for related substances. and then aged at 5° C. and 25° C. Aliquots were taken and analyzed for related substances periodically for 14 days. Results showed no change in impurity profile at either condition through 14 days.

Wet SDD was analyzed for impurities after storage at 5° C. and 25° C. for 1 and 2 weeks and compared to the impurity profiles of the ingoing compound of Formula (I) and the SDD that was secondarily dried immediately after spray drying. The impurity profiles were similar to that of the initial dried sample and the ingoing compound of Formula (I) through 2 weeks of storage.

The wet SDD stability samples were characterized for physical stability by DSC, PXRD, and SEM. DSC thermograms showed a single $T_g$ at 81° C., indicative of a homogeneous dispersion with no phase separation. The PXRD diffractograms did not show any evidence of crystals after storage at either condition. SEM images showed a typical morphology of mostly inflated spheres with some broken particles.

Example 3: Preparation of a 1000 g Batch of a Spray-Dried Dispersion Containing 25% of the Compound of Formula (I) and 75% PVP/VA 64

A 1000 g batch of the spray-dried dispersion containing 25% of the compound of Formula (I) and 75% PVP/VA 64 was prepared as described in Example 2 for the 1.5 kg and 3.5 kg batches. Briefly, acetone (90% (w/w) of the total mixture) was added to the mixing tank followed by the addition of 250.0 g of the compound of Formula (I) (2.5% (w/w) of the total mixture). The mixture was mixed for 30 minutes in the dark at a temperature range of 15° C. to 27° C. At the end of the mixing period, the solution was clear and free of undissolved solids. The PVP/VA 64 (750.0 g, 7.5% (w/w) of the total mixture) was then added and the mixture was stirred for an additional 30 minutes in the dark at a temperature range of 15° C. to 27° C. At the end of the mixing period, the solution was clear and free of undissolved solids.

Figure 5:
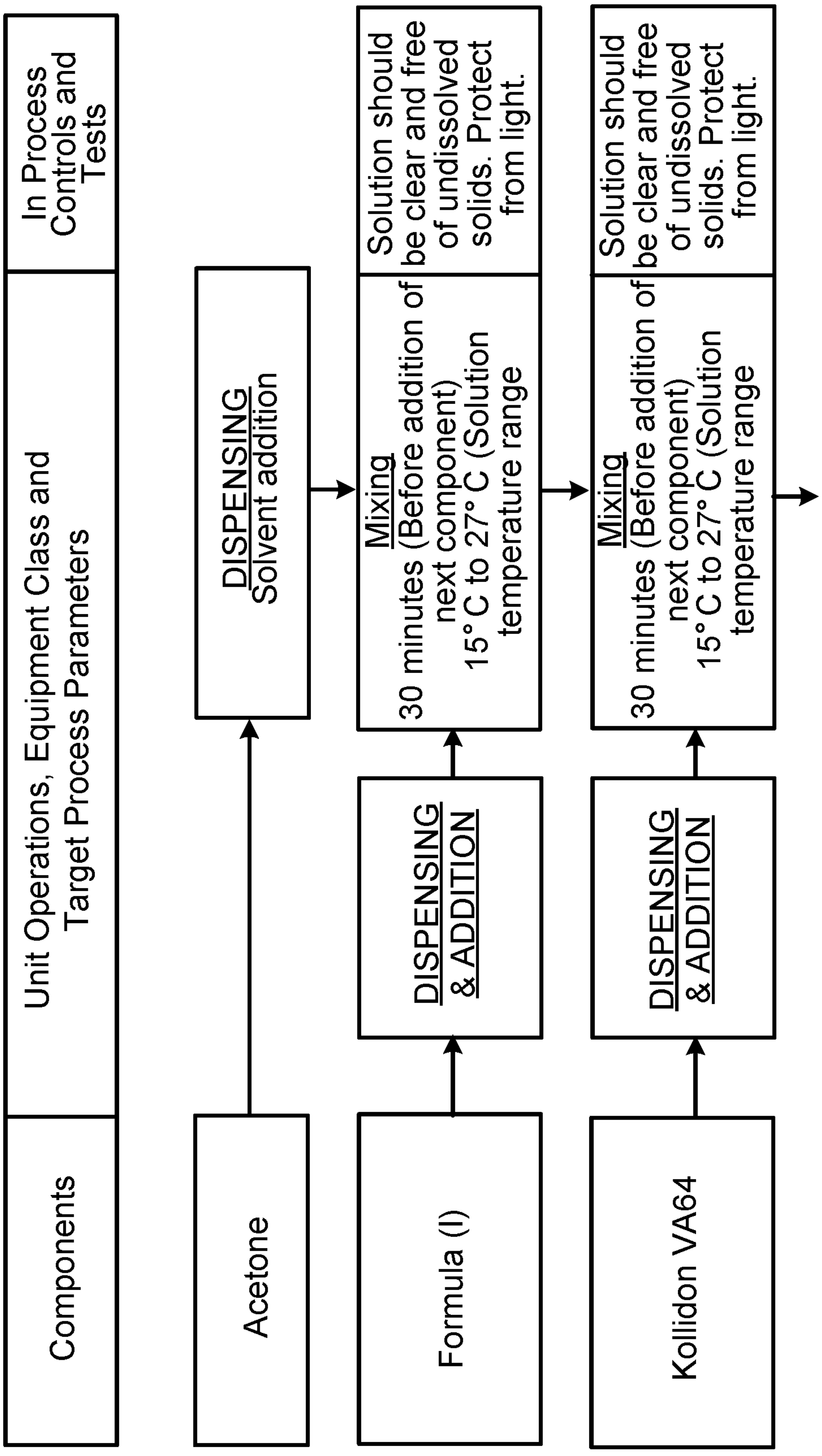
FIG. 5 is a flow diagram of the spray drying manufacturing process used to prepare a 1000 g batch of a SDD containing 25% of the compound of Formula (I) and 75% PVP/VA 64.
Figure 5:
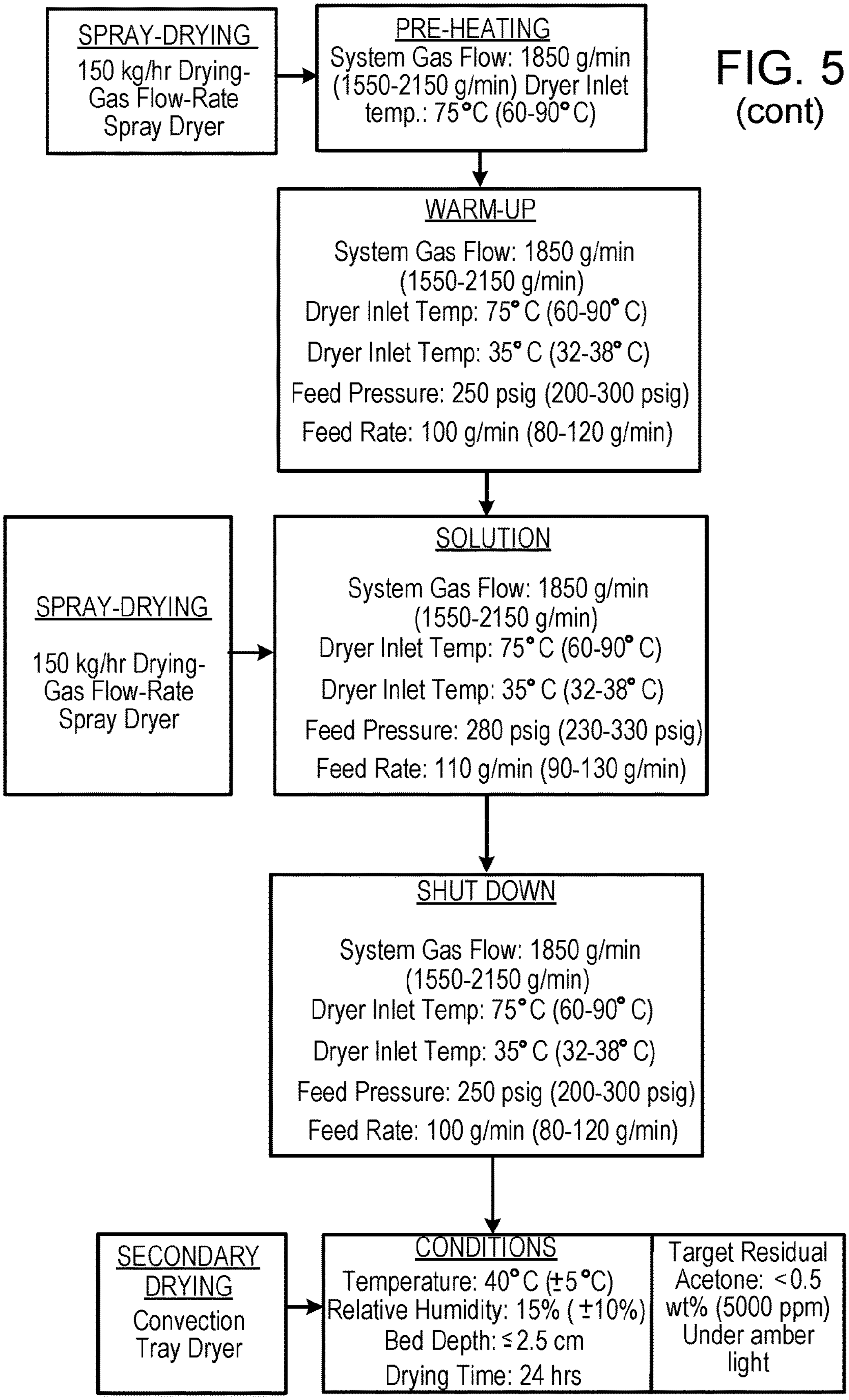

The solution was pumped and atomized in a drying chamber. The spray-dried dispersions were prepared in a Pharmaceutical Spray Dryer with 100 kg/hr drying gas capacity (PSD-1). The inlet temperature was set at 75° C. (varied between 60° C.-90° C.). The outlet temperature was set at 35° C. (varied between 32° C.-38° C.). The feed pressure was set at 280 psig (varied between 230-330 psig). The feed rate was set at 110 g/min (varied between 90-130 g/min). The spray dried powder was then dried in a convection tray dryer with a bed depth of <2.5 cm at 40° C. (±5° C.) and 15% relative humidity (±10%) for 24 hours under amber light. The residual acetone after drying was <0.5 wt % (5000 ppm). FIG. 5 is a flow diagram of the manufacturing process.

Example 4: Preparation of Spray-Dried Dispersion Formulations of the Compound of Formula (I) for Clinical Use The spray-dried dispersion (SDD) containing 25% compound of Formula (I) and 75% PVP/VA 64, prepared as described above, was formulated as a suspension or a capsule for clinical use.

Suspension Preparation

A suspension that contained 50 mg of the SDD was prepared as follows. A 30 mL amber dosing bottle was tared on a balance. 200.0 mg SDD (50 mgA)+5% was then weighed into the dosing bottle. Using a 10-mL syringe, 5.0 mL of water (purified, USP) was added to the dosing bottle and the bottle was capped and shaken moderately for 30 seconds. The SDD suspension was stored in an amber vial at 2-8° C. prior to use, and dosed within 24 hours of preparation.

Capsule Preparation

An empty hard gelatin capsule, size 0 (Capsugel, Morristown, NJ), was placed on a balance and the weight was recorded. 200.0 mg SDD (50 mgA)±5% was then weighed onto weigh paper or an equivalent. All contents were transferred to the capsule using a ProFunnel device for Size 0 capsules. The filled capsule was placed on the balance and the weight was recorded. The weight of the empty capsule was subtracted from the filled weight, ensuring that the weight of the SDD within the capsule was 200.0 mg SDD±5%, or from 190.0 mg to 210.0 mg. The capsule was securely closed with the head, assuring it clicked into place. The capsules were stored in an amber vial at 2-8° C. prior to use, and were dosed within 24 hours of preparation.

Example 5: Dog Relative Bioavailability and Food Effect Study

Four spray-dried dispersions (SDDs), formulated in 0.25% methylcellulose as a suspension, were prepared: (1) 25% compound of Formula (I)/75% HPMCAS-L; (2) 10% compound of Formula (I)/90% HPMCAS-L; (3) 25% compound of Formula (I)/75% methyl methacrylate copolymer (1:1) (methyl methacrylate copolymer sold under the trademark EUDRAGIT® L100); and (4) 25% compound of Formula (I)/75% PVP/VA 64. A clinical capsule formulation was prepared as a reference formulation (Reference Formulation 1 from Table 5, above).

Dogs (two cohorts, six dogs in each) were dosed in six sessions, including fasted state sessions and fed sessions (high fat diet), with 50 mg dose of one of the SDDs or reference per dog in a 3-way crossover design. Each session had a 3-day washout in between. All formulations were well tolerated. The study design is shown in Table 15, below.

TABLE 15

Study design

| | Session 1 (Fasted) | Session 2 (Fed) | Session 3 (Fasted) | Session 4 (Fed) | Session 5 (Fasted) | Session 6 (Fed) |
|---|---|---|---|---|---|---|
| Cohort 1 | | | | | | |
| Dog 1001 | Reference | Reference | SDD 1 | SDD 1 | SDD 2 | SDD 2 |
| Dog 1002 | Reference | Reference | SDD 1 | SDD 1 | SDD 2 | SDD 2 |
| Dog 2001 | SDD 1 | SDD 1 | SDD 2 | SDD 2 | Reference | Reference |
| Dog 2002 | SDD 1 | SDD 1 | SDD 2 | SDD 2 | Reference | Reference |
| Dog 3001 | SDD 2 | SDD 2 | Reference | Reference | SDD 1 | SDD 1 |
| Dog 3002 | SDD 2 | SDD 2 | Reference | Reference | SDD 1 | SDD 1 |
| Cohort 2 | | | | | | |
| Dog 4001 | Reference | Reference | SDD 3 | SDD 3 | SDD 4 | SDD 4 |
| Dog 4002 | Reference | Reference | SDD 3 | SDD 3 | SDD 4 | SDD 4 |
| Dog 5001 | SDD 3 | SDD 3 | SDD 4 | SDD 4 | Reference | Reference |
| Dog 5002 | SDD 3 | SDD 3 | SDD 4 | SDD 4 | Reference | Reference |
| Dog 6001 | SDD 4 | SDD 4 | Reference | Reference | SDD 3 | SDD 3 |
| Dog 6002 | SDD 4 | SDD 4 | Reference | Reference | SDD 3 | SDD 3 |

Figure 6A:
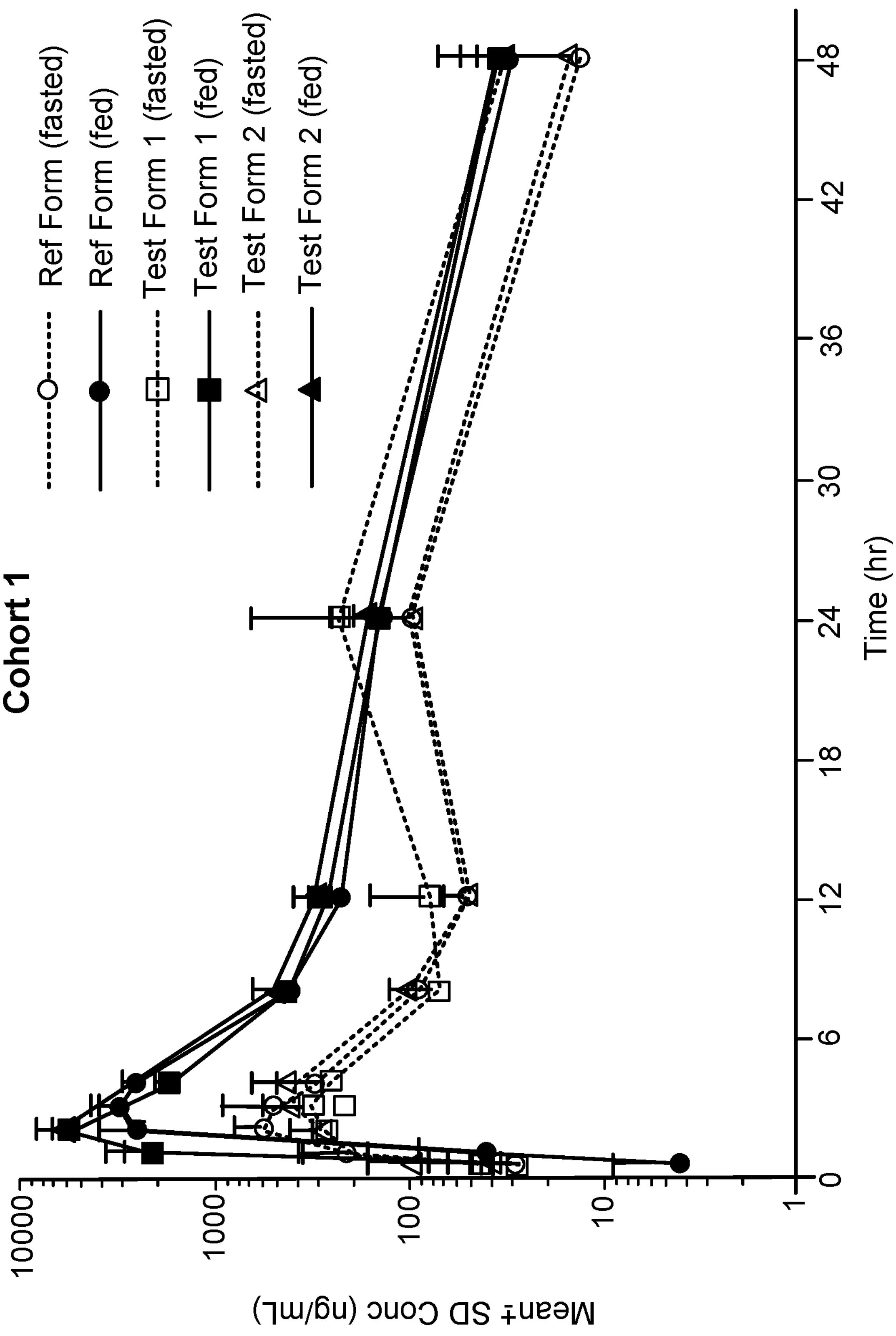
FIGS. 6A and 6B are line graphs showing the pharmacokinetic (PK) results of a bioavailability and food effect study in dogs.
Figure 6B:
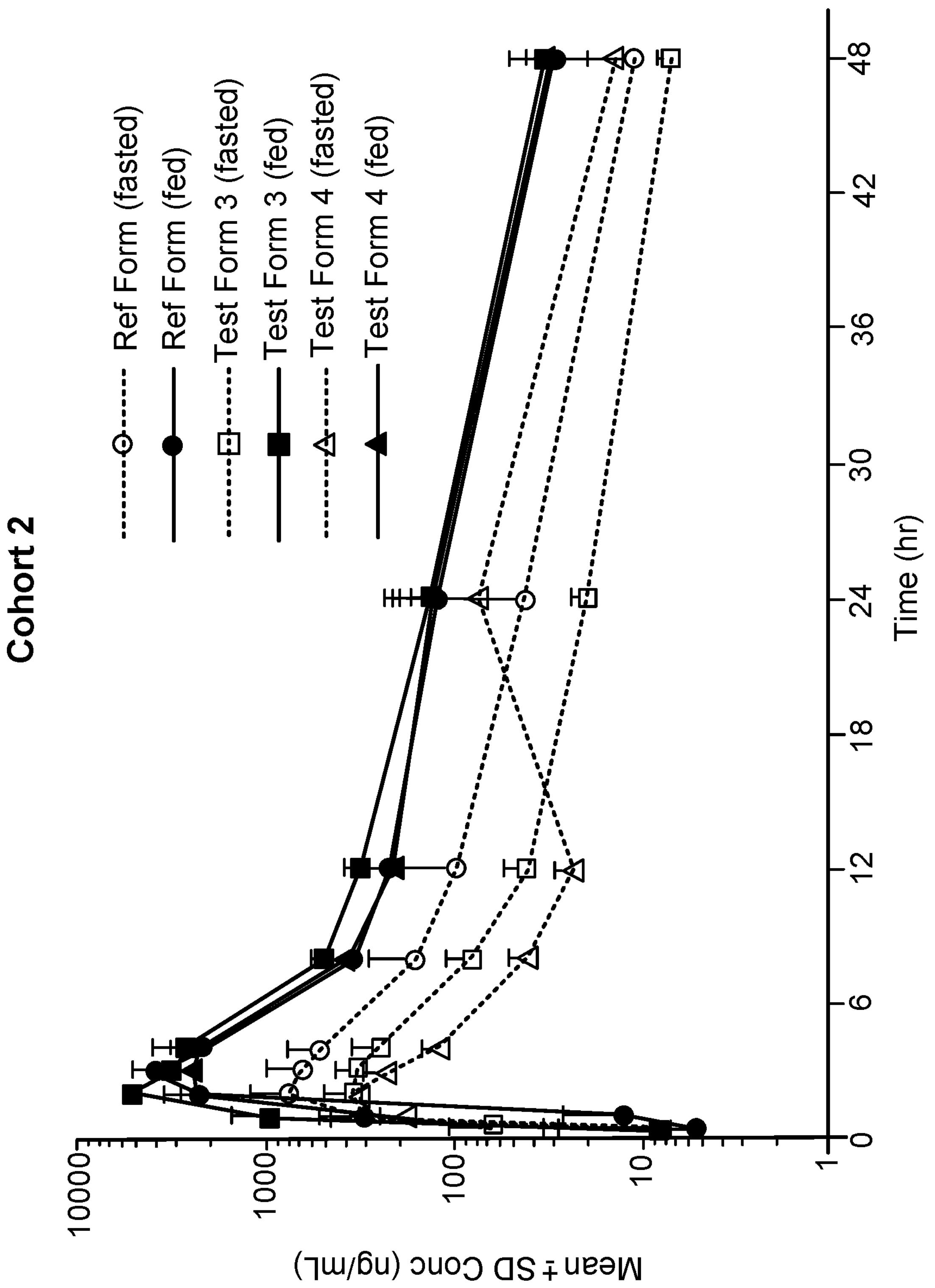

The area under the plasma concentration versus time curve from 0 hours extrapolated to infinity ($AUC_{0-\infty}$), maximum plasma concentration ($C_{max}$), the apparent terminal half-life ($t_{1/2}$), and the time to achieve maximum plasma concentration ($t_{max}$) were calculated. Results are shown in Table 16, below, and in FIGS. 6A and 6B.

TABLE 16

Pharmacokinetic results

| | | Fasted [Mean (% coefficient of variation (CV))] | | Fed [Mean (% CV)] | | Ratio of Fed/Fasted [Mean (% CV)] | |
|---|---|---|---|---|---|---|---|
| Cohort | Form | $C_{max}$ (ng/mL) | $AUC_{inf}$ (hr * ng/mL) | $C_{max}$ (ng/mL) | $AUC_{inf}$ (hr * ng/mL) | $C_{max}$ | AUC |
| 1 (N = 4)* | Ref | 652 (55.5) | 5170 (69.4) | 3650 (19.5) | 20100 (22) | 6.9 (48) | 5.5 (69.2) |
| | SDD 1 | 524 (62.7) | 2870 (62.9) | 5760 (25.6) | 22800 (14.6) | 15.4 (66.9) | 8 (89.6) |
| | SDD 2 | 487 (45.7) | 3950 (26.4) | 4220 (27.4) | 18100 (26.8) | 16.5 (40.7) | 6.3 (34.6) |

TABLE 16-continued

| Pharmacokinetic results | | | | | | | |
|---|---|---|---|---|---|---|---|
| | | Fasted [Mean (% coefficient of variation (CV))] | | Fed [Mean (% CV)] | | Ratio of Fed/Fasted [Mean (% CV)] | |
| Cohort | Form | $C_{max}$ (ng/mL) | $AUC_{inf}$ (hr * ng/mL) | $C_{max}$ (ng/mL) | $AUC_{inf}$ (hr * ng/mL) | $C_{max}$ | AUC |
| 2 (N = 6) | Ref | 854 (40.2) | 5520 (59.1) | 4220 (27.4) | 18100 (26.8) | 5.8 (46.5) | 4.1 (49.2) |
| | SDD 3 | 453 (28.3) | 2830 (21.6) | 5320 (13.5) | 23800 (26.1) | 12.6 (30.3) | 8.6 (22.2) |
| | SDD 4 | 353 (20.1) | 1840 (21.9) | 3060 (20.7) | 17200 (20.5) | 8.9 (29.3) | 8.4 (46.1) |

*Animals 2001 and 2002 were excluded from summary statistics due to emesis in all 3 fed sessions, which resulted in notably lower exposures The results showed that $t_{1/2}$ and $t_{max}$ were similar among the formulations, and comparable between the fed and fasted states. Under the fed state with a high fat meal, exposures increased and inter-animal variability decreased. The food effect was more notable with the spray-dried dispersion formulations, especially for peak exposure ($C_{max}$).

Compared to the reference form, SDD 4 (25% compound of Formula (I)/75% PVP/VA 64) appeared to have lower inter-animal variability, lower exposures under the fasted state, and slightly lower $C_{max}$ but relatively comparable AUC in the fed state.

Example 6: Phase 1 Study to Evaluate the Pharmacokinetics, Effect of Food on Pharmacokinetics, and Safety of the Compound of Formula (I) in Healthy Adult Subjects The present study was designed to evaluate the pharmacokinetics (PK) of the compound of Formula (I) as well as to evaluate the effect of a fed condition on the PK of the compound of Formula (I). The 50 mg dose was chosen for this study because it was within the tested dose range in completed Phase 1 and Phase 2 trials and was well tolerated in those studies. The objectives of the study were: to evaluate the PK of the compound of Formula (I) 50 mg in healthy adult subjects; to evaluate the effect of food on the PK of the compound of Formula (I) 50 mg; and to evaluate the safety and tolerability of the compound of Formula (I) 50 mg.

Study Design

This was a Phase 1, open-label, randomized, 2-period crossover study of the PK and the effect of food on the PK of the compound of Formula (I) in 16 healthy male and female adult subjects, 18 to 55 years of age.

After providing informed consent, subjects were screened for eligibility to participate in the study up to 28 days prior to Day 1 of treatment period 1. Eligible subjects were admitted to the clinical unit on Day −1 and randomized to 1 of the 2 treatment sequences (16 subjects [8 males and 8 females]; see Table 17, below). On Day 1 of each treatment period, subjects received a single dose of the compound of Formula (I) 50 mg under fasted or fed conditions. There were 21 days between doses.

TABLE 17

| Treatment sequences | | |
|---|---|---|
| Treatment sequence | Treatment period I | Treatment period 2 |
| 1 | Formula (I) - fasted | Formula (I) - fed |
| 2 | Formula (I) - fed | Formula (I) - fasted |

Subjects were required to fast for at least 4 hours before check-in on Day −1. In the fasted condition, subjects were required to fast overnight for at least 10 hours prior to dosing and continued to fast for an additional 4 hours after dosing. In the fed condition, subjects were required to fast overnight for at least 10 hours and then ingest a liquid dietary supplement with study drug (liquid dietary supplement was consumed within 30 minutes) and not consume any other food for 4 hours after dosing. During both treatment periods, water was not permitted for 1 hour before dosing until 2 hours after dosing except for the water/liquid dietary supplement provided for study drug dosing. Vanilla-flavored nutritional composition sold under the trademark ENSURE PLUS® was used as the liquid dietary supplement.

On Day 1 of each treatment period, subjects were dosed with the compound of Formula (I) 50 mg. Blood samples were collected for PK analysis over a period of 36 hours during the in-house stay. Subjects remained in the unit on the day of dosing and were discharged on Day 2 of each treatment period, following completion of all required procedures. On the mornings of Days 8 and 15 of each treatment period, subjects returned to the clinical unit on an outpatient basis for PK blood sample collection and safety assessments. On Day 21 of treatment period 1, subjects arrived at the site and had Day 21 assessments completed in the evening, and they stayed overnight at the site and began Day 1 of treatment period 2 the following day. A final follow-up study visit was conducted on Day 22 of treatment period 2 (21±2 days after treatment period 2 dosing) or upon early termination.

During each treatment period, blood samples for PK analysis were collected within 45 minutes before dosing, and at approximately 30 minutes, and 1, 2, 3, 4, 5, 6, 7, 8, 9, 10, 12, 16, 24, 36, 168, 336, and 504 hours after dosing.

Figure 7:
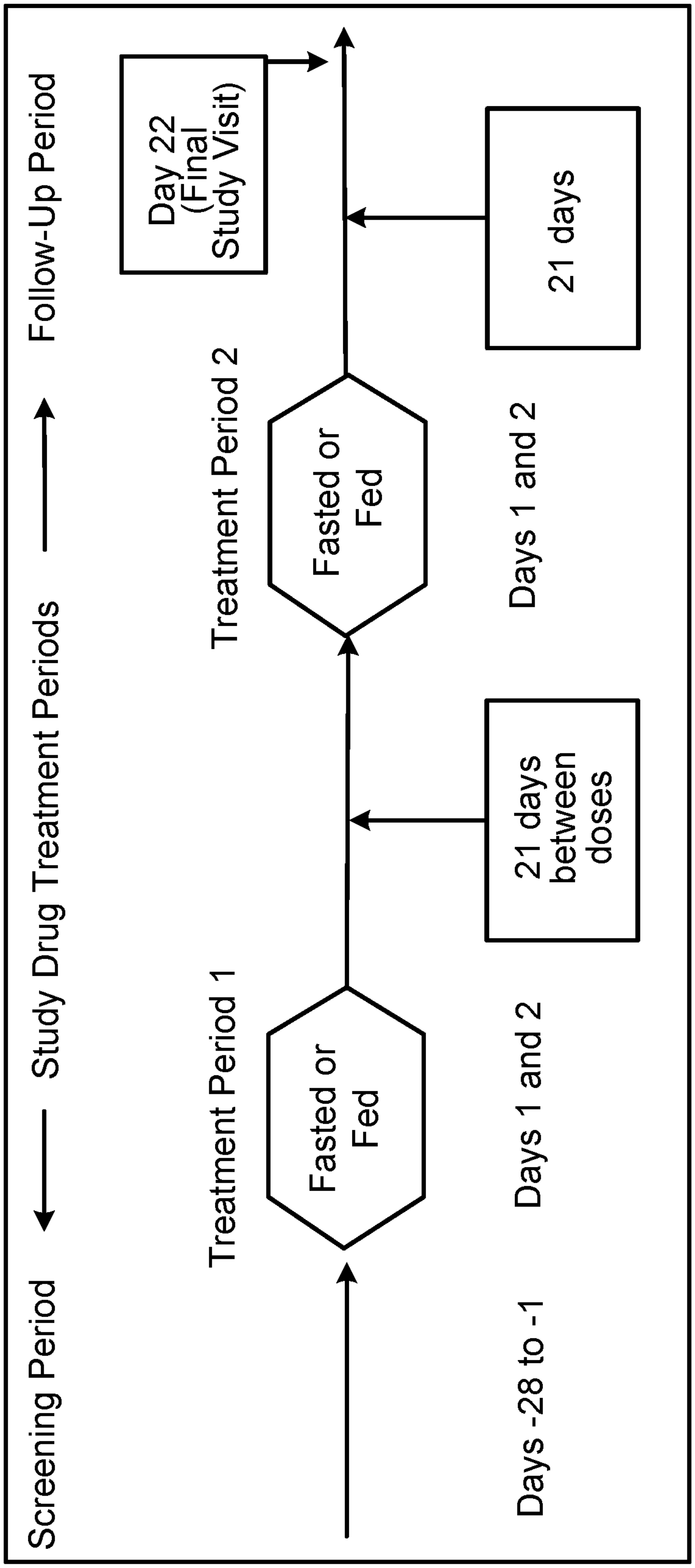
FIG. 7 is a flow chart showing the study design of a Phase 1 study of the pharmacokinetics and food effect of the compound of Formula (I) in healthy adult subjects.

Safety assessments (including clinical safety laboratory tests, vital sign measurements, physical examinations, and electrocardiograms (ECGs)) were conducted at scheduled times throughout the study. Adverse events (AEs) and the use of concomitant medications were monitored throughout the study. FIG. 7 illustrates the study design.

Test Product, Dose and Mode of Administration

The compound of Formula (I) was supplied as an encapsulated, lipidic semi-solid containing 50 mg of the compound of Formula (I) as free base equivalent for oral administration. Subjects swallowed a single capsule with approximately 240 mL of water in the fasted condition. Subjects swallowed a single capsule with a liquid dietary supplement (nutritional composition sold under the trademark ENSURE PLUS® [237 mL container]) with up to an additional 120 mL of water in the fed condition.

Duration of Treatment

The duration of study participation for each adult subject was approximately 10 weeks, including up to 28 days of screening, 2 days of dosing separated by 21 days, and a final follow-up study visit 21 days after receiving the last dose of study drug during treatment period 2.

Criteria for Evaluation

Pharmacokinetics

The following plasma PK parameters were calculated for the compound of Formula (I):

- Area under the plasma concentration versus time curve from 0 hours to last measurable concentration ($AUC_{0-tlast}$)
- Area under the plasma concentration versus time curve from 0 to 24 hours ($AUC_{0-24}$)
- Area under the plasma concentration versus time curve from 0 hours extrapolated to infinity ($AUC_{0-\infty}$)
- Maximum plasma concentration ($C_{max}$)
- Time to achieve maximum plasma concentration ($t_{max}$)
- Delay time between time of dosing and time of appearance of measurable test article ($T_{lag}$)
- Apparent terminal half-life ($t_{1/2}$)
- Apparent terminal rate constant ($\lambda z$)
- Apparent mean residence time (MRT)
- Molar AUC ratio of the hydroxylated metabolite of the compound of Formula (I) to the parent drug the compound of Formula (I)

The following plasma PK parameters were calculated only for the compound of Formula (I):

- Apparent systemic clearance after oral administration (CL/F)
- Apparent volume of distribution during terminal phase after oral administration (Vz/F)

Safety

Safety was monitored throughout the study and included the following assessments:

- Adverse events (AEs)
- Clinical laboratory tests (hematology, coagulation, clinical chemistry, and urinalysis)
- Vital sign measurements (including orthostatic blood pressure and pulse rate)
- Physical examinations
- 12-lead electrocardiograms (ECGs)

Statistical Methods

Pharmacokinetic parameters were calculated using non-compartmental methods and summarized by condition (fed or fasted) using descriptive statistics. Two-sided 90% confidence intervals were calculated for the ratio under the fed condition vs. under the fasted condition for $AUC_{0-\infty}$, $AUC_{0-tlast}$, and $C_{max}$ for the compound of Formula (I) and the hydroxylated metabolite of the compound of Formula (I).

Safety data were summarized with descriptive statistics.

Pharmacokinetics

Pharmacokinetic Assessments

PK plasma samples for analyses of the compound of Formula (I) and the hydroxylated metabolite of the compound of Formula (I) were collected at the following times during each treatment period:

- Day 1: within 45 minutes before dosing, and at approximately 30 minutes, and 1, 2, 3, 4, 5,6, 7, 8, 9, 10, 12, and 16 hours after dosing.
- Day 2: approximately 24 and 36 hours after dosing.
- Day 8: approximately 168 hours after dosing.
- Day 15: approximately 336 hours after dosing.
- Approximately 504 hours after dosing (for treatment period 1, this sample was collected in the morning at least 30 minutes prior to the predose sample on Day 1 of treatment period 2).
- Final study visit for subjects who terminate early: 1 sample.

Blood samples on Day 1 were collected within 5 minutes of the scheduled sampling times (other than the predose sample). Blood samples on Days 2, 8, and 15 were collected within 2 hours of the scheduled sampling time. The 504 hour blood sample for treatment period 2 had a ±2-day window. A PK sample was to be collected from subjects who terminated early. The exact time of sampling in hour and minutes was recorded.

Bioanalytical Methods

Plasma samples were analyzed for the compound of Formula (I) and for its hydroxylated metabolite by inVentiv Health, Princeton NJ, in compliance with Good Laboratory Practice (GLP) and relevant Standard Operating Procedures (SOPs).

The concentrations of the compound of Formula (I) and the hydroxylated metabolite of the compound of Formula (I) were quantified in plasma samples according to validated methods using tandem mass spectrometry in positive ion mode. This method was validated for the analysis of the compound of Formula (I) and the hydroxylated metabolite of the compound of Formula (I) in 25.0 μL dipotassium ethylenediaminetetraacetic acid ($K_2$-EDTA) human plasma samples over concentration ranges of 5.00 to 2500 ng/mL and 0.500 and 250 ng/mL, respectively. All analytical results were within acceptable limits. Incurred sample reanalysis (ISR) was successfully conducted in this study for both analytes.

Results

Pharmacokinetic Results

Eight male and eight female subjects were enrolled. The mean age was 37.1 years (range, 21 to 55 years). The majority of subjects were White (93.8%) and of Hispanic ethnicity (81.3%). The mean weight at screening was 160.28 lbs (range, 102.0 to 222.2 lbs) and mean body mass index (BMI) was 25.50 $kg/m^2$ (range, 20.7 to 30.5 $kg/m^2$). The randomization was well balanced with respect to demographics and baseline characteristics.

All 16 subjects were included in the safety analysis set. No subjects were excluded from the safety analysis set and no subject had his or her PK data excluded from analysis.

Figure 8A:
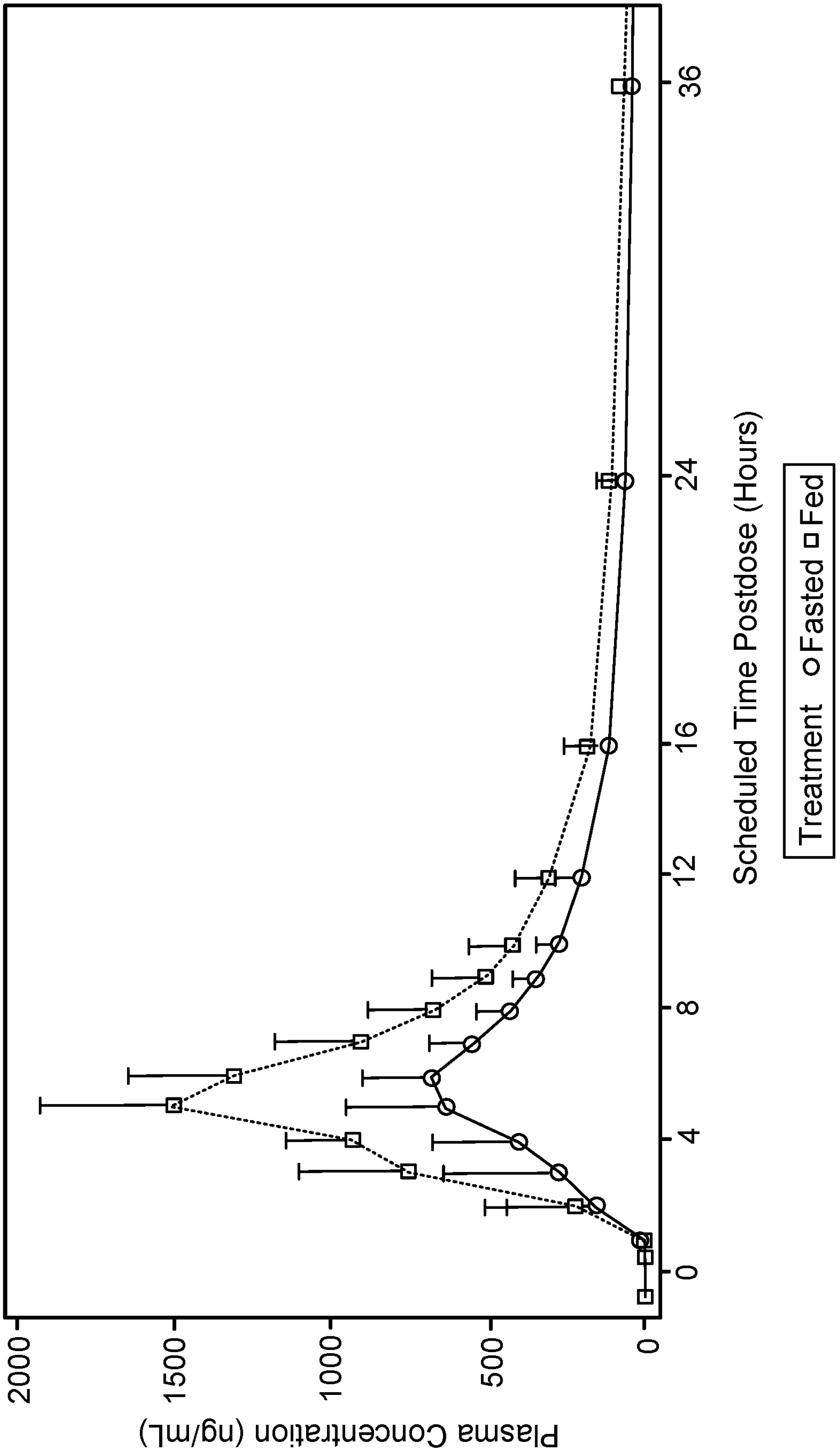
FIGS. 8A and 8B are line graphs showing the mean plasma concentration versus time profiles for the compound of Formula (I) under fasted and fed conditions, respectively, in healthy adult subjects.
Figure 8B:
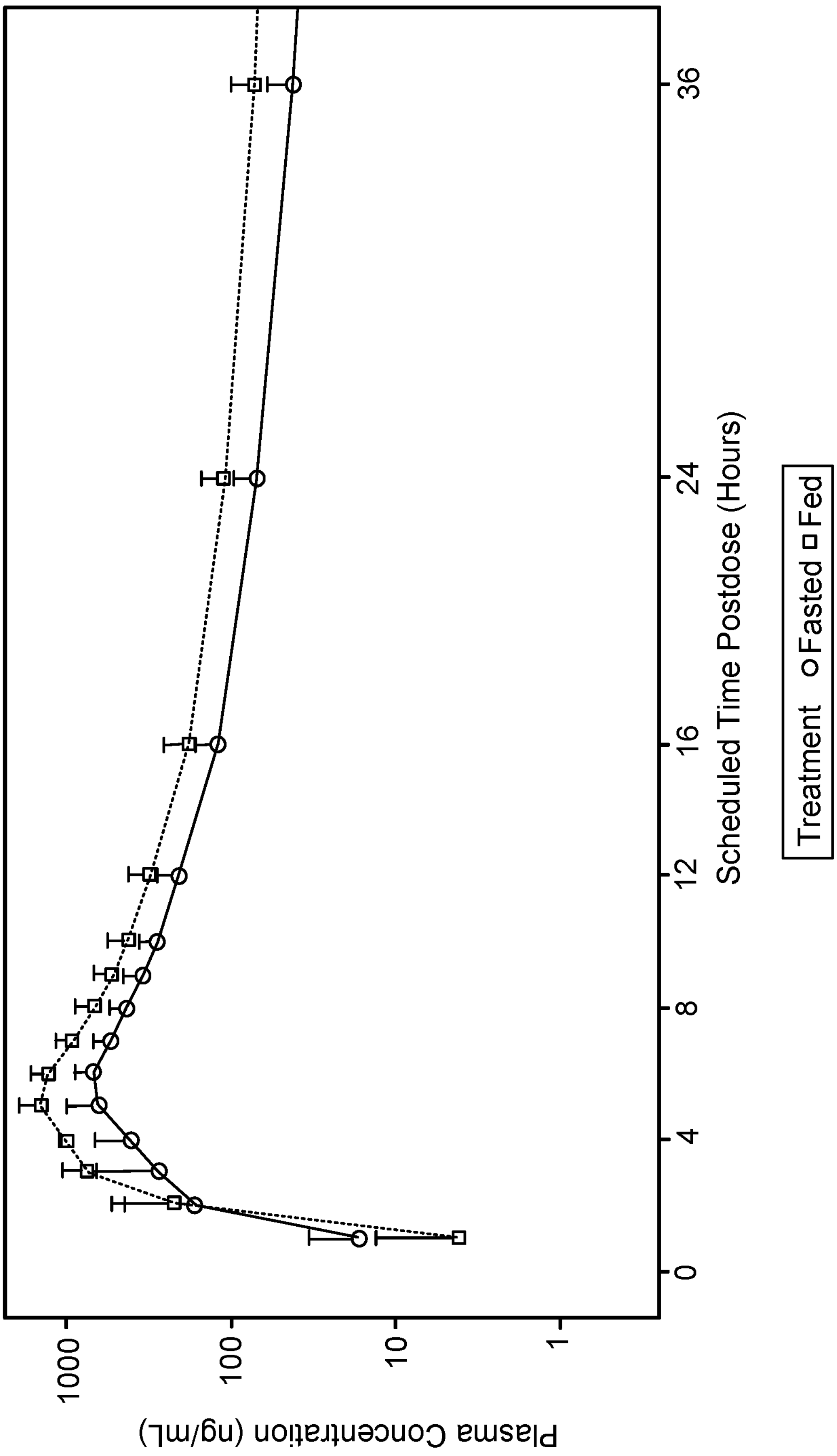

The mean plasma concentration versus time profiles for the compound of Formula (I) under fasted and fed conditions are presented in FIGS. 8A and 8B, respectively. The compound of Formula (I) was slowly absorbed after oral administration in both fasted and fed conditions. Mean plasma concentrations were lower in the fasted than in the fed condition.

PK parameters for the compound of Formula (I) after treatment with the compound of Formula (I) under fasted and fed conditions are summarized in Table 18, below, where $AUC_{0-24}$=area under the plasma concentration vs. time curve from 0 to 24 hours, $AUC_{0-tlast}$=AUC from 0 hours to last measurable concentration, $AUC_{0-\infty}$=AUC from 0 hours extrapolated to infinity, CL/F=apparent systemic clearance after oral administration, CV=coefficient of variation, $C_{max}$=maximum plasma concentration, CV(%)=coefficient of variation, max=maximum, min=minimum, MRT=apparent mean residence time, PK=pharmacokinetic, SD=standard deviation, $t_{1/2}$=apparent terminal half-life, $T_{lag}$=delay time between time of dosing and time of appearance of measurable test article, $t_{max}$=time to maximum plasma concentration, VZ/F=apparent volume of distribution during the terminal phase after oral administration.

The PK data for $t_{max}$, $T_{lag}$, $t_{1/2}$, MRT, and Vz/F were rounded to 2 significant figures and all other parameters ($AUC_{0-24}$, $AUC_{0-tlast}$, $AUC_{0-\infty}$, $C_{max}$, and CL/F) were rounded to 3 significant figures. The last significant figure was rounded up if the digit to the right of it was ≥5, and was rounded down if the digit to the right of it was ≤4.

TABLE 18

Summary of Formula (I) PK parameters (safety analysis set)

| Parameter Statistic | Fasted Formula (I) (50 mg) (N = 16) | Fed Formula (I) (50 mg) (N=15) |
|---|---|---|
| $AUC_{0-24}$ (ng × hr/mL) | | |
| Mean (SD) | 5590 (2230) | 9950 (2540) |
| Geometric CV % | 32.7 | 26.2 |
| $AUC_{0-tlast}$ (ng × hr/mL) | | |
| Mean (SD) | 8020 (5110) | 16200 (5450) |
| Geometric CV % | 53.6 | 39.7 |
| $AUC_{0-\infty}$ (ng × hr/mL) | | |
| Mean (SD) | 9440 (2990) [n = 7] | 17800 (4990) [n = 12] |
| Geometric CV % | 39.7 | 28.1 |
| $C_{max}$ (ng/mL) | | |
| Mean (SD) | 731 (301) | 1550 (392) |
| Geometric CV % | 36.6 | 24.2 |
| $t_{max}$ (hours) | | |
| Median (min, max) | 6.0 (3.0, 6.0) | 5.0 (3.0, 6.0) |
| $T_{lag}$ (hours) | | |
| Mean (SD) | 0.63 (0.22) | 0.94 (0.37) |
| $t_{1/2}$ (hours) | | |
| Mean (SD) | 33 (17) [n = 7] | 42 (6.8) [n = 12] |
| Geometric CV % | 99 | 15 |
| MRT (hours) | | |
| Mean (SD) | 28 (11) [n = 7] | 30 (5.0) [n = 12] |
| Geometric CV % | 49 | 16 |
| CL/F (L/hr) | | |
| Mean (SD) | 6.0 (2.7) [n = 7] | 3.0 (0.82) [n = 12] |
| Geometric CV % | 40 | 28 |
| VZ/F (L) | | |
| Mean (SD) | 240 (120) [n = 7] | 180 (57) [n = 12] |
| Geometric CV % | 67 | 30 |

As seen in Table 18, above, administration of the compound of Formula (I) 50 mg under fed compared with fasted conditions resulted in a higher mean $C_{max}$ of the compound of Formula (I) (approximately 2-fold higher; 1550 vs. 731 ng/mL), a longer $t_{1/2}$ (42 vs. 33 hours), a slightly shorter median $t_{max}$ (5.0 vs. 6.0 hours), and a higher mean $AUC_{0-\infty}$ (approximately 2-fold higher; 17800 vs. 9440 ng×hr/mL). The compound of Formula (I) geometric mean ratios for $C_{max}$ and $AUC_{0-tlast}$ for fed vs. fasted conditions were 218.6% and 215.2%, respectively, indicating that the compound of Formula (I) absorption was approximately 2-fold greater when administered with food. The upper and lower 9000 confidence interval (CI) bounds for both $C_{max}$ (187.400 and 255.1%, respectively) and $AUC_{0-tlast}$ (1820.9% and 253.1%, respectively) were outside of the "no-effect" range of 80.00% to 125.00%, indicating that there was a food effect on the compound of Formula (I) exposure.

Figure 9A:
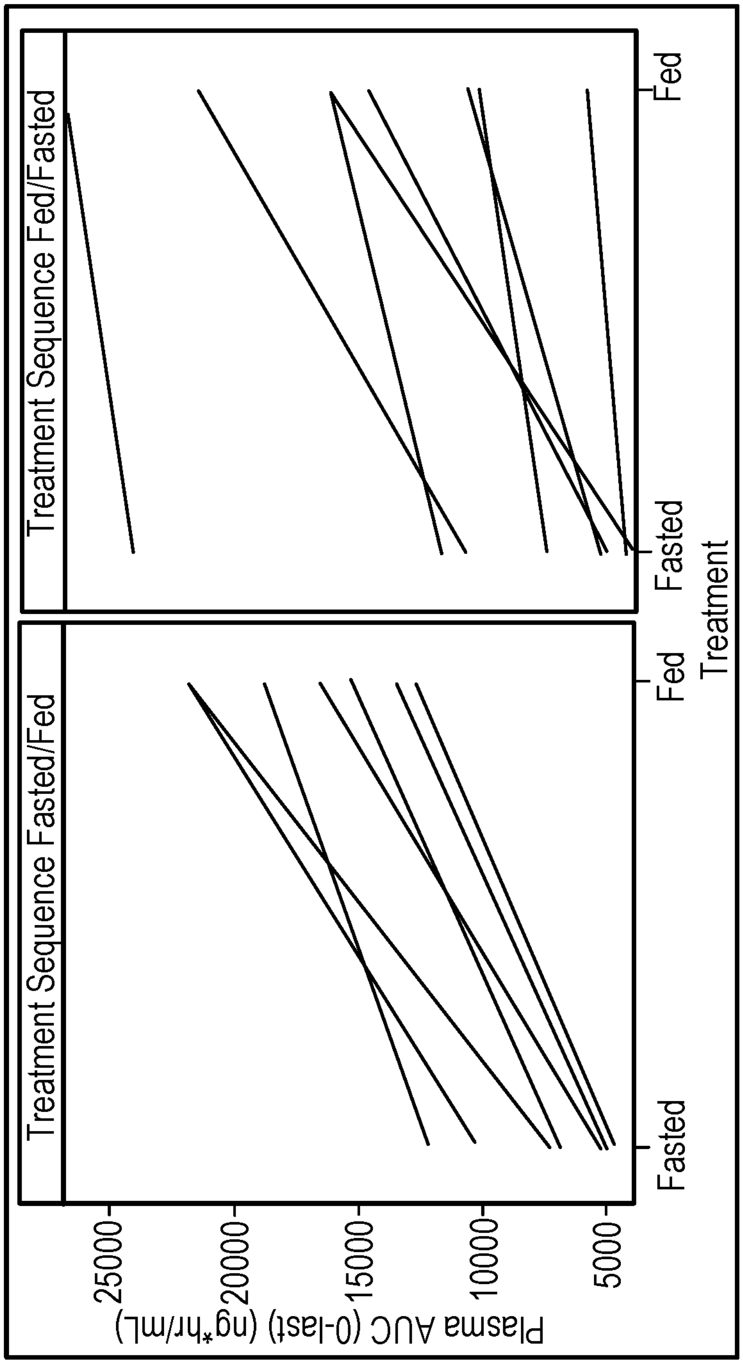
FIGS. 9A-9C are spaghetti plots of the pharmacokinetics of the compound of Formula (I) in healthy adult subjects under fasted and fed conditions.
Figure 9B:
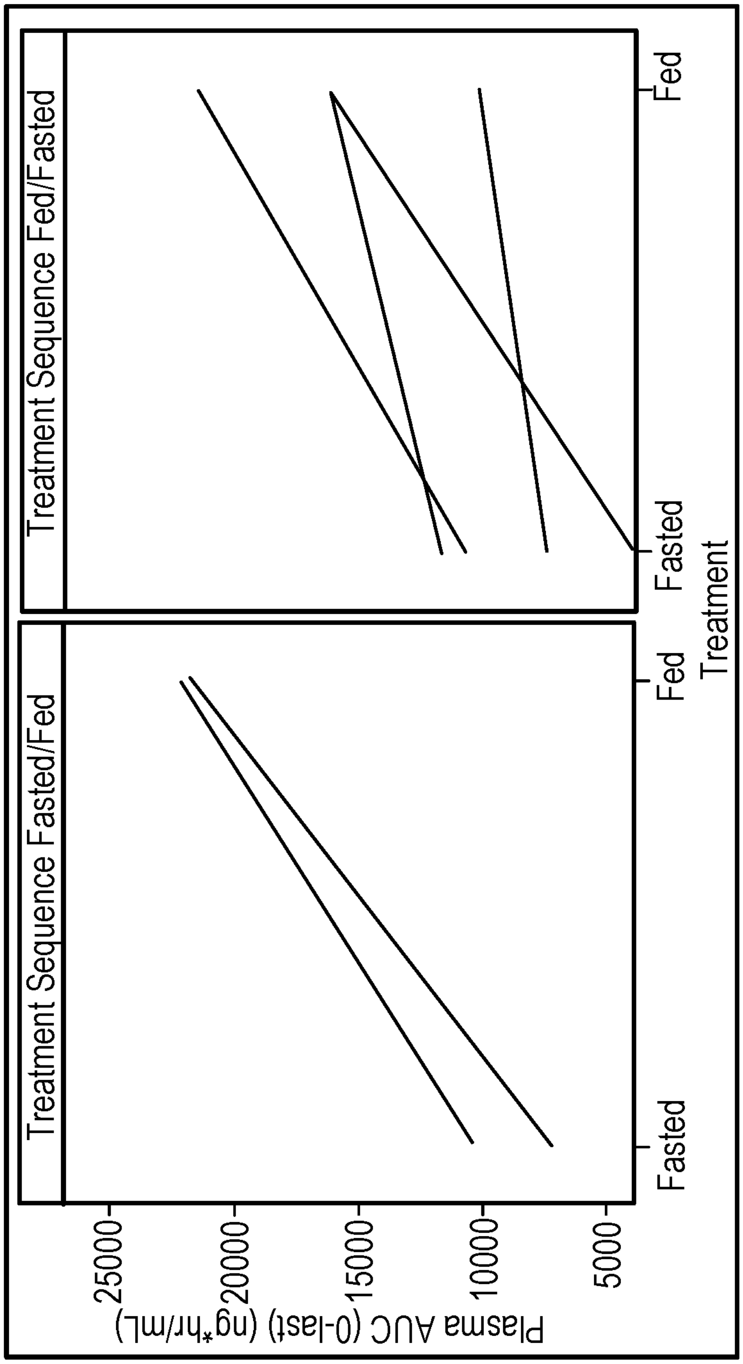
Figure 9C:
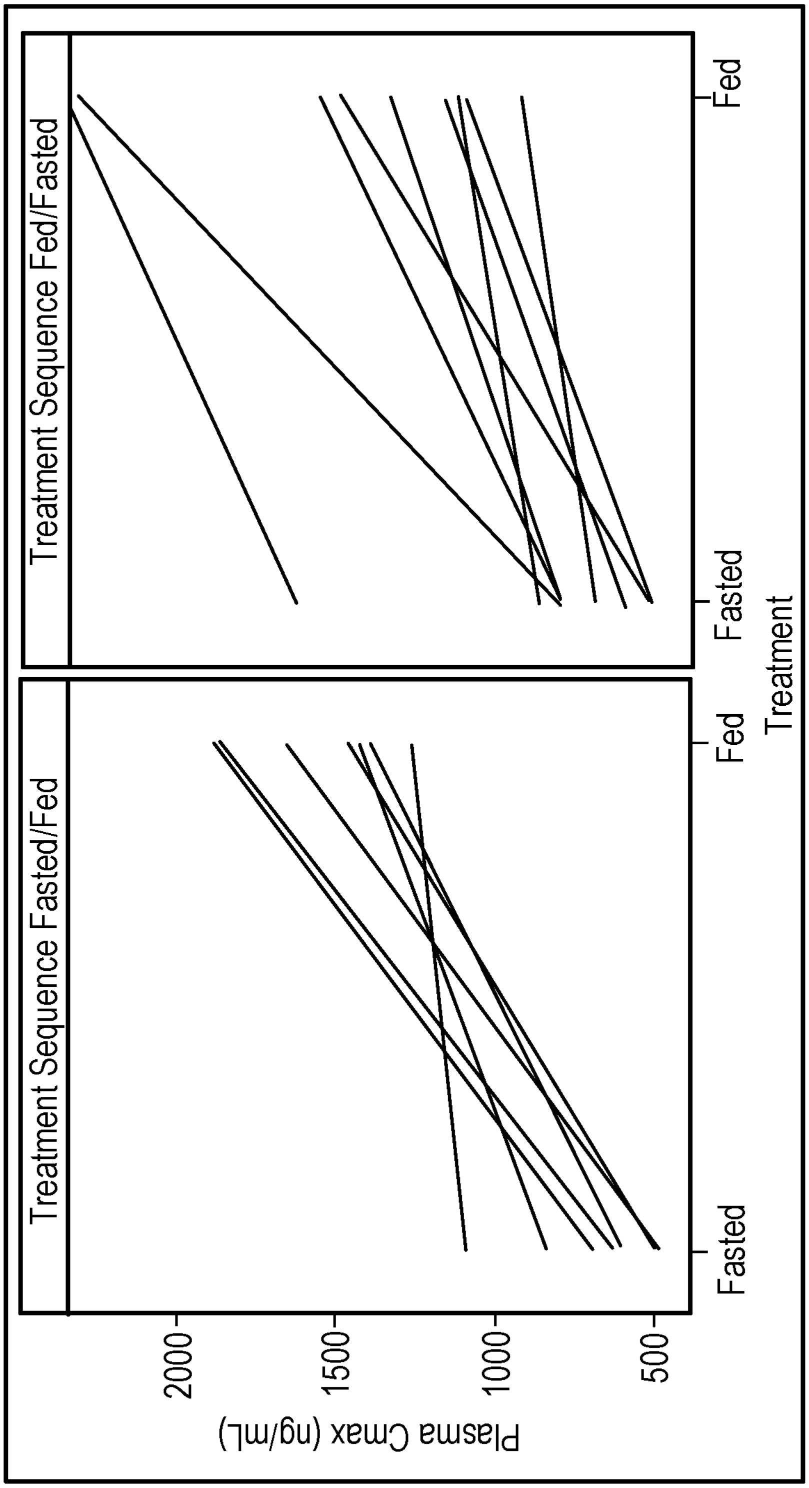

Frequency distribution of $T_{lag}$ and $t_{max}$ values are presented in Table 19 and Table 20, respectively. Spaghetti plots for the compound of Formula (I) $AUC_{0-tlast}$, $AUC_{0-\infty}$ and $C_{max}$ are shown in FIGS. 9A, 9B, and 9C, respectively.

TABLE 19

Frequency distribution of plasma Formula (I) $T_{lag}$ values by treatment (safety analysis set)

| $T_{lag}$ (hr) | Statistic | Fasted (Formula (I) 50 mg) (N = 16) | Fed (Formula (I) 50 mg) (N = 15) |
|---|---|---|---|
| 0.50 | n (%) | 11 (68.8%) | 3 (20.0%) |
| 0.53 | n (%) | 1 (6.3%) | 0 (0.0%) |
| 0.55 | n (%) | 0 (0.0%) | 1 (6.7%) |
| 1.00 | n (%) | 4 (25.0%) | 8 (53.3%) |
| 1.02 | n (%) | 0 (0.0%) | 1 (6.7%) |
| 1.03 | n (%) | 0 (0.0%) | 1 (6.7%) |
| 2.00 | n (%) | 0 (0.0%) | 1 (6.7%) |

TABLE 20

Frequency distribution of plasma Formula (I) $T_{max}$ values by treatment (safety analysis set)

| $T_{max}$ (hr) | Statistic | Fasted (Formula (I) 50 mg) (N = 16) | Fed (Formula (I) 50 mg) (N = 15) |
|---|---|---|---|
| 3.00 | n (%) | 1 (6.3%) | 2 (13.3%) |
| 4.02 | n (%) | 1 (6.3%) | 0 (0.0%) |
| 5.00 | n (%) | 4 (25.0%) | 8 (53.3%) |
| 5.03 | n (%) | 0 (0.0%) | 1 (6.7%) |
| 5.05 | n (%) | 0 (0.0%) | 1 (6.7%) |
| 6.00 | n (%) | 10 (62.5%) | 2 (13.3%) |
| 6.02 | n (%) | 0 (0.0%) | 1 (6.7%) |

The compound of Formula (I) was slowly absorbed after oral administration in the fasted and fed conditions. In the fasted condition, the mean compound of Formula (I) $C_{max}$ was approximately 53% lower than in the fed condition (731 vs. 1550 ng/mL). Due to a prolonged elimination phase, $t_{1/2}$ values and therefore, $AUC_{0-\infty}$ values could not be determined for some the compound of Formula (I) concentration-time profiles. Mean $AUC_{0-\infty}$ was approximately 47% lower in the fasted condition than in the fed condition (9440 vs. 17800 ng×hr/mL) for those subjects for whom $AUC_{0-\infty}$ could be determined. Mean $AUC_{0-tlast}$ was approximately 50% lower in the fasted condition than in the fed condition (8020 vs. 16200 ng×hr/mL). Median $t_{max}$ was slightly longer in the fasted condition than in the fed condition (6.0 vs. 5.0 hours) and mean $t_{1/2}$ was shorter in the fasted condition than in the fed condition (33 vs. 42 hours) for those subjects for whom a $t_{1/2}$ could be determined. Variability in the compound of Formula (I) PK (geometric CV %) for AUC, $C_{max}$, $t_{1/2}$, and apparent mean residence time (MRT) was lower in the fed condition compared with the fasted condition.

The geometric mean ratios and associated 90% CIs for $AUC_{0-tlast}$ and $C_{max}$ for the compound of Formula (I) after treatment with the compound of Formula (I) for the fed vs. fasted condition are provided in Table 21, below, where $AUC_{0-tlast}$=AUC from 0 hours to last measurable concentration, $C_{max}$=maximum plasma concentration, and PK=pharmacokinetic.

TABLE 21

| Formula (I) geometric mean ratios for PK exposure parameters under fed vs. fasted conditions (safety analysis set) | | |
|---|---|---|
| Parameter | Ratio[a] (%) (Fed vs. Fasted Condition) | 90% Confidence Interval[b] |
| $AUC_{0\text{-}tlast}$ (ng × hr/mL) | 215.2 | 182.9, 253.1 |
| $C_{max}$ (ng/mL) | 218.6 | 187.4, 255.1 |

[a]Ratio of geometric least-squares means was based on a mixed model using log-transformed (base 10) data.
[b]The 90% confidence interval for geometric mean ratio was based on least-squares means using log-transformed (base 10) data.

The compound of Formula (I) geometric mean ratios for $C_{max}$ and $AUC_{0\text{-}tlast}$ for the fed vs. fasted conditions were 218.6% and 215.2%, respectively, indicating that the compound of Formula (I) absorption was approximately 2-fold greater when administered with food. The upper and lower 90% CI bounds for both $C_{max}$ (187.4%, 255.1%) and $AUC_{0\text{-}tlast}$ (182.9%, 253.1%) were outside of the "no-effect" range of 80.00% to 125.00%, indicating that there was a food effect on the compound of Formula (I) exposure. Due to the missing $AUC_{0\text{-}\infty}$ values, the food effect on overall exposure was not assessed using $AUC_{0\text{-}\infty}$ values.

CONCLUSION

Administration of the compound of Formula (I) 50 mg under fed compared with fasted conditions resulted in a higher mean $C_{max}$ of the compound of Formula (I) (approximately 2-fold higher; 1550 vs. 731 ng/mL), a longer $t_{1/2}$ (42 vs. 33 hours), a slightly shorter median $t_{max}$ (5.0 vs. 6.0 hours), and a higher mean $AUC_{0\text{-}\infty}$ (approximately 2-fold higher; 17800 vs. 9440 ng×hr/mL).

The compound of Formula (I) geometric mean ratios for $C_{max}$ and $AUC_{0\text{-}tlast}$ for fed vs. fasted conditions were 218.6% and 215.2%, respectively, indicating that the compound of Formula (I) absorption was approximately 2-fold greater when administered with food. The upper and lower 90% CI bounds for both $C_{max}$ (187.4%, 255.1%) and $AUC_{0\text{-}tlast}$ (182.9%, 253.1%) were outside of the "no-effect" range of 80.00% to 125.00%, indicating that there was a food effect on the compound of Formula (I) exposure. Similar results were observed with the hydroxylated metabolite of the compound of Formula (I). Overall, these results indicate that the compound of Formula (I) 50 mg was well tolerated in healthy subjects when administered under fasted or fed conditions and that the total AUC and $C_{max}$ were increased when the compound of Formula (I) was taken with food.

Example 7: Phase 1 Study to Evaluate the Relative Bioavailability, Effect of Food on Pharmacokinetics, and Safety of Formulations of the Compound of Formula (I) in Healthy Adult Subjects A Phase 1 study to compare the relative bioavailability of a 50 mg dose of different formulations of the compound of Formula (I) as well as to evaluate the effect of fasting and fed conditions on the pharmacokinetics (PK) of the compound of Formula (I) was designed. The 50 mg dose was chosen for this study because it is within the tested dose range in completed Phase 1 and Phase 2 trials and was well tolerated in those studies. The objectives of the study are: to evaluate the PK and compare the relative bioavailability of the compound of Formula (I) 50 mg formulations in healthy adult subjects; to evaluate the effect of food on the PK of the compound of Formula (I) 50 mg formulations; and to evaluate the safety and tolerability of the compound of Formula (I) 50 mg formulations.

Study Design

This is a Phase 1, open-label, randomized, three-period crossover study of the relative bioavailability and the effect of food on the PK of the compound of Formula (I) 50 mg in healthy adult subjects. During treatment period 1 and treatment period 2, subjects will receive a single dose of the compound of Formula (I) 50 mg administered as an encapsulated, lipidic semi-solid (reference) and 1 of 2 different spray-dried dispersion (SDD) test formulations (suspension or capsule) under fed conditions, and during treatment period, three subjects will receive the same SDD test formulation under fasted conditions.

A total of 36 healthy adult subjects will be randomized to 1 of 4 treatment sequences (9 subjects per sequence; approximately equal distribution of males and females per sequence; see Table 22, below). There will be 21 days between each dose.

TABLE 22

| Treatment sequences | | | |
|---|---|---|---|
| Treatment sequence | Treatment period 1 (Fed) | Treatment period 2 (Fed) | Treatment period 3 (Fasted) |
| 1 | Reference | SDD suspension | SDD suspension |
| 2 | SDD suspension | Reference | SDD suspension |
| 3 | Reference | SDD capsule | SDD capsule |
| 4 | SDD capsule | Reference | SDD capsule |

After providing informed consent, subjects will be screened for eligibility to participate in the study. Screening will begin up to 28 days prior to Day 1 of treatment period 1. Eligible subjects will be admitted to the clinical unit on Day −1, and randomized to 1 of the 4 treatment sequences on Day 1 of treatment period 1. During treatment periods 1 and 2, subjects will fast overnight for at least 10 hours and then ingest a liquid dietary supplement (vanilla-flavored nutritional composition sold under the trademark ENSURE PLUS®, 237 mL container) with the study drug and not consume any other food for 4 hours after dosing. During treatment period 3, subjects will fast overnight for at least 10 hours prior to dosing and continue to fast for an additional 4 hours after dosing. During all treatment periods, water will not be permitted for 1 hour before dosing until 2 hours after dosing except for the water/liquid dietary supplement provided for study drug dosing.

On Day 1 of each treatment period, subjects will be dosed with the compound of Formula (I) 50 mg and have blood samples collected for PK analysis. Subjects will complete a taste satisfaction questionnaire after study drug ingestion on Day 1 of treatment period 3 (only for subjects who receive the SDD suspension under the fasted condition). Subjects will remain in the unit on the day of dosing and will be discharged on Day 2 of each treatment period, following completion of all required procedures, including collection of the 36-hour PK sample. On the mornings of Days 8 and 15 of each treatment period, subjects will return to the clinical unit on an outpatient basis for PK blood sample collection and safety assessments. On Day 21 of treatment period 1 and treatment period 2, subjects will arrive at the site and have Day 21 assessments completed, and they will stay overnight at the site and begin Day 1 of treatment period 2 or treatment period 3 the following day. A final follow-up study visit will be conducted on Day 22 of treatment period 3 (21±2 days after treatment period 3 dosing) or upon early termination.

Figure 10:
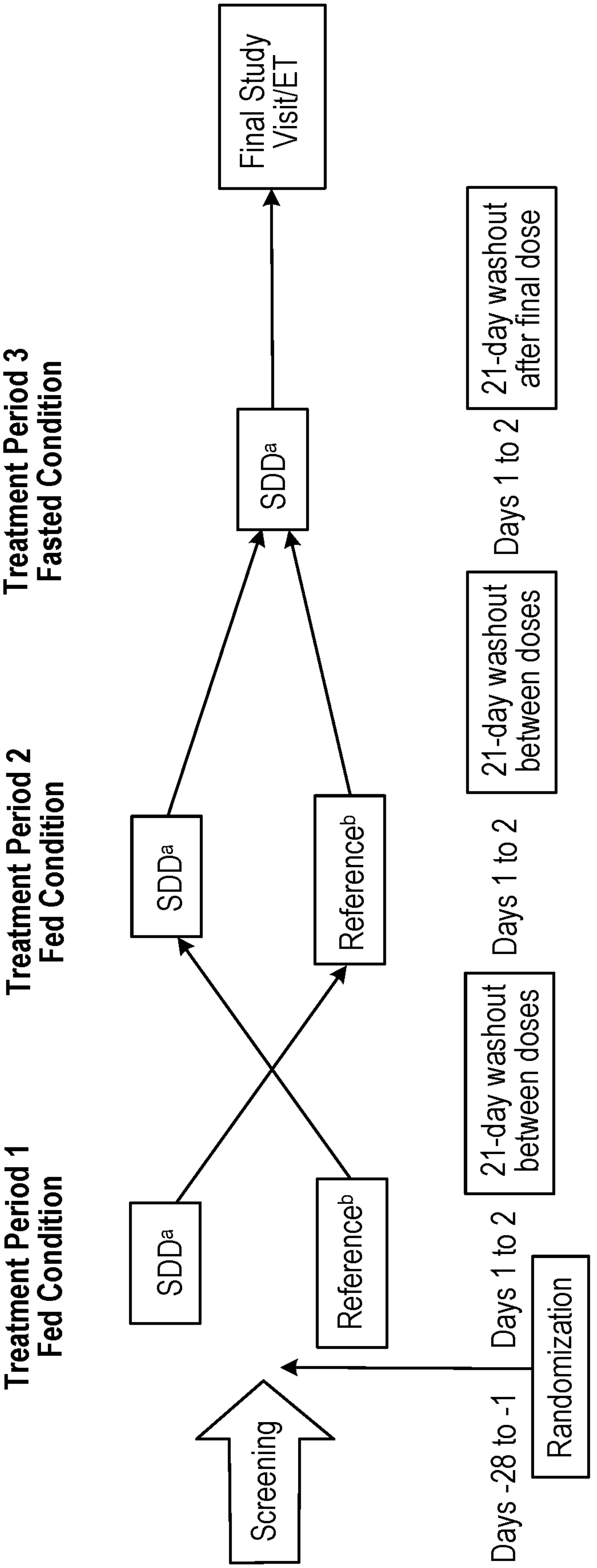
FIG. 10 is a flow chart showing the study design of a Phase 1 study of the bioavailability, pharmacokinetics and food effect of the compound of Formula (I) in healthy adult subjects.

Blood samples for PK analysis and safety assessments will be collected/conducted at scheduled times throughout the study. The study design schematic is shown in FIG. 10.

Duration of Treatment

The expected duration of study participation for each healthy adult subject will be approximately 13 weeks, including up to 28 days of screening, 3 doses each separated by 21 days, and a final follow-up study visit 21 days after receiving the last dose of study drug during treatment period 3.

Test Product, Dose, and Mode of Administration

The compound of Formula (I) will be supplied as two different test formulations for oral administration: as powder in bottles for constitution into a suspension (20 mL) and as powder-filled capsules. The compound of Formula (I) test formulations will contain 50 mg of the compound of Formula (I) as free base equivalent. Subjects must swallow the study drug with a liquid dietary supplement (nutritional composition sold under the trademark ENSURE PLUS® [237 mL container]) with an additional 100 mL of water (SDD capsule formulation) or with an additional 80 mL of water (SDD suspension formulation) during treatment period 1 or 2. Subjects must swallow the study drug with 330 mL of water (SDD capsule formulation) or 310 mL of water (SDD suspension formulation) during treatment period 3.

Reference Therapy, Dose, and Mode of Administration

The compound of Formula (I) reference formulation (encapsulated, lipidic semi-solid formulation) will be supplied as capsules for oral administration. The compound of Formula (I) reference capsules will contain 50 mg of the compound of Formula (I) as free base equivalent. Subjects must swallow a single capsule with a liquid dietary supplement (nutritional composition sold under the trademark ENSURE PLUS® [237 mL container]) with an additional 100 mL of water during treatment period 1 or 2.

Criteria for Evaluation

Pharmacokinetics

Blood samples for assessment of plasma concentrations of the compound of Formula (I) and metabolites will be collected within 45 minutes before dosing, and at approximately 30 minutes, and 1, 2, 3, 4, 5, 6, 7, 8, 9, 10, 12, 16, 24, 36, 168, 336, and 504 hours after dosing.

The following plasma PK parameters will be calculated for the compound of Formula (I) and metabolites:

- Area under the plasma concentration versus time curve from 0 hours to the time of the last measurable concentration ($AUC_{0\text{-}tlast}$)
- Area under the plasma concentration curve extrapolated from 0 hours to infinity ($AUC_{0\text{-}\infty}$)
- Maximum plasma concentration ($C_{max}$)
- Time to achieve maximum plasma concentration ($t_{max}$)
- Delay time between time of dosing and time of appearance of measurable test article ($T_{lag}$)
- Apparent terminal half-life ($t_{1/2}$)
- Apparent terminal rate constant (λz)
- Apparent mean residence time (MRT)
- Molar AUC ratio of primary metabolite(s) to the parent drug the compound of Formula (I)

The following plasma PK parameters will be calculated only for the compound of Formula (I):

- Apparent systemic clearance after oral administration (CL/F)
- Apparent volume of distribution during terminal phase after oral administration (Vz/F)

Other Assessment

A taste satisfaction questionnaire will be administered.

Safety Assessments

Safety will be monitored throughout the study and will include the following assessments:

- AEs
- Clinical laboratory tests (hematology, coagulation, clinical chemistry, and urinalysis)
- Vital sign measurements (including orthostatic blood pressure and pulse rate)
- Physical examinations
- 12-lead electrocardiogram (ECG)

Statistical Methods

Pharmacokinetic parameters will be calculated using non-compartmental methods and summarized by formulation using descriptive statistics. Two-sided 90% confidence intervals will be calculated for the ratio of each test formulation (SDD suspension and SDD capsule) vs. the reference formulation for $AUC_{0\text{-}\infty}$, $AUC_{0\text{-}tlast}$, and $C_{max}$ for the compound of Formula (I) and metabolites under fed conditions. Further, two-sided 90% confidence intervals will be calculated for the ratio of each test formulation under fasted conditions vs. under fed conditions for $AUC_{0\text{-}\infty}$, $AUC_{0\text{-}tlast}$, and $C_{max}$ for the compound of Formula (I) and metabolites.

Safety and taste satisfaction questionnaire data will be summarized with descriptive statistics.

Results

Pharmacokinetic Results

Pharmacokinetic results are shown in Tables 23-26, below.

TABLE 23

Summary of Plasma Pharmacokinetic Parameters (Safety Analysis Set - SDD Suspension Group)

| | | Compound of Formula (I) Plasma Concentration | |
|---|---|---|---|
| Parameter (units) Statistic | Reference Capsule (Fed) (N = 18) | SDD Suspension (Fed) (N = 18) | SDD Suspension (Fasted) (N = 18) |
| $AUC_{0\text{-}tlast}$ (ng × hr/mL) | | | |
| Mean (SD) | 16600 (7880) | 5980 (3960) | 737 (417) |
| Geom CV (%) | 46.8 | 72.8 | 68.7 |
| $AUC_{0\text{-}\infty}$ | | | |

TABLE 23-continued

Summary of Plasma Pharmacokinetic Parameters (Safety Analysis Set - SDD Suspension Group)

| Parameter (units) Statistic | Reference Capsule (Fed) (N = 18) | Compound of Formula (I) Plasma Concentration SDD Suspension (Fed) (N = 18) | SDD Suspension (Fasted) (N = 18) |
|---|---|---|---|
| (ng × hr/mL) | | | |
| Mean | 17400 (8010) | 6500 (4180) | 893 (480) |
| Geom CV (%) | 45.4 | 71.7 | 60.1 |
| $C_{max}$ (ng/mL) | | | |
| Mean (SD) | 1480 (506) | 672 (323) | 72.3 (44.9) |
| Geom CV (%) | 32.1 | 57.9 | 57.5 |
| $t_{max}$ (hr) | | | |
| Median (min, max) | 5.0 (3.0, 6.0) | 5.0 (5.0, 10) | 7.0 (5.0, 12) |
| $T_{lag}$ (hr) | | | |
| Mean (SD) | 1.0 (0.31) | 0.85 (0.29) | 1.2 (0.65) |
| $t_{1/2}$ (hr) | | | |
| Mean (SD) | 50 (20) | 19 (6.1) | 9.0 (0.46) |
| Geom CV (%) | 140 | 93 | 23 |
| MRT (hr) | | | |
| Mean (SD) | 36 (43) | 23 (24) | 17 (2.9) |
| Geom CV (%) | 84 | 62 | 18 |
| CL/F (L/hr) | | | |
| Mean (SD) | 3.4 (1.4) | 11 (8.0) | 80 (54) |
| Geom CV (%) | 45 | 72 | 63 |
| Vz/F (L) | | | |
| Mean (SD) | 180 (260) | 210 (140) | 970 (560) |
| Geom CV (%) | 93 | 77 | 53 |
| $T_{last}$ (hr) | | | |
| Mean (SD) | 170 (140) | 77 (110) | 31 (7.6) |
| Geom CV (%) | 120 | 92 | 30 |

TABLE 24

Geometric Mean Ratios for Pharmacokinetic Exposure Parameters by formulation and fed vs fasted (Safety Analysis Set - SDD Suspension Group)

| Analyte Parameter (units) Compound of Formula (I) | Treatment Comparison | Ratio (%) | 90% CI |
|---|---|---|---|
| $AUC_{0\text{-}tlast}$ (ng × hr/mL) | SDD Suspension (Fed) vs. Reference Capsule (Fed) | 32.2 | (26.4%, 39.4%) |
| $AUC_{0\text{-}\infty}$ (ng × hr/mL) | SDD Suspension (Fed) vs. Reference Capsule (Fed) | 33.5 | (27.7%, 40.6%) |
| $C_{max}$ (ng/mL) | SDD Suspension (Fed) vs. Reference Capsule (Fed) | 42.2 | (34.8%, 51.2%) |
| $AUC_{0\text{-}tlast}$ (ng × hr/mL) | SDD Suspension (Fasted) vs. Reference Capsule (Fed) | 4.4 | (3.4%, 5.7%) |
| $AUC_{0\text{-}\infty}$ (ng × hr/mL) | SDD Suspension (Fasted) vs. Reference Capsule (Fed) | 5.0 | (3.8%, 6.5%) |
| $C_{max}$ (ng/mL) | SDD Suspension (Fasted) vs. Reference Capsule (Fed) | 4.5 | (3.8%, 5.4%) |

TABLE 25

Summary of Plasma Pharmacokinetic Parameters (Safety Analysis Set - SDD Capsule Group)

| Parameter (units) Statistic | Reference Capsule (Fed) (N = 18) | Compound of Formula (I) Plasma Concentration SDD Capsule (Fed) (N = 18) | SDD Capsule (Fasted) (N = 17) |
|---|---|---|---|
| $AUC_{0\text{-}tlast}$ (ng × hr/mL) | | | |
| Mean (SD) | 19500 (7960) | 9470 (4670) | 1840 (1650) |
| Geom CV (%) | 50.4 | 48.0 | 78.7 |
| $AUC_{0\text{-}\infty}$ (ng × hr/mL) | | | |
| Mean | 20100 (7850) | 10000 (4610) | 2120 (1830) |
| Geom CV (%) | 47.1 | 44.9 | 73.7 |
| $C_{max}$ (ng/mL) | | | |
| Mean (SD) | 1770 (494) | 1110 (449) | 143 (110) |
| Geom CV (%) | 25.7 | 44.5 | 74.1 |
| $t_{max}$ (hr) | | | |
| Median (min, max) | 5.0 (5.0, 8.0) | 5.0 (3.0, 6.0) | 7.0 (6.0, 12) |
| $T_{lag}$ (hr) | | | |
| Mean (SD) | 1.0 (0.38) | 1.3 (0.49) | 1.2 (0.88) |
| $t_{1/2}$ (hr) | | | |
| Mean (SD) | 35 (18) | 26 (20) | 14 (11) |
| Geom CV (%) | 69 | 98 | 49 |
| MRT (hr) | | | |
| Mean (SD) | 28 (12) | 25 (14) | 21 (9.2) |
| Geom CV (%) | 45 | 55 | 31 |
| CL/F (L/hr) | | | |
| Mean (SD) | 3.0 (1.5) | 5.9 (2.4) | 36 (18) |
| Geom CV (%) | 47 | 45 | 74 |
| Vz/F (L) | | | |
| Mean (SD) | 130 (61) | 190 (140) | 630 (380) |
| Geom CV (%) | 47 | 75 | 72 |
| $T_{last}$ (hr) | | | |
| Mean (SD) | 170 (96) | 100 (89) | 44 (32) |
| Geom CV (%) | 91 | 100 | 39 |

TABLE 26

Geometric Mean Ratios for Pharmacokinetic Exposure Parameters by formulation and fed vs fasted (Safety Analysis Set - SDD Suspension Group)

| Analyte Parameter (units) | Treatment Comparison | Ratio (%) | 90% CI |
|---|---|---|---|
| Compound of Formula (I) | | | |
| $AUC_{0\text{-}tlast}$ (ng × hr/mL) | SDD Capsule (Fed) vs. Reference Capsule (Fed) | 48.2 | (41.4%, 56.1%) |
| $AUC_{0\text{-}\infty}$ (ng × hr/mL) | SDD Capsule (Fed) vs. Reference Capsule (Fed) | 49.7 | (43.1%, 57.2%) |
| $C_{max}$ (ng/mL) | SDD Capsule (Fed) vs. Reference Capsule (Fed) | 59.8 | (51.7%, 69.2%) |
| $AUC_{0\text{-}tlast}$ (ng × hr/mL) | SDD Capsule (Fasted) vs. Reference Capsule (Fed) | 8.0 | (5.7%, 11.2%) |
| $AUC_{0\text{-}\infty}$ (ng × hr/mL) | SDD Capsule (Fasted) vs. Reference Capsule (Fed) | 9.0 | (6.6%, 12.4%) |
| $C_{max}$ (ng/mL) | SDD Capsule (Fasted) vs. Reference Capsule (Fed) | 6.7 | (4.9%, 9.2%) |

Example 8: Phase 2 Study of the Compound of Formula (I) in Adult Subjects with Congenital Adrenal Hyperplasia A Phase 2 study to assess the safety, tolerability, pharmacokinetics (PK), and pharmacodynamics (PD) of the compound of Formula (I) in adult subjects with classic congenital adrenal hyperplasia (CAH) was designed. The objectives of the study are: to assess the safety and tolerability of two ascending doses of the compound of Formula (I) in adult subjects with CAH; to evaluate the effect of repeated doses of the compound of Formula (I) on endogenous levels of PD biomarkers in adult subjects with CAH; and to evaluate plasma exposures following repeated doses of the compound of Formula (I) administered nightly.

The lower dose strength selected for this study, the compound of Formula (I) 50 mg, was well tolerated in both single and repeat-dose safety and PK studies in healthy volunteers. Doses up to 100 mg were also well tolerated in both single-dose and repeat-dose Phase 1 studies in healthy volunteers, and importantly, in a large Phase 2 study in non-elderly female and male subjects with major depressive disorder receiving the compound of Formula (I) during an 8-week, double-blind treatment period. Furthermore, the anticipated steady state exposures with the selected the compound of Formula (I) doses, using the predicted $C_{max}$ and AUC, are within the acceptable safety margins defined by the nonclinical toxicology studies that have been conducted to date.

Study Design

A Phase 2, open-label, multiple-dose, dose-escalation study to assess the safety, tolerability, PK, and PD of the compound of Formula (I) in approximately 30 adult female and male subjects (18 to 50 years of age) with a documented medical diagnosis of classic 21-hydroxylase deficiency CAH was designed. The study will include a sequential-cohort design with four compound of Formula (I) dose cohorts: 50 mg and 100 mg, with each dose administered for 14 consecutive days:

- Cohort 1: compound of Formula (I) 50 mg once daily with a bottle of vanilla-flavored Ensure Plus® (~237 mL) at approximately 2200 hours.
- Cohort 2: compound of Formula (I) 100 mg once daily with a bottle of vanilla-flavored Ensure Plus® (~237 mL) at approximately 2200 hours.
- Cohort 3: compound of Formula (I) 100 mg once daily with the evening meal at approximately 1900 hours.
- Cohort 4: compound of Formula (I) 100 mg twice daily with breakfast at approximately 0700 hours and with the evening meal at approximately 1900 hours.

There will be an approximate 2-week period to evaluate safety and tolerability data before proceeding from Cohort 1 to Cohort 2. Subjects who previously completed the current study in Cohort 1 or Cohort 2 may reenroll to participate in Cohorts 3 or 4 (in addition to new subjects). Table 27 below depicts the dose cohorts, doses, and number of subjects per cohort.

TABLE 27

Dose cohorts, doses, and number of subjects

| Cohort | Compound of Formula (I) Dose | Approximate Dosing Time(s) | Number of Subjects |
|---|---|---|---|
| 1 | 50 mg | 2200 hours | 8-10 |
| 2 | 100 mg | 2200 hours | 8-10 |
| 3 | 100 mg | 1900 hours | 8-10 |
| 4 | 100 mg | 0700 and 1900 hours | Up to 8 |

Subjects will be screened for eligibility to participate in the study for up to approximately 3 weeks (Days −28 to −8). Subjects who reenroll and have had a stable medication regimen for CAH since their last visit in this study do not have to undergo screening; those who reenroll and have had a change to their medication regimen for CAH must undergo a second screening visit. During screening, subjects will provide a single blood sample in the morning between 0700 and 1000 hours (prior to first morning dose of hydrocortisone) to determine their 17-hydroxyprogesterone (17-OHP) levels for study entry.

Eligible subjects who have a screening 17-OHP level ≥1,000 ng/dL will be admitted to the study center for 1 night and have baseline serial PD samples collected over a 24-hour period beginning in the evening of Day −7. Baseline serial PD samples will be collected at approximately 2145, 2300, 2400, 0100, 0200, 0400, 0600, 0800, 1000, 1200, 1400, 1600, and 2200 hours. The subjects' usual morning dose of steroidal treatments will be administered after the 1000 hours PD sample is collected on Day −6. Subjects will be discharged on Day −6 after the last PD sample is collected.

Subjects within each dose cohort will be admitted to the study center on Days 1 and 14 (first and last day of dosing). Subjects will have a blood sample collected on Day 1 for CYP21A2 genotyping. Baseline safety assessments will be collected on Day 1 prior to the first dose of study drug. Study drug (the compound of Formula (I) 50 or 100 mg) will be administered at approximately 2200 hours for Cohorts 1 and 2 and at approximately 1845, 2000, 2100, 2200, 2300, 2400, 0100, 0200, 0400, 0600, 0800, 1000, 1200, 1400, 1800, 1900, and 2200 hours for Cohorts 3 and 4. The subjects' usual morning dose of steroidal treatments will be administered after the 1000 hours PD sample is collected on Day −6. Subjects will be discharged on Day −6 after the last PD sample is collected.

Subjects in Cohorts 1 and 2 will be admitted to the study center on Days 1 and 14 (first and last day of dosing). Subjects will have a blood sample collected on Day 1 for cytochrome P450 (CYP) 21A2 genotyping. Baseline safety assessments will be collected on Day 1 prior to the first dose of study drug. Study drug (compound of Formula(I) 50 mg or 100 mg) will be administered at approximately 2200 hours. The subjects' usual morning dose of concurrent steroidal treatments will be administered after the 12-hour post-dose PK/PD samples are collected (at approximately 1000 hours) on Day 2 and after the 16-hour post-dose PK/PD samples are collected (at approximately 1400 hours) on Day 15. Subjects will be discharged from the study center the evening on Days 2 and 15 following completion of all study-related procedures for those days. Prior to this discharge on Day 2, study drug will be administered at the study center at approximately 2200 hours. Study drug will then be self-administered nightly at home at approximately 2200 hours on Days 3 to 13. Subjects will take their usual morning dose of concurrent steroidal treatments at approximately 1000 hours on Days 3 to 14. On Day 7 during the treatment period, PK, PD, and safety assessments will be conducted in an outpatient setting at the study center.

Subjects in Cohorts 3 and 4 will have a blood sample collected on Day 1 for CYP21A2 genotyping (only for subjects who have not previously participated in Cohorts 1 or 2). Baseline safety assessments will be collected on Day 1 prior to the first dose of study drug. For Cohort 3, study drug (compound of Formula(I) 100 mg) will be administered at home on Days 1 to 13 at approximately 1900 hours with each subject's evening meal. For Cohort 4, study drug compound of Formula(I) 100 mg) will be administered at home on Days 2 to 14 at approximately 0700 hours with each subject's breakfast and on Days 1 to 13 at approximately 1900 hours with each subjects' evening meal. For both cohorts, the Day 14 evening dose will be administered at the study site. Subjects will take their usual morning dose of concurrent steroidal treatments at approximately 1000 hours on Days 1 to 14. On Day 7 during the treatment period, PK, PD, and safety assessments will be conducted in an outpatient setting at the study center. Subjects will be admitted to the study center on Day 14 (last day of dosing). On Day 14, subjects will receive study drug in the study center at approximately 1900 hours with a standard (moderate fat/moderate calorie) evening meal. The subjects' usual morning dose of concurrent steroidal treatments will be administered after PK/PD samples are collected at approximately 1400 hours on Day 15. Subjects will be discharged from the study center the evening on Day 15 following completion of all study-related procedures.

Figure 11:
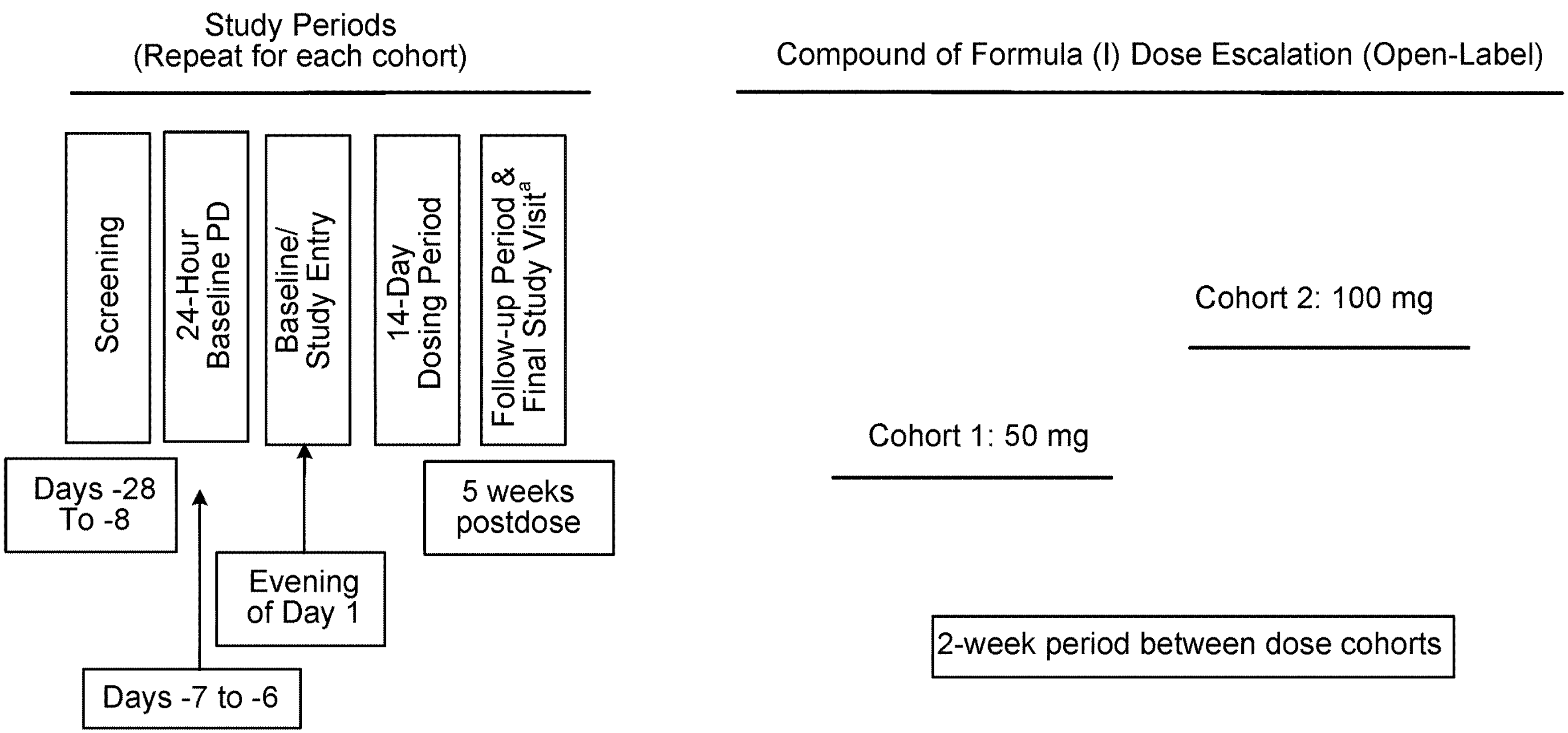
FIG. 11 shows the study design of a Phase 2 study of the compound of Formula (I) in adult subjects with congenital adrenal hyperplasia.

For all cohorts, follow-up visits on Days 21, 28, and 35 will be conducted at the study center or the subject's home by a qualified home healthcare provider (based on the subject's preference). A final study visit will be conducted at the study site approximately 5 weeks after the last dose of study drug (on Day 49 or early termination). There will be a visit window of −8 hours for Day 7, −8 hours/+3 days for Days 21, 28, and 35, and +7 days for the final study visit. Safety, tolerability, PK, and PD will be assessed at scheduled times throughout the study. The study design schematic is shown in FIG. 11.

Dose Escalation Procedure

Cohort 1 will consist of approximately 8 to 10 subjects who will receive a daily dose of the compound of Formula (I) 50 mg at approximately 2200 hours for 14 days (subjects will receive study drug at the site on Days 1, 2, and 14, and self-administer study drug at home on Days 3 to 13). Following the completion of Day 15 assessments for all subjects in the Cohort 1, a medical monitor will review the accumulated safety and tolerability results to ensure there are no safety concerns with proceeding to the 100 mg dose (Cohorts 2 and 3), and to determine if a maximum tolerated dose (MTD) has been reached. If the MTD is reached, no dose escalation will occur. There will be an approximate 2-week period between Cohorts 1 and 2 to accommodate this safety review. A similar procedure will be used prior to proceeding to the 100 mg twice daily dose (Cohort 4).

If the medical monitor determines that it is safe to proceed to the compound of Formula (I) 100 mg, subjects in Cohort 2 will be administered the compound of Formula (I) 100 mg daily for 14 days. Dosing for Cohorts 3 and 4 may begin simultaneously with Cohort 2.

During the 14-day dosing period for any cohort, dosing may be postponed or halted if one or more subjects experience a severe or serious adverse event (AE), or if the type, frequency, or severity of AEs becomes unacceptable. If dosing is postponed, the medical monitor will review all available safety, tolerability, and PK data before allowing any further subjects to receive study drug.

Study Population

Approximately 30 adult female and male subjects (18 to 50 years of age) with a documented medical diagnosis of classic 21-hydroxylase deficiency CAH, who meet all protocol eligibility criteria, will be enrolled. Subjects who previously completed the current study in Cohort 1 or Cohort 2 may reenroll to participate in Cohorts 3 or 4 (in addition to new subjects).

Duration of Treatment

The expected duration of study participation for each subject is approximately 11 weeks, including up to approximately 3 weeks for screening, a 24-hour PD baseline period (approximately 7 days prior to the first day of dosing), 14 days of dosing, and a follow-up period of approximately 5 weeks. The total duration of the study will be an additional 8 to 11 weeks for subjects who reenroll.

Test Product, Dose, and Mode of Administration

The compound of Formula (I) will be supplied as capsules containing 50 mg of the compound of Formula (I) free base for oral administration (see, e.g., Reference 1 formulation as described in Example 9). Doses of the compound of Formula (I) are 50 mg and 100 mg, administered in oral capsule form. Each dose of study drug for Cohorts 1 and 2 is to be administered with a bottle of vanilla-flavored nutritional composition sold under the trademark ENSURE PLUS® (~237 mL). Each dose of study drug for Cohort 3 is to be administered with each subject's evening meal at approximately 1900 hours. Each dose of study drug for Cohort 4 is to be administered with each subject's breakfast at approximately 1900 hours (i.e., a total daily dose of 200 mg).

Criteria for Evaluation

Cohorts 1 and 2

Blood samples to evaluate 24-hour PD baseline will be collected on Days −7 to −6 at approximately 2145, 2300, 2400, 0100, 0200, 0400, 0600, 0800, 1000, 1200, 1400, 1600, and 2200 hours. Blood samples to evaluate PK and PD parameters of the compound of Formula (I) will be collected on Days 1 to 2 and Days 14 to 15 at: 15 minutes pre-dose and at 1, 2, 3, 4, 6, 8, 10, 12, 14, 16, 20, and 24 hours post-dose; Day 7 (at approximately 24 hours post-dose); Days 21, 28, and 35 (at approximately 168, 336, and 504 hours post-dose); and at the final study visit (Day 49 or early termination).

Cohorts 3 and 4

Blood samples to evaluate 24-hour PD baseline will be collected on Days −7 to −6 at approximately 1845, 2000, 2100, 2200, 2300, 2400, 0100, 0200, 0400, 0600, 0800, 1000, 1200, 1400, 1800, 1900, and 2200 hours. Blood samples to evaluate PK and PD parameters of the compound of Formula (I) will be collected on Days 14 to 15 at the following times (for Cohort 4, all times are relative to evening dosing unless otherwise indicated): 15 minutes predose and at 1, 2, 3, 4, 5, 6, 7, 9, 11, 13, 15, 17, 19, 23, 24, and 27 hours postdose; Day 7 (at 24 hours postdose for Cohort 3 or at 12 hours post morning dose but prior to the evening dose for Cohort 4); Days 21, 28, and 35 (at approximately 168, 336, and 504 hours postdose); and at the final study visit (Day 49 or early termination).

Pharmacokinetics

The following plasma PK parameters will be calculated for the compound of Formula (I) and metabolites:

- Area under the plasma concentration versus time curve from 0 hours to last measurable concentration ($AUC_{0\text{-}tlast}$)
- Area under the plasma concentration versus time curve from 0 to 24 hours ($AUC_{0\text{-}24}$)
- Maximum plasma concentration ($C_{max}$)
- Time to maximum plasma concentration ($t_{max}$)
- Delay time between time of dosing and time of appearance of measurable test article ($T_{lag}$)
- Terminal half-life ($t_{1/2}$)
- Apparent terminal rate constant (λz)
- Apparent mean residence time (MRT)
- Additional PK parameters for Day 14 only:
- Average plasma concentration at steady state ($C_{avg}$)
- Percent fluctuation at steady state (% fluctuation)
- Accumulation index at steady state
- Apparent systemic clearance after oral administration (CL/F) (the compound of Formula (I) only)

Pharmacodynamics

Primary: Morning 17-OHP (serum; ng/dL) from the 0600, 0800, and 1000 hour samples (8-, 10-, and 12-hour post-dose samples from Cohorts 1 and 2 and 11-, 13-, and 15-hour postdose samples from Cohorts 3 and 4.

Secondary: 17-OHP at all other times, androstenedione (serum; ng/dL), testosterone (serum; ng/dL), cortisol (serum; g/dL), and adrenocorticotropic hormone (plasma ACTH; pg/mL).

Safety

Safety and tolerability will be monitored throughout the study and will include the following assessments:

- Adverse events
- Clinical laboratory tests—clinical chemistry (including creatine kinase, myoglobin, total and conjugated bilirubin), hematology, coagulation (prothrombin time, aPTT, d-dimer, fibrinogen), and urinalysis (including quantitative myoglobin, casts and crystals)
- Vital signs
- Physical examinations (including musculoskeletal exam)
- 12-lead electrocardiograms (ECGs)
- Columbia-Suicide Severity Rating Scale (C-SSRS)
- Brief Psychiatric Rating Scale (BPRS)

Statistical Methods

Safety, PK, and PD variables will be summarized within each dose cohort (the compound of Formula (I) 50 mg and 100 mg) using descriptive statistics. Summaries of PD measures will include both observed values and changes from pre-dose.

Results

Pharmacokinetic Results

Eight subjects (four female and four male) were enrolled in this study and completed Cohort 1. Age, sex, and BMI information for the study participants is shown in Table 28, below.

TABLE 28

Cohort 1 Subjects

| Subject ID | Age (years) | Sex (Male/Female) | BMI ($kg/m^2$) |
|---|---|---|---|
| 001 | 37 | Female | 24.9 |
| 002 | 25 | Female | 32.0 |
| 003 | 49 | Male | 37.2 |
| 004 | 36 | Male | 25.0 |
| 005 | 27 | Female | 25.5 |
| 006 | 19 | Male | 21.7 |
| 007 | 25 | Male | 27.5 |
| 008 | 31 | Female | 34.4 |

Figure 12A:
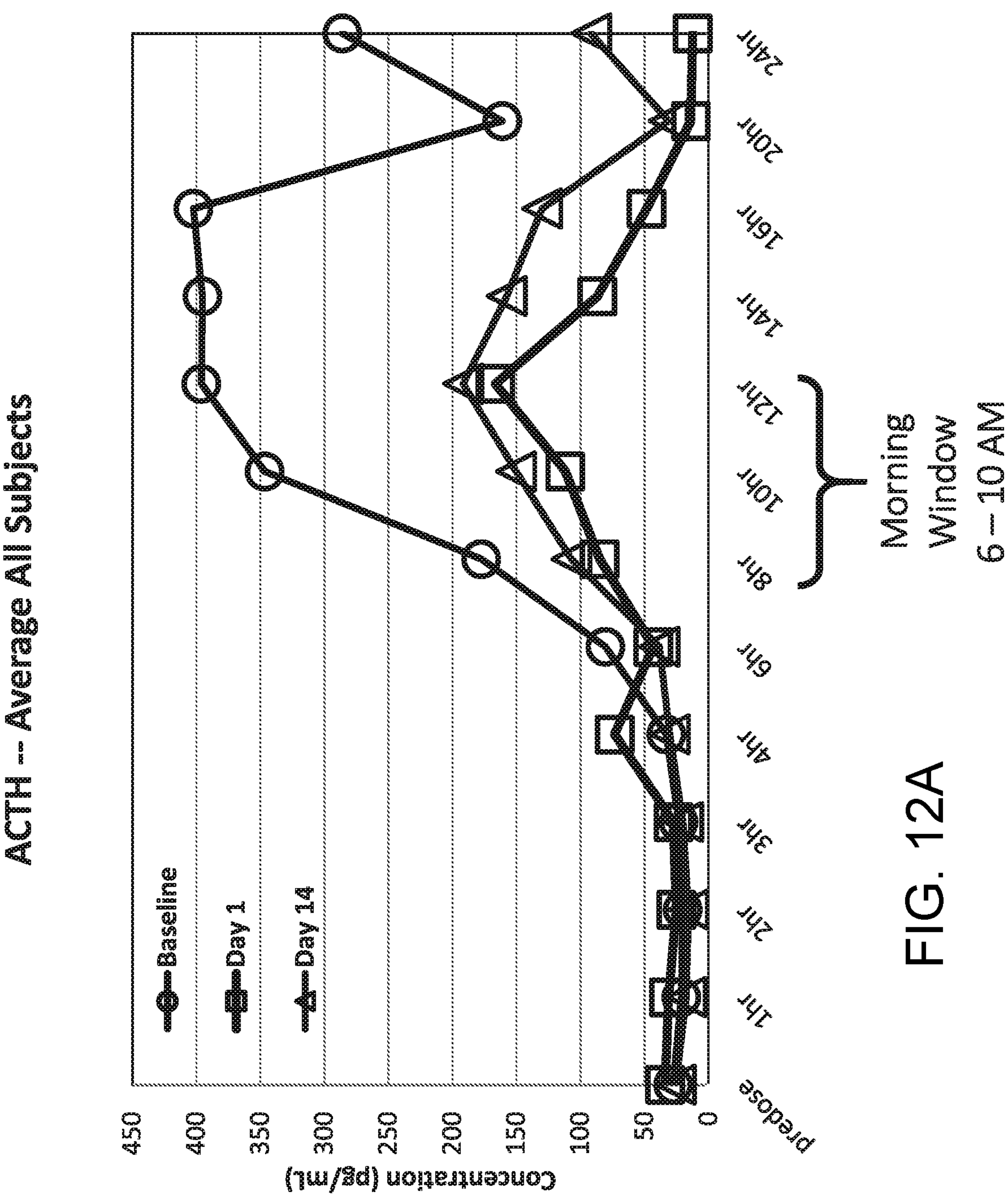
FIGS. 12A and 12B show the arithmetic mean values for adrenocorticotropic hormone (ACTH) (FIG. 12A) and 17-hydroxyprogesterone (17-OHP) (FIG. 12B) for all 8 Cohort 1 subjects plotted at each time point for pre-treatment baseline (circles), day 1 (squares), and day 14 (triangles).
Figure 12B:
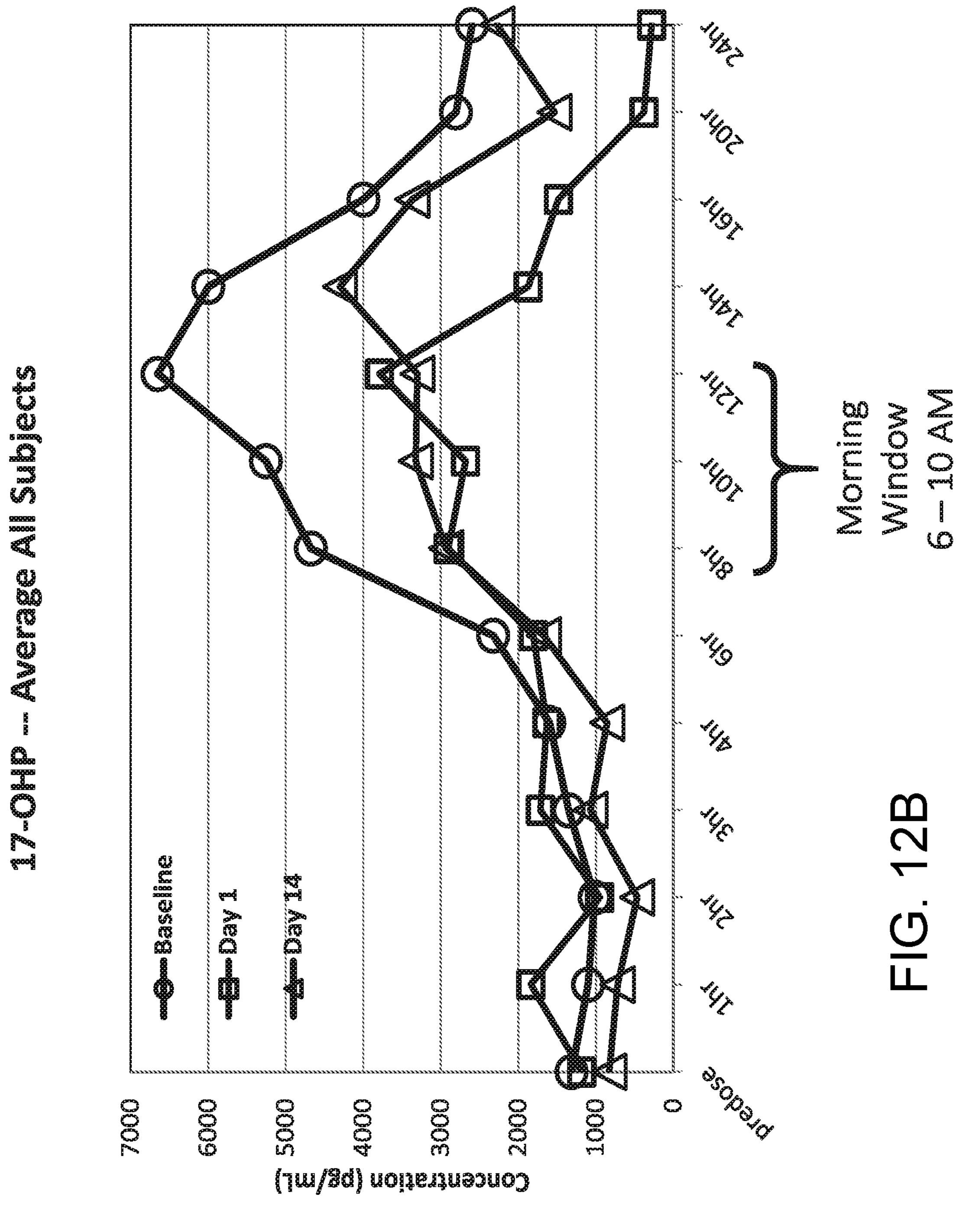

The subjects received a daily dose of the compound of Formula (I) at 50 mg at approximately 2200 hours (~10 p.m. or bedtime) for 14 days. Arithmetic mean values for ACTH (FIG. 12A) and 17-OHP (FIG. 12B) for all 8 Cohort 1 subjects were plotted at each timepoint for Pre-treatment Baseline, Day 1, and Day 14. Both ACTH and 170HP concentration profiles at day 1 and day 14 show clear reductions from the baseline mean profiles. Cohort 1 mean PK parameters of $T_{max}$, $C_{max}$, and $AUC_{24}$ for the compound of Formula (I) are shown in Table 29 below. These PK parameters are consistent with observations from Phase 1 studies in healthy volunteers.

TABLE 29

Cohort 1 Mean PK parameters of $T_{max}$, $C_{max}$, and $AUC_{24}$

| | Day 1 | | | Day 14 | | |
|---|---|---|---|---|---|---|
| | $T_{max}$ | $C_{max}$ | $AUC_{24}$ | $T_{max}$ | $C_{max}$ | $AUC_{24}$ |
| Mean | 5.4 | 1305 | 10,292 | 4.4 | 1349 | 14,297 |
| CV % | 30 | 25 | 24 | 32 | 15 | 24 |

Additional measurements of cohort 1 and cohort 2 mean PK parameters of $T_{max}$, $C_{max}$, and $AUC_{24}$ for the compound of Formula (I) on Day 1 of dosing are shown in Table 30 below.

TABLE 30

Mean PK parameters of $T_{max}$, $C_{max}$, and $AUC_{24}$ on Day 1 of dosing

| | Cohort 1 50 mg-Ensure | | | Cohort 2 100 mg-Ensure | | |
|---|---|---|---|---|---|---|
| Day 1 | $T_{max}$* (h) | $C_{max}$ (ng/ml) | $AUC_{24}$ (h * ng/ml) | $T_{max}$ (h) | $C_{max}$ (ng/ml) | $AUC_{24}$* (h ng/ml) |
| G.Mean | 6 | 1,270 | 10,411 | 4 | 2,370 | 24,725 |
| CV % | — | 25 | 24 | — | 21 | 42 |
| N | 8 | 8 | 8 | 8 | 4 | 4 |

*Median

Additional measurements of cohort 1, cohort 2 and cohort 3 mean PK parameters of $T_{max}$, $C_{max}$, and $AUC_{24}$ for the compound of Formula (I) on Day 14 of dosing are shown in Table 31 below.

TABLE 31

Mean PK parameters of Tmax, Cmax, and AUC24 on Day 14 of dosing

| | Cohort 1 50 mg- Ensure | | | Cohort 2 100 mg-Ensure | | | Cohort 3 100 mg w/evening Meal | | |
|---|---|---|---|---|---|---|---|---|---|
| Day 14 | Tmax* (h) | Cmax (ng/ml) | AUC24 (h * ng/ml) | Tmax (h) | Cmax (ng/ml) | AUC24 (h * ng/ml) | Tmax (h) | Cmax (ng/ml) | AUC24 (h * ng/ml) |
| G. Mean | 4 | 1,335 | 14,070 | 4 | 3,379 | 35,416 | 3 | 3,650 | 34,706 |
| CV % | | 15 | 24 | | 31 | 37 | | 32 | 15 |
| N | 8 | 8 | 8 | 6 | 6 | 6 | 8 | 8 | 8 |

*Median

Figure 13A:
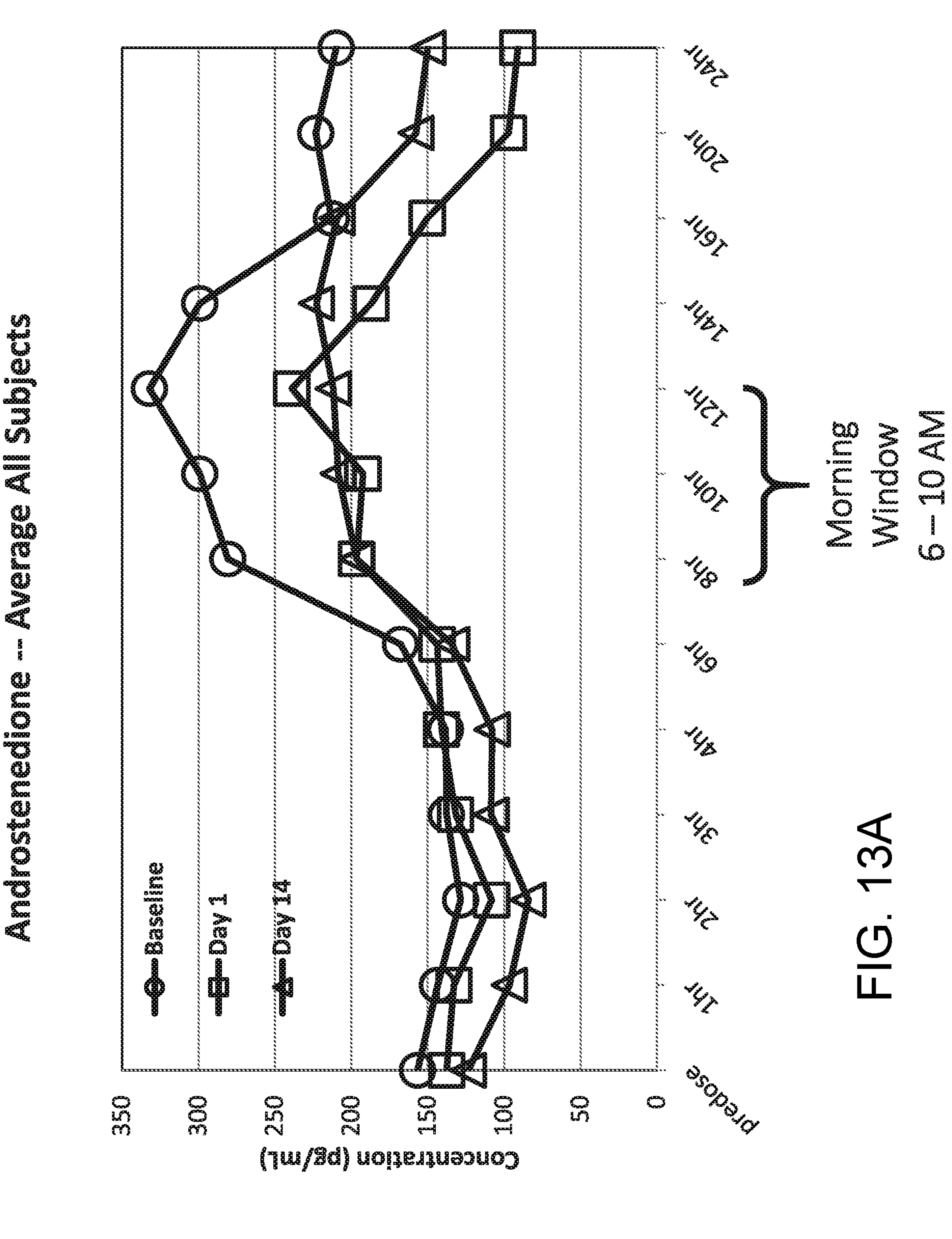
FIGS. 13A and 13B show arithmetic mean values for androstenedione (FIG. 13A) and testosterone (FIG. 13B) for all 8 Cohort 1 subjects were plotted at each timepoint for pre-treatment baseline (circles), day 1 (squares), and day 14 (triangles).
Figure 13B:
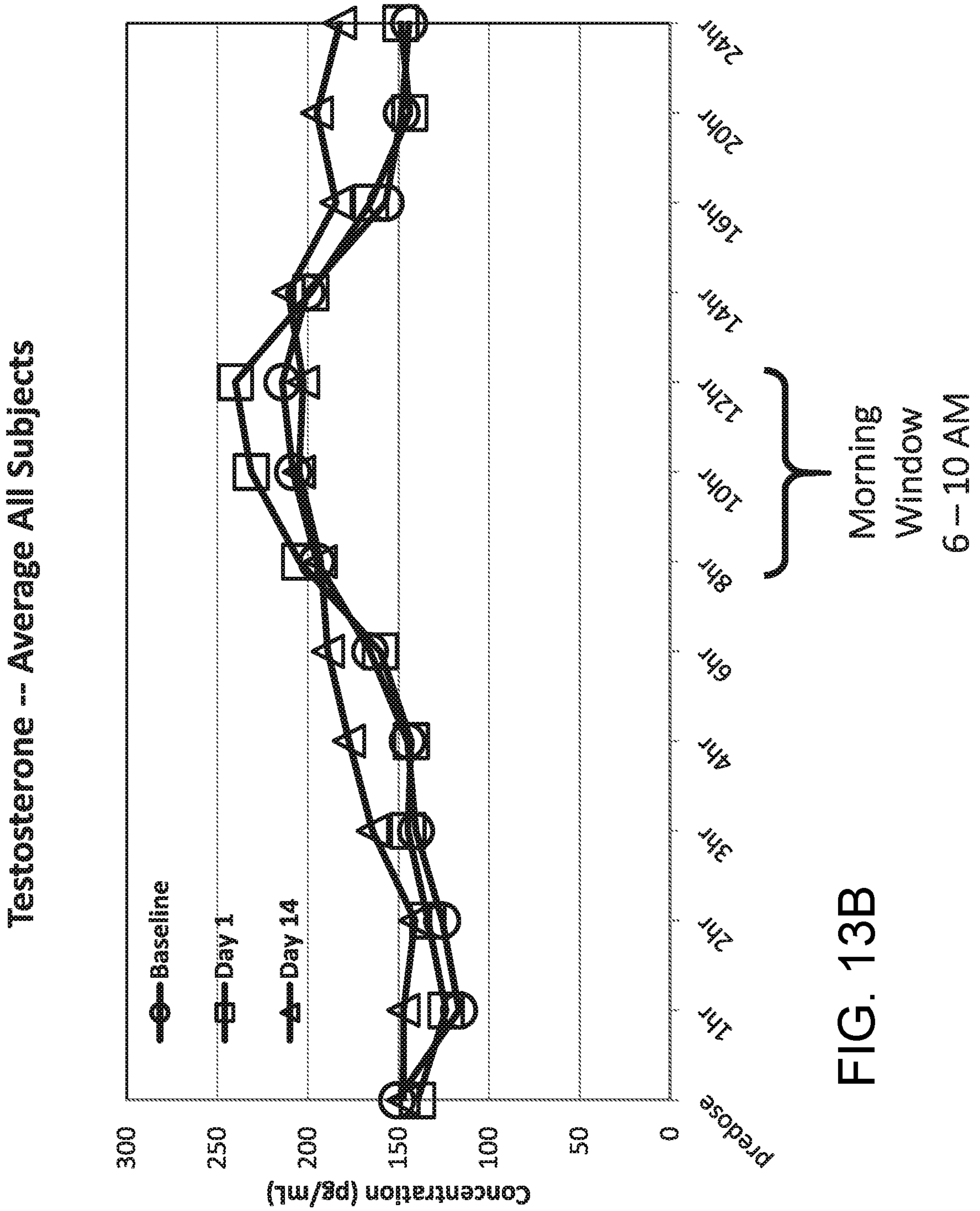

Arithmetic mean values for androstenedione (FIG. 13A) and testosterone (FIG. 13B) for all 8 Cohort 1 subjects were plotted at each timepoint for Pre-treatment Baseline, day 1, and day 14. The androstenedione concentration profile on Day 1 and Day 14 shows a clear reduction from the baseline mean profile.

Figure 14A:
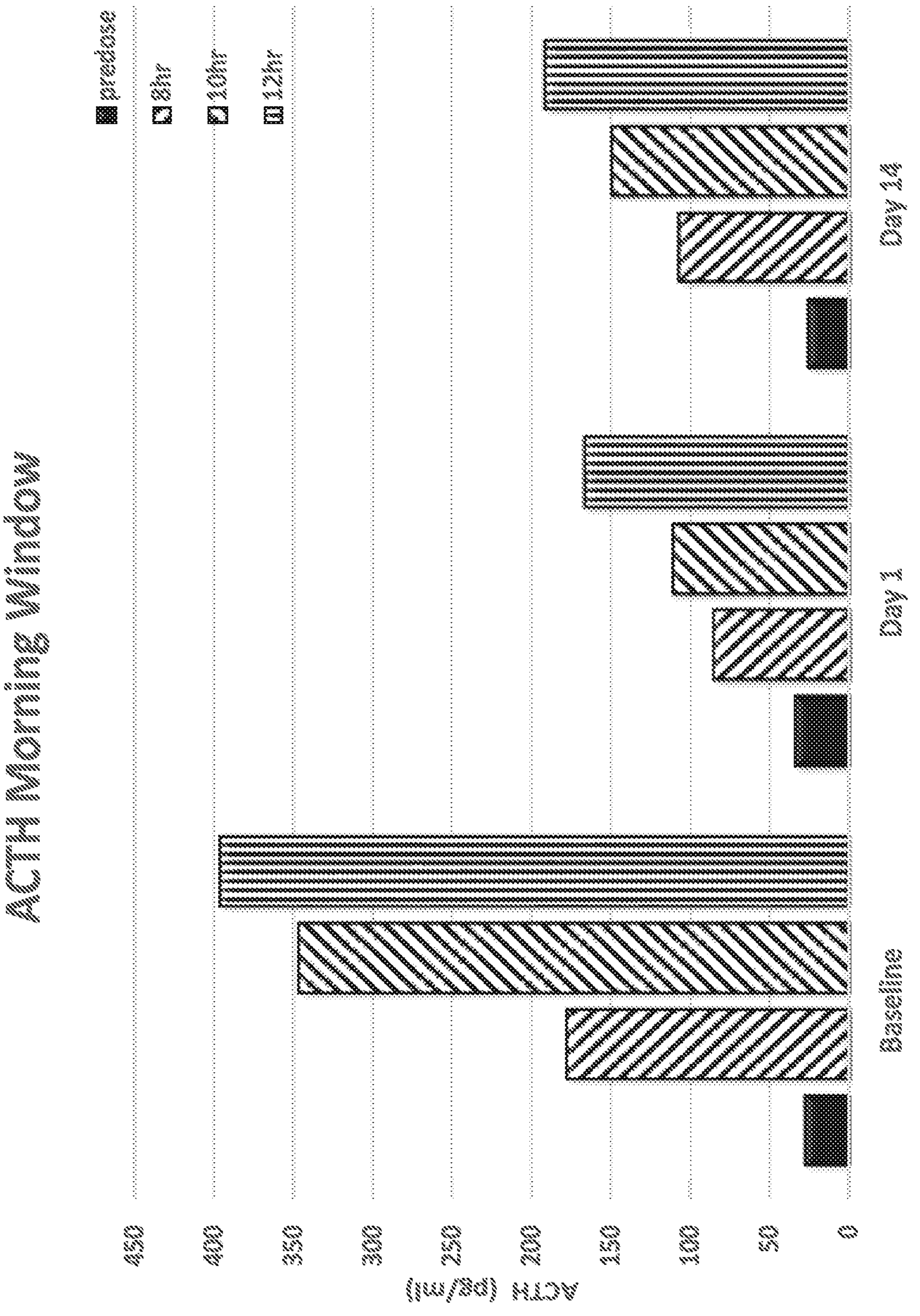
FIGS. 14A and 14B show the reduction of ACTH at timepoints 8-, 10-, and 12-hours postdose.
Figure 14B:
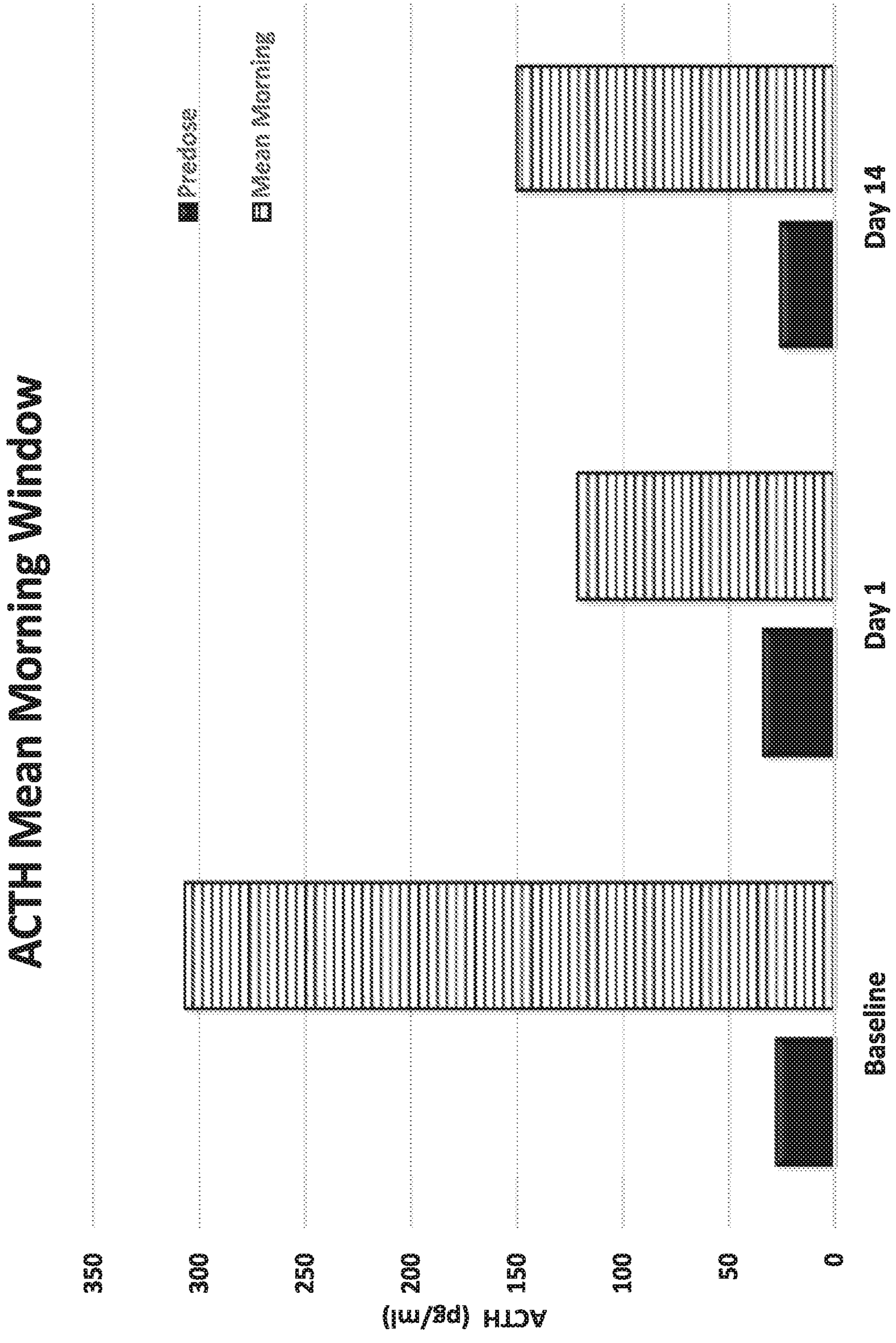

When focusing exclusively on the critical morning window period (timepoints at 8-, 10-, and 12-hours postdose) from 6:00 a.m. to 10:00 a.m., the levels of ACTH show marked reductions from baseline at each of the 3 timepoints on Days 1 and 14 (FIG. 14A). Arithmetic mean values across all three timepoints show >=50% reductions from baseline at Day 1 and Day 14 (FIG. 14B).

Figure 15A:
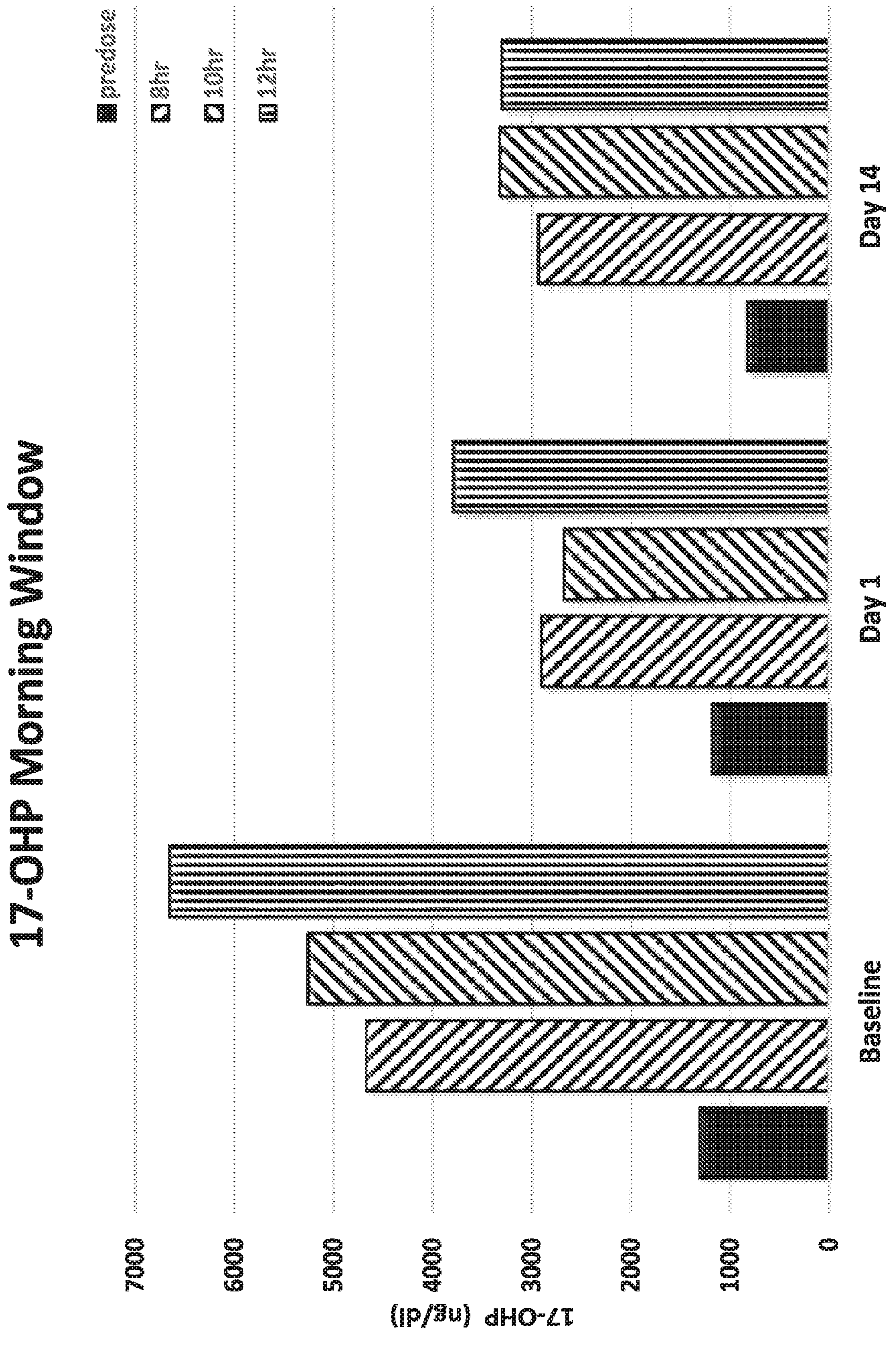
FIGS. 15A and 15B show the reduction of 17-OHP at timepoints 8-, 10-, and 12-hours postdose.
Figure 15B:
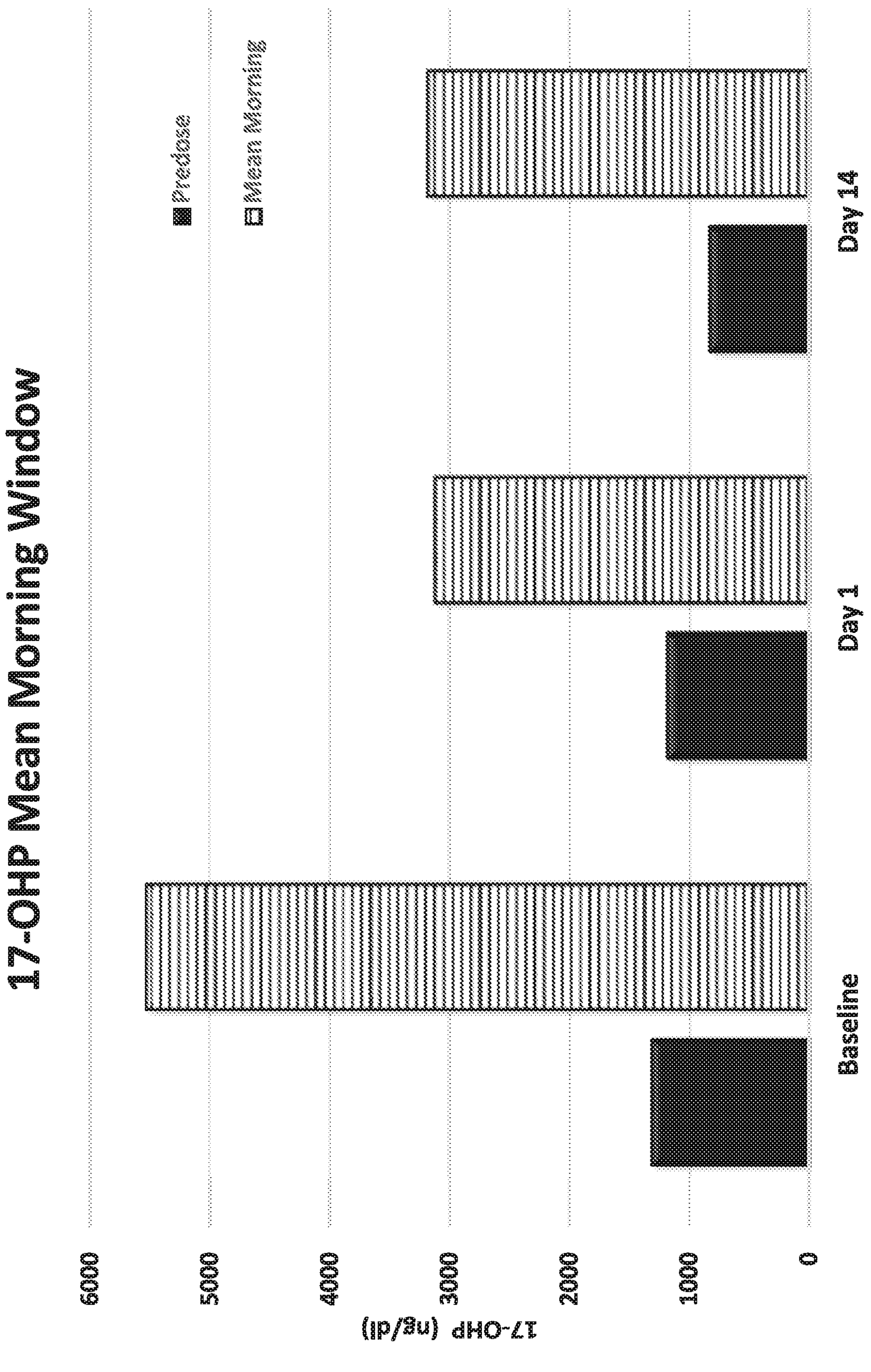

When focusing exclusively on the critical morning window period (timepoints at 8-, 10-, and 12-hours postdose) from 6:00 a.m. to 10:00 a.m., the levels of 17-OHP show marked reductions from baseline at each of the 3 timepoints on Days 1 and 14 (FIG. 15A). Arithmetic mean values across all three timepoints show >=40% reductions from baseline at Day 1 and Day 14 (FIG. 15B).

Figure 16A:
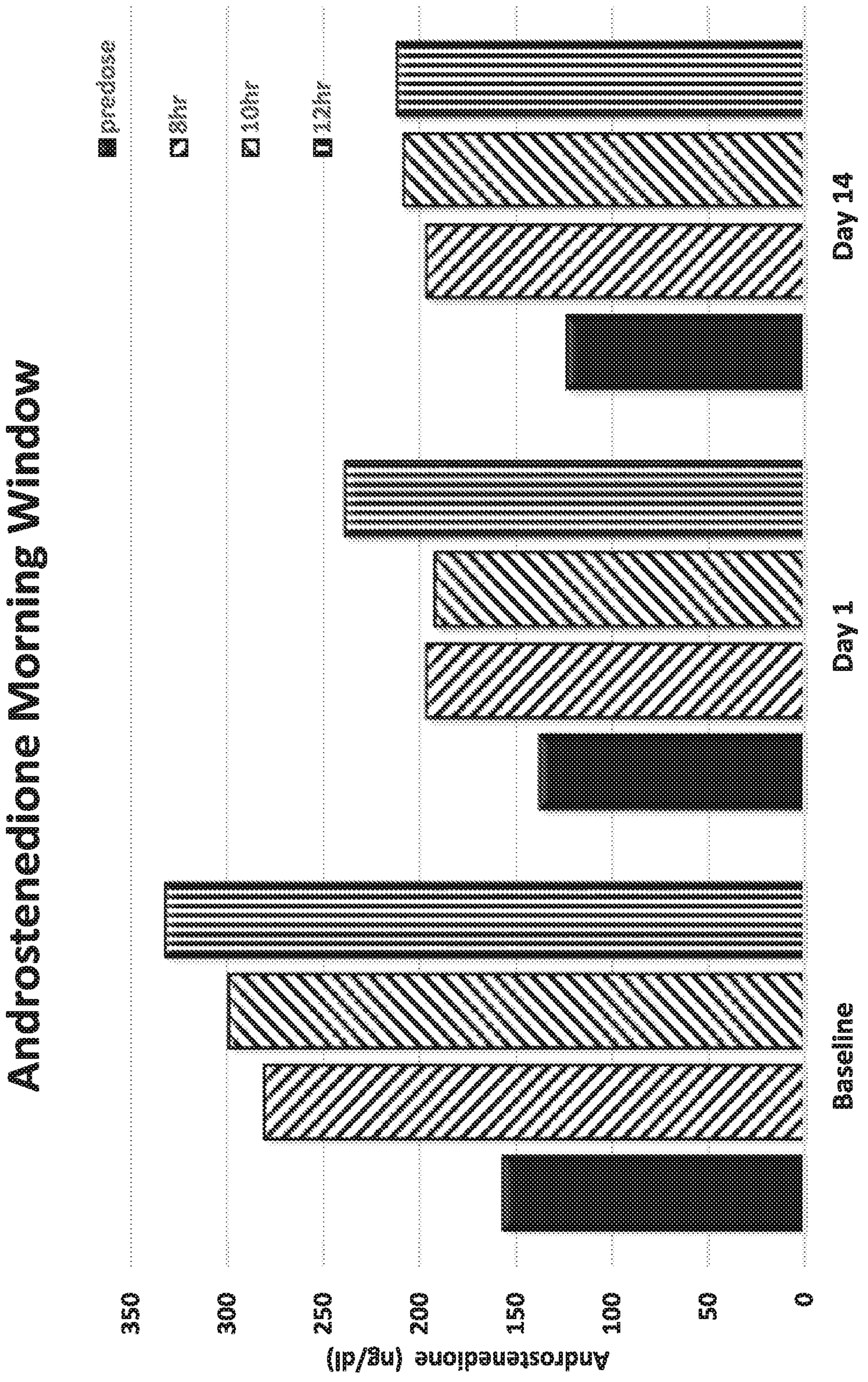
FIGS. 16A and 16B show the reduction of androstenedione at timepoints 8-, 10-, and 12-hours postdose.
Figure 16B:
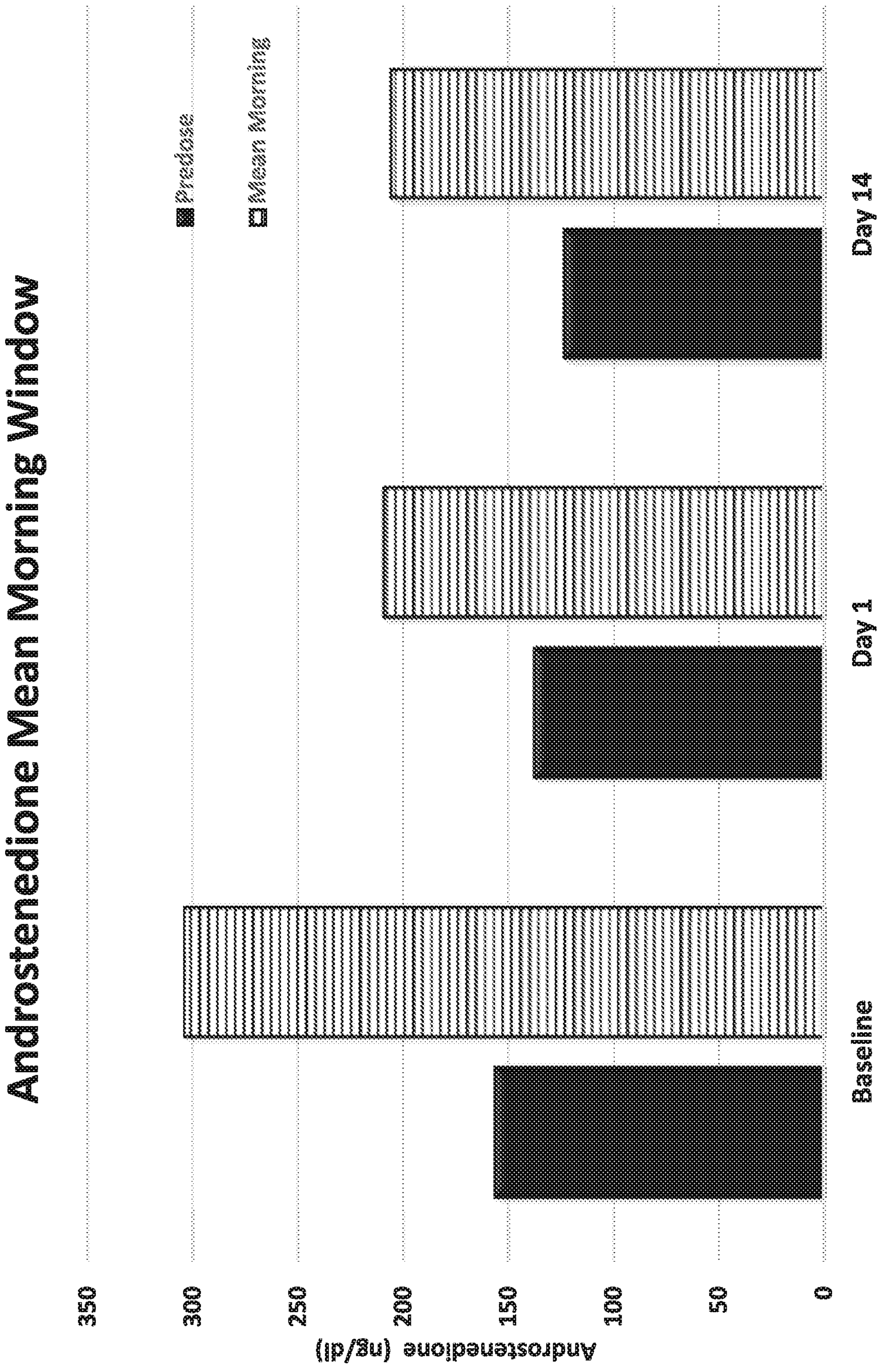
Figure 17A:
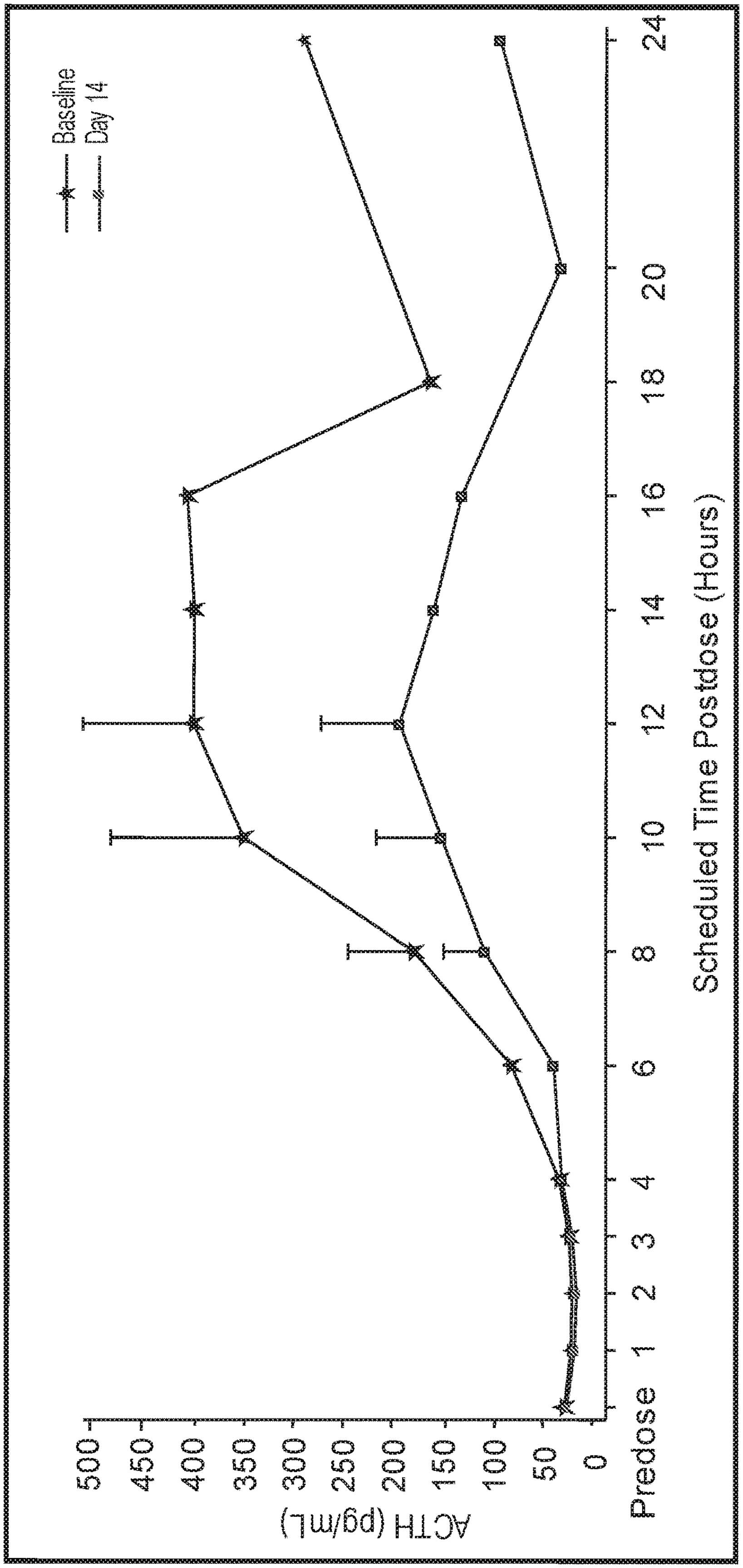
FIG. 17A shows the plasma ACTH Mean Blood Concentrations following the compound of Formula (I) 50 mg Dose qhs (Cohort 1; n=8). Error bars represent the standard error of the mean for each morning window timepoint. ACTH normal ranges: Female 6 to 58 pg/mL; Male 7 to 69 pg/mL.
Figure 17B:
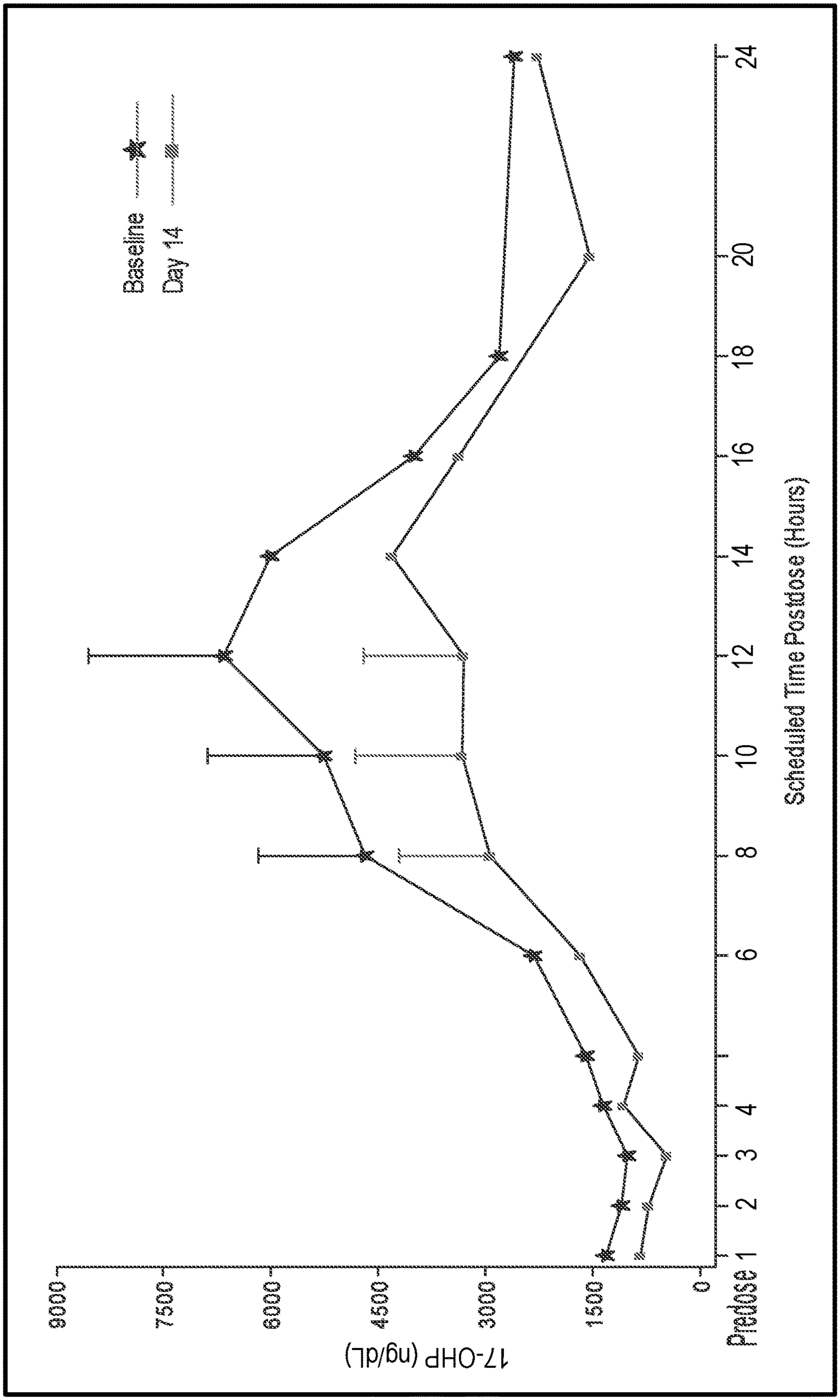
FIG. 17B shows the serum 17-OHP Mean Blood Concentrations following the compound of Formula (I) 50 mg Dose qhs (Cohort 1; n=8). Error bars represent the standard error of the mean for each morning window timepoint. 17-OHP normal ranges: Female<207 ng/dL; Male<139 ng/dL.
Figure 17C:
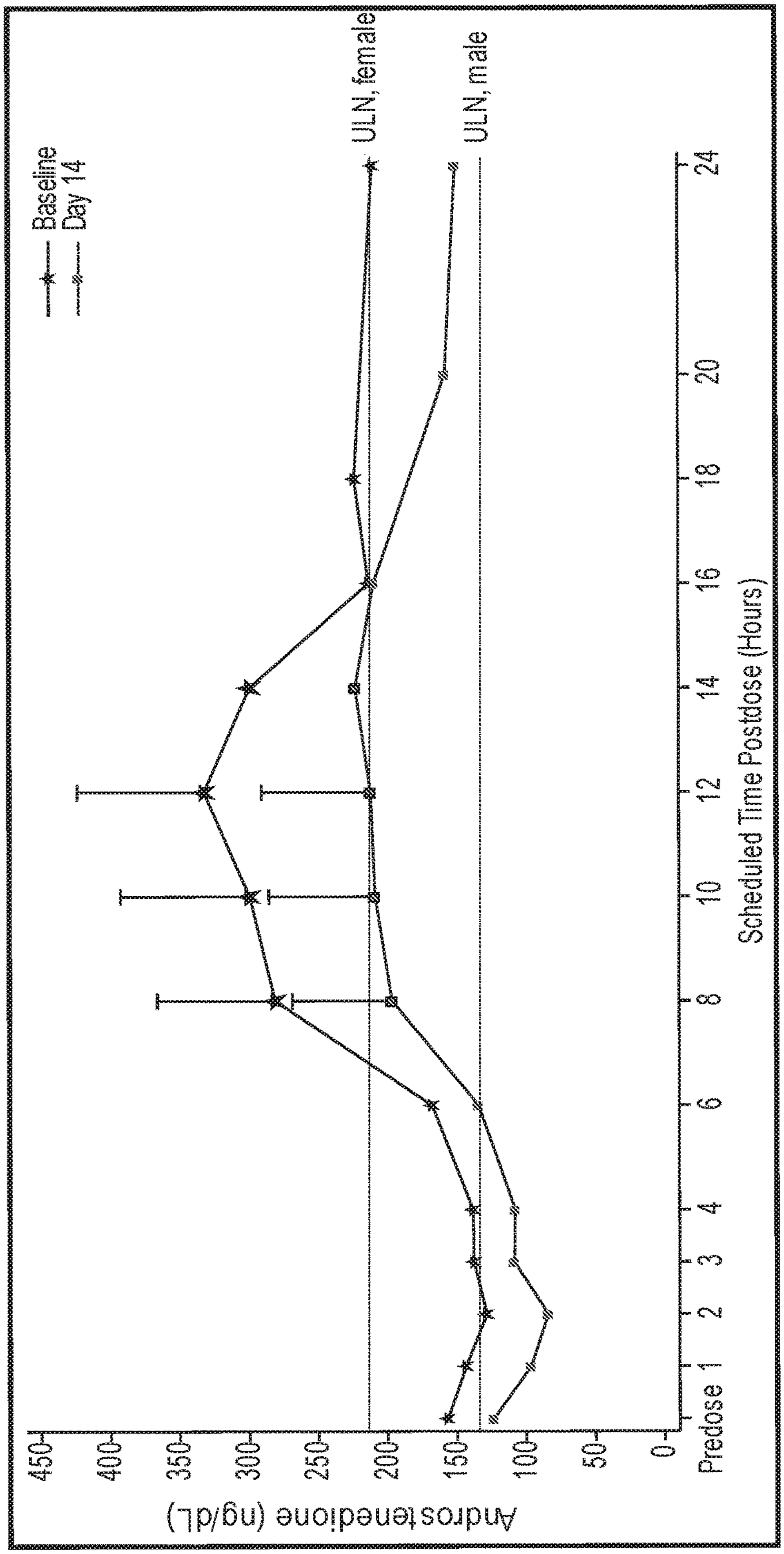
FIG. 17C: shows the serum Androstenedione Mean Blood Concentrations following the compound of Formula (I) 50 mg Dose qhs (Cohort 1; n=8). Error bars represent the standard error of the mean for each morning window timepoint. Androstenedione normal ranges: Female 26 to 214 ng/mL; Male 33 to 134 ng/mL.
Figure 18A:
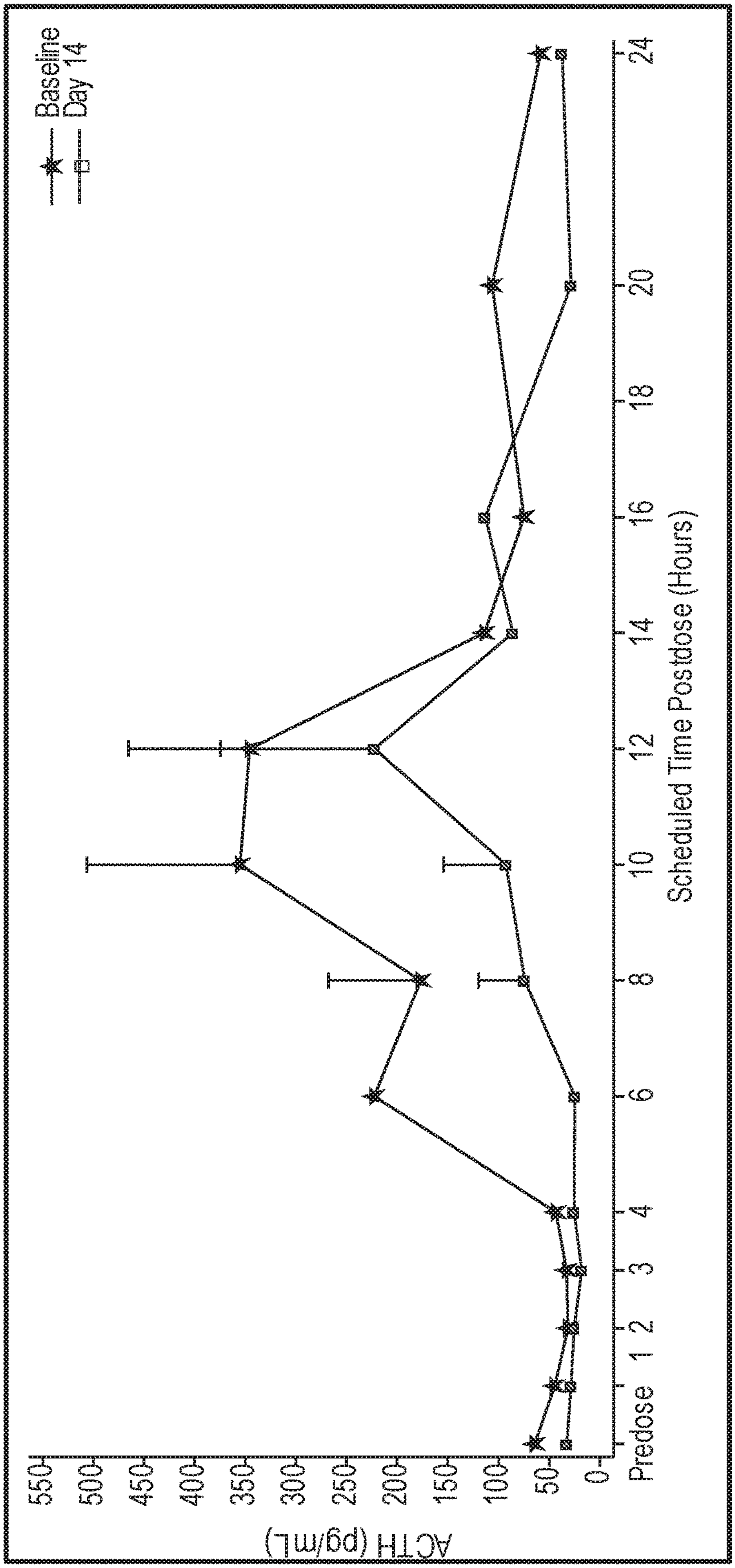
FIG. 18A shows the plasma ACTH Mean Blood Concentrations following the compound of Formula (I) 100 mg Dose qhs (Cohort 2; n=4). Error bars represent the standard error of the mean for each morning window timepoint. ACTH normal ranges: Female 6 to 58 pg/mL; Male 7 to 69 pg/mL.
Figure 18B:
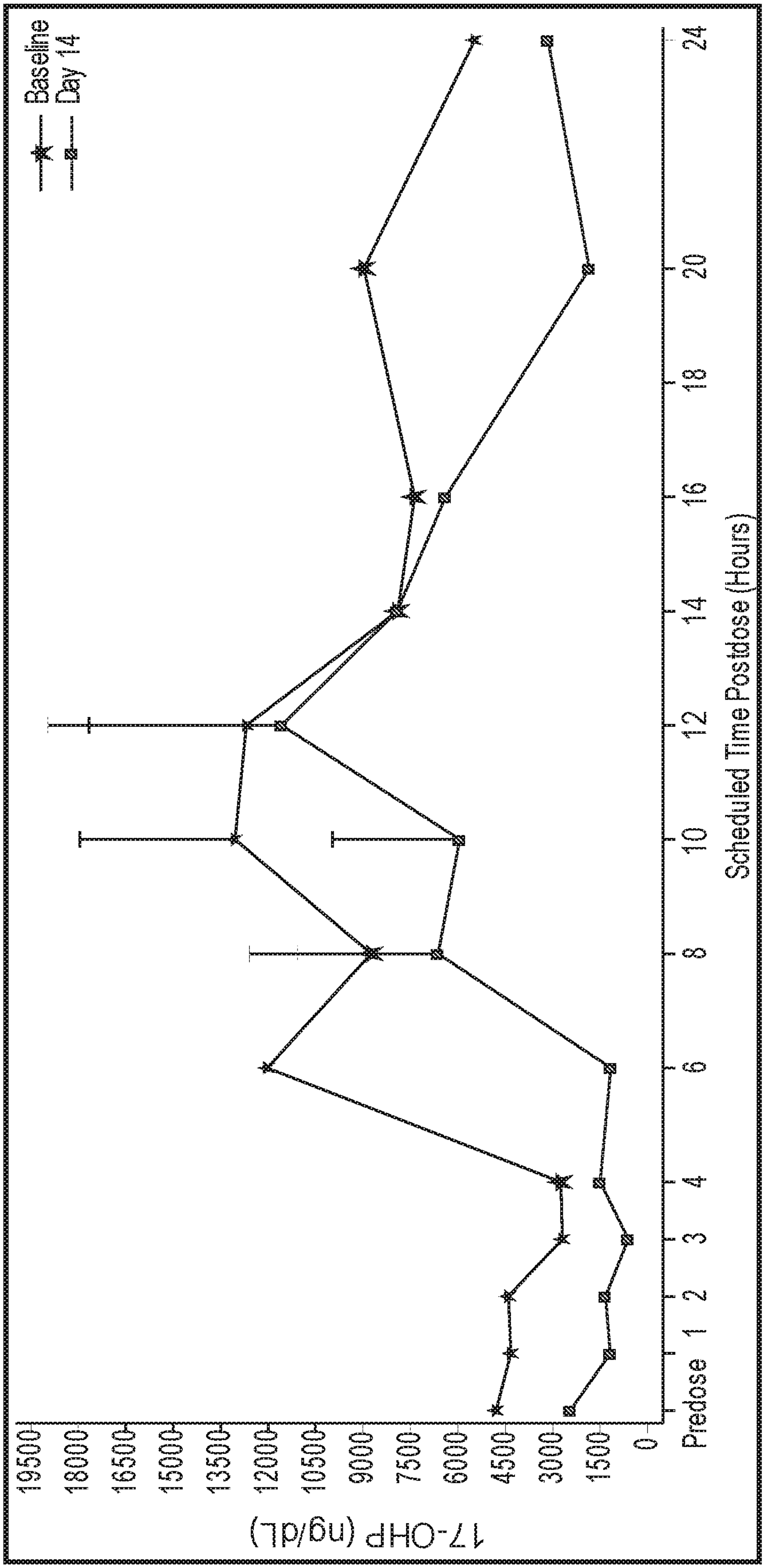
FIG. 18B shows the serum 17-OHP Mean Blood Concentrations following the compound of Formula (I) 100 mg Dose qhs (Cohort 2; n=4). Error bars represent the standard error of the mean for each morning window timepoint. 17-OHP normal ranges: Female<207 ng/dL; Male<139 ng/dL.
Figure 18C:
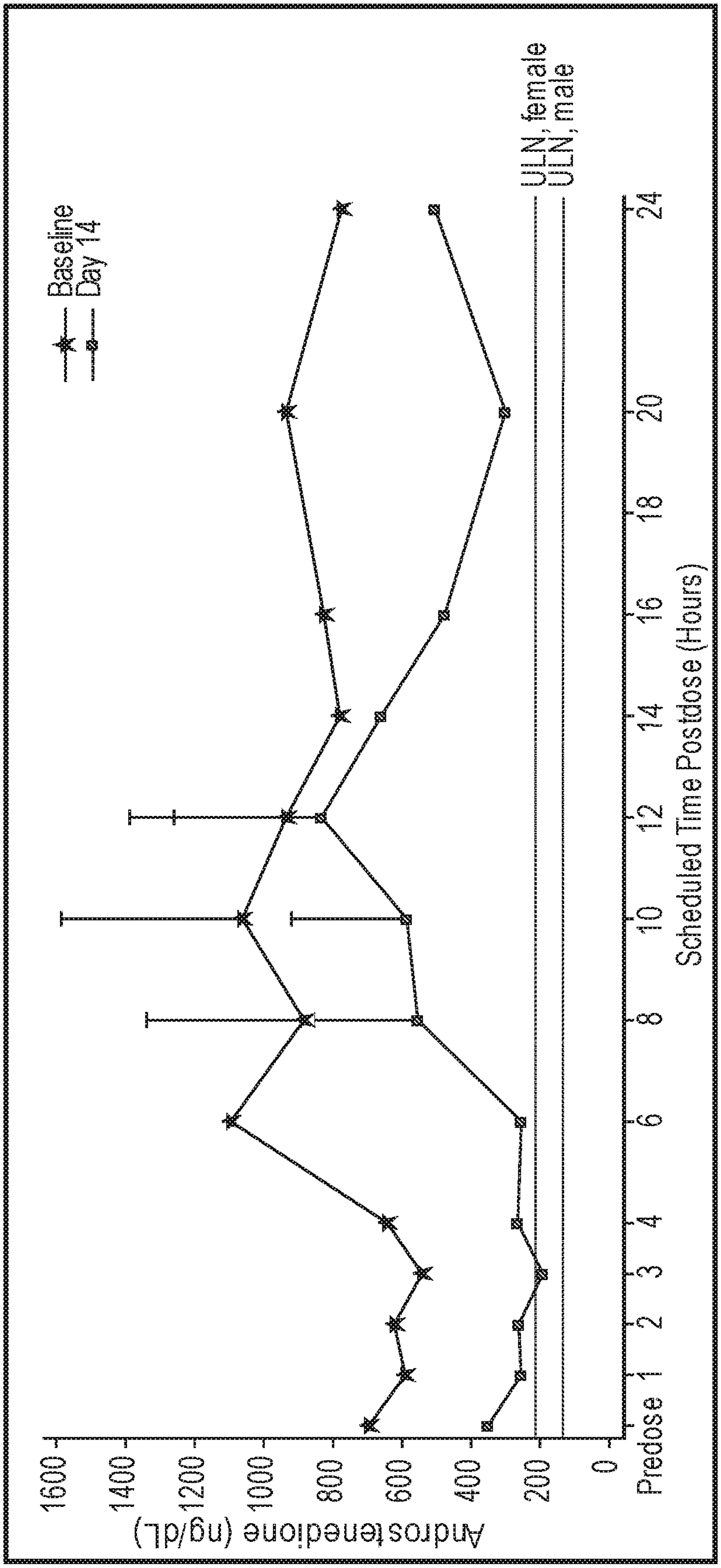
FIG. 18C shows the serum Androstenedione Mean Blood Concentrations following the compound of Formula (I) 100 mg Dose qhs (Cohort 2; n=4). Error bars represent the standard error of the mean for each morning window timepoint. Androstenedione normal ranges: Female 26 to 214 ng/mL; Male 33 to 134 ng/mL.
Figure 19A:
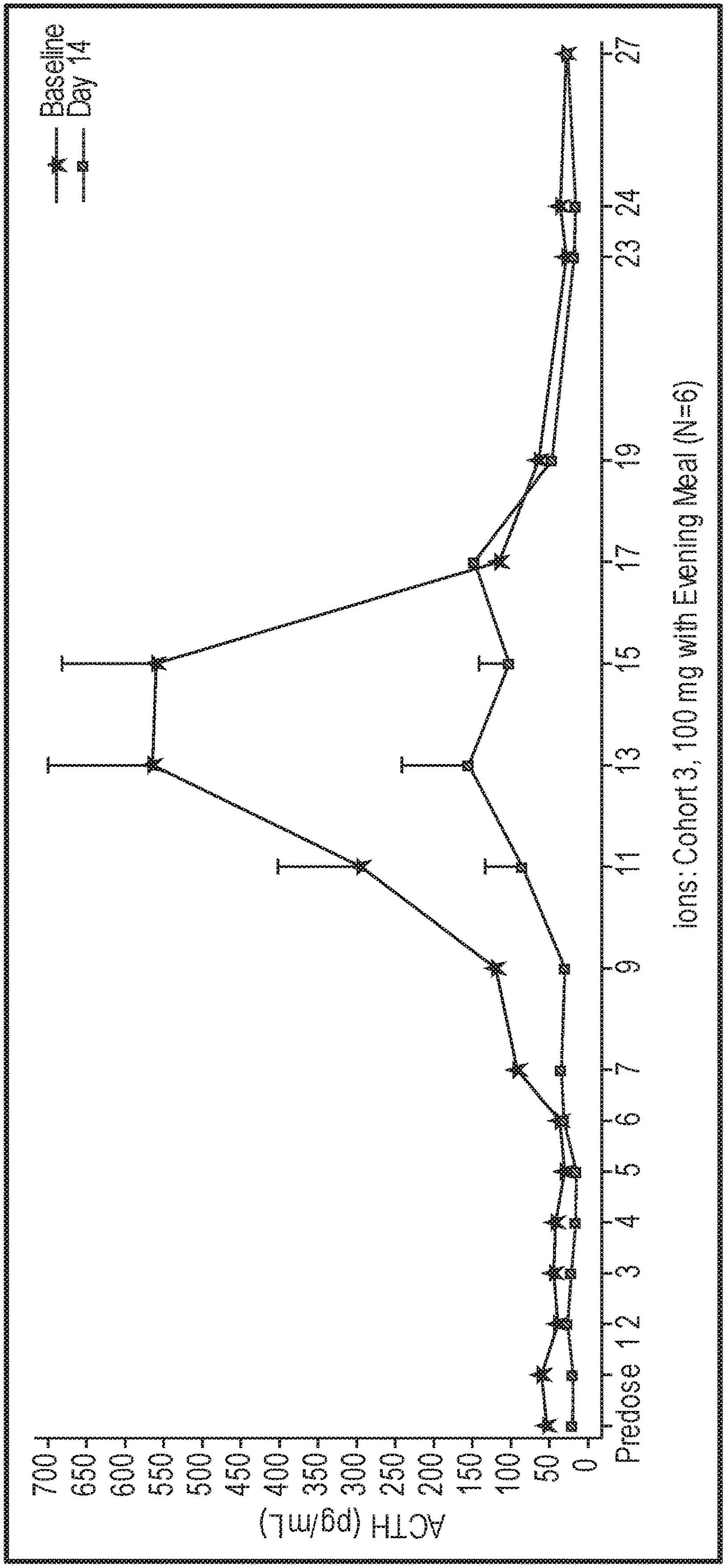
FIG. 19A shows the plasma ACTH Mean Blood Concentrations following the compound of Formula (I) 100 mg Dose with Evening Meal (Cohort 3). Error bars represent the standard error of the mean for each morning window timepoint. ACTH normal ranges: Female 6 to 58 pg/mL; Male 7 to 69 pg/mL.
Figure 19B:
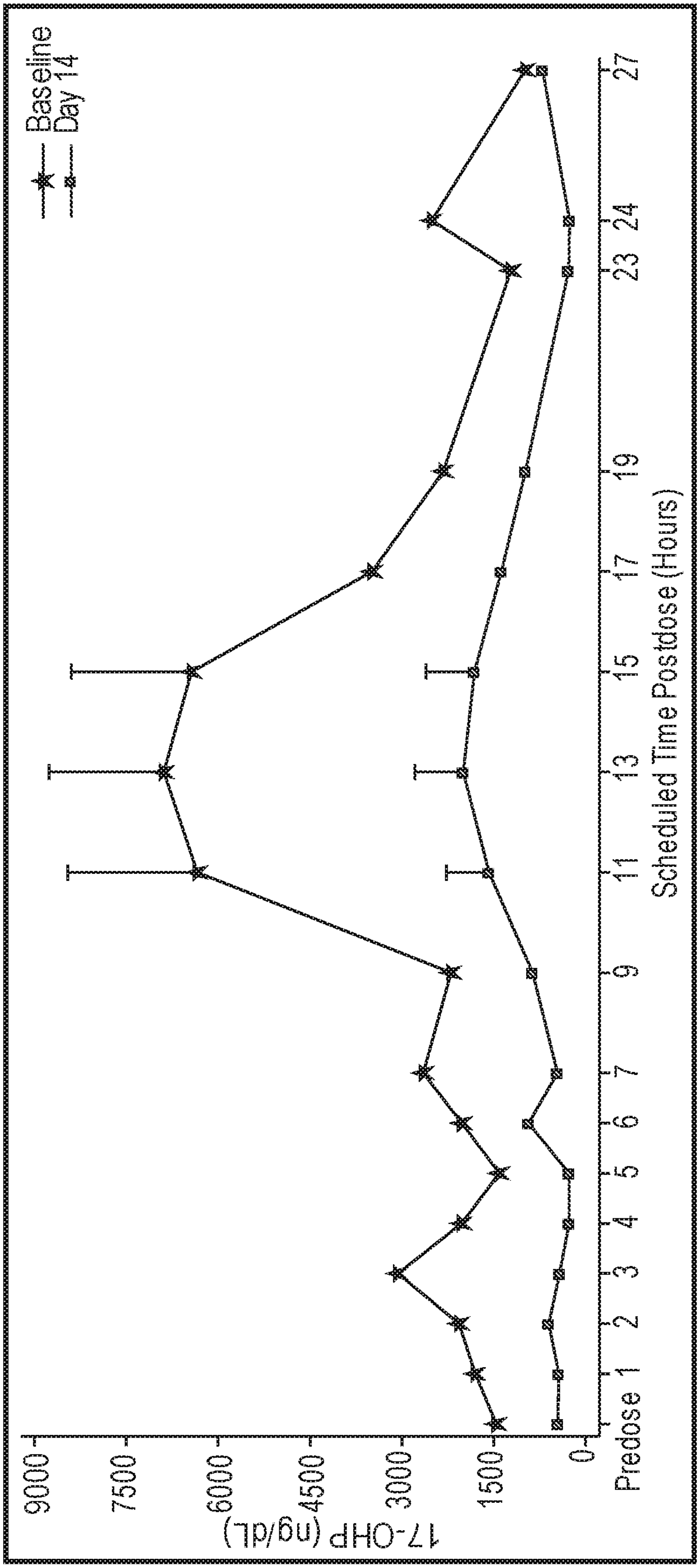
FIG. 19B shows the serum 17-OHP Mean Blood Concentrations following the compound of Formula (I) 100 mg Dose with Evening Meal (Cohort 3). Error bars represent the standard error of the mean for each morning window timepoint. 17-OHP normal ranges: Female<207 ng/dL; Male<139 ng/dL.
Figure 19C:
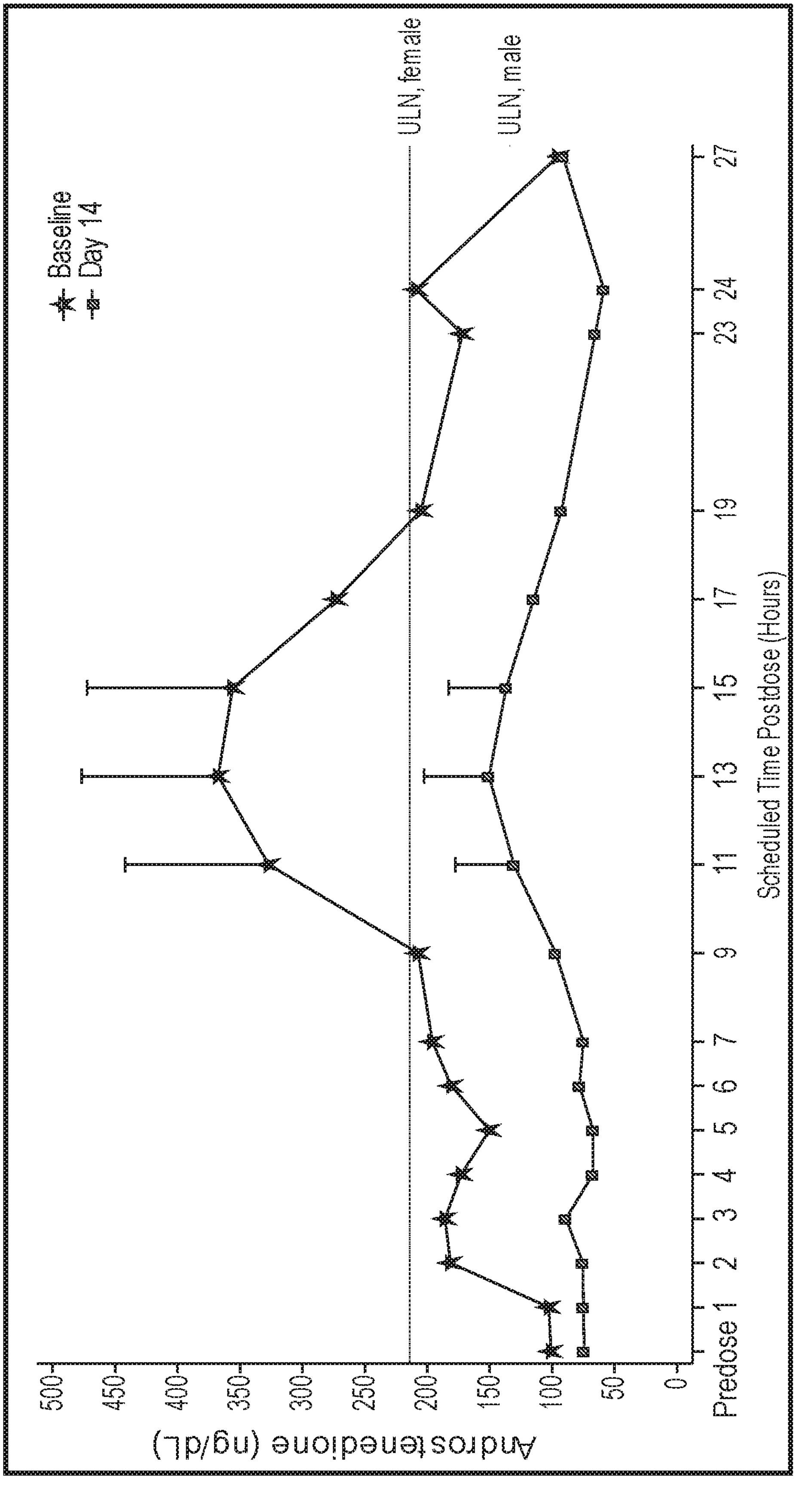
FIG. 19C shows the serum Androstenedione Mean Blood Concentrations following the compound of Formula (I) 100 mg Dose with Evening Meal (Cohort 3). Error bars represent the standard error of the mean for each morning window timepoint. Androstenedione normal ranges: Female 26 to 214 ng/mL; Male 33 to 134 ng/mL.

When focusing exclusively on the critical morning window period (timepoints at 8-, 10-, and 12-hours postdose) from 6:00 a.m. to 10:00 a.m., the levels of androstenedione show marked reductions from baseline at each of the 3 timepoints on Days 1 and 14 (FIG. 16A). Arithmetic mean values across all three timepoints show >=30% reductions from baseline at Day 1 and Day 14 (FIG. 16B).

A summary of reduction in 17-OHP and androstenedione in cohort 1 is shown in Table 32. Further, the androstenedione levels of three subjects was normalized by the treatment for the three subjects with Subject ID Nos. 001, 002, and 006).

TABLE 32

Cohort 1 Summary of Reduction in 17-OHP and Androstenedione at each timepoint in the morning window (6 a.m. to 10 a.m.)

| Subject | Sex/ | Dosing | 17-OHP % change from baseline | | | Androstenedione % change from baseline | | |
|---|---|---|---|---|---|---|---|---|
| ID | Age | Day | 6 AM | 8 AM | 10 AM | 6 AM | 8 AM | 10 AM |
| 001 | F/37 | D 1 | −61.4 | 14.7 | −24.1 | −42.0 | 2.0 | −19.5 |
| | | D 14 | −90.3 | −67.2 | −37.2 | −84.6 | −58.6 | −55.1 |
| 002 | F/25 | D 1 | −96.0 | −95.5 | 45.4 | −68.0 | −66.7 | −21.7 |
| | | D 14 | −37.7 | −58.6 | −24.9 | −34.2 | −47.8 | −38.7 |
| 003 | M/49 | D 1 | −11.8 | −46.6 | −34.0 | −13.4 | −47.1 | −22.7 |
| | | D 14 | −24.5 | −5.2 | −22.9 | −7.5 | −10.8 | −16.0 |
| 004 | M/36 | D 1 | −13.7 | 17.1 | 10.1 | 4.5 | 15.9 | 3.0 |
| | | D 14 | −53.6 | −46.8 | −35.8 | −13.8 | −15.2 | −21.2 |
| 005 | F/27 | D 1 | −24.4 | −83.6 | −52.2 | −35.6 | −50.3 | −33.5 |
| | | D 14 | −78.8 | −95.1 | −86.3 | 26.7 | −13.7 | −10.9 |
| 006 | M/19 | D 1 | −5.1 | −1.1 | −97.8 | −10.0 | −18.5 | −78.9 |
| | | D 14 | −25.4 | −20.4 | −98.3 | −67.8 | −62.7 | −92.1 |
| 007 | M/25 | D 1 | −50.0 | −28.0 | −27.4 | −24.8 | −30.0 | −15.8 |
| | | D 14 | 14.9 | 4.0 | −7.1 | −4.8 | −36.8 | −30.2 |
| 008 | F/31 | D 1 | −64.5 | −80.7 | −92.8 | −12.2 | 7.0 | −9.3 |
| | | D 14 | −59.0 | −65.2 | −89.1 | 74.5 | 99.4 | 59.2 |

TABLE 33

Cohort 1 Summary of PK parameters of $T_{max}$, $C_{max}$, and $AUC_{24}$ for each subject at days 1 and 14

| | Day 1 | | | Day 14 | | |
|---|---|---|---|---|---|---|
| Subject ID | $T_{max}$ (h) | $C_{max}$ (ng/ml) | $AUC_{24}$ (h * ng/ml) | $T_{max}$ (h) | $C_{max}$ (ng/ml) | $AUC_{24}$ (h * ng/ml) |
| 001 | 6 | 1830 | 14,487 | 6 | 1570 | 20,863 |
| 002 | 6 | 1210 | 11,829 | 4 | 1610 | 15,494 |
| 003 | 6 | 1060 | 11,068 | 3 | 1310 | 15,599 |
| 004 | 4 | 1670 | 9,669 | 3 | 1160 | 10,180 |
| 005 | 8 | 961 | 9,266 | 6 | 1550 | 15,130 |
| 006 | 4 | 1030 | 6,574 | 3 | 1090 | 10,288 |
| 007 | 6 | 1550 | 8,239 | 6 | 1170 | 12,880 |
| 008 | 3 | 1130 | 11,209 | 4 | 1330 | 13,944 |
| Mean | 5.4 | 1305 | 10,292 | 4.4 | 1349 | 14,297 |
| CV % | 30 | 25 | 24 | 32 | 15 | 24 |
| N | 8 | 8 | 8 | 8 | 8 | 8 |

After 14 days of once-daily compound of Formula (I) administration, a majority of participants in Cohorts 1-3 showed reduced serum concentrations of adrenal androgens and precursors. Mean changes from baseline (±standard deviation) in Cohort 1 were as follows: 17-OHP, −2341.0±1535.0 ng/dL; androstenedione, −98.4±98.7 ng/dL; and ACTH, −157.0±194.9 pg/mL. Mean reductions were larger in Cohort 2 (17-OHP, −4406.0±5516.1; androstenedione, -362.8±354.0; ACTH, −180.9±155.2) and Cohort 3 (17-OHP, −4760.1±4018.2; androstenedione, −210.9±188.6; ACTH, −358.9±177.6), suggesting a possible dose response. FIGS. 17A-17C, 18A-18C, and 19A-19C depict results from Cohorts 1, 2, and 3, respectively.

SUMMARY

The results from this ongoing Phase II open-label study demonstrated a reduction of at least 50 percent from baseline in 17-hydroxyprogesterone (17-OHP) and adrenocorticotropic hormone (ACTH) levels in more than 50 percent of CAH patients in cohort 1 treated with the compound of Formula (I) for 14 days (i.e., 6 of 8 patients in cohort 1 had a reduction of >50% from baseline levels of 17-OHP during at least one morning window timepoint, see, e.g., Table 32). Meaningful reductions were also observed in other biomarkers, including androstenedione (i.e., 4 of these patients also had a reduction of ≥50% from baseline levels of androstenedione during at least one morning window timepoint, see, e.g., Table 32). The greater reductions in biomarkers in cohorts 2 and 3, treated with double the dose of the compound of Formula (I) compared with cohort 1, suggest a possible dose response. Further, the compound of Formula (I) was well-tolerated with a relatively small number of mild adverse events (AEs) reported (e.g., headache, ovulation pain, fatigue, localized infection (toe), dizziness, nausea, URI, contusion with the most common being headache). No clinically significant findings from routine labs, vital signs, or electrocardiograms were found.

Example 9: Reference Formulation 1 of the Compound of Formula (I)

Figure 20:
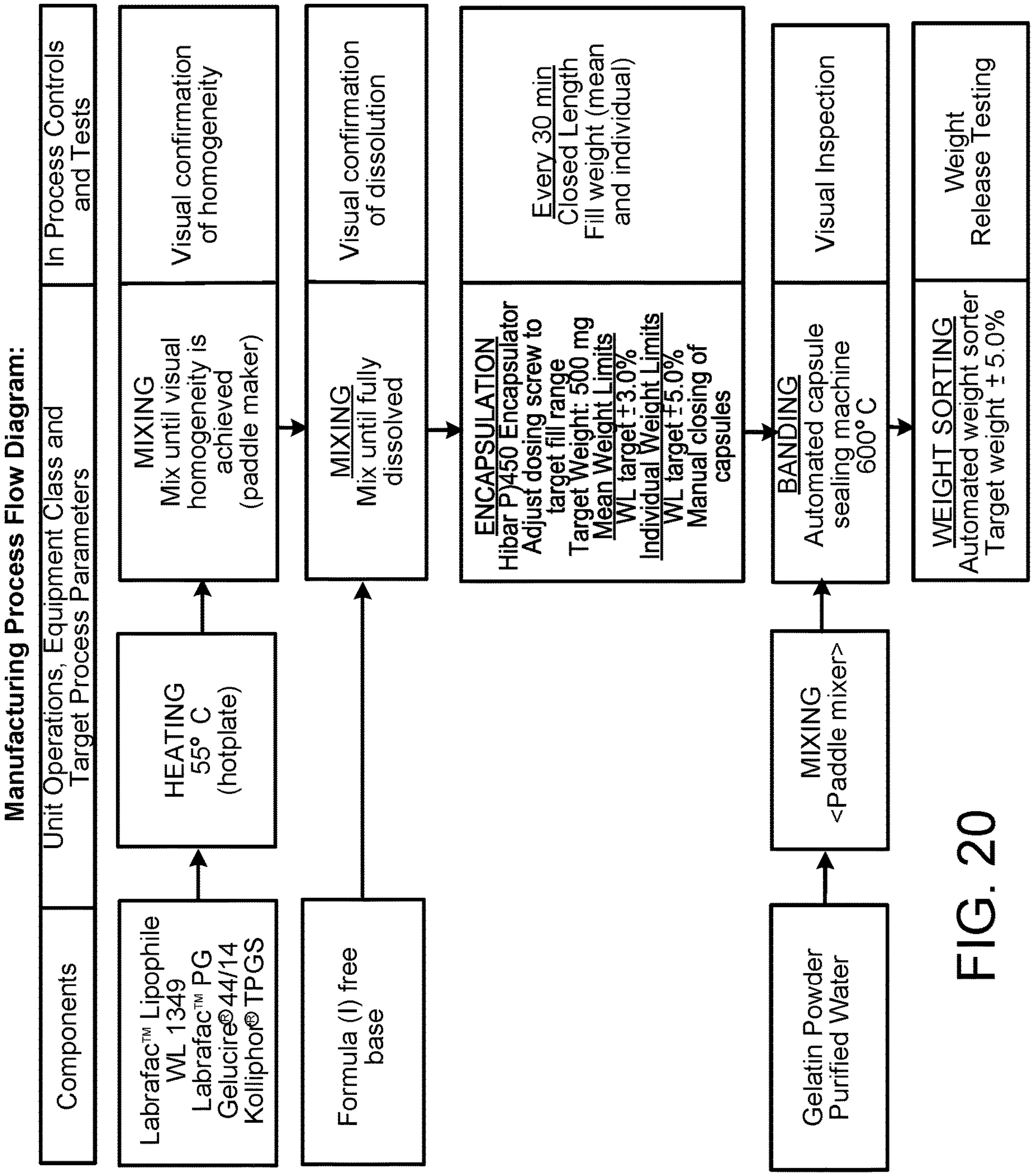
FIG. 20 is a scheme showing the manufacturing process for forming 50 mg capsules of the compound of Formula (I).
Figure 21:
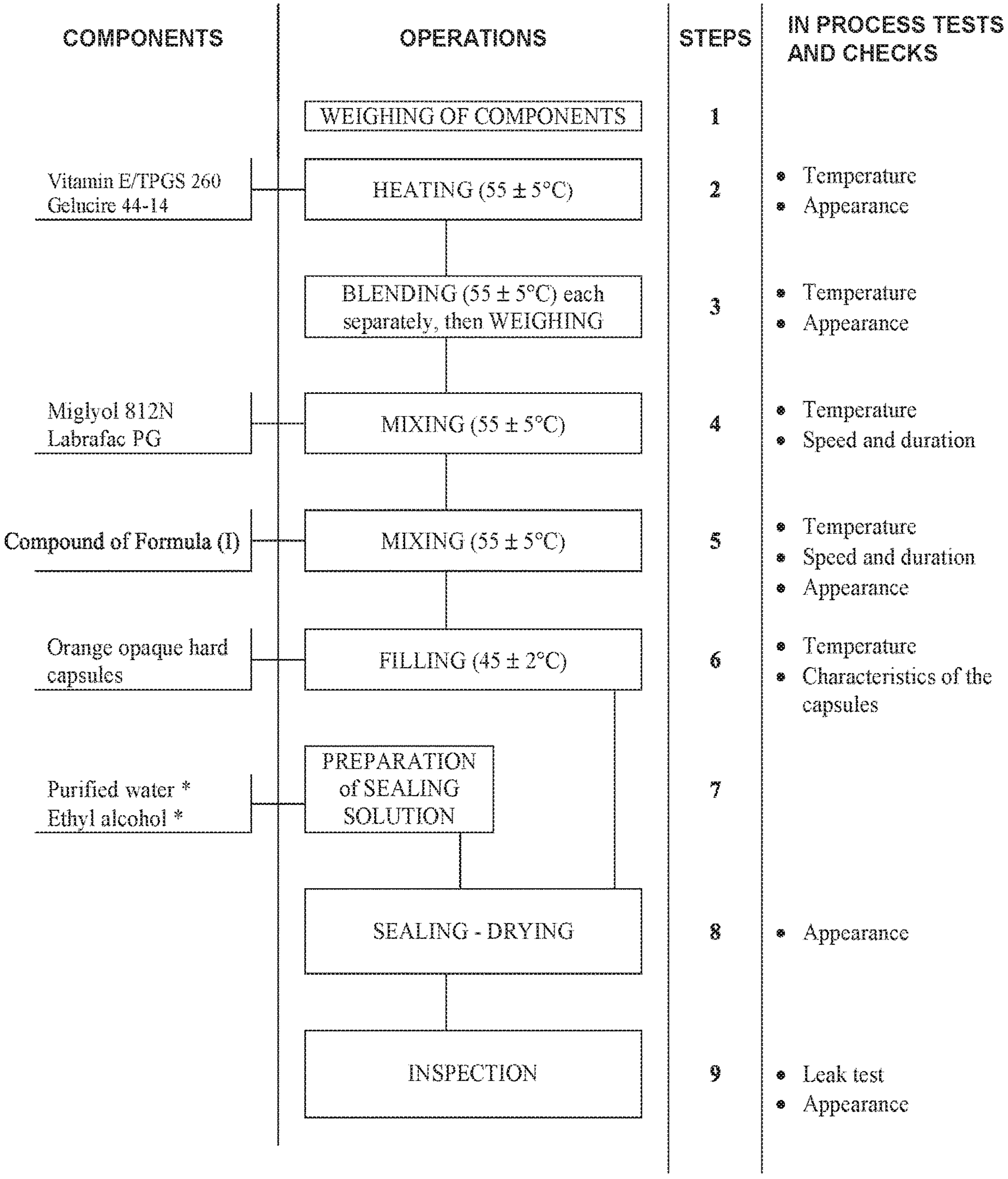
FIG. 21 is an alternative scheme showing the manufacturing process for forming 50 mg capsules of the compound of Formula (I).

Tables 34A and 34B show Reference formulation 1 of the compound of Formula (I) as used in the clinical studies described in Examples 6 and 8, above. An example manufacturing process is shown in FIG. 20. Another example manufacturing process is shown in FIG. 21.

TABLE 34A

| | | | 50 mg Capsule | |
|---|---|---|---|---|
| Component | Quality Standard | Function | Weight (mg/unit) | % (w/w) |
| Compound of Formula (I), free base | In-house | Active Ingredient | 50.0 | 10.0 |
| Medium-Chain Triglycerides (sold under the trademark LABRAFAC ™ LIPOPHILE WL1349) | NF | Oily Phase Vehicle | 196.0 | 39.2 |
| Propylene Glycol Dicaprylate/Dicaprate, (sold under the trademark LABRAFAC ™ PG) | NF | Emulsifying Agent | 102.0 | 20.4 |
| Lauroyl Polyoxyl-32 Glycerides (sold under the trademark GELUCIRE ® 44/14) | NF | Nonionic Surfactant & Solubilizing Agent | 95.0 | 19.0 |
| Vitamin E Polyethylene Glycol Succinate (sold under the trademark KOLLIPHOR ® TPGS) | USP/NF | Solubilizing Agent | 57.0 | 11.4 |
| Total Emulsion Weight | | | 500.0 | 100.0 |
| Gelatin Capsule Shell. Size #00, Swedish Orange cap/body; (sold under the trademark CONI-SNAP ®) | Non Pharmacopoeial | Capsule Shell | — | — |
| Gelatin Powder, 220 Bloom | USP | Capsule shell banding agent | — | — |
| Purified Water | USP | Capsule shell banding solvent | — | — |

TABLE 34B

| | | | 50 mg Capsule | |
|---|---|---|---|---|
| Component | Quality Standard | Function | Weight (mg/unit) | % (w/w) |
| Compound of Formula (I), free base | In-house | Active Ingredient | 50.0 | 10.0 |
| Medium-Chain Triglycerides (caprylic:capric acid 60:40; sold under the trademark MIGLYOL 812N) | Ph. Eur./NF | Vehicle | 195.85 | 39.2 |
| Propylene Glycol Dicaprylocaprate, (sold under the trademark LABRAFAC ™ PG) | Ph. Eur. | Vehicle | 102.15 | 20.4 |
| Lauroyl macrogolglycerides type 1500-Lauroyl polyoxylglycerides type 1500 (sold under the trademark GELUCIRE ® 44/14) | Ph. Eur./NF | Surfactant | 95.0 | 19.0 |

TABLE 34B-continued

| Component | Quality Standard | Function | 50 mg Capsule Weight (mg/unit) | 50 mg Capsule % (w/w) |
|---|---|---|---|---|
| Vitamin E Polyethylene Glycol Succinate, 260 mg/g d-alpha tocopherol (Vitamin E/TPGS 260) | NF | Surfactant | 57.0 | 11.4 |
| Total Emulsion Weight | | | 500.0 | 100.0 |
| Orange opaque hard capsule, size 0, composed of gelatin, titanium dioxide and red ferric oxide (sold under the trademark SWEDISH ORANGE ®) | Non Pharmacopoeial | Capsule Shell | — | — |
| Ethanol (96%) and Purified Water | USP | Capsule shell banding solvent | — | — |

Example 10: Study Evaluating Effect of Ensure Plus, Ensure Pudding, Milk and High Fat Meal on Reference Capsule Study Design This is a Phase 1, open-label, randomized, four-period crossover study to evaluate the effect of food with different levels of fat and caloric content on the PK, safety, and tolerability of the compound of Formula (I) in healthy adult subjects.

A total of 16 healthy adult subjects (8 males and 8 females) will be randomly assigned to 1 of 4 treatment sequences (4 subjects per sequence [2 males and 2 females per sequence]; see Table 35 below). During each treatment period, subjects will receive a single dose of the compound of Formula (I) 100 mg administered with the appropriate meal, according to the randomization scheme. There will be a washout of at least 21 days between each dose.

TABLE 35

| Treatment Sequence | Treatment Period 1 | Treatment Period 2 | Treatment Period 3 | Treatment Period 4 |
|---|---|---|---|---|
| 1 | Reference meal | Test meal 1 | Test meal 2 | Test meal 3 |
| 2 | Test meal 1 | Test meal 3 | Reference meal | Test meal 2 |
| 3 | Test meal 2 | Reference meal | Test meal 3 | Test meal 1 |
| 4 | Test meal 3 | Test meal 2 | Test meal 1 | Reference meal |

Reference meal: vanilla-flavored Ensure Plus ®
Test meal 1: Low fat, low caloric content meal 1
Test meal 2: Low fat, low caloric content meal 2
Test meal 3: standard high fat, high caloric content meal After providing informed consent, subjects will be screened for eligibility to participate in the study. Screening will begin up to 28 days before Day 1 of treatment period 1. Eligible subjects will be admitted to the clinical unit on Day −1 and randomized to 1 of the 4 treatment sequences on Day 1 of treatment period 1. During each treatment period, subjects will fast overnight for at least 10 hours until the start of the assigned meal, according to the randomization scheme, and ingest the study drug at approximately 0800 hours. Subjects must complete the entire meal within the specified time period and should not consume any other food for 4 hours after dosing. For all treatment periods, water will not be permitted for 1 hour before dosing until 2 hours after dosing except for the water provided with study drug dosing and planned meals.

On Day 1 of each treatment period, subjects will be dosed with the compound of Formula (I) 100 mg. Blood samples will be collected for PK analysis over a period of 36 hours during the in-house stay. During each treatment period, subjects will remain in the clinic on the day of dosing and will be discharged on Day 2 after completing all required procedures. On the mornings of Days 8 and 15 of each treatment period, subjects will return for an outpatient visit to the clinic for PK blood sample collection and safety assessments. On Day 21 of treatment periods 1 to 3, subjects will arrive at the site and have Day 21 assessments completed and they will stay overnight at the site and begin Day 1 of the subsequent treatment period the following day. A final follow-up study visit will be conducted on Day 22 of treatment period 4 (21±2 days after treatment period 4 dosing) or upon early termination.

Blood samples for PK d/conducted at scheduled times throughout the study.

Study Population

Sixteen healthy adult subjects (8 males and 8 females) between 18 and 55 years of age, inclusive, who meet all protocol eligibility criteria, will be enrolled.

Duration of Treatment

The expected duration of study participation for each healthy adult subject will be approximately 16 weeks, including up to 28 days of screening, 4 days of dosing with at least 21 days between consecutive doses, and a final follow-up study visit 21 days (±2 days) after receiving the last dose of study drug during treatment period 4.

Test Product, Dose, and Mode of Administration

The compound of Formula (I) will be supplied as capsules for oral administration (encapsulated, lipidic semi-solid formulation, e.g., Example 9). The compound of Formula (I) capsules will contain 50 mg of the compound of Formula (I) as free base equivalent. During each treatment period, subjects will receive two 50 mg capsules (100 mg) of the study drug along with a meal and water as defined by the randomization scheme. The food, water, and study drug administration are as follows:

- Reference meal: Two capsules of study drug will be administered approximately 5 minutes after the start of a liquid dietary supplement (i.e., Ensure Plus® [237 mL container]) and an additional 120 mL of water for study drug dosing.
- Test meal 1: Two capsules of study drug will be administered approximately 5 minutes after the start of a low fat, low caloric meal 1 with 120 mL of water for study drug dosing.

Test meal 2: Two capsules of study drug will be administered approximately 5 minutes after the start of a low fat, low caloric meal 2 with 120 mL of water for study drug dosing.

Test meal 3: Two capsules of study drug will be administered approximately 30 minutes after the start of a high fat, high caloric meal with 120 mL of water for study drug dosing.

Criteria for Evaluation

Pharmacokinetics

Blood samples for assessment of plasma concentrations of the compound of Formula (I) and metabolites will be collected within 45 minutes before dosing, and at approximately 30 minutes, and 1, 2, 3, 4, 5, 6, 7, 8, 9, 10, 12, 16, 24, 36, 168, 336, and 504 hours after dosing. The following plasma PK parameters will be calculated for the compound of Formula (I) and metabolites:

Area under the plasma concentration versus time curve from 0 hours to last measurable concentration ($AUC_{0-tlast}$)

Area under the plasma concentration versus time curve from 0 hours extrapolated to infinity ($AUC_{0-\infty}$)

Maximum plasma concentration ($C_{max}$)

Time to achieve maximum plasma concentration ($t_{max}$)

Delay time between time of dosing and time of appearance of measurable test article ($T_{lag}$)

Apparent terminal half-life ($t_{1/2}$)

Apparent terminal rate constant (λz)

Apparent mean residence time (MRT)

Molar AUC ratio of primary metabolite(s) to the parent drug compound of Formula (I).

The following plasma PK parameters will be calculated only for the compound of Formula (I):

Apparent systemic clearance after oral administration (CL/F)

Apparent volume of distribution during terminal phase after oral administration (Vz/F)

Safety Assessments

Safety will be monitored throughout the study and will include the following assessments:

Adverse events (AEs)

Clinical laboratory tests (hematology, coagulation, clinical chemistry, and urinalysis)

Vital sign measurements (including orthostatic blood pressure and pulse rate)

Physical examinations 12-lead electrocardiograms (ECGs)

Statistical Methods

Pharmacokinetic parameters will be calculated using non-compartmental methods and summarized by meal type (test meal/reference meal) using descriptive statistics. Two-sided 90% confidence intervals will be calculated for the ratio of each test meal versus the reference meal for $AUC_{0-\infty}$, $AUC_{0-tlast}$, and $C_{max}$ for the compound of Formula (I) and metabolites. Safety data will be summarized with descriptive statistics.

Results

Pharmacokinetic Results

Pharmacokinetic results are shown in Table 36 below.

TABLE 36

Summary of Plasma Pharmacokinetic Parameters

| Parameter (units) Statistic | Ensure Plus (Fed) (N = 18) | Compound of Formula (I) Plasma Concentration<br>Ensure Pudding (Fed) (N = 18) | Whole Milk (Fed) (N = 17) | High Fat Meal (Fed) (N = 17) |
|---|---|---|---|---|
| $AUC_{0-tlast}$ (ng × hr/mL) | | | | |
| Mean (SD) | 36703 (17400) | 34077 (11597) | 35561 (15866) | 55487 (23242) |
| Geom CV (%) | 58 | 39.7 | 44.6 | 41.9 |
| $AUC_{0-\infty}$ (ng × hr/mL) | | | | |
| Mean | 45386 (19648) | 40037 (9515) | 46737 (17395) | 63755 (19139) |
| Geom CV (%) | 43.3 | 23.8 | 38.8 | 31 |
| $C_{max}$ (ng/mL) | | | | |
| Mean (SD) | 3090 (1070) | 3038 (984) | 2835 (1005) | 4336 (1938) |
| Geom CV (%) | 39.7 | 34.9 | 34.5 | 53.6 |
| $t_{max}$ (hr) | | | | |
| Median (min, max) | 5.0 (2.0, 10.0) | 5.0 (4.0, 6.0) | 5.0 (4.0, 7.0) | 5.0 (4.0, 7.0) |
| $T_{lag}$ (hr) | | | | |
| Mean (SD) | 0.38 (0.46) | 0.20 (0.25) | 0.16 (0.31) | 0.29 (0.37) |
| $t_{1/2}$ (hr) | | | | |
| Mean (SD) | 361 (263) | 373 (196) | 373 (143) | 326 (120) |
| Geom CV (%) | 61.1 | 48.6 | 37.1 | 33.8 |
| CL/F (L/hr) | | | | |
| Mean (SD) | 2.49 (0.956) | 2.636 (0.659) | 2.427 (0.975) | 1.706 (0.526) |
| Geom CV (%) | 41.2 | 24.8 | 38.8 | 31.1 |
| Vz/F (L) | | | | |
| Mean (SD) | 1254 (906) | 1414 (720) | 1308 (627) | 816 (378) |
| Geom CV (%) | 72.7 | 58.4 | 61.3 | 54.9 |

Example 11: Spray-Dried Dispersion Granule Formulation of the Compound of Formula (I) (SDD-G)

Figure 22A:
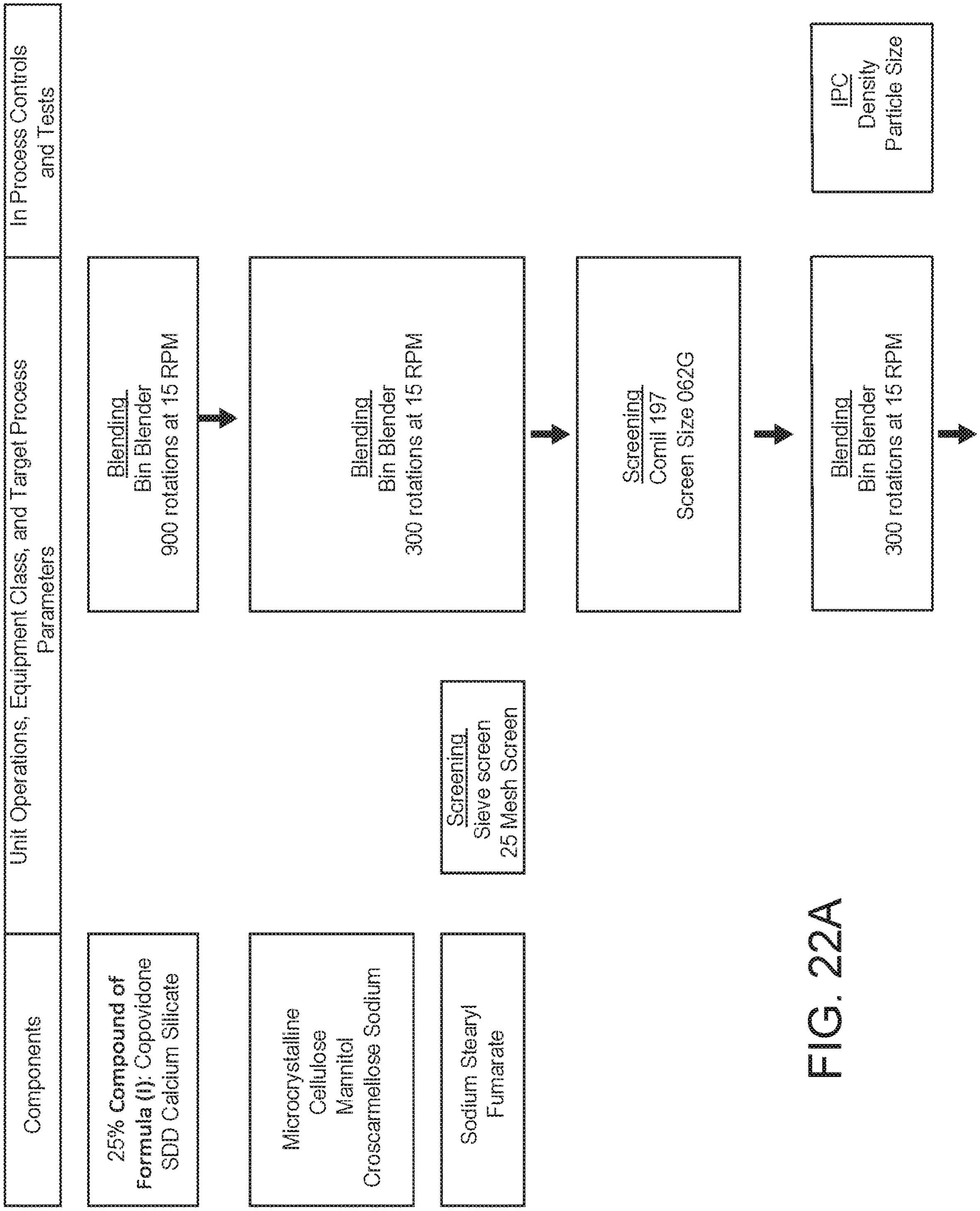
FIGS. 22A and 22B show a scheme showing the manufacturing process for forming SDD granules of the compound of Formula (I).
Figure 22B:
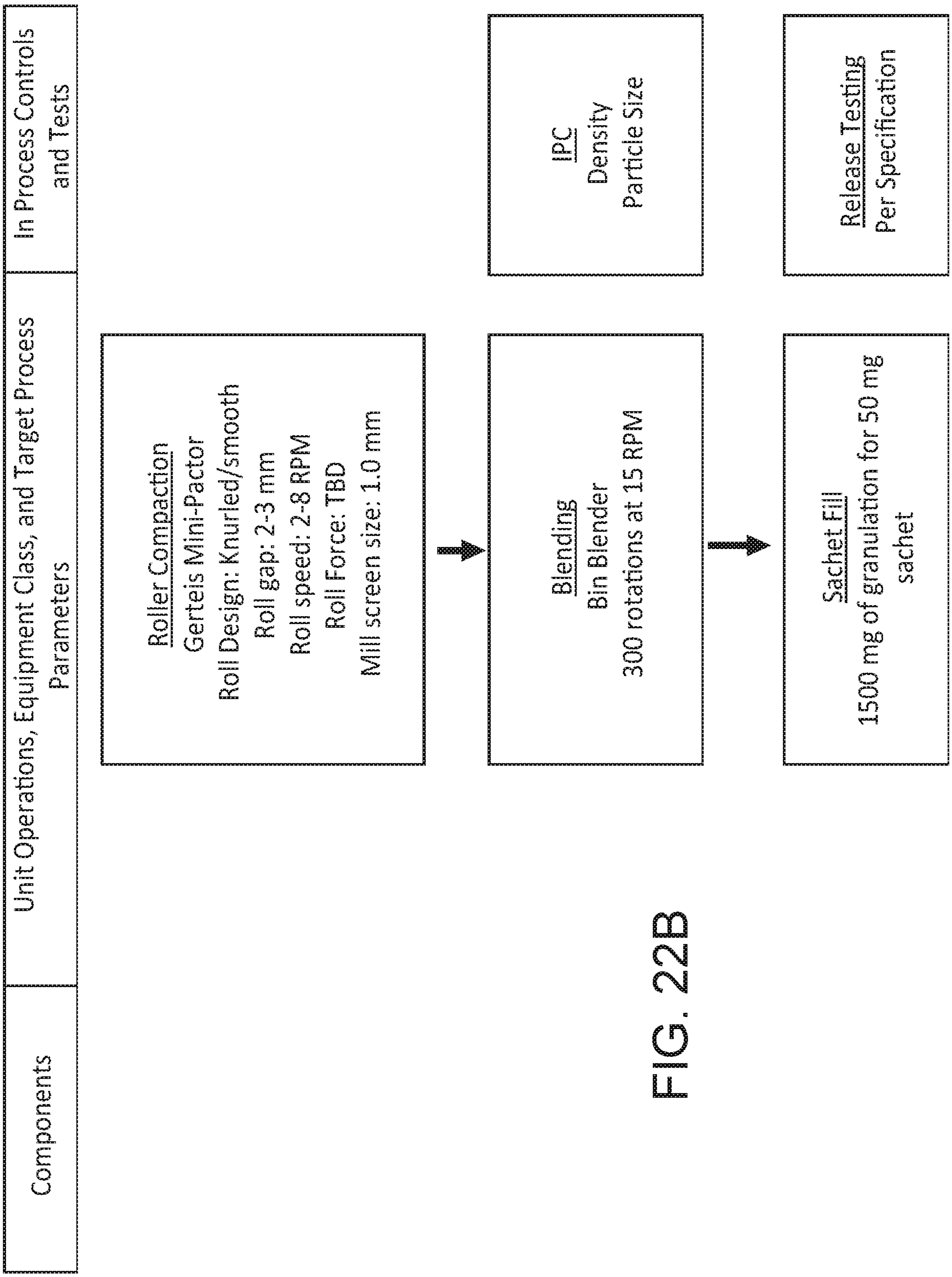

Table 37 shows a granule formulation of the compound of Formula (I) using a SDD prepared according to Example 3, above. An example manufacturing process is shown in FIG. 22A and FIG. 22B.

TABLE 37

| | | | 50 mg Sachet | | Batch |
|---|---|---|---|---|---|
| Component | Quality Standard | Function | Weight (mg/unit) | % (w/w) | Weight (g) |
| Example 3, SDD | In-house | Drug Substance | 200.0 | 13.33 | 40 |
| Calcium Silicate (sold under the trademark ZEOPHARM 250) | NF | Glidant | 10.0 | 0.67 | 2 |
| Mannitol (sold under the trademark PEARLITOL 200SD) | NF/EP/JP | Filler | 832.5 | 55.5 | 166.5 |
| Microcrystalline Cellulose (sold under the trademark AVICEL PH-102) | NF/EP/JP | Filler | 300.0 | 20.0 | 60 |
| Croscarmellose Sodium (sold under the trademark AC-DI-SOL ®) SD711 | NF/EP/JP | Disintegrant | 150.0 | 10.0 | 30 |
| Sodium Stearyl Fumarate | NF/EP/JP | Lubricant | 7.5 | 0.5 | 1.5 |
| Total | | | 1500 | 100.0 | 300 |

Example 12: Liquid Formulation 1 of the Compound of Formula (I)

Figure 23:
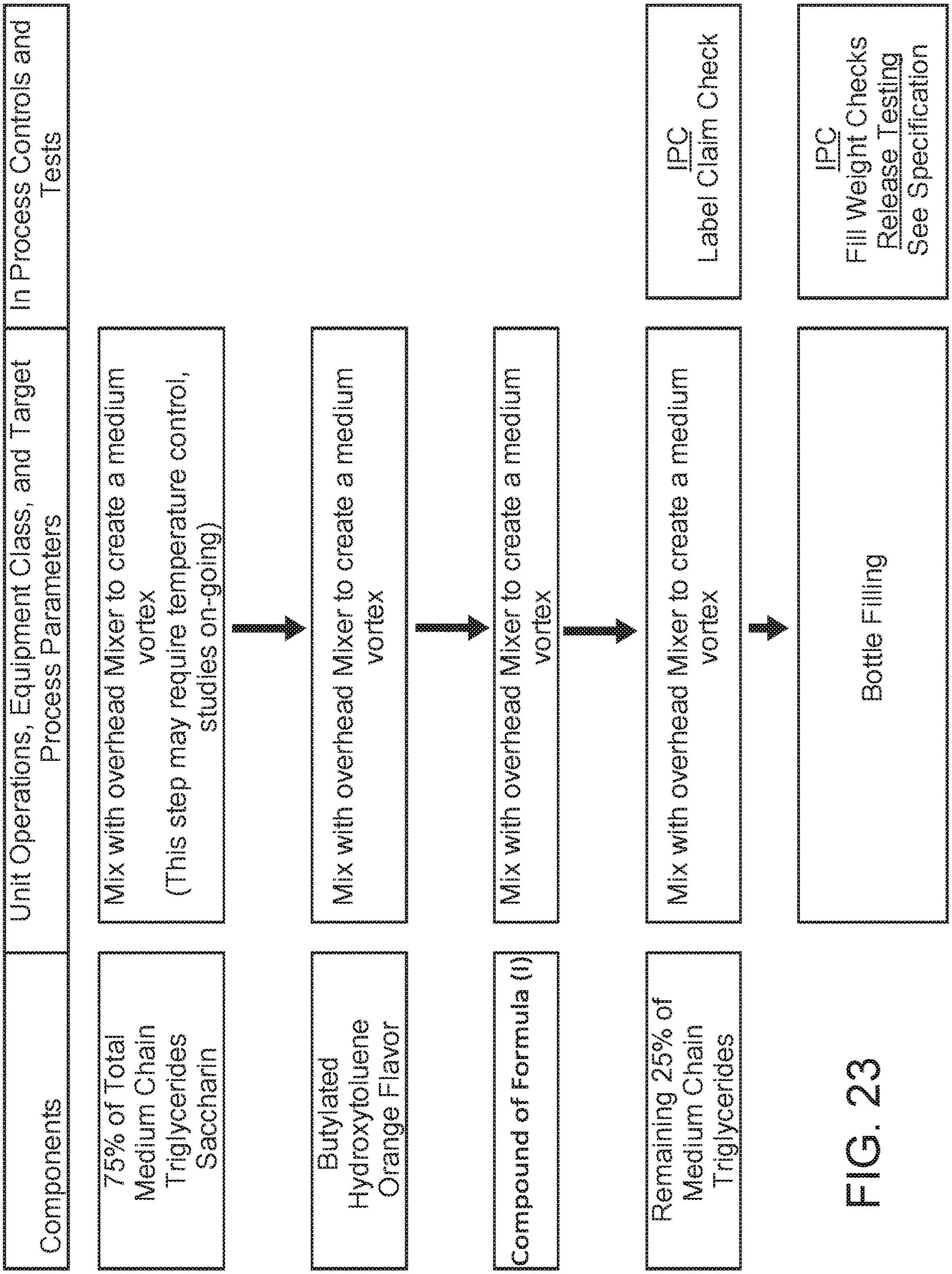
FIG. 23 is a scheme showing the manufacturing process for forming 50 mg/nL liquid formulation 1 of the compound of Formula (I).

Table 38 shows liquid formulation 1 of the Compound of Formula (I) free base. An example manufacturing process is shown in FIG. 23.

TABLE 38

| | | | 50 mg/mL Oral Solution | | Batch |
|---|---|---|---|---|---|
| Component | Quality Standard | Function | Weight (mg/mL) | % (w/v) | Weight (g) |
| Compound of Formula (I) FB | In-house | Drug Substance | 50.0 | 5 | 20.03 |
| Saccharin | NF/EP | Sweetener | 1.5 | 0.15 | 0.61 |
| Butylated hydroxytoluene | NF/EP | Anti-oxidant | 1.7 | 0.17 | 0.69 |
| FONA orange flavor | NF | Flavor | 1.0 | 0.1 | 0.41 |
| LABRAFAC ™ LIPOPHILE WL1349 | NF/EP | Liquid Vehicle | to 1 mL | 94.58 | 358.87 |
| Total | | | 1 mL | 100.0 | 380.6 |

Example 13: Liquid Formulation 2 of the Compound of Formula (I)

Figure 24:
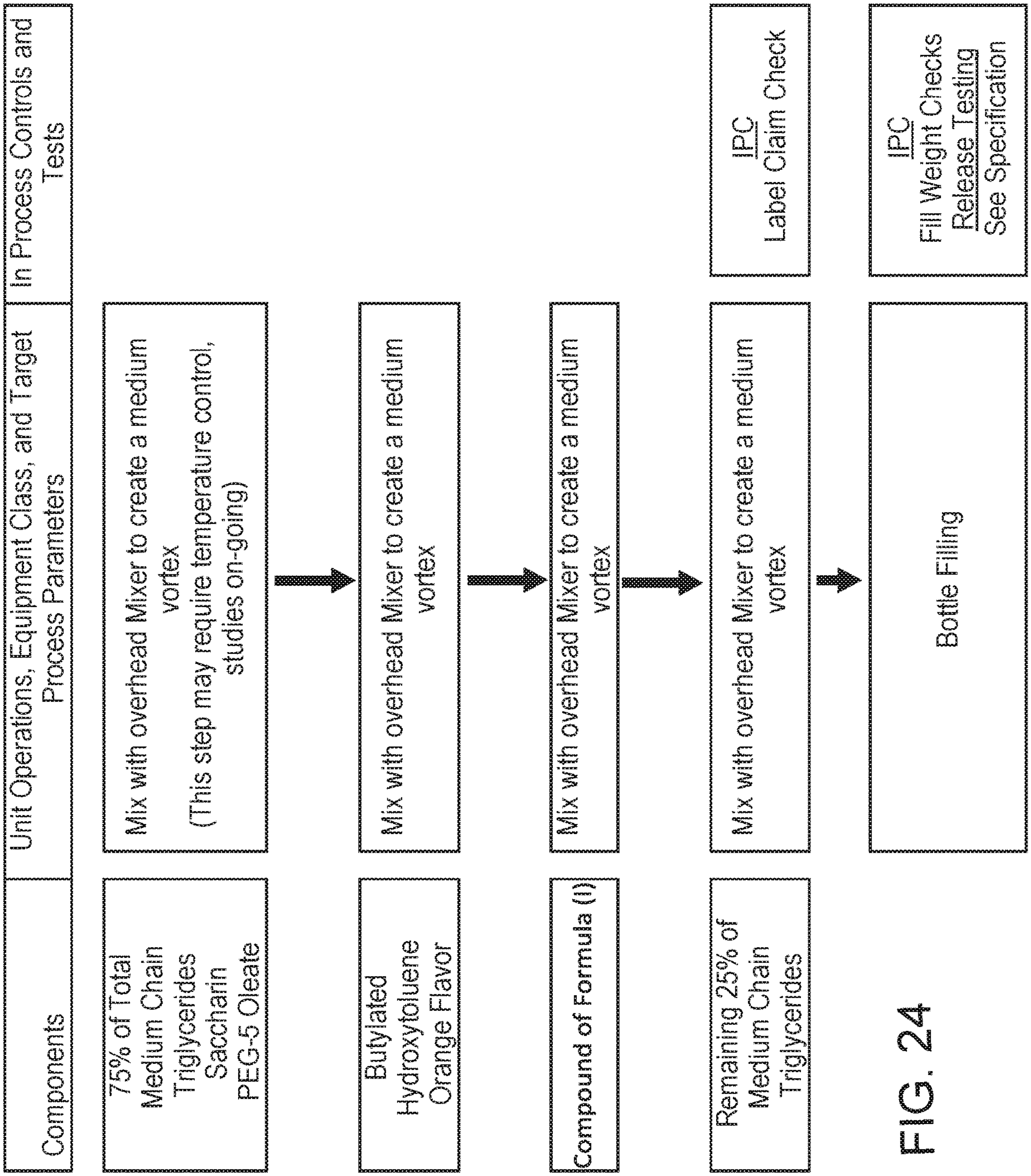
FIG. 24 is a scheme showing the manufacturing process for forming 50 mg/nL liquid formulation 2 of the compound of Formula (I).

Table 39 shows liquid formulation 2 of the Compound of Formula (I) free base. An example manufacturing process is shown in FIG. 24.

TABLE 39

| | | | 50 mg/mL Oral Solution | | Batch |
|---|---|---|---|---|---|
| Component | Quality Standard | Function | Weight (mg/mL) | % (w/v) | Weight (g) |
| Compound of Formula (I) FB | In-house | Drug Substance | 50.0 | 5 | 20.17 |
| Saccharin | NF/EP | Sweetener | 1.5 | 0.15 | 0.61 |
| Butylated hydroxytoluene | NF/EP | Anti-oxidant | 1.7 | 0.17 | 0.68 |

TABLE 39-continued

| Component | Quality Standard | Function | 50 mg/mL Oral Solution Weight (mg/mL) | % (w/v) | Batch Weight (g) |
|---|---|---|---|---|---|
| LABRAFIL M 1944 CS | NF/EP | Surfactant | 200.0 | 20 | 80.16 |
| FONA orange flavor | NF | Flavor | 1.0 | 0.1 | 0.40 |
| LABRAFAC ™ LIPOPHILE WL1349 | NF/EP | Liquid Vehicle | to 1 mL | 74.58 | 278.68 |
| Total | | | 1 mL | 100.0 | 380.7 |

Example 14: A Phase I, Open-Label Study to Evaluate the Pharmacokinetics, Relative Bioavailability, Effect of Food, Safety and Tolerability of Different Compound of Formula (I) Prototype Formulations in Healthy Adult Subjects

Methodology

This is a single center, open-label, randomized, single dose 4-period crossover study in healthy adult subjects designed to investigate the pharmacokinetic (PK) and safety of up to 4 compound of Formula (I) liquid lipidic prototype formulations (compound of Formula (I) Oral Solution, Prototype Formulations, 50 mg/mL), a compound of Formula (I) spray dried dispersion formulation (compound of Formula (I) Granule for Sprinkle, 25-50 mg) and compound of Formula (I), 50 mg Capsules (Reference). It is planned to enroll 36 subjects to be allocated as 3 cohorts of 12 subjects per cohort, with 6 sub-cohorts of 6 subjects per sub-cohort. In each of these 6 sub-cohorts, 6 subjects will be assigned to one of 3 sub-cohorts where a single oral dose of Investigational Medicinal Product (IMP) is administered in 4 dosing periods (Periods 1 to 4) in multiple fed or fasted states or to one of 3 sub-cohorts where a single oral dose of IMP is administered in 2 dosing periods (Periods 1 and 2) only in the fed state. Within each sub-cohort, subjects will also be randomized before administration of the first dose of IMP in Period 1 to one of the following treatment sequences (Table 40):

TABLE 40

| Sub-Cohort | Sequence | Number of Subjects | Total Number of Periods Dosed | Regimen Period 1 | Period 2 | Period 3 | Period 4 |
|---|---|---|---|---|---|---|---|
| 1A | ABEF | 3 | 4 | Regimen A | Regimen B | Regimen E | Regimen F |
| | BAEF | 3 | 4 | Regimen B | Regimen A | Regimen E | Regimen F |
| 1B | AB | 3 | 2 | Regimen A | Regimen B | N/A | N/A |
| | BA | 3 | 2 | Regimen B | Regimen A | N/A | N/A |
| 2A | ADEF | 3 | 4 | Regimen A | Regimen D | Regimen E | Regimen F |
| | DAEF | 3 | 4 | Regimen D | Regimen A | Regimen E | Regimen F |
| 2B | AD | 3 | 2 | Regimen A | Regimen D | N/A | N/A |
| | DA | 3 | 2 | Regimen D | Regimen A | N/A | N/A |
| 3A | ACEF | 3 | 4 | Regimen A | Regimen C | Regimen E | Regimen F |
| | CAEF | 3 | 4 | Regimen C | Regimen A | Regimen E | Regimen F |
| 3B | AC | 3 | 2 | Regimen A | Regimen C | N/A | N/A |
| | CA | 3 | 2 | Regimen C | Regimen A | N/A | N/A |

At informed consent, subjects will agree either to participate in 2 study periods or 4 study periods. Once placed into a sub-cohort, the order in which subjects receive the study treatments will be randomized based on the schedule above.

Subjects will receive up to 4 regimens in up to 4 periods in an order according to the randomization schedule within each sub-cohort.

The effect of different prandial states on the PK of the compound of Formula (I) may be explored in Periods 3 and 4 by administering in the fasted state or after an alternative meal (e.g. high fat, standard or light breakfast, etc.).

The proposed regimens are presented in Table 41 below:

TABLE 41

| Regimen | Investigational Medicinal Product | Dose | Route of Administration | Prandial State |
|---|---|---|---|---|
| A | Compound of Formula (I), 50 mg Capsules (Reference) | 50 mg | Oral | Fed (Ensure Plus) |

TABLE 41-continued

| Regimen | Investigational Medicinal Product | Dose | Route of Administration | Prandial State |
|---|---|---|---|---|
| B | Compound of Formula (I) Oral Solution, Prototype Formulation 1, 50 mg/mL | 50 mg | Oral | Fed (Ensure Plus) |
| C | Compound of Formula (I) Oral Solution, Prototype Formulation 2, 50 mg/mL | 50 mg | Oral | Fed (Ensure Plus) |
| D | Compound of Formula (I) Granule for Sprinkle, 25-50 mg | 50 mg | Oral | Fed (Ensure Plus) |
| E | Compound of Formula (I) Oral Solution, Prototype Formulation 1 | 100 mg | Oral | Fed (Ensure Plus) |
| F | Compound of Formula (I) Oral Solution, Granule for Sprinkle | 50 mg | Oral | Fed (altentative meal) |

Study Design:

Subjects will be screened for eligibility to participate in the study up to 28 days before the first dose of IMP in Period 1. Each study period will follow the same study design. Subjects will be admitted to the clinical unit on the evening prior to IMP administration (Day −1). For Periods 1 and 2 (Regimen A and one of either Regimens B, C or D), all subjects will receive the compound of Formula (I) formulations in the morning according to the randomization schedule in the fed state with a liquid dietary supplement (Ensure Plus). For Periods 3 and 4 (Regimens E and F), subjects will receive the compound of Formula (I) formulations in the morning according to the randomization schedule in the fed state with a liquid dietary supplement or an alternate prandial state (fasted or alternative meal). IMP administration will be performed on Day 1 with an appropriate interval between subjects based on logistical requirements (approximately 10 min). Meals will be standardized for each treatment regimen across periods.

Subjects will remain in the clinical unit until 36 h post-dose when they will be discharged. Subjects will return to the clinical unit at 168 h (7 days) and 336 h (14 days) post-dose for a PK blood sample and safety assessments. The minimum washout between IMP dosing occasions will be 14 days between Periods 1 and 2 and 21 days or more to accommodate interim data reviews between Periods 2 and 3 and between Periods 3 and 4.

There will be a follow-up phone call 18 to 24 days post-final visit to ensure the ongoing wellbeing of subjects.

Following the completion of Period 2 for all cohorts, there will be an interim data review during which the PK and safety data will be reviewed, plus any relevant emerging Chemistry, Manufacturing and Control (CMC) stability study information, to determine the formulation, dose level and prandial state in which to administer the IMP in Period 3 (Regimen E). There will be a similar interim review following completion of Period 3 (administration of Regimen E) to determine the formulation, dose level and prandial state in which to administer the IMP in Period 4 (Regimen F). The criteria for the interim decisions will be based on available compound of Formula (I) PK data: e.g., $C_{max}$, $T_{max}$, AUC(0-36), $F_{rel}$ and safety data.

Number of Subjects Planned:

It is planned to enroll 36 healthy male and female (non-pregnant, non-lactating) subjects in 6 sub-cohorts of 6 subjects per sub-cohort. These sub-cohorts will be combined in sets of 2 to create 3 cohorts of n=12 for Periods 1 and 2 to target data in 10 evaluable subjects in each cohort for the primary objectives per formulation variant. A total of 18 subjects, 6 from each of Sub-Cohorts 1A, 2A and 3A participating in Periods 1 and 2, will additionally participate in Periods 3 and 4 with a target of a minimum of 6 evaluable subjects. A subject will be considered evaluable for a particular regimen if they have received an IMP and has completed sufficient planned PK assessments up to 336 h (14 days) after dosing for that regimen to allow for the assessment of study endpoints. A subject will be considered evaluable for a particular comparison (e.g., food effect, relative bioavailability) if they have received both IMPs under comparison and have sufficient PK data up to 14 days after each regimen to allow for assessment of study endpoints.

Subjects withdrawn due to an IMP-related adverse event (AE) will not be replaced. Subjects who are withdrawn for other reasons may be replaced as required by agreement between the principal investigator (PI) and sponsor to ensure sufficient numbers of evaluable subjects at the end of each study period. Replacement subjects may be required to be dosed with specific formulations from the previous regimens in order to obtain the minimum number of evaluable subjects required for interim decisions and to obtain data in any other regimen that is required to fulfil the study objective comparisons, with the exception that any previously dosed IMP that has been considered sub-optimal will not be dosed. Up to 8 replacement subjects in total may be enrolled into the study. The maximum number of subjects that may be dosed is 44 in total.

If a subject withdraws from Sub-Cohort 1A, 2A or 3A after Period 2, it is acceptable to replace them with a subject from Sub-Cohort 1B, 2B or 3B provided the subject signs an updated consent form agreeing to participate in four treatment periods. At the discretion of the investigator, such a subject may not be required to undergo repeat screening procedures.

Duration of Study:

For subjects enrolled to receive single dose administration on 4 separate occasions in Periods 1 to 4 (Sub-Cohorts 1A, 2A and 3A), the estimated time from screening until the follow-up phone call is approximately 15 to 16 weeks.

For subjects enrolled to receive single dose administration on 2 separate occasions in Periods 1 to 2 only (Sub-Cohorts 1B, 2B and 3B), the estimated time from screening until the follow-up phone call is approximately 8 to 9 weeks.

Pharmacokinetic Assessments:

The plasma concentration data for a compound of Formula (I) will be analyzed for final reporting by Quotient Sciences and for interim reviews by Neurocrine Biosciences, Inc. (NBI), using Phoenix WinNonlin v8.0 or a more recent version (Certara USA, Inc., USA). NBI will be responsible for PK analysis for interim review.

PK analysis of the concentration time data obtained will be performed using appropriate non-compartmental techniques to obtain estimates of the following PK parameters (Table 42) where possible and appropriate:

TABLE 42

| | |
|---|---|
| $T_{lag}$ | Time prior to the first measurable (non-zero) concentration |
| $T_{max}$ | Time to maximum plasma concentration |
| $C_{max}$ | Maximum plasma concentration |
| $AUC_{0-tlast}$ | Area under the plasma concentration versus time curve (AUC) from 0 h to last measurable concentration |
| $AUC_{0-inf}$ | AUC from 0 h extrapolated to infinity |
| $AUC_{extrap}$ | Percentage of $AUC_{0-inf}$ extrapolated beyond the last measurable concentration |
| Lambda-z | Slope of the apparent terminal phase |
| $T_{1/2}$ | Apparent terminal half-life |
| CL/F[a] | Apparent systemic clearance after oral administration |
| Vd/F[a] | Apparent volume of distribution based on the area after a single oral administration |
| MRT | Mean residence time |
| MPR $AUC_{0-tlast}$ | Metabolite to parent ratio based on $AUC_{0-tlast}$ |
| MPR $AUC_{0-inf}$ | Metabolite to parent ratio based on $AUC_{0-inf}$ |

Taste Assessments:

Taste will be assessed for each IMP formulation and vehicle (e.g., Ensure Plus, soft food) using a questionnaire designed for this purpose and adapted for this specific study as required.

The questionnaire will ask subjects to rate the acceptability of smell, sweetness, bitterness, flavor, mouth feel, and aftertaste on a 6-point scale, and overall experience on a 5-point scale for each IMP formulation independently of any previous formulations.

Statistical Methodology:

Descriptive summaries for all safety data, PK assessments and taste questionnaire data will be provided. No hypothesis testing will be performed for the safety or taste questionnaire data.

Periods 1 and 2—for Each Cohort Separately

Relative Bioavailability

Statistical modelling will be performed on the natural log-transformed compound of Formula (I) PK parameters (AUC(0-tlast), AUC(0-inf) and Cmax) to assess relative bioavailability (Frel) using a mixed effects model with terms for regimen, period and sequence as fixed effects and subject within sequence as a random effect. Ratios of geometric means (GMRs) and 90% confidence interval (CI) for the relevant comparison of interest, i.e., between each of the prototype formulations (compound of Formula (I) Oral Solution, Prototype Formulation 1, 50 mg/mL, e.g., Example 12; compound of Formula (I) Oral Solution, Prototype Formulation 2, 50 mg/mL, e.g., Example 13; and compound of Formula (I) Granule for Sprinkle, 25-50 mg, e.g. Example 11 [Regimens B, C and D, respectively]) and compound of Formula (I), 50 mg Capsules, e.g., Example 9 (Reference; Regimen A) will be presented.

All Periods (Periods 1 to 4)

Food Effect

Statistical modelling will be performed on the compound of Formula (I) PK parameters AUC(0-tlast), AUC(0-inf) and Cmax to assess for the effects of food, if relevant. The natural log-transformed PK parameters will be analyzed for bioavailability using a mixed effects model with terms for prandial state (and meal type if applicable) as a fixed effect and subject as a random effect. Ratios of geometric means and 90% CI for the relevant comparisons of interest will be presented where the ratio is defined as fasted/fed or test meal/reference meal (if applicable).

Relative Bioavailability

Statistical modelling will be performed on the natural log-transformed compound of Formula (I) PK parameters (AUC(0-tlast), AUC(0-inf) and Cmax) to assess relative bioavailability using a mixed effects model with terms for regimen as a fixed effect and subject as a random effect. Ratios of geometric means and 90% CI for the relevant comparison of interest i.e., between each of the prototype formulations (Regimens E and F, IMPs to be determined by interim reviews following completion of Periods 2 and 3) and compound of Formula (I), 50 mg Capsules (Reference; Regimen A) will be presented.

Results

Preliminary PK data is summarized in Table 43 below:

TABLE 43

| Preliminary Data from Periods 1 and 2 | | | | |
|---|---|---|---|---|
| | A- Reference | B-Oral Solution 1 | C-Oral Solution 2 | D- SDD Granule |
| N | 35 | 12 | 12 | 12 |
| Tmax* (h) | 5 (2, 6) | 6 (5, 7) | 5 (5, 7) | 5 (5, 7) |
| Cmax (ng/ml) | 1361 (33) | 790 (31) | 1082 (46) | 1075 (35) |
| AUC36 (h*ng/ml) | 9452 (30) | 5556 (34) | 7582 (37) | 6691 (41) |

*Geometric Mean/CV % for AUC and Cmax; Median for Tmax

Example 15. Compound of Formula (I) Crystalline Free Base Form I

Example 15A

Scheme 1: Preparation of 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (Compound of Formula (I), Form I)

Scheme 1

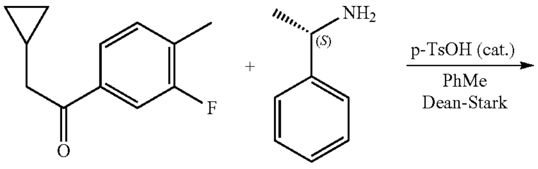

1-A 2-A

-continued

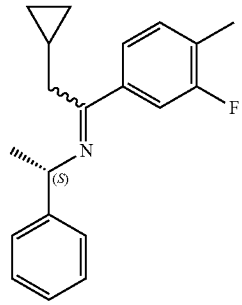

3-A

Sponge ("Raney") Nickel
(70 wt %)
EtOH

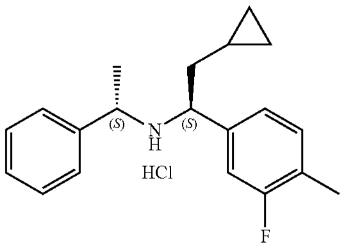

4-A

Pd/C
(10 wt %)
MeOH

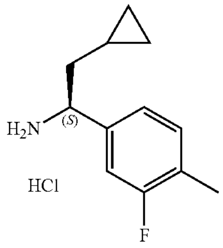

5-A

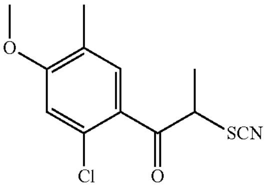

6-A

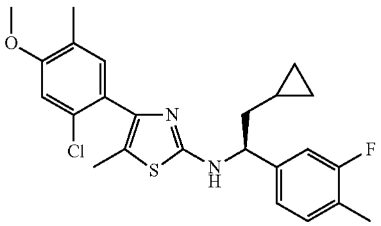

7-A 1. n-$Bu_4NBr$, MTBE
KOH, 5 °C

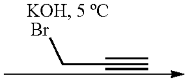

2. EtOH

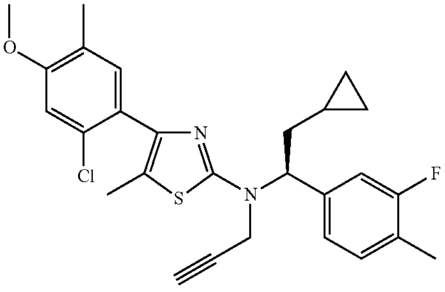

1

Step 1: Preparation of (S)-2-cyclopropyl-1-(3-fluoro-4-methylphenyl)-N-(1-phenylethyl)ethan-1-imine (Compound 3-A)

Compound 3-A

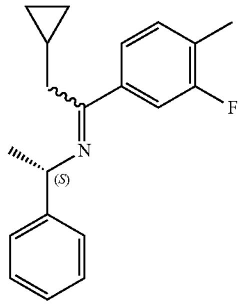

A mixture of 2-cyclopropyl-1-(3-fluoro-4-methylphenyl) ethan-1-one (1-A, 150.7 kg, 1 eq., as a 27.6% w/w solution in toluene, Example 15C), (S)-(−)-1-Phenylethylamine (2-A, 112.9 kg, 1.19 eq.), and p-toluenesulfonic acid (7.4 kg, 0.05 eq.) is refluxed at 110-120° C. for 23-25 h in a reactor set up in a Dean-Stark configuration. The solvent is then removed at 125-135° C. under atmospheric pressure until distillation halts and a portion of toluene (275 kg, 2.24 w/w) is added to afford a suspension. The suspension is refluxed at 110-120° C. for 23-25 h. The mixture is cooled to 22° C. and washed twice with aqueous $NH_4Cl$ (10%, 301.2 kg, 0.72 eq.) and once with aqueous $NaHCO_3$ (5%, 301.2 kg, 0.23 eq., check pH 8-9). The solvent is removed at 125-135° C. and atmospheric pressure to a target volume of 256 L, the mixture is filtered over celite, the cake is washed with toluene (25 kg). The resulting mixture containing compound 3-A is used directly in the next step without isolation. The yield is determined by correcting for the LOD and GC-FID purity of the sample (208.4 kg, 90.0% corrected, 0.89% Compound 2-A). EI-MS: 294.1 $[M-H]^+$, 190.1 $[M-C_6H_5CH(CH_3)]^+$, 105.1 $[C_6H_5CH(CH_3)]^+$.

Step 2: Preparation of (S)-2-cyclopropyl-1-(3-fluoro-4-methylphenyl)-N-((S)-1-phenylethyl)ethan-1-amine hydrochloride (Compound 4-A)

Compound 4-A

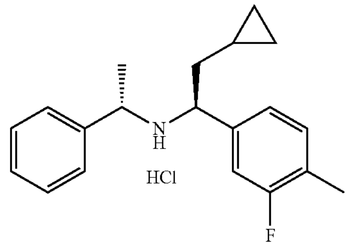

Sponge nickel catalyst (144 kg, 0.70 w/w, shipped as a 50% w/w suspension in water) is added to a hydrogenation reactor, equipped with a dip tube capable of removing material from the top of the mass inside, minimizing the amount of water introduced. The supernatant is discarded, ethanol (329.3 kg, 1.58 w/w, anhydrous) is added, the suspension is stirred and then allowed to settle. This process is repeated four more times and the Karl Fisher (KF) of the supernatant is checked (≤1% $H_2O$ w/w). Compound 3-A (208.4 kg, 1 eq., as a 62.6% solution in toluene) is added to the mixture in the hydrogenation reactor and ethanol (387.6 kg, 1.86 w/w) is used to rinse the addition flask into the hydrogenation reactor. The hydrogenation reactor is pressurized/depressurized twice with nitrogen (2 bar) and twice with hydrogen (5 bar) then pressurized with hydrogen (9.8-10.2 bar) and heated to 33-37° C. and stirred for 17-19 h. The system is depressurized/pressurized three times with nitrogen (1 bar) and the suspension is filtered and washed with three times with ethanol (493.8 kg, 2.37 w/w). HCl (concentrated, 83.4 kg, 1.07 eq.) is added and the mixture stirred 25-35 min at 20-24° C. The mixture is concentrated by distillation at 78-80° C. and atmospheric pressure to remove water with a distillate target volume of 1167 L (5.6 L/kg, Compound 3-A) and the KF of the solution is checked (<1.5% $H_2O$ w/w). The mixture is stirred at 48-52° C. for 55-65 min, then 68-72° C. for 55-65 min, then cooled to 20-24° C. at a rate of 12° C./h and stirred for 25-35 min, then cooled to 0-4° C. at a rate of 10° C./h and stirred for 55-65 min. The suspension is filtered, the cake is washed twice with precooled ethanol (329.2 kg, 1.58 w/w, 0° C.), and the collected solid is dried at 40° C. to afford compound 4-A (156.5 kg, 66.4% uncorrected). $^{1}$H NMR (400 MHz, DMSO-d6) δ ppm-0.33-0.06 (m, 2H) 0.11-0.31 (m, 3H) 1.57 (d, J=6.57 Hz, 3H) 1.95 (br t, J=7.07 Hz, 2H) 2.26 (d, J=1.26 Hz, 3H) 3.68 (br d, J=7.83 Hz, 1H) 3.92 (br t, J=6.44 Hz, 1H) 6.98 (dd, J=7.71, 1.14 Hz, 1H) 7.28-7.36 (m, 2H) 7.37-7.50 (m, 5H). ESI-MS: 298.2 m/z $[M+H]^+$.

Step 3: Preparation of (S)-2-cyclopropyl-1-(3-fluoro-4-methylphenyl)ethan-1-amine hydrochloride (Compound 5-A)

Compound 5-A

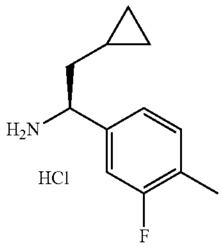

Compound 4-A (156.5 kg, 1.00 eq.) and Pd/C (7.8 kg, 10% Pd basis) are added to an inerted hydrogenation reactor. The reactor is then pressurized/depressurized twice with nitrogen (2 bar) and then methanol (494.5 kg, 3.16 w/w) is added. The reactor is depressurized/pressurized three times with nitrogen (2 bar) then three times with hydrogen (5 bar), pressurized with hydrogen (9.8-10.2 bar), heated to 58-62° C. and stirred for 7-9 h. The reaction mixture is cooled to 20-24° C. The reactor is depressurized/pressurized three times with nitrogen (1 bar) and the suspension is filtered and washed three times with methanol (492.9 kg, 3.15 w/w). The solution is concentrated at 63-67° C. and atmospheric pressure to a distillate target volume of 1408 L (9.0 L/kg Compound 4-A). n-Heptane (1173.8 kg, 7.5 w/w) is added and the mixture is refluxed at 65-80° C. and atmospheric pressure in Dean-Stark configuration to remove methanol. The suspension is cooled to 31-35° C. and filtered, the cake washed with n-heptane (147.1 kg, 0.94 w/w), and the solid dried at 40° C. (101.0 kg, 93.8% uncorrected, 99.2% ee). $^{1}$H NMR (400 MHz, DMSO-d6) δ ppm-0.12-0.14 (m, 2H) 0.26-0.42 (m, 2H) 0.44-0.55 (m, 1H) 1.70-1.83 (m, 2H) 2.23 (d, J=1.52 Hz, 3H) 4.24 (t, J=7.33 Hz, 1H) 7.22-7.29 (m, 1H) 7.29-7.36 (m, 1H) 7.40 (dd, J=10.99, 1.39 Hz, 1H). ESI-MS: 194.2 $[M+H]^+$, 177.0 $[M-NH_2]^+$.

Step 4: Preparation of (S)-4-(2-chloro-4-methoxy-5-methylphenyl)-N-(2-cyclopropyl-1-(3-fluoro-4-methylphenyl)ethyl)-5-methylthiazol-2-amine (Compound 7-A)

Compound 7-A

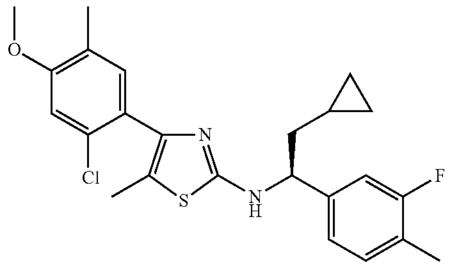

A mixture of n-heptane (146 kg), water (142 kg), Compound 5-A (57.4 kg), and aqueous sodium hydroxide (30% w/w, 41.0 kg) was stirred together. The layers were partitioned, and the aqueous layer removed. The organic layer was washed with water (170 kg) and the layers partitioned. The organic layer was set aside using n-heptane (40 kg) to rinse and n-heptane (145 kg) and 1-(2-chloro-4-methoxy-5-methylphenyl)-2-thiocyanatopropan-1-one (6-A, 66.1 kg) were added to the reactor and heated to 85° C. The previously set aside organic layer containing the free base of Compound 5-A was added at 84-85° C. to the reactor and rinsed with n-heptane (20 kg). The resulting mixture was stirred for 2 h at 83° C. Subsequently, the solvent was switched to methanol by four put-and-take additions/vacuum distillations of methanol (180 kg) at 55° C. with the target volume being 287 L remaining in the reactor. The suspension was cooled to 5° C. and water (570 kg) was added over 4 h at 5-10° C., with the first 60 kg added very slowly. The suspension was aged 2 h at ° C. and then isolated by filtration and washed with a mixture of methanol/water (91/115 kg) and then a mixture of methanol/water (134/57 kg). The yellow solid was dried at 25° C. and 1 mbar for 17 h then 40° C. and 1 mbar for 22 h to afford Compound 7-A (97.4 kg, 87.5% yield). $^{1}$H NMR (400 MHz, DMSO-d6) δ ppm-0.01-0.14 (m, 2H) 0.29-0.42 (m, 2H) 0.61-0.73 (m, 1H) 1.47 (dt, J=13.83, 6.85 Hz, 1H) 1.76 (dt, J=13.89, 7.20 Hz, 1H) 2.00 (s, 3H) 2.11 (s, 3H) 2.19 (d, J=1.01 Hz, 3H) 3.82 (s, 3H) 4.54 (q, J=7.58 Hz, 1H) 7.00 (s, 1H) 7.06 (d, J=0.76 Hz, 1H) 7.08-7.14 (m, 2H) 7.18-7.23 (m, 1H) 7.89 (d, J=8.08 Hz, 1H). ESI-MS: 445.3 m/z [M+H]+.

Step 5: Preparation of 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (Compound of Formula (I))

Compound of Formula (I)

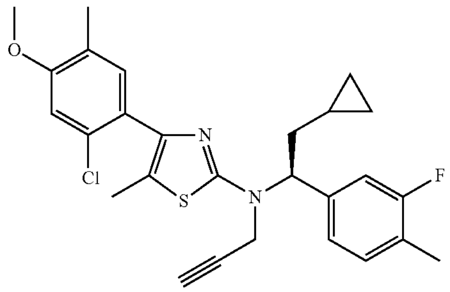

A mixture of methyl tert-butyl ether (MTBE) (279 kg), tetra-n-butylammonium bromide (10.5 kg), and Compound 7-A (95.4 kg) were heated at 60° C. external temperature for 30 min and then cooled to 0° C. Aqueous potassium hydroxide (52.4% w/w, 364 kg) and propargyl bromide (39.4 kg as an 80% w/w solution in toluene, 1.19 eq.) were added at 0-5° C. and the biphasic mixture aged 14.5 h at 4-6° C. with vigorous stirring. Subsequently, water (191 kg) was added and the aqueous layer was discharged. The organic layer was washed twice with water (382 kg) and once with aqueous acetic acid (5.26% w/w, 190 kg) at 20° C. The mixture is polish filtered, rinsed with ethanol (11 kg) and then the solvent switched to ethanol by 3 put-and-take additions/vacuum distillations of ethanol (300 kg) at 25-30° C. for the first cycle and then 35-40° C. with the target volume of each cycle being 250 L remaining in the reactor. Ethanol (164 kg) was added and the mixture heated at 60° C. external for 0.5 h before it was cooled to 25° C. in 1 h and seeded with authentic compound of Formula (I) (0.340 kg) which may be prepared as described below in Example 15B. The suspension was aged for 5 h, cooled to 0° C. in 2 h, aged 12 h, filtered, and washed twice with ethanol (24 kg each) pre-cooled to 0° C. The white solid was dried at 40° C. and 1 mbar for 19 h to yield 80.15 kg of the compound of Formula (I), Form I (77.2% yield). $^1$H NMR (400 MHz, DMSO-d6) δ ppm 0.14 (qt, J=8.59, 4.42 Hz, 2H) 0.29-0.48 (m, 2H) 0.61-0.82 (m, 1H) 1.89 (dt, J=14.08, 6.98 Hz, 1H), 2.07 (br d, J=7.83 Hz, 1H) 2.10 (s, 3H) 2.14 (s, 3H) 2.20 (d, J=1.01 Hz, 3H) 3.11 (t, J=2.27 Hz, 1H) 3.83 (s, 3H) 3.94-4.22 (m, 2H) 5.26 (t, J=7.58 Hz, 1H) 7.05 (s, 1H) 7.10-7.36 (m, 4H). ESI-MS: 483.2 m/z $[M+H]^+$.

Figure 25:
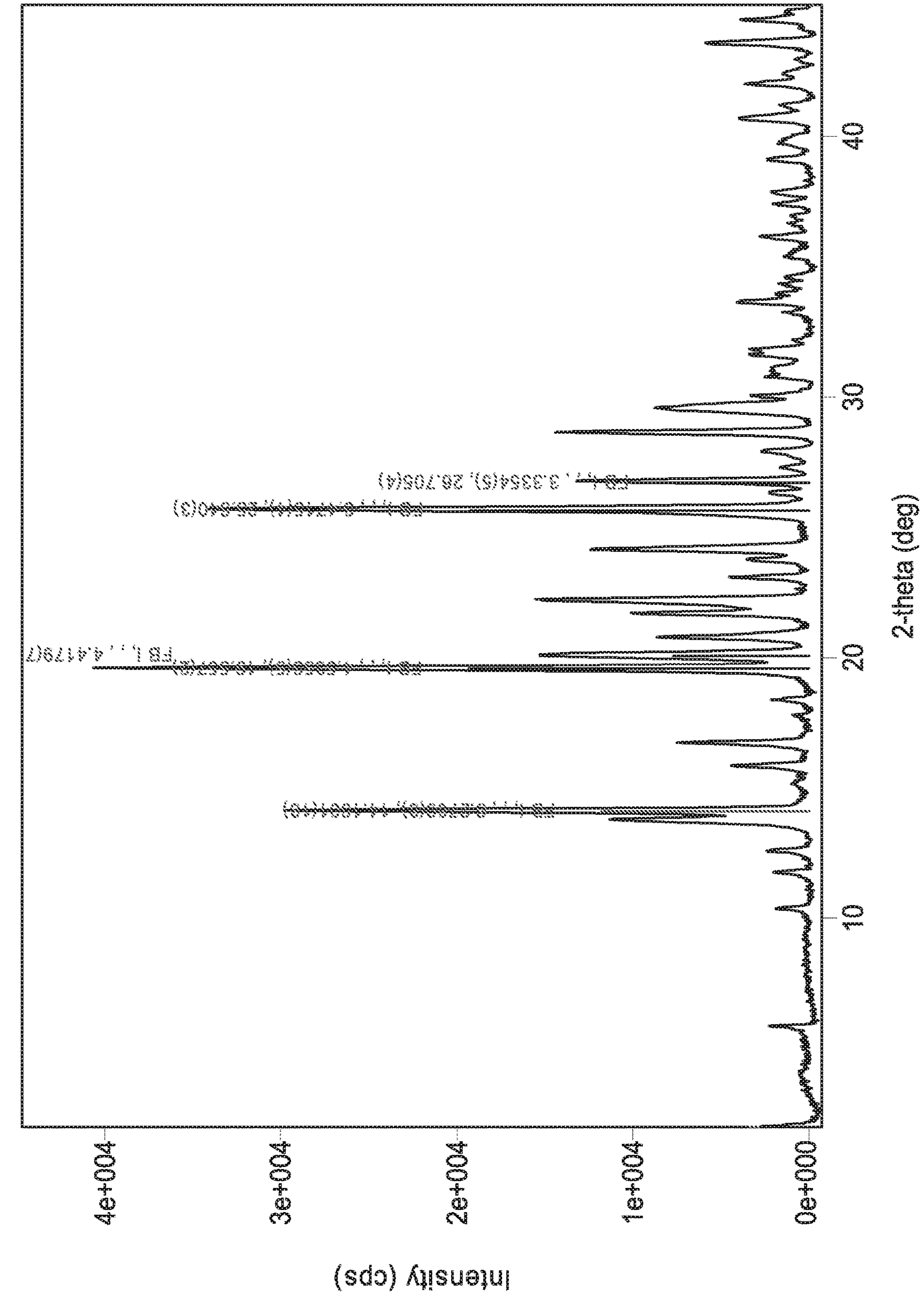
FIG. 25 is an XRPD spectrum of the compound of Formula (I) free base crystalline form I.
Figure 26:
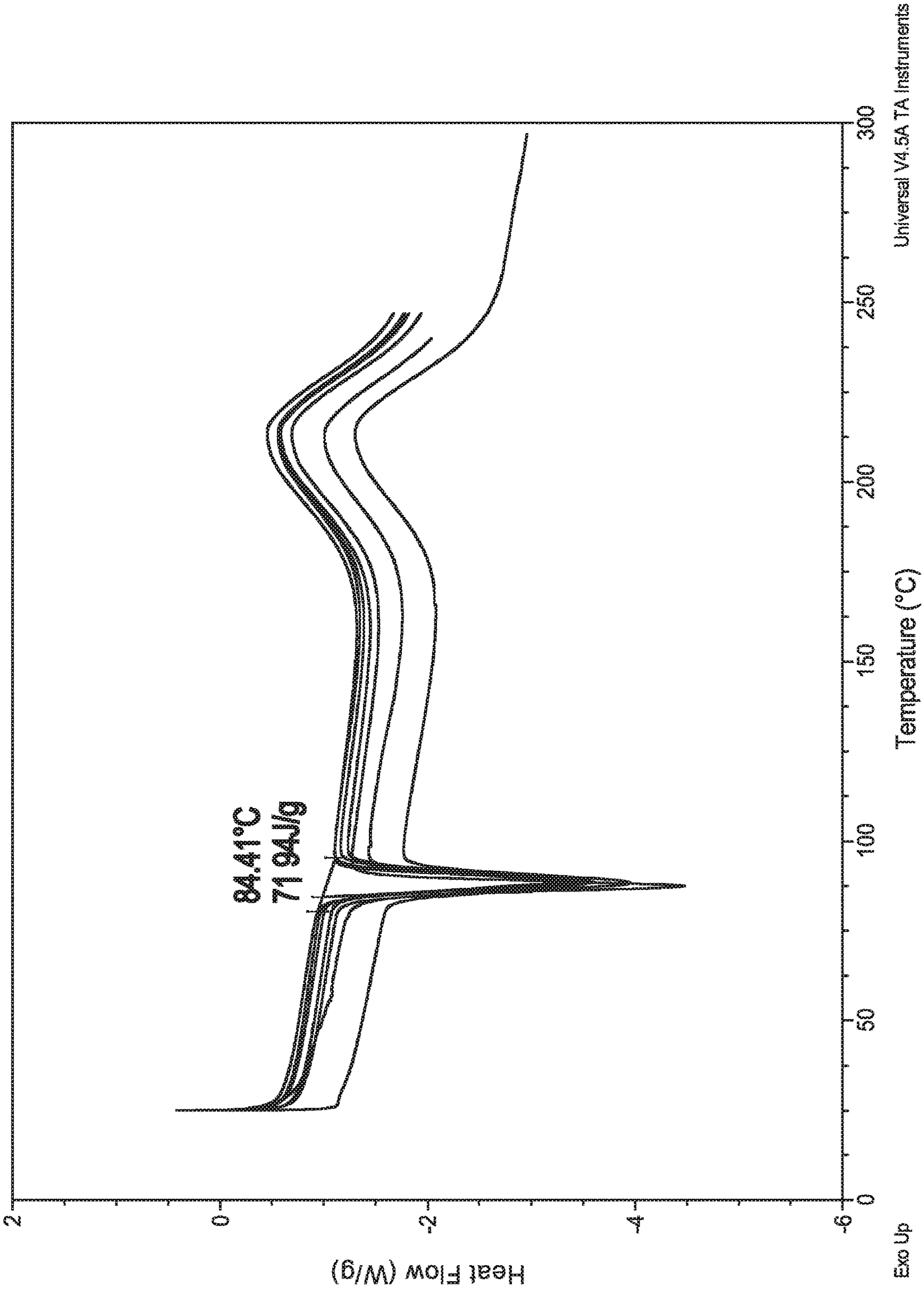
FIG. 26 is a differential scanning calorimetry (DSC) spectrum of the compound of Formula (I) free base crystalline form I.

The crystallinity of the crystalline free base Compound of Formula (I), Form I was confirmed by XRPD (FIG. 25, Table 44) and further supported by DSC (FIG. 26), indicating the crystalline compound having an onset of melt at about 84.4° C. (71.9 J/g). TGA of the crystalline free base exhibited about 0.6% of weight loss due to solvent/$H_2O$.

TABLE 44

XRPD Peak Data for the Compound of Formula (I) Crystalline Free Base Form I

| 2-Theta (°) | Height (cps) |
|---|---|
| 5.901(15) | 1221(101) |
| 10.367(11) | 1280(103) |
| 11.762(13) | 1377(107) |
| 12.582(11) | 1591(115) |
| 13.802(2) | 7326(247) |
| 14.1541(16) | 20179(410) |
| 15.173(14) | 449(61) |
| 15.854(7) | 2906(156) |
| 16.746(5) | 5113(206) |
| 18.366(7) | 1171(99) |
| 19.586(2) | 27789(481) |
| 20.100(4) | 10759(299) |
| 20.794(4) | 5441(213) |
| 21.730(5) | 7125(244) |
| 22.239(7) | 10370(294) |
| 23.056(11) | 3482(170) |
| 23.714(7) | 2300(138) |
| 24.115(7) | 8402(265) |
| 25.666(4) | 26173(467) |
| 26.296(6) | 1505(112) |
| 26.752(4) | 9919(288) |
| 27.264(7) | 1016(92) |
| 27.874(7) | 2092(132) |
| 28.623(3) | 10560(297) |
| 29.546(6) | 5811(220) |
| 30.025(3) | 2248(137) |
| 30.737(10) | 1333(105) |

TABLE 44-continued

XRPD Peak Data for the Compound of Formula (I) Crystalline Free Base Form I

| 2-Theta (°) | Height (cps) |
|---|---|
| 31.017(19) | 1406(108) |
| 31.588(10) | 2292(138) |
| 31.809(8) | 2212(136) |
| 32.126(13) | 593(70) |
| 33.200(16) | 839(84) |
| 33.613(13) | 2996(158) |
| 33.914(13) | 1156(98) |
| 34.276(16) | 1008(92) |
| 34.564(12) | 1056(94) |
| 35.397(18) | 816(82) |
| 36.073(10) | 1928(127) |
| 36.67(3) | 562(68) |
| 37.347(9) | 1553(114) |
| 37.776(12) | 1573(114) |
| 39.070(7) | 1890(125) |
| 39.743(15) | 1042(93) |
| 40.643(9) | 2808(153) |
| 41.106(8) | 1107(96) |
| 41.984(11) | 2686(150) |
| 42.376(16) | 986(91) |
| 42.901(16) | 492(64) |
| 43.543(10) | 4744(199) |
| 44.419(16) | 2810(153) |

Example 15B

Preparation of 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (Compound of Formula (I), seed batch)

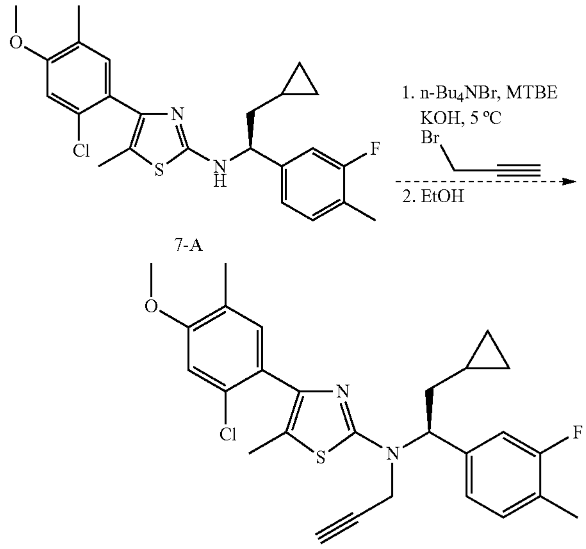

7-A

1

A mixture of MTBE, tetra-n-butylammonium bromide, and Compound 7-A cooled to 0° C. is treated with aqueous potassium hydroxide and propargyl bromide maintaining the temperature at 0-5° C. The resulting biphasic mixture is aged 23 h at 4-6° C. Subsequently, water and MTBE are added and the aqueous layer is discharged. The organic layer is washed twice with water and once with aqueous acetic acid at 20° C. Ethanol is added and then the solvent switched to ethanol by 3 put-and-take additions/vacuum distillations of ethanol at 35-40° C. with a target volume of each cycle remaining in the vessel, except for the third cycle where the mixture is concentrated to dryness. Ethanol is added to the vessel and the mixture heated at 60° C. external for 0.5 h before it is cooled to 20° C. in 1 h and aged 18 h affording a suspension. The suspension is cooled to 0° C., aged 6 h, filtered, and washed twice with ethanol pre-cooled to 0° C. to afford a solid. The solid is dried at 40° C. under vacuum to afford the compound of Formula (I).

Example 15C

Scheme 2: Preparation of 2-cyclopropyl-1-(3-fluoro-4-methylphenyl)ethan-1-one (Compound 1-A)

Scheme 2

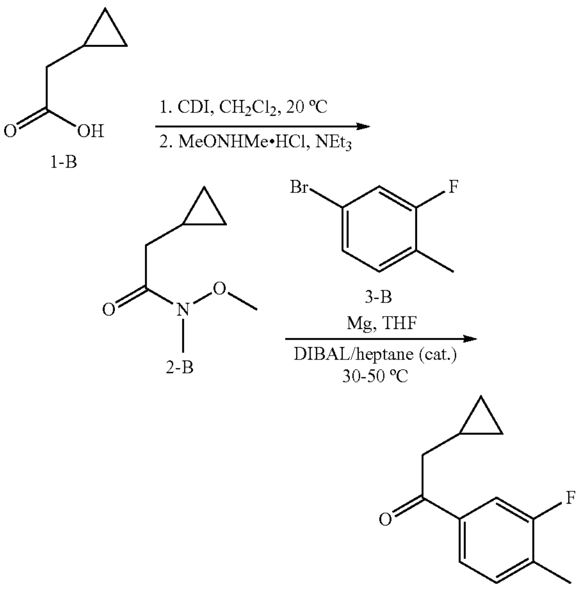

1-B
2-B
3-B
1-A

Step 1: Preparation of 2-cyclopropyl-N-methoxy-N-methylacetamide (Compound 2-B)

Compound 2-B

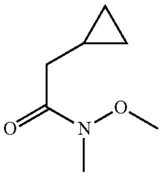

A suspension of 1,1'-Carbonyldiimidazole (152.6 kg, 1.01 eq.) in DCM (682 kg, 513 L, 7.3 w/w relative to 2-cyclopropylacetic acid) was treated with a solution of 2-cyclopropylacetic acid (1-B, 93.6 kg, 1 eq.) in DCM (248 kg, 186 L, 2.65 w/w) over at least 1 h, keeping the temperature <25° C. and compensating for significant effervescence. The resulting mixture is stirred for 15 min at 22° C. and then N,O-dimethylhydroxylamine·HCl (93.3 kg, 1.03 eq.) is added in portions, keeping the temperature <30° C. Subsequently, triethylamine (46.4 kg, 0.49 eq.) is added to the stirring mixture at 20-25° C. The resulting mixture is stirred at 22° C. at least 1 h. The mixture is washed once with $KHSO_4$ solution (0.24 M, 357.1 kg, 0.09 eq.), once with $KHSO_4$ solution (0.40 M, 365.4 kg, 0.15 eq.), once with $KHSO_4$ solution (0.80 M, 384.5 kg, 0.30 eq.), and once with $NaHCO_3$ solution (0.60 M, 393.1 kg, 0.24 eq.). Residual DCM is removed by three put-and-takes of THF (166.6 kg, 1.78 w/w) and vacuum distillation (50-60° C., to minimum volume/until distillation stops). THE (333.2 kg. 3.56 w/w) is added and the yield is determined by correcting for the LOD and GC-FID purity of the sample (131.5 kg, 98.2% corrected). $^1$H-NMR (400 MHz, DMSO-d6) δ: −0.01-0.03 (m, 2H) 0.32-0.36 (m, 2H) 0.81-0.90 (br m, 1H) 2.18 (d, J=6.80 Hz, 2H) 2.97 (s, 3H) 3.53 (s, 3H). ESI-MS: 144.0 [M+H]$^+$.

Step 2: Preparation of 2-cyclopropyl-1-(3-fluoro-4-methylphenyl)ethan-1-one (Compound 1-A)

Compound 1-A

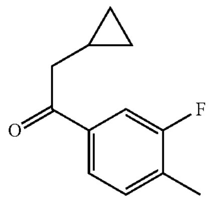

Mg (turnings, 28.6 kg, 1.37 eq.) are suspended in THE (244.7 kg, 2.0 w/w) and DIBAL-H (1 M in n-heptane, 18.9 kg, 0.03 eq.) is added dropwise at 30° C., The resulting mixture is stirred at 30° C. for at least 10 min and then 4-bromo-2-fluoro-1-methylbenzene (3-B, neat, 21.1 kg, 0.13 eq.) is added over at least 30 min at 30-50° C. Subsequently, the mixture is treated with a solution of 4-bromo-2-fluoro-1-methylbenzene (3-B, 191.6 kg, 1.18 eq.) in THE (414.5 kg, 3.37 w/w) at 30-50° C. over 3 h or less. The mixture is stirred at 30° C. for at least 1 h. Subsequently, the mixture is treated with 2-cyclopropyl-N-methoxy-N-methylacetamide (2-B, 123.0 kg, 1 eq., 25.9% w/w solution in THF) over at least 1 h at 15-25° C. The resulting mixture is stirred at 20-25° C. for at least 1 h. The stirring mixture is then treated with aqueous HCl (3 M, 10.3% w/w, 668.9 kg, 2.24 eq.) at 10-25° C. and the resulting mixture is stirred at least 2 h (check pH 3.0-3.5). The layers are separated, and the aqueous layer is combined with heptane (290.3 kg, 2.36 w/w). The layers are separated, and the organic layer is washed once with $NaHCO_3$ solution (0.63 M, 211.6 kg, 0.15 eq.) and once with NaCl solution (2.57 M, 213.0 kg, 0.55 eq.). The residual solvents are removed by vacuum distillation at 58-62° C. until distillation stops and then one put-and-take of toluene (275.5 kg, 2.24 w/w) at 107-117° C. until distillation stops. Toluene (275.5 kg, 2.24 w/w) is added and the yield is determined by correcting for the LOD and GC-FID purity of the sample (150.7 kg, 91.3% corrected). $^1$H NMR (400 MHz, DMSO-d6) δ ppm 0.07-0.21 (m, 2H) 0.40-0.54 (m, 2H) 1.02 (ttt, J=8.16, 8.16, 6.68, 6.68, 4.86, 4.86 Hz, 1H) 2.30 (d, J=1.77 Hz, 3H) 2.91 (d, J=6.57 Hz, 2H) 7.44 (t, J=7.83 Hz, 1H) 7.57-7.78 (m, 2H). ESI-MS: 193.1 [M+H]$^+$.

Example 16: Compound of Formula (I) Crystalline Tosylate Salt Form 1

Approximately 20 mg of the Compound of Formula (I) was weighed into a vial. Using a positive displacement pipette, 250 μL of solvent (IPA) was added to the vial along with a stir bar. The vial was placed in an aluminum block on a Reacti-Therm mixer and heated to 60° C. for ~1 hour. A molar equivalent of para-toluenesulfonic acid was added to the vial (20 μL of a 2M solution in water) and allowed to stir. The sample was slow cooled back to room temperature along with mild Nitrogen gas for evaporation. Precipitate was collected, left to dry overnight, and then analyzed by XRPD, DSC, and TGA.

The crystallinity of the crystalline tosylate form 1 was confirmed by XRPD (FIG. 27, Table 45) and further supported by DSC (FIG. 28), indicating the crystalline compound having an onset of melt at about 156° C. (22.2 Jlg). TGA of the crystalline compound is provided in FIG. 28, and exhibited about 0.500 of weight loss due to solvent/$H_2O$.

TABLE 45

XRPD Peak Data for the Compound of Formula (I) Crystalline Tosylate Form 1

| 2-Theta (°) | Height (cps) |
|---|---|
| 8.112(9) | 957(89) |
| 9.124(2) | 12296(320) |
| 9.471(2) | 4519(194) |
| 10.525(3) | 8507(266) |
| 11.316(3) | 10211(292) |
| 13.182(5) | 6158(227) |
| 13.494(6) | 1598(115) |
| 14.249(9) | 2197(135) |
| 15.208(9) | 1746(121) |
| 15.711(7) | 1437(109) |
| 16.252(5) | 5723(218) |
| 16.692(3) | 3848(179) |
| 17.540(4) | 1578(115) |
| 19.031(6) | 6774(238) |
| 19.265(4) | 6491(233) |
| 19.499(10) | 3152(162) |
| 20.401(3) | 8581(267) |
| 20.656(4) | 3040(159) |
| 21.142(3) | 11498(310) |
| 21.703(6) | 4979(204) |
| 21.870(11) | 5331(211) |
| 22.277(5) | 3701(176) |
| 22.769(3) | 10159(291) |
| 23.297(3) | 14954(353) |
| 23.532(4) | 3597(173) |
| 23.810(3) | 9590(283) |
| 24.73(2) | 2325(139) |
| 25.47(4) | 1704(119) |
| 26.087(5) | 2413(142) |
| 26.71(3) | 422(59) |
| 27.210(6) | 1648(117) |
| 27.593(5) | 2825(153) |
| 28.472(4) | 6417(231) |
| 29.51(3) | 1423(109) |
| 29.98(3) | 849(84) |
| 30.63(6) | 1262(103) |
| 30.77(3) | 1121(97) |
| 31.577(3) | 5563(215) |
| 32.74(4) | 874(85) |
| 33.73(4) | 1111(96) |
| 34.415(13) | 2054(131) |
| 34.799(11) | 706(77) |
| 35.139(15) | 1320(105) |
| 35.682(16) | 1028(93) |
| 38.39(4) | 751(79) |
| 39.743(17) | 1790(122) |
| 40.219(16) | 762(80) |
| 41.23(3) | 925(88) |
| 43.16(3) | 1540(113) |
| 44.288(12) | 1142(98) |

OTHER EMBODIMENTS

It is to be understood that the foregoing description is intended to illustrate and not limit the scope of the disclosure, which is defined by the scope of the appended claims. Other aspects, advantages, and modifications are within the scope of the following claims.

What is claimed is:

1. A pharmaceutical composition comprising:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (compound of Formula (I)):

(I)

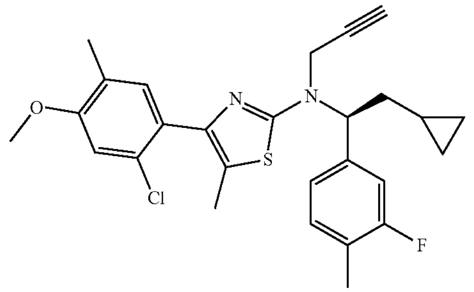

or a pharmaceutically acceptable salt thereof; and (b) an oily phase vehicle which is medium-chain triglycerides;

(c) a nonionic surfactant selected from the group consisting of oleoyl polyoxyl-6 glycerides, linoleoyl polyoxyl-6 glycerides, polysorbate 80, polysorbate 20, lauroyl polyoxyl-32 glycerides, poloxamer, PEG-32 stearate, and PEG-32 hydrogenated palm glycerides;

(d) an emulsifying agent which is propylene glycol dicaprylate/dicaprate; and (e) a solubilizing agent which is vitamin E polyethylene glycol succinate.

2. The pharmaceutical composition of claim 1, wherein the compound of Formula (I), or a pharmaceutically acceptable salt thereof, is the free base.

3. The pharmaceutical composition of claim 1, comprising from 5 wt % to 15 wt % of the compound of Formula (I), or a pharmaceutically acceptable salt thereof, based on the weight of the free base.

4. The pharmaceutical composition of claim 3, wherein the compound of Formula (I), or a pharmaceutically acceptable salt thereof, is the free base.

5. The pharmaceutical composition of claim 1, comprising about 10 wt % of the compound of Formula (I), or a pharmaceutically acceptable salt thereof, based on the weight of the free base.

6. The pharmaceutical composition of claim 5, wherein the compound of Formula (I), or a pharmaceutically acceptable salt thereof, is the free base.

7. The pharmaceutical composition of claim 1, comprising from 35 wt % to 45 wt % of the oily phase vehicle.

8. The pharmaceutical composition of claim 7, wherein the compound of Formula (I), or a pharmaceutically acceptable salt thereof, is the free base.

9. The pharmaceutical composition of claim 1, comprising about 39 wt % of the oily phase vehicle.

10. The pharmaceutical composition of claim 9, wherein the compound of Formula (I), or a pharmaceutically acceptable salt thereof, is the free base.

11. The pharmaceutical composition of claim 1, comprising from 15 wt % to 25 wt % of the emulsifying agent.

12. The pharmaceutical composition of claim 11, wherein the compound of Formula (I), or a pharmaceutically acceptable salt thereof, is the free base.

13. The pharmaceutical composition of claim 1, comprising about 20 wt % of the emulsifying agent.

14. The pharmaceutical composition of claim 13, wherein the compound of Formula (I), or a pharmaceutically acceptable salt thereof, is the free base.

15. The pharmaceutical composition of claim 1, comprising from 15 wt % to 25 wt % of the nonionic surfactant.

16. The pharmaceutical composition of claim 15, wherein the compound of Formula (I), or a pharmaceutically acceptable salt thereof, is the free base.

17. The pharmaceutical composition of claim 1, comprising about 19 wt % of the nonionic surfactant.

18. The pharmaceutical composition of claim 17, wherein the compound of Formula (I), or a pharmaceutically acceptable salt thereof, is the free base.

19. The pharmaceutical composition of claim 1, wherein the nonionic surfactant is lauroyl polyoxyl-32 glycerides.

20. The pharmaceutical composition of claim 19, wherein the compound of Formula (I), or a pharmaceutically acceptable salt thereof, is the free base.

21. The pharmaceutical composition of claim 1, comprising from 5 wt % to 15 wt % of the solubilizing agent.

22. The pharmaceutical composition of claim 21, wherein the compound of Formula (I), or a pharmaceutically acceptable salt thereof, is the free base.

23. The pharmaceutical composition of claim 1, comprising about 11 wt % of the solubilizing agent.

24. The pharmaceutical composition of claim 23, wherein the compound of Formula (I), or a pharmaceutically acceptable salt thereof, is the free base.

25. The pharmaceutical composition of claim 1, comprising:

(a) from 1 wt % to 20 wt % of the compound of Formula (I), or a pharmaceutically acceptable salt thereof, based on the weight of the free base;
(b) from 20 wt % to 50 wt % of the oily phase vehicle;
(c) from 15 wt % to 25 wt % of the nonionic surfactant;
(d) from 15 wt % to 25 wt % of the emulsifying agent; and
(e) from 5 wt % to 15 wt % of the solubilizing agent.

26. The pharmaceutical composition of claim 25, wherein the compound of Formula (I), or a pharmaceutically acceptable salt thereof, is the free base.

27. The pharmaceutical composition of claim 1, comprising:

(a) from 5 wt % to 15 wt % of the compound of Formula (I), or a pharmaceutically acceptable salt thereof, based on the weight of the free base;
(b) from 35 wt % to 45 wt % of the oily phase vehicle;
(c) from 15 wt % to 25 wt % of the nonionic surfactant;
(d) from 15 wt % to 25 wt % of the emulsifying agent; and
(e) from 5 wt % to 15 wt % of the solubilizing agent.

28. The pharmaceutical composition of claim 27, wherein the compound of Formula (I), or a pharmaceutically acceptable salt thereof, is the free base.

29. The pharmaceutical composition of claim 1, comprising:

(a) about 10 wt % of the compound of Formula (I), or a pharmaceutically acceptable salt thereof, based on the weight of the free base;
(b) about 39 wt % of the oily phase vehicle;
(c) about 19 wt % of the nonionic surfactant;
(d) about 20 wt % of the emulsifying agent; and
(e) about 11 wt % of the solubilizing agent.

30. The pharmaceutical composition of claim 29, wherein the compound of Formula (I), or a pharmaceutically acceptable salt thereof, is the free base.

31. The pharmaceutical composition of claim 1, comprising:

(a) 10 wt % of the compound of Formula (I), or a pharmaceutically acceptable salt thereof, based on the weight of the free base;
(b) 39.2 wt % of the oily phase vehicle;
(c) 19.0 wt % of a nonionic surfactant;
(d) 20.4 wt % of the emulsifying agent; and
(e) 11.4 wt % of the solubilizing agent.

32. The pharmaceutical composition of claim 1, formulated in a unit dosage form, wherein the compound of Formula (I), or a pharmaceutically acceptable salt thereof, is present in an amount of from 5 mg to 200 mg, based on the weight of the free base.

33. The pharmaceutical composition of claim 32, wherein the compound of Formula (I), or a pharmaceutically acceptable salt thereof, is the free base.

34. The pharmaceutical composition of claim 32, wherein the compound of Formula (I), or a pharmaceutically acceptable salt thereof, is present in an amount of about 100 mg, based on the weight of the free base.

35. The pharmaceutical composition of claim 34, wherein the compound of Formula (I), or a pharmaceutically acceptable salt thereof, is the free base.

36. The pharmaceutical composition of claim 32, wherein the compound of Formula (I), or a pharmaceutically acceptable salt thereof, is present in an amount of about 50 mg, based on the weight of the free base.

37. The pharmaceutical composition of claim 36, wherein the compound of Formula (I), or a pharmaceutically acceptable salt thereof, is the free base.

38. The pharmaceutical composition of claim 32, wherein the compound of Formula (I), or a pharmaceutically acceptable salt thereof, is present in an amount of about 25 mg, based on the weight of the free base.

39. The pharmaceutical composition of claim 38, wherein the compound of Formula (I), or a pharmaceutically acceptable salt thereof, is the free base.

40. The pharmaceutical composition of claim 32, wherein the pharmaceutical composition is in a capsule form.

41. The pharmaceutical composition of claim 40, wherein the compound of Formula (I), or a pharmaceutically acceptable salt thereof, is the free base.

42. The pharmaceutical composition of claim 1, comprising 39.2 wt % of the oily phase vehicle.

43. The pharmaceutical composition of claim 42, wherein the compound of Formula (I), or a pharmaceutically acceptable salt thereof, is the free base.

44. The pharmaceutical composition of claim 1, comprising:

(a) about 10 wt % of the compound of Formula (I), or a pharmaceutically acceptable salt thereof, based on the weight of the free base;
(b) from 35 wt % to 45 wt % of the oily phase vehicle;
(c) from 15 wt % to 25 wt % of the nonionic surfactant;
(d) from 15 wt % to 25 wt % of the emulsifying agent; and
(e) from 5 wt % to 15 wt % of the solubilizing agent.

45. The pharmaceutical composition of claim 44, wherein the compound of Formula (I), or a pharmaceutically acceptable salt thereof, is the free base.

46. The pharmaceutical composition of claim 31, wherein the compound of Formula (I), or a pharmaceutically acceptable salt thereof, is the free base.

47. A pharmaceutical composition, comprising:

(a) 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound of Formula (I)):

(I)

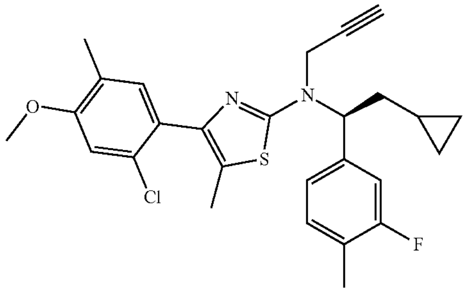

or a pharmaceutically acceptable salt thereof;

(b) medium-chain triglycerides;

(c) lauroyl polyoxyl-32 glycerides;

(c) propylene glycol dicaprylate/dicaprate; and (e) vitamin E polyethylene glycol succinate.

48. The pharmaceutical composition of claim 47, wherein the compound of Formula (I), or a pharmaceutically acceptable salt thereof, is the free base.

49. A pharmaceutical composition, comprising:

(a) about 10 wt % 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound of Formula (I)):

(I)

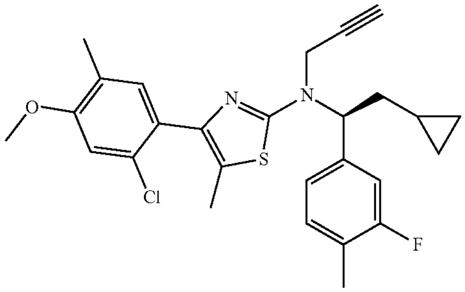

or a pharmaceutically acceptable salt thereof, based on the weight of the free base, (b) from 35 wt % to 45 wt % of medium-chain triglycerides;

(c) from 15 wt % to 25 wt % of lauroyl polyoxyl-32 glycerides;

(d) from 15 wt % to 25 wt % of propylene glycol dicaprylate/dicaprate; and (e) from 5 wt % to 15 wt % of vitamin E polyethylene glycol succinate.

50. The pharmaceutical composition of claim 49, wherein the compound of Formula (I), or a pharmaceutically acceptable salt thereof, is the free base.

51. The pharmaceutical composition of claim 49, comprising:

(a) about 10 wt % of the compound of Formula (I), based on the weight of the free base;

(b) about 39 wt % of medium-chain triglycerides;

(c) about 19 wt % of lauroyl polyoxyl-32 glycerides;

(d) about 20 wt % of propylene glycol dicaprylate/dicaprate; and (e) about 11 wt % of vitamin E polyethylene glycol succinate.

52. The pharmaceutical composition of claim 51, wherein the compound of Formula (I), or a pharmaceutically acceptable salt thereof, is the free base.

* * * * *